United States Patent
Carceller González et al.

(10) Patent No.: US 12,195,783 B2
(45) Date of Patent: Jan. 14, 2025

(54) METHODS TO DETERMINE KDM1A TARGET ENGAGEMENT AND CHEMOPROBES USEFUL THEREFOR

(71) Applicant: Oryzon Genomics S.A., Madrid (ES)

(72) Inventors: Elena Carceller González, Sant Cugat (ES); Tamara Maes, Castelldefels (ES); Cristina Mascaro Crusat, Barcelona (ES); Alberto Ortega Muñoz, Barcelona (ES)

(73) Assignee: Oryzon Genomics S.A., Madrid (ES)

( * ) Notice: Subject to any disclaimer, the term of this patent is extended or adjusted under 35 U.S.C. 154(b) by 0 days.

(21) Appl. No.: 17/644,604

(22) Filed: Dec. 16, 2021

(65) Prior Publication Data
US 2022/0389478 A1 Dec. 8, 2022

Related U.S. Application Data

(62) Division of application No. 17/313,226, filed on May 6, 2021, now abandoned, which is a division of application No. 16/085,024, filed as application No. PCT/EP2017/056330 on Mar. 16, 2017, now Pat. No. 11,034,991.

(30) Foreign Application Priority Data

Mar. 16, 2016 (EP) ..................... 16382119

(51) Int. Cl.
*G01N 33/58* (2006.01)
*C07D 495/04* (2006.01)
*C12Q 1/26* (2006.01)

(52) U.S. Cl.
CPC ............. *C12Q 1/26* (2013.01); *C07D 495/04* (2013.01); *G01N 33/58* (2013.01)

(58) Field of Classification Search
CPC ...................................................... G01N 33/58
See application file for complete search history.

(56) References Cited

U.S. PATENT DOCUMENTS 11,034,991 B2 * 6/2021 Carceller González ..................... A61P 25/00

FOREIGN PATENT DOCUMENTS

| | | |
|---|---|---|
| EP | 2743256 A1 | 6/2014 |
| EP | 2907802 A1 | 8/2015 |
| JP | 2007-524357 | 8/2007 |
| JP | 2013-505903 | 2/2013 |
| JP | 2013-525331 | 6/2013 |
| JP | 2013-535460 | 9/2013 |
| JP | 2014-515013 | 6/2014 |
| JP | 2014-532619 | 12/2014 |
| JP | 2015-502335 | 1/2015 |
| WO | WO2004/072232 | 8/2004 |
| WO | WO2008/054827 | 5/2008 |
| WO | WO2011/035941 | 3/2011 |
| WO | WO-2011035941 A1 * | 3/2011 ........... A61K 31/075 |
| WO | WO2011/131697 | 10/2011 |
| WO | WO2012/013728 | 2/2012 |
| WO | WO2012/135113 | 10/2012 |
| WO | WO2013/022047 | 2/2013 |
| WO | WO2013/057320 | 4/2013 |
| WO | WO2013/057322 | 4/2013 |
| WO | WO2014/058071 | 4/2014 |
| WO | WO2014/151282 | 9/2014 |

OTHER PUBLICATIONS

Wang, Rongsheng E. et al., "Biotinylated Quercetin as an Intrinsic Photoaffinity Proteomics Probe for the Identification of Quercetin Target Proteins," *Bioorganic & Medicinal Chemistry*, vol. 19, pp. 4710-4720 (2011).
Sanchez, Laura M. et al., "Examination of the Mode of Action of the Almiramide Family of Natural Products Against the Kinetoplastid Parasite *Trypanosoma brucei*," *Journal of Natural Products*, vol. 76, pp. 630-641 (2013).
McAllister, Tom E. et al., "Recent Progress in Histone Demethylase Inhibitors," *Journal of Medicinal Chemistry*, vol. 59, No. 4, pp. 1308-1329 (2016).
Ourailidou, Maria E. et al., "Towards the development of activity-based probes for detection of lysine-specific demethylase-1 activity," *Bioorganic & Medicinal Chemistry*, vol. 25, No. 3, pp. 847-856 (2017).
Szewczuk, Lawrence M. et al., Mechanistic Analysis of a Suicide Inactivator of Histone Demethylase LSD1, *Biochemistry*, vol. 46, No. 23, pp. 6892-6902 (2007).

(Continued)

*Primary Examiner* — John S Kenyon
(74) *Attorney, Agent, or Firm* — FINNEGAN, HENDERSON, FARABOW, GARRETT & DUNNER, LLP

(57) ABSTRACT

The invention relates to methods to determine KDM1A target engagement and chemoprobes useful therefor. In particular, the invention relates to non-peptidic KDM1A chemoprobes carrying a tag or label that can be used to assess KDM1A target engagement in cells and tissues. These chemoprobes can also be used to identify KDM1A interacting factors and analyze expression levels of KDM1A.

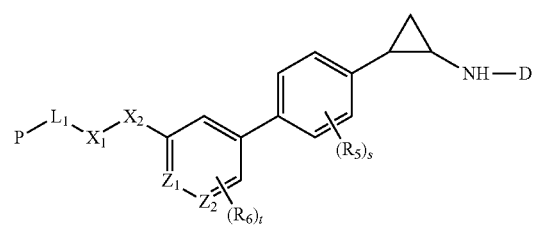

(II)

13 Claims, 11 Drawing Sheets
Specification includes a Sequence Listing.

(56) References Cited

OTHER PUBLICATIONS

McGrath, John P. et al., "Pharmacological Inhibition of the Histone Lysine Demethylase KDM1A Suppresses the Growth of Multiple Acute Myeloid Leukemia Subtypes," *Cancer Research*, vol. 76, No. 7, pp. 1975-1988 (2016), PMID 26837761, doi: 10.1158/0008-5472. CAN-15-2333.
International Search Report of International Application No. PCT/EP2017/056330, Dec. 7, 2017.
Written Opinion of the International Searching Authority of International Application No. PCT/EP2017/056330.

* cited by examiner

THP-1 cells

SEQUENCE LISTING

<160> NUMBER OF SEQ ID NOS: 2

<210> SEQ ID NO 1
<211> LENGTH: 852
<212> TYPE: PRT
<213> ORGANISM: Homo sapiens
<220> FEATURE:
<223> OTHER INFORMATION: KDM1A protein

<400> SEQUENCE: 1

Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
                20                  25                  30

Asn Gly Ser Glu Val Ala Ala Gln Pro Ala Gly Leu Ser Gly Pro Ala
            35                  40                  45

Glu Val Gly Pro Gly Ala Val Gly Glu Arg Thr Pro Arg Lys Lys Glu
        50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Arg Asn Ala Lys
130                 135                 140

Ala Glu Lys Glu Lys Lys Leu Pro Pro Pro Pro Gln Ala Pro Pro
145                 150                 155                 160

Glu Glu Glu Asn Glu Ser Glu Pro Glu Glu Pro Ser Gly Val Glu Gly
                165                 170                 175

Ala Ala Phe Gln Ser Arg Leu Pro His Asp Arg Met Thr Ser Gln Glu
            180                 185                 190

Ala Ala Cys Phe Pro Asp Ile Ile Ser Gly Pro Gln Gln Thr Gln Lys
        195                 200                 205

Val Phe Leu Phe Ile Arg Asn Arg Thr Leu Gln Leu Trp Leu Asp Asn
210                 215                 220

Pro Lys Ile Gln Leu Thr Phe Glu Ala Thr Leu Gln Gln Leu Glu Ala
225                 230                 235                 240

Pro Tyr Asn Ser Asp Thr Val Leu Val His Arg Val His Ser Tyr Leu
                245                 250                 255

Glu Arg His Gly Leu Ile Asn Phe Gly Ile Tyr Lys Arg Ile Lys Pro
            260                 265                 270

Leu Pro Thr Lys Lys Thr Gly Lys Val Ile Ile Gly Ser Gly Val
        275                 280                 285

Ser Gly Leu Ala Ala Ala Arg Gln Leu Gln Ser Phe Gly Met Asp Val
290                 295                 300

Thr Leu Leu Glu Ala Arg Asp Arg Val Gly Gly Arg Val Ala Thr Phe
305                 310                 315                 320

Arg Lys Gly Asn Tyr Val Ala Asp Leu Gly Ala Met Val Val Thr Gly
                325                 330                 335

Leu Gly Gly Asn Pro Met Ala Val Val Ser Lys Gln Val Asn Met Glu
            340                 345                 350

Leu Ala Lys Ile Lys Gln Lys Cys Pro Leu Tyr Glu Ala Asn Gly Gln

```
                355                 360                 365
Ala Val Pro Lys Glu Lys Asp Glu Met Val Glu Gln Glu Phe Asn Arg
        370                 375                 380
Leu Leu Glu Ala Thr Ser Tyr Leu Ser His Gln Leu Asp Phe Asn Val
385                 390                 395                 400
Leu Asn Asn Lys Pro Val Ser Leu Gly Gln Ala Leu Glu Val Val Ile
                405                 410                 415
Gln Leu Gln Glu Lys His Val Lys Asp Glu Gln Ile Glu His Trp Lys
        420                 425                 430
Lys Ile Val Lys Thr Gln Glu Glu Leu Lys Glu Leu Leu Asn Lys Met
                435                 440                 445
Val Asn Leu Lys Glu Lys Ile Lys Glu Leu His Gln Gln Tyr Lys Glu
        450                 455                 460
Ala Ser Glu Val Lys Pro Pro Arg Asp Ile Thr Ala Glu Phe Leu Val
465                 470                 475                 480
Lys Ser Lys His Arg Asp Leu Thr Ala Leu Cys Lys Glu Tyr Asp Glu
                485                 490                 495
Leu Ala Glu Thr Gln Gly Lys Leu Glu Glu Lys Leu Gln Glu Leu Glu
        500                 505                 510
Ala Asn Pro Pro Ser Asp Val Tyr Leu Ser Ser Arg Asp Arg Gln Ile
                515                 520                 525
Leu Asp Trp His Phe Ala Asn Leu Glu Phe Ala Asn Ala Thr Pro Leu
        530                 535                 540
Ser Thr Leu Ser Leu Lys His Trp Asp Gln Asp Asp Phe Glu Phe
545                 550                 555                 560
Thr Gly Ser His Leu Thr Val Arg Asn Gly Tyr Ser Cys Val Pro Val
                565                 570                 575
Ala Leu Ala Glu Gly Leu Asp Ile Lys Leu Asn Thr Ala Val Arg Gln
        580                 585                 590
Val Arg Tyr Thr Ala Ser Gly Cys Glu Val Ile Ala Val Asn Thr Arg
                595                 600                 605
Ser Thr Ser Gln Thr Phe Ile Tyr Lys Cys Asp Ala Val Leu Cys Thr
        610                 615                 620
Leu Pro Leu Gly Val Leu Lys Gln Gln Pro Pro Ala Val Gln Phe Val
625                 630                 635                 640
Pro Pro Leu Pro Glu Trp Lys Thr Ser Ala Val Gln Arg Met Gly Phe
                645                 650                 655
Gly Asn Leu Asn Lys Val Val Leu Cys Phe Asp Arg Val Phe Trp Asp
        660                 665                 670
Pro Ser Val Asn Leu Phe Gly His Val Gly Ser Thr Thr Ala Ser Arg
                675                 680                 685
Gly Glu Leu Phe Leu Phe Trp Asn Leu Tyr Lys Ala Pro Ile Leu Leu
        690                 695                 700
Ala Leu Val Ala Gly Glu Ala Gly Ile Met Glu Asn Ile Ser Asp
705                 710                 715                 720
Asp Val Ile Val Gly Arg Cys Leu Ala Ile Leu Lys Gly Ile Phe Gly
                725                 730                 735
Ser Ser Ala Val Pro Gln Pro Lys Glu Thr Val Val Ser Arg Trp Arg
        740                 745                 750
Ala Asp Pro Trp Ala Arg Gly Ser Tyr Ser Tyr Val Ala Ala Gly Ser
                755                 760                 765
Ser Gly Asn Asp Tyr Asp Leu Met Ala Gln Pro Ile Thr Pro Gly Pro
        770                 775                 780
```

```
Ser Ile Pro Gly Ala Pro Gln Pro Ile Pro Arg Leu Phe Phe Ala Gly
785                 790                 795                 800

Glu His Thr Ile Arg Asn Tyr Pro Ala Thr Val His Gly Ala Leu Leu
                805                 810                 815

Ser Gly Leu Arg Glu Ala Gly Arg Ile Ala Asp Gln Phe Leu Gly Ala
                820                 825                 830

Met Tyr Thr Leu Pro Arg Gln Ala Thr Pro Gly Val Pro Ala Gln Gln
            835                 840                 845

Ser Pro Ser Met
    850

<210> SEQ ID NO 2
<211> LENGTH: 16
<212> TYPE: PRT
<213> ORGANISM: Artificial Sequence
<220> FEATURE:
<223> OTHER INFORMATION: Epitope of mAb825

<400> SEQUENCE: 2

Ala Met Tyr Thr Leu Pro Arg Gln Ala Thr Pro Gly Val Pro Ala Gln
1               5                   10                  15
```

METHODS TO DETERMINE KDM1A TARGET ENGAGEMENT AND CHEMOPROBES USEFUL THEREFOR

This application is a continuation of application Ser. No. 17/313,226 filed May 6, 2021, which is a divisional of application Ser. No. 16/085,024 filed Sep. 14, 2018, which is a national stage filing under 35 U.S.C. § 371 of International Patent Application No. PCT/EP2017/056330, filed on Mar. 16, 2017, and which claims benefit of European Patent Application No. 16382119.2, filed Mar. 16, 2016, all of which are incorporated herein by reference.

FIELD OF THE INVENTION

The invention relates to methods to determine KDM1A target engagement and chemoprobes useful therefor. In particular, the invention relates to non-peptidic KDM1A chemoprobes carrying a tag or label that can be used to assess KDM1A target engagement in cells and tissues. These chemoprobes can also be used to identify KDM1A interacting factors and analyze expression levels of KDM1A.

BACKGROUND

Covalent modifications of histones are closely related to the control of gene transcription. Chromatin modifications constitute an epigenetic code that is dynamically 'written' and 'erased' by specialized proteins, and 'read' or interpreted by proteins that translate the code into gene expression changes. Acetylation, phosphorylation and methylation of histones is mediated by histone acetyl (HATs), phospho- and methyl transferases (PRMTs, HMTs), and can be reversed by deacetylases (HDACs), phosphatases and demethylases (KDMs).

KDMs are classified in 2 families with distinct enzymatic mechanisms of action: FAD-dependent amine oxidases (KDM1), which demethylate H3K4me1/2, and JmjC domain-containing KDMs, which are Fe(II)-dependent enzymes that catalyze the demethylation of mono-, di- and trimethylated lysines.

KDM1A (Lysine Specific Demethylase-1, also known as LSD1 or AOF2) belongs to the family of FAD-dependent amine oxidases and demethylates histone lysines via a hydride transfer from the N6-methyl group of the methylated lysine to the FAD cofactor, forming an unstable imine intermediate that is further hydrolyzed to liberate formaldehyde. This catalytic mechanism permits demethylation of secondary and tertiary but not of quaternary amines, limiting the substrate to mono and dimethylated lysines. During the demethylation reaction, the FAD cofactor is reduced to FADH2 and subsequently reoxidized to FAD, a process in which $H_2O_2$ is released. KDM1A is structurally related to the family of the monoamine oxidases, which include MAO-A, MAO-B, SMOX and IL11. KDM1A is a key enzyme involved in various biological processes including hematopoiesis, embryonic development, neurodevelopment, and viral biology. Increased or inappropriate KDM1A expression has been described in leukemogenesis and in solid tumors. KDM1A has been recognized as an interesting target for the development of new drugs to treat cancer, neurological diseases and other conditions, and a number of KDM1A inhibitors are currently under preclinical or clinical development for use in human therapy.

Assessment of KDM1A target engagement by KDM1A inhibitors in cells or tissues has been analyzed most frequently indirectly, through measurement of me2H3K4 accumulation, or by assessment of changes in gene expression. However, inhibition of histone lysine modifiers often leads to local rather than global changes in histone marks, histone modifications can be modulated by more than one cellular enzyme (for example H3K4 can be methylated by the SET/MLL proteins, and the methylation can be reversed by the KDM1 and KDM5 demethylases), and it is not always clear if a given change in histone mark is a direct or indirect consequence of treatment.

A NanoBRET assay that assesses LSD1 detachment from H3 histones upon KDM1A inhibition has also been described (JP McGrath et al., Cancer Res 2016, epub 2 Feb. 2016, PMID: 26837761). However, said assay requires transfection of cells with modified KDM1A and H3 constructs, and cannot readily be applied to samples obtained from animals or from human subjects.

A reliable method for the quantitative assessment of inhibitor engagement to KDM1A in cells and tissues, amenable to the analysis of clinical samples, is thus needed.

SUMMARY OF THE INVENTION

The invention relates to methods for the direct determination of KDM1A target engagement in a sample which is based on the determination of free KDM1A using specific KDM1A chemoprobes as described herein and in the appended claims. The methods as described herein can be used to quantify KDM1A target engagement of a KDM1A inhibitor in all kinds of samples, including clinical samples. The invention also relates to said KDM1A chemoprobes and to further uses thereof, as described herein and in the appended claims.

BRIEF DESCRIPTION OF THE DRAWINGS

FIG. 6C: detection of free KDM1A by AlphaLISA in the presence of 5 uM ORY-1001 as described in Example 6.

FIG. 8A: KDM1A Target engagement in MV(4;11) leukemic cells; FIG. 8B: KDM1A Target engagement in THP-1 leukemic cells; FIG. 8C: KDM1A Target engagement in LNCap prostate cancer cells.

FIG. 9C: KDM1A Target engagement in brain of SAMP8 mice treated with Compound C as described in example 8.

DETAILED DESCRIPTION OF THE INVENTION

Definitions

Figure 1A:
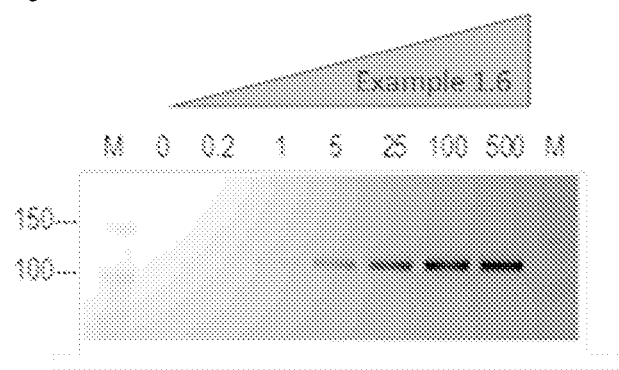
FIGS. 1A and 1B: KDM1A Western blot of pull down of cellular protein extracts described in example 3 using the chemoprobe example 1.6 (FIG. 1A) and of cell protein extracts treated with ORY-1001 (FIG. 1B) according to conditions detailed in example 3.

As used in the specification and appended claims, unless specified to the contrary, the following terms have the meaning indicated below.

Sample: any tissue, cells, protein extract, recombinant protein to which the methods of the invention described herein is to be applied. A sample or the subject from which the sample has been obtained may have been treated with a KDM1A inhibitor.

Reference sample: any tissue, cells, protein extract, recombinant protein that is chosen to serve as a reference to the sample. A reference sample or the subject from which the reference sample has been obtained may have been treated with a vehicle, may have been obtained prior to treatment with a KDM1A inhibitor, or may have been obtained when the effect of the KDM1A inhibitor has ceased completely.

Subject: human or animal organism.

In vitro: outside the context of a living organism; i.e. not in vivo.

Free KDM1A: enzymatically active KDM1A enzyme present in a sample, i.e. KDM1A not bound by a KDM1A inhibitor. Free KDM1A is available for binding to a KDM1A chemoprobe.

Total KDM1A: all KDM1A enzyme present in a sample, whether free, inhibited by a KDM1A inhibitor, or bound by a KDM1A chemoprobe.

Level: the amount of signal of free KDM1A or total KDM1A in a sample or subject determined by the methods described herein. The amount of signal can also be obtained from raw signal readouts by data processing. Data processing may comprise operations to remove background signal, eliminate outliers, average and/or normalize the raw signal using methods described in the literature. The level can also refer to the concentration/absolute amount of free KDM1A or total KDM1A in a sample, calculated by interpolating the signal of free KDM1A or total KDM1A in a calibration curve generated using a dilution series of samples with known free KDM1A or total KDM1A concentrations/amounts.

KDM1A inhibitor: herein is a non-peptidic compound that inhibits the enzymatic activity of KDM1A. The term KDM1A inhibitor will be used herein exclusively for a compound that is not a KDM1A chemoprobe according to the invention.

Non-peptidic compound: a compound that does not contain a chain of at least 3 amino acid monomers linked by peptide (amide) bonds. The presence of an (single) amide bond will not in itself be sufficient to term a compound as peptidic.

KDM1A chemoprobe (also termed chemoprobe): compound that selectively binds and inhibits KDM1A and incorporates a label or tag for detection, particularly a compound of formula I, II, IIa, III, IIIa as described herein and in the appended claims. The term KDM1A chemoprobe will be used herein exclusively for a compound that is not a KDM1A inhibitor according to the invention.

Tag: herein tag will be used to describe a moiety that can be incorporated into a molecule, for example into a KDM1A chemoprobe, that can be recognized and used in capture, recovery, isolation, purification or detection procedure of that molecule or of complexes involving that molecule.

Label: herein label will be used to describe a moiety that can be incorporated into a molecule, for example into a KDM1A chemoprobe or detection agent, and that directly gives rise to a signal, for example a fluorescent, bioluminescent, isotope, mass spectrometry label. A label can also be used as a tag if a suitable capture agents is available, for example a fluorescein moiety can be recognized and captured by an anti-fluorescein antibody.

Capture agent: agent that recognizes and binds the tag and that can be used to capture the chemoprobe or chemoprobe complexes from their crude biological source. In this invention, the capture agent can also be an agent that can be used to capture KDM1A or KDM1A containing complexes from their crude biological source.

Detection agent: agent that recognizes and binds a tag and that can be used to detect the KDM1A chemoprobe or KDM1A chemoprobe bound complexes, or an agent that can be used to detect KDM1A or a KDM1A containing complex in a sample.

Irreversible KDM1A inhibitor: a KDM1A inhibitor that reacts with KDM1A or its cofactor and changes it chemically (e.g. via covalent bond formation), irreversibly inactivating the KDM1A enzyme activity. Examples of irreversible KDM1A inhibitors include FAD binding KDM1A inhibitors.

Reversible KDM1A inhibitor: a KDM1A inhibitor that binds non-covalently to KDM1A or its cofactor and reversibly inactivates the KDM1A enzyme activity.

Target engagement: the target engagement of a KDM1A inhibitor is a measure for the degree of occupation of KDM1A by a KDM1A inhibitor.

Pharmacodynamics: herein, the study of the time dependent relation of the dose of KDM1A inhibitor administered, and the KDM1A target engagement.

Antibody as used herein is intended to include monoclonal antibodies, polyclonal antibodies, and chimeric antibodies, as well as Fab fragments, ScFv and the like.

KDM1A Chemoprobes

In one aspect, the invention relates to compounds that can be used as KDM1A chemoprobes, for use in the methods as described herein.

Accordingly, the invention provides a compound of formula (I)

$$P-L-Z \quad (I)$$

or a salt thereof,
wherein:
P is a tag or label;
L is a divalent $C_{6-100}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(═O)—, —NR¹—, —NR¹—C(═O)—, —C(═O)—NR¹—, —NR¹—C(═O)—NR¹—, —NR¹—C(═S)—NR¹—, —O—C(═O)—NR¹—, —NR¹—C(═O)—O—, —C(═O)—O—, —O—C(═O)—, —SO₂—NR¹— and —NR¹—SO₂—, and wherein L provides a distance of at least 6 atoms between P and Z;
R¹ is hydrogen or $C_{1-4}$ alkyl; and
Z is a radical of a KDM1A inhibitor.

As used herein in connection with Z, a radical of a KDM1A inhibitor is meant to be a KDM1A inhibitor where a H atom is replaced by the connecting bond.

In the compounds of formula (I) the KDM1A inhibitor can be an irreversible KDM1A inhibitor or a reversible KDM1A inhibitor. Preferably, the KDM1A inhibitor is an irreversible KDM1A inhibitor and thus Z preferably is a radical of an irreversible KDM1A inhibitor.

KDM1A inhibitors for use in the context of a compound of formula (I) include any of the compounds disclosed under the section "KDM1A inhibitors" below.

Preferably, the KDM1A inhibitor is a selective KDM1A inhibitor, e.g. a selective irreversible KDM1A inhibitor. As used herein, a "selective KDM1A inhibitor" refers to a KDM1A inhibitor which exhibits a selectivity of at least 10-fold for KDM1A over other FAD-dependent monoamine oxidases, particularly MAO-A and MAO-B. More preferably, the compound exhibits a selectivity of at least 30-fold for KDM1A over other FAD-dependent monoamine oxidases, particularly MAO-A and MAO-B, and still more preferably of at least 50-fold for KDM1A over other FAD-dependent monoamine oxidases, particularly MAO-A and MAO-B. The ability of a compound to inhibit KDM1A and other FAD-dependent monoamine oxidases, particularly MAO-A and MAO-B are preferably to be determined in accordance with the assays described in the appended Examples.

In some embodiments, the KDM1A inhibitor in a compound of formula (I) is not parnate, also known as tranylcypromine, which is not a selective KDM1A inhibitor.

In the compounds of formula (I) the KDM1A inhibitor is preferably an irreversible KDM1A inhibitor comprising a 2-cyclyl-cyclopropylamino moiety, preferably a 2-(hetero) arylcyclopropylamino compound, as defined herein.

In certain embodiments, in the compounds of formula (I) Z is a radical of an irreversible KDM1A inhibitor disclosed in WO2010/043721, WO2010/084160, WO2011/035941, WO2011/042217, WO2011/131697, WO2012/013727, WO2012/013728, WO2012/045883, WO2013/057320, WO2013/057322, WO2012/135113, WO2013/022047, WO2014/058071, WO2010/143582, US2010/0324147, WO2011/131576, WO2014/084298, WO2014/086790, WO2014/164867, WO2015/021128, WO2015/123408, WO2015/123424, WO2015/123437, WO2015/123465, WO2015/156417 or WO2015/181380. In certain embodiments, in the compounds of formula (I) Z is a radical of an irreversible KDM1A inhibitor disclosed in WO2010/043721, WO2010/084160, WO2011/035941, WO2011/042217, WO2011/131697, WO2012/013727, WO2012/013728, WO2012/045883, WO2013/057320, WO2013/057322, WO2012/135113, WO2013/022047, WO2014/058071, WO2010/143582, US2010/0324147, WO2011/131576, WO2014/084298, WO2014/086790, WO2014/164867, WO2015/021128, WO2015/123408, WO2015/123424, WO2015/123437, WO2015/123465, WO2015/156417, WO2015/181380, WO2016/123387, WO2016/130952, WO2016/172496, WO2016/177656, WO2017/027678 or CN106045862.

In certain embodiments, the KDM1A inhibitor is preferably a compound of formula (A), (B), (C), (D), (E), (F), (G), (H), (J), (K), (L), (M) or (N), as described in more detail below. More preferably, the KDM1A inhibitor is a compound of formula (C), (F), (H), (J), (K), (L), (M) or (N). Still more preferably, the KDM1A inhibitor is a compound from the lists of examples provided below for compounds of formulae (C), (F), (H), (J), (K) or (L). Preferably, in the compounds of the invention described herein the KDM1A inhibitor is (trans)-N1-((1R,2S)-2-phenylcyclopropyl)cyclohexane-1,4-diamine (also known as ORY-1001 or RG6016) or a salt thereof.

The invention also relates to a compound of formula (I) wherein Z is a group of formula Z1

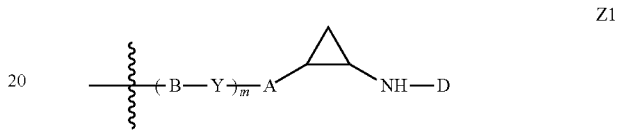

Z1 wherein:
A is aryl or heteroaryl, wherein said aryl or said heteroaryl is optionally substituted;
B is aryl, heteroaryl or heterocycloalkyl, wherein B is optionally substituted;
m is 0 or 1;
Y is a bond, —($C_{1-4}$ alkylene)-O—, —($C_{1-4}$ alkylene)-NR²—, —($C_{0-4}$ alkylene)-C(═O)—NR²—, or —($C_{0-4}$ alkylene)-NR²—C(═O)—R² is hydrogen or $C_{1-4}$ alkyl;
D is hydrogen, —($C_{1-4}$ alkylene)-CO—NR³R⁴, cyclyl or —($C_{1-4}$ alkylene)-cyclyl, wherein cyclyl and the cyclyl moiety in the —($C_{1-4}$ alkylene)-cyclyl are each optionally substituted;
R³ and R⁴ are each independently selected from hydrogen, $C_{1-4}$ alkyl and —($C_{0-4}$ alkylene)-cyclyl, wherein the cyclyl moiety in the —($C_{0-4}$ alkylene)-cyclyl is optionally substituted, or R³ and R⁴ are linked together to form together with the N atom to which they are bound a heterocyclic ring which may contain one or more additional heteroatoms selected from N, O and S and which is optionally substituted;
and the groups —(B—Y)$_m$-A- and —NH-D on the cyclopropyl ring are in trans configuration.

In any chemical drawings depicted herein, the waved line (interrupted bond) refers to the attachment point of the group (Z1 in this case, or any other group, as applicable) to the remainder of the compound (i.e. to L in the case of Z1).

In Z1, D is hydrogen, —($C_{1-4}$ alkylene)-CO—NR³R⁴, cyclyl or —($C_{1-4}$ alkylene)-cyclyl, wherein cyclyl and the cyclyl moiety in the —($C_{1-4}$ alkylene)-cyclyl are each optionally substituted.

Preferably, D is —($C_{1-4}$ alkylene)-CO—NR³R⁴, cyclyl or —($C_{1-4}$ alkylene)-cyclyl, wherein cyclyl and the cyclyl moiety in the —($C_{1-4}$ alkylene)-cyclyl are each optionally substituted.

More preferably, D is cyclyl or —($C_{1-4}$ alkylene)-cyclyl, wherein cyclyl and the cyclyl moiety in the —($C_{1-4}$ alkylene)-cyclyl are each optionally substituted.

Still more preferably, D is cycloalkyl, benzocycloalkyl, heterocycloalkyl or —($C_{1-4}$ alkylene)-cyclyl, wherein the cycloalkyl, the benzocycloalkyl, the heterocycloalkyl and the cyclyl moiety in the —($C_{1-4}$ alkylene)-cyclyl are each optionally substituted.

In some embodiments, D is optionally substituted cycloalkyl or optionally substituted benzocycloalkyl, preferably optionally substituted cycloalkyl. Even more preferably, D is a group of formula

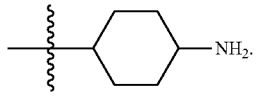

In some embodiments, D is optionally substituted heterocycloalkyl, for example D is optionally substituted piperidinyl, preferably optionally substituted 4-piperidinyl.

In some embodiments, D is —($C_{1-4}$ alkylene)-cyclyl wherein the cyclyl moiety in the —($C_{1-4}$ alkylene)-cyclyl is optionally substituted.

In some embodiments, D is —($C_{1-4}$ alkylene)-cycloalkyl wherein the cycloalkyl in the —($C_{1-4}$ alkylene)-cycloalkyl is optionally substituted. In some embodiments, D is cyclopropylmethyl.

In some embodiments, D is —($C_{1-4}$ alkylene)-heterocycloalkyl, wherein the heterocycloalkyl in the —($C_{1-4}$ alkylene)-heterocycloalkyl is optionally substituted. In some embodiments, D is —$CH_2$-heterocycloalkyl, more preferably —$CH_2$-(4-piperidinyl), wherein the heterocycloalkyl in the —$CH_2$-heterocycloalkyl and the 4-piperidinyl in the —$CH_2$-(4-piperidinyl) are each optionally substituted. In some embodiments, D is a group of formula

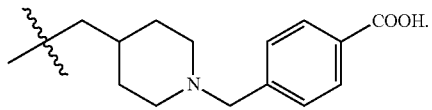 [SMILES: *CC1CCN(Cc2ccc(C(=O)O)cc2)CC1]

In some embodiments, D is a group of formula

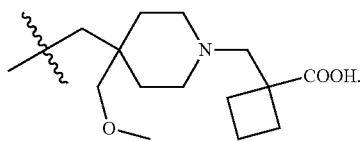 [SMILES: *CC1(COC)CCN(CC2(C(=O)O)CCC2)CC1]

In some embodiments, D is —($C_{1-4}$ alkylene)-heteroaryl, preferably —$CH_2$-heteroaryl, wherein the heteroaryl in the —($C_{1-4}$ alkylene)-heteroaryl and the heteroaryl in the —$CH_2$-heteroaryl is optionally substituted. Preferably, the heteroaryl in D is a monocyclic 5- or 6-membered heteroaryl, which is optionally substituted. In some embodiments, D is a group of formula

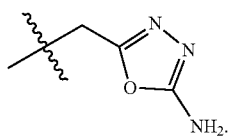 [SMILES: *Cc1nnc(N)o1]

In Z1, Y is a bond, —($C_{1-4}$ alkylene)-O—, —($C_{1-4}$ alkylene)-$NR^2$—, —($C_{0-4}$ alkylene)-C(═O)—$NR^2$—, or —($C_{0-4}$ alkylene)-$NR^2$—C(═O)—. Although both orientations are possible for Y groups, preferably Y groups are linked to A through the O, NR2 or C(═O) groups, respectively, and are linked to B through the alkylene groups.

Preferably Y is a bond, —$CH_2$—O—, —C(═O)—$NR^2$—, or —$NR^2$—C(═O)—. More preferably, Y is a bond.

In Z1, A is aryl or heteroaryl, wherein said aryl or said heteroaryl is optionally substituted. In relation to A, aryl and heteroaryl relate to an aryl or heteroaryl group as defined below. In addition, in relation to A, aryl and heteroaryl also encompasses ring systems comprising at least an aromatic ring. Thus rings comprising an aromatic ring like phenyl or an heteroaromatic ring like pyridyl fused to a non-aromatic carbocyclic or heterocyclic ring are also included, for example 2,3-dihydrobenzofuran. Preferably, the two points of attachment of ring A to the remainder of the molecule are on the aromatic ring.

Preferably, A is optionally substituted phenyl. In some embodiments, A is unsubstituted phenyl.

In Z1, B is aryl, heteroaryl or heterocycloalkyl, wherein B is optionally substituted. Preferably, B is aryl or heteroaryl, wherein B is optionally substituted. More preferably, B is optionally substituted aryl, preferably optionally substituted phenyl. In some embodiments, B is unsubstituted phenyl.

In some embodiments, m is 1 and Y is bond, more preferably m is 1, Y is bond, and B is optionally substituted aryl, preferably optionally substituted phenyl. In some embodiments, B is unsubstituted phenyl.

In some embodiments, m is 0.

The invention further provides a compound of formula (I) as defined above, wherein Z is a group of formula Z2

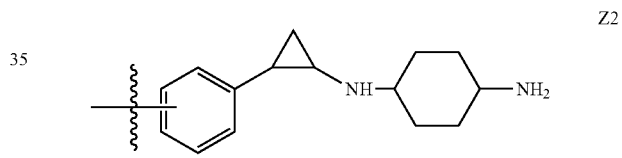

wherein the phenyl ring is optionally substituted, and wherein the substituents on the cyclopropyl ring are in trans configuration. In some embodiments, the phenyl ring is unsubstituted.

The invention further provides a compound of formula (I) as defined above, wherein Z is a group of formula Z3a or Z3b

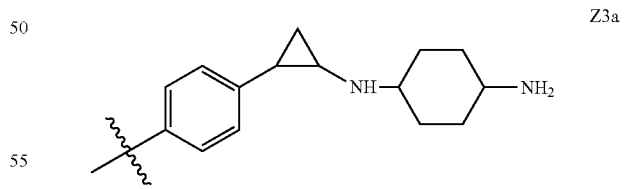

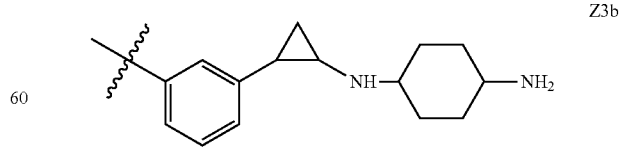

wherein in Z3a and Z3b the phenyl rings are optionally substituted and the substituents on the cyclopropyl ring are in trans configuration. In some embodiments, the phenyl rings are unsubstituted.

The invention further provides a compound of formula (I) as defined above, wherein Z is a group of formula Z4:

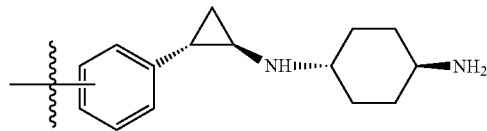

wherein the phenyl ring is optionally substituted. Preferably, the phenyl ring is unsubstituted.

The invention further provides a compound of formula (I) as defined above, wherein Z is a group of formula Z5a or Z5b:

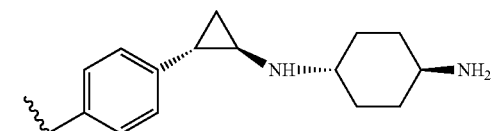

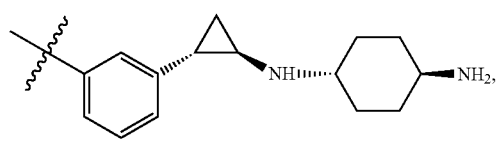

wherein in Z5a and Z5b the phenyl rings are optionally substituted. Preferably, the phenyl rings are unsubstituted.

In a compound of formula (I), P is a tag or label. Examples of tags or labels that can be used in a compound of formula (I) include the tags and labels described in more detail in the corresponding section, below.

In a compound of formula (I), L is a divalent $C_{6-100}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— and —NR$^1$—SO$_2$—, and wherein L provides a distance of at least 6 atoms between P and Z.

Preferably, in the compounds of formula (I) L is a divalent $C_{30}$-$C_{80}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— and —NR$^1$—SO$_2$—, and wherein L provides a distance between P and Z of 25 to 70 atoms.

More preferably, L is a divalent $C_{40}$-$C_{70}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— and —NR$^1$—SO$_2$—, and wherein L provides a distance between P and Z of 35 to 65 atoms.

In some embodiments, L comprises a heteroalkylene group of 6 to 70 atoms, preferably of 6 to 50 atoms.

Preferably, in a compound of formula (I) L comprises a group of formula (i) or (ii):
(i) —(CH$_2$CH$_2$O)$_n$—(CH$_2$)$_p$—, wherein n is an integer from 6 to 20, preferably from 8 to 18, and p is an integer from 1 to 5; or
(ii) —(CH$_2$CH$_2$O)$_x$—(CH$_2$)$_q$-G-(CH$_2$CH$_2$O)$_y$(CH$_2$)$_r$—, wherein G is —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, or —O—C(=O)—, preferably G is —NR$^1$—C(=O)— or —C(=O)—NR$^1$—, one of x and y is an integer from 1 to 18 and the other from x and y is an integer from 0 to 17 provided that x+y is from 4 to 18, preferably x+y is from 6 to 16, and each of q and r is an integer independently selected from 1 to 5.

More preferably, in a compound of formula (I) L comprises a group of formula (i) or (ii):
(i) —(CH$_2$CH$_2$O)$_n$—(CH$_2$)$_p$—, wherein n is an integer from 6 to 20, preferably from 8 to 18, and p is an integer from 1 to 5; or
(ii) —(CH$_2$CH$_2$O)$_x$—(CH$_2$)$_q$-G-(CH$_2$CH$_2$O)$_y$(CH$_2$)$_r$—, wherein G is —NR$^1$—C(=O)— or —C(=O)—NR$^1$—, one of x and y is an integer from 1 to 18 and the other from x and y is an integer from 0 to 17 provided that x+y is from 4 to 18, preferably x+y is from 6 to 16, and each of q and r is an integer independently selected from 1 to 5.

Still more preferably, in a compound of formula (I) L comprises a group of formula —(CH$_2$CH$_2$O)$_n$—(CH$_2$)$_p$—, wherein n is an integer from 6 to 20, preferably from 8 to 18, and p is an integer from 1 to 5.

Preferably, L comprises a group of formula X$_1$—X$_2$—X$_3$, wherein X$_1$ is linked to the remainder of L and X$_3$ is linked to Z, and wherein:
X$_1$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$—, —NR$^1$—SO$_2$— or —O—;
X$_2$ is C$_{0-5}$ alkylene;
X$_3$ is arylene or heteroarylene, wherein said arylene and said heteroarylene are each optionally substituted.

Preferably, X$_1$ is —NHC(=O)—, —C(=O)NH—, —SO$_2$—NH— or —NH—SO$_2$—, more preferably X$_1$ is —NHC(=O)— or —C(=O)NH—, still more preferably —NHC(=O)—.

Preferably, X$_3$ is connected to X$_1$—X$_2$ and to Z in a 1,3 disposition. More preferably, X$_3$ is a group of formula:

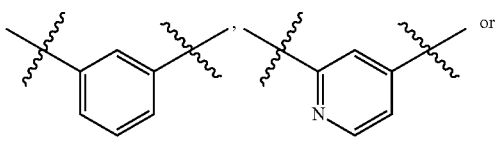

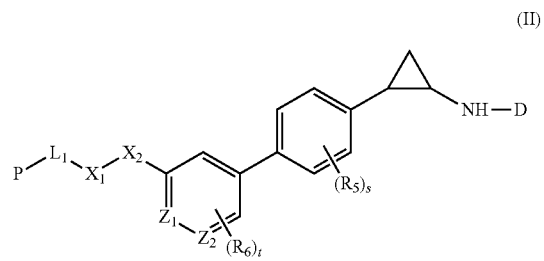

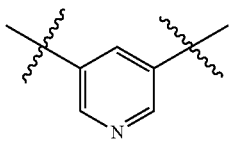

wherein each ring is optionally substituted. Still more preferably, wherein $X_3$ is a group of formula:

which is optionally substituted. In some embodiments, $X_3$ is unsubstituted.

Preferably, $X_2$ is $C_{1-5}$ alkylene, more preferably $-(CH_2)_{1-5}-$.

In some embodiments, L comprises a group of formula $X_1-X_2-X_3$, wherein $X_1$ is $-NHC(=O)-$ or $-C(=O)NH-$, $X_2$ is $C_{1-5}$ alkylene and $X_3$ is a group of formula:

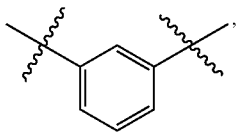 [SMILES: *c1cccc(*)c1]

Preferably, L comprises a group of formula $X_1-X_2-X_3$, wherein $X_1-X_2-X_3$ is a group of formula:

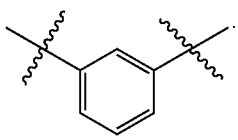 [SMILES: *c1cccc(*)c1]

wherein the group is linked to Z through the phenyl ring and to the remainder of L through the N atom.

Particularly preferred compounds for use as KDM1A chemoprobes according to the invention include the compounds of formula (II).

Accordingly, the invention provides a compound of formula II or a salt thereof, wherein:

P is a tag or label;

D is cyclyl or $-(C_{1-4}$ alkylene)-cyclyl, wherein cyclyl and the cyclyl moiety in the $-(C_{1-4}$ alkylene)-cyclyl are each optionally substituted;

$L_1$ is a divalent $C_{6-90}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of $-C(=O)-$, $-NR^1-$, $-NR^1-C(=O)-$, $-C(=O)-NR^1-$, $-NR^1-C(=O)-NR^1-$, $-NR^1-C(=S)-NR^1-$, $-O-C(=O)-NR^1-$, $-NR^1-C(=O)-O-$, $-C(=O)-O-$, $-O-C(=O)-$, $-SO_2-NR^1-$ and $-NR^1-SO_2-$, and wherein $L_1$ provides a distance of at least 3 atoms between P and $X_1$;

$R^1$ is hydrogen or $C_{1-4}$ alkyl;

$X_1$ is $-C(=O)-$, $-NR^1-$, $-NR^1-C(=O)-$, $-C(=O)-NR^1-$, $-NR^1-C(=O)-NR^1-$, $-NR^1-C(=S)-NR^1-$, $-O-C(=O)-NR^1-$, $-NR^1-C(=O)-O-$, $-C(=O)-O-$, $-O-C(=O)-$, $-SO_2-NR^1-$, $-NR^1-SO_2-$ or $-O-$;

$X_2$ is $C_{0-5}$ alkylene;

one of $Z_1$ and $Z_2$ is CH or N, and the other of $Z_1$ and $Z_2$ is CH;

s and t are each independently selected from 0, 1 and 2;

$R_5$ and $R_6$ are at each occurrence independently selected from $C_{1-4}$ alkyl, halo, $-NH_2$, $-NR^aR^c$, $-CN$, $-OH$, $-OR^c$, halo$C_{1-4}$ alkyl, cyclyl, cyclyl$C_{1-4}$ alkyl-, and $C_{1-4}$ alkyl-O-$C_{1-4}$ alkyl;

$R^a$ is selected from hydrogen, $C_{1-4}$ alkyl and halo$C_{1-4}$ alkyl;

$R^c$ is independently selected from $C_{1-4}$ alkyl, halo$C_{1-4}$ alkyl, cyclyl, cyclyl$C_{1-4}$ alkyl-, and $C_{1-4}$ alkyl-O-$C_{1-4}$ alkyl-; and wherein the phenyl and $-NH-D$ groups on the cyclopropyl ring are in trans configuration.

In another aspect, the invention provides a compound of formula (IIa)
or a salt thereof

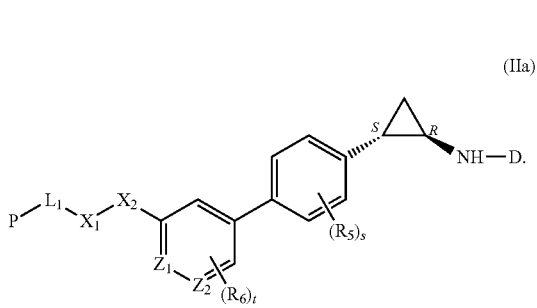

(IIa)

wherein the meanings for the various substituents are as defined above.

Throughout this document, the symbols R and S on the cyclopropyl ring are meant to indicate absolute configuration on this ring.

Still more preferably, D is cycloalkyl, benzocycloalkyl, heterocycloalkyl or —($C_{1-4}$ alkylene)-cyclyl, wherein the cycloalkyl, the benzocycloalkyl, the heterocycloalkyl and the cyclyl moiety in the —($C_{1-4}$ alkylene)-cyclyl are each optionally substituted.

In some embodiments, in a compound of formula (II) or (IIa), D is optionally substituted cycloalkyl or optionally substituted benzocycloalkyl, preferably optionally substituted cycloalkyl. Even more preferably, D is a group of formula

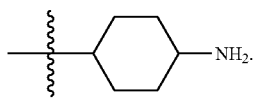

In some embodiments, in a compound of formula (II) or (IIa), D is optionally substituted heterocycloalkyl, for example D is optionally substituted piperidinyl, preferably optionally substituted 4-piperidinyl.

In some embodiments, in a compound of formula (II) or (IIa), D is —($C_{1-4}$ alkylene)-cyclyl wherein the cyclyl moiety in the —($C_{1-4}$ alkylene)-cyclyl is optionally substituted.

In some embodiments, in a compound of formula (II) or (IIa), D is —($C_{1-4}$alkylene)-cycloalkyl wherein the cycloalkyl in the —($C_{1-4}$ alkylene)-cycloalkyl is optionally substituted. In some embodiments, D is cyclopropylmethyl.

In some embodiments, in a compound of formula (II) or (IIa), D is —($C_{1-4}$ alkylene)-heterocycloalkyl, wherein the heterocycloalkyl in the —($C_{1-4}$ alkylene)-heterocycloalkyl is optionally substituted. In some embodiments, D is —$CH_2$-heterocycloalkyl, more preferably —$CH_2$-(4-piperidinyl), wherein the heterocycloalkyl in the —$CH_2$-heterocycloalkyl and the 4-piperidinyl in the —$CH_2$-(4-piperidinyl) are each optionally substituted. In some embodiments, D is a group of formula

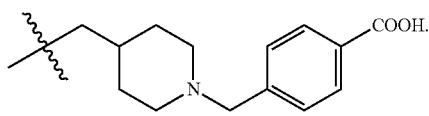 [SMILES: *CC1CCN(Cc2ccc(C(=O)O)cc2)CC1]

In some embodiments, D is a group of formula

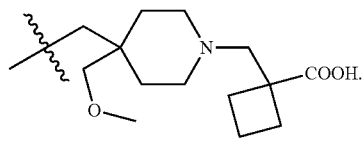 [SMILES: *CC1(COC)CCN(CC2(C(=O)O)CCC2)CC1]

In some embodiments, in a compound of formula (II) or (IIa), D is —($C_{1-4}$ alkylene)-heteroaryl, preferably —$CH_2$—heteroaryl, wherein the heteroaryl in the —($C_{1-4}$ alkylene)-heteroaryl and the heteroaryl in the —$CH_2$-heteroaryl is optionally substituted. Preferably, the heteroaryl in D is a monocyclic 5- or 6-membered heteroaryl, which is optionally substituted. In some embodiments, D is a group of formula

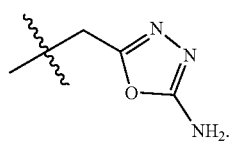

In a further aspect, the invention provides a compound of formula (III), or a salt thereof

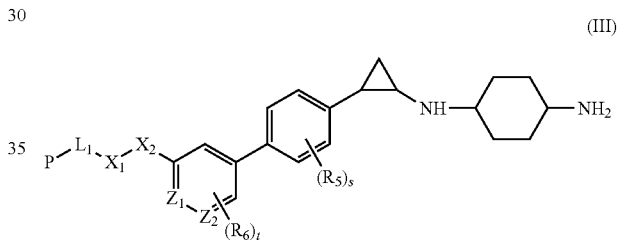

(III)

wherein the substituents on the cyclopropyl ring are in trans configuration, wherein the meanings for the various substituents are as defined above.

A particularly preferred compound is a compound of formula (IIIa), or a salt thereof

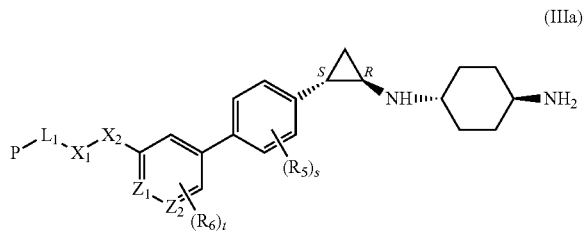

(IIIa)

wherein the meanings for the various substituents are as defined above.

Preferably, in a compound of formula (II), (IIa), (III) or (IIIa), $X_1$ is —$NR^1$—C(=O)—, —C(=O)—$NR^1$—, —$SO_2$—$NR^1$— or —$NR^1$—$SO_2$—, more preferably $X_1$ is —NHC(=O)—, —C(=O)NH—, —$SO_2$—NH— or —NH—$SO_2$—, still more preferably $X_1$ is —NHC(=O)— or —C(=O)NH—, and even more preferably $X_1$ is —NHC(=O)—.

Preferably, in a compound of formula (II), (IIa), (III) or (IIIa), $X_2$ is $C_{1-5}$ alkylene, preferably —($CH_2$)$_{1-5}$—.

Preferably, in a compound of formula (II), (IIa), (III) or (IIIa) $X_1$—$X_2$ is a group of formula

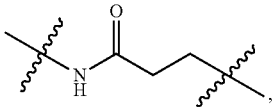 [SMILES: *CCC(=O)N*]

wherein the group is linked to the ring through the carbon atom and to $L_1$ through the N atom.

Preferably, in a compound of formula (II), (IIa), (III) or (IIIa) each of $Z_1$ and $Z_2$ is CH.

Preferably, in a compound of formula (II), (IIa), (III) or (IIIa), $R_5$ and $R_6$ are each independently selected from halo and $C_{1-4}$alkyl.

In some embodiments, each of s and t is 0.

Preferably, in a compound of formula (II), (IIa), (III) or (IIIa), $L_1$ is a group of formula $X_4$—$X_5$, wherein $X_4$ is linked to P and $X_5$ is linked to $X_1$, wherein:
$X_4$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— or —NR$^1$—SO$_2$—; and
$X_5$ is a group of formula (i) or (ii):
(i) —(CH$_2$CH$_2$O)$_n$—(CH$_2$)$_p$—, wherein n is an integer from 6 to 20, preferably from 8 to 18, and p is an integer from 1 to 5; or
(ii) —(CH$_2$CH$_2$O)$_x$—(CH$_2$)$_q$-G-(CH$_2$CH$_2$O)$_y$(CH$_2$)$_r$-, wherein G is —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, or —O—C(=O)—, preferably G is —NR$^1$—C(=O)— or —C(=O)—NR$^1$—, one of x and y is an integer from 1 to 18 and the other from x and y is an integer from 0 to 17 provided that x+y is from 4 to 18, preferably x+y is from 6 to 16, and each of q and r is an integer independently selected from 1 to 5.

More preferably, in a compound of formula (II), (IIa), (III) or (IIIa), $L_1$ is a group of formula $X_4$—$X_5$, wherein $X_4$ is linked to P and $X_5$ is linked to $X_1$, wherein:
$X_4$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— or —NR$^1$—SO$_2$—; and
$X_5$ is a group of formula (i) or (ii):
(i) —(CH$_2$CH$_2$O)$_n$—(CH$_2$)$_p$—, wherein n is an integer from 6 to 20, preferably from 8 to 18, and p is an integer from 1 to 5; or
(ii) —(CH$_2$CH$_2$O)$_x$—(CH$_2$)$_q$-G-(CH$_2$CH$_2$O)$_y$(CH$_2$)$_r$-, wherein G is —NR$^1$—C(=O)— or —C(=O)—NR$^1$—, one of x and y is an integer from 1 to 18 and the other from x and y is an integer from 0 to 17 provided that x+y is from 4 to 18, preferably x+y is from 6 to 16, and each of q and r is an integer independently selected from 1 to 5.

Still more preferably, in a compound of formula (II), (IIa), (III) or (IIIa), $L_1$ is a group of formula $X_4$—$X_5$, wherein $X_4$ is linked to P and $X_5$ is linked to $X_1$, wherein:
$X_4$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— or —NR$^1$—SO$_2$—; and
$X_5$ is a group of formula —(CH$_2$CH$_2$O)$_n$—(CH$_2$)$_p$—, wherein n is an integer from 6 to 20, preferably from 8 to 18, and p is an integer from 1 to 5.

A particularly suitable class of compounds for use as chemoprobes in the methods of the invention is a compound of formula (II), preferably of formula (IIa), or a salt thereof, wherein:
P is a tag or label;
D is cyclyl or —(C$_{1-4}$ alkylene)-cyclyl, wherein cyclyl and the cyclyl moiety in the —(C$_{1-4}$ alkylene)-cyclyl are each optionally substituted, preferably D is cycloalkyl, benzocycloalkyl, heterocycloalkyl or —(C$_{1-4}$ alkylene)-cyclyl, wherein the cycloalkyl, the benzocycloalkyl, the heterocycloalkyl and the cyclyl moiety in the —(C$_{1-4}$ alkylene)-cyclyl are each optionally substituted, and more preferably D is optionally substituted cycloalkyl, optionally substituted heterocycloalkyl, —CH$_2$-heterocycloalkyl wherein the heterocycloalkyl in the —CH$_2$-heterocycloalkyl is optionally substituted, or —CH$_2$-heteroaryl wherein the heteroaryl in the —CH$_2$-heteroaryl is optionally substituted;
$L_1$ is a group of formula $X_4$—$X_5$, wherein $X_4$ is linked to P and $X_5$ is linked to $X_1$, wherein:
$X_4$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— or —NR$^1$—SO$_2$—;
$X_5$ is a group of formula —(CH$_2$CH$_2$O)$_n$—(CH$_2$)$_p$—, wherein n is an integer from 6 to 20, preferably from 8 to 18, and p is an integer from 1 to 5;
$X_1$ is —NR$^1$—C(=O)—, —C(=O)—NR$^1$—, —SO$_2$—NR$^1$— or —NR$^1$—SO$_2$—, preferably $X_1$ is —NHC(=O)—, —C(=O)NH—, —SO$_2$—NH— or —NH—SO$_2$—, more preferably $X_1$ is —NHC(=O)— or —C(=O)NH—, and still more preferably $X_1$ is —NHC(=O)—; and $X_2$ is C$_{1-5}$ alkylene, preferably —(CH$_2$)$_{1-5}$—; and more preferably $X_1$—$X_2$ is a group of formula

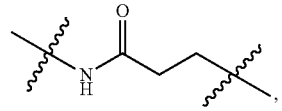 [SMILES: *CCC(=O)N*]

wherein the group is linked to the ring through the carbon atom and to $L_1$ through the N atom;
each of $Z_1$ and $Z_2$ is CH; and
each of s and t is 0.

Still more preferred compounds for use as chemoprobes in the methods of the invention is a compound of formula (III), preferably of formula (IIIa), or a salt thereof

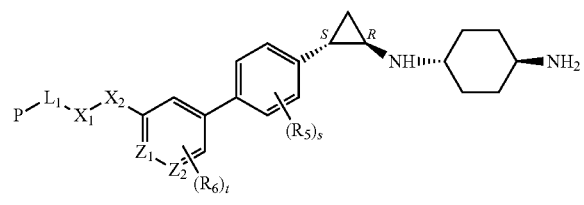

(IIIa)

wherein:

P is a tag or label;

L$_1$ is a group of formula X$_4$—X$_5$, wherein X$_4$ is linked to P and X$_5$ is linked to X$_1$, wherein:

X$_4$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— or —NR$^1$—SO$_2$—;

X$_5$ is a group of formula —(CH$_2$CH$_2$O)$_n$—(CH$_2$)$_p$—, wherein n is an integer from 6 to 20, preferably from 8 to 18, and p is an integer from 1 to 5;

X$_1$ is —NR$^1$—C(=O)—, —C(=O)—NR$^1$—, —SO$_2$—NR$^1$— or —NR$^1$—SO$_2$—, preferably X$_1$ is —NHC(=O)—, —C(=O)NH—, —SO$_2$—NH— or —NH—SO$_2$—, more preferably X$_1$ is —NHC(=O)— or —C(=O)NH—, and still more preferably X$_1$ is —NHC(=O)—; and X$_2$ is C$_{1-5}$ alkylene, preferably —(CH$_2$)$_{1-5}$—; and more preferably X$_1$—X$_2$ is a group of formula

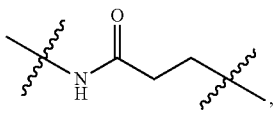 [SMILES: *CCC(=O)N*]

wherein the group is linked to the ring through the carbon atom and to L$_1$ through the N atom;

each of Z$_1$ and Z$_2$ is CH; and each of s and t is 0.

Throughout this document, divalent chemical groups depicted using specific chemical formulae, such as X$_1$, X$_2$, X$_3$ etc are preferably oriented in the direction in which they are written. As an example, if in a compound of formula (IIIa) X$_1$ is —NHC(=O)—, this group is preferably oriented so that the N atom is bound to L$_1$ and the C atom is bound to the X$_2$ group.

In some of the embodiments described above, certain cyclic groups are defined to be optionally substituted. This means that the group can be unsubstituted or can have one or more substituents. Examples of optional substituents for cyclic groups include, without limitation, the following groups:

C$_{1-4}$ alkyl, cyclyl, cyclylC$_{1-4}$alkyl-, —NH$_2$, —NR$^a$R$^c$, —NO$_2$, halo, haloC$_{1-4}$alkyl, haloC$_{1-4}$ alkoxy, C$_{1-4}$alkyl-O—C$_{1-4}$alkyl-, —CN, —C(=O)—NH$_2$, —C(=O)—NR$^a$R$^c$, —NR$^a$—C(=O)—R$^c$, —S(=O)—R$^c$, —S(=O)$_2$—R$^c$, —NR$^a$—S(=O)$_2$—R$^c$, —S(=O)$_2$—NH$_2$, —S(=O)$_2$—NR$^a$R$^c$, —OH, —OR$^c$, —C(=O)—R$^c$, —C(=O)—OH, —C(=O)—OR$^c$, —O—C(=O)—R$^c$, —NR$^a$—C(=O)—OR$^c$, —O—C(=O)—NR$^a$R$^c$, wherein:

each R$^a$ and R$^b$ are independently selected from hydrogen, C$_{1-4}$ alkyl and haloC$_{1-4}$ alkyl; and each R$^c$ is independently selected from C$_{1-4}$alkyl, haloC$_{1-4}$alkyl, cyclyl, cyclylC$_{1-4}$alkyl-, and C$_{1-4}$alkyl-O—C$_{1-4}$alkyl-.

In a compound of formula (I), (II), (IIa), (III) and (IIIa), P is a tag or label. Examples of tags or labels that can be used in said compounds include the tags and labels described in more detail in the corresponding section below. In some embodiments, P is a tag. In some embodiments, P is biotin or a biotin derivative.

In some embodiments, P is a label. In some embodiments, P is fluorescent label. In some embodiments, P is fluorescein or a fluorescein derivative.

Preferably, P is biotin or a biotin derivative.

Thus, in a compound of formula (II), (IIa), (III) or (IIIa), it is preferred that X$_4$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— or —NR$^1$—SO$_2$—; and that P is biotin or a biotin derivative.

Accordingly, it is particularly preferred that P—X$_4$— is selected from the groups listed below:

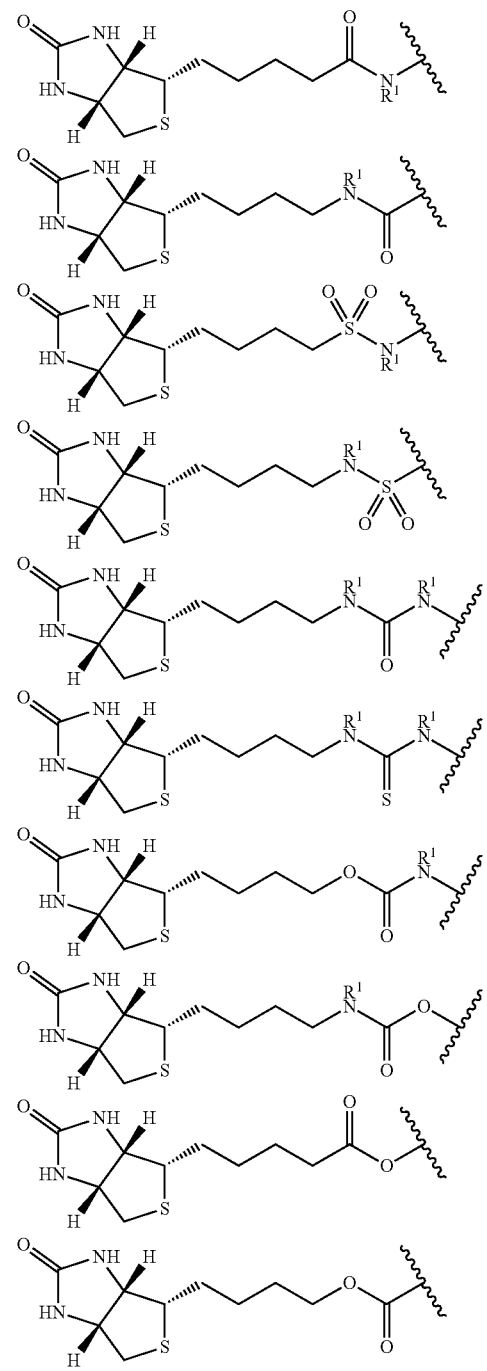

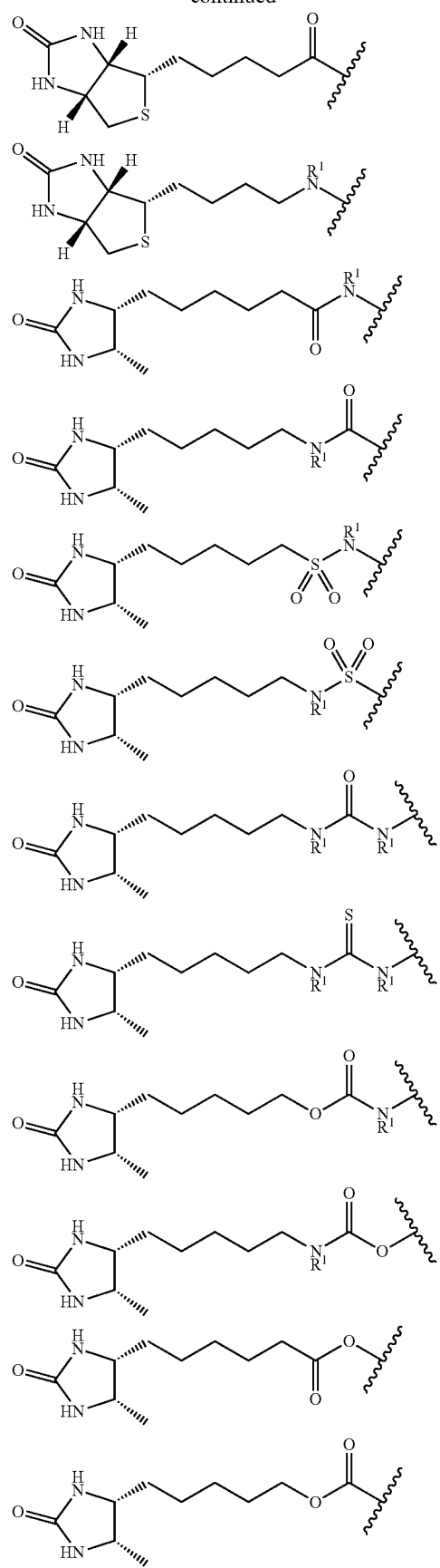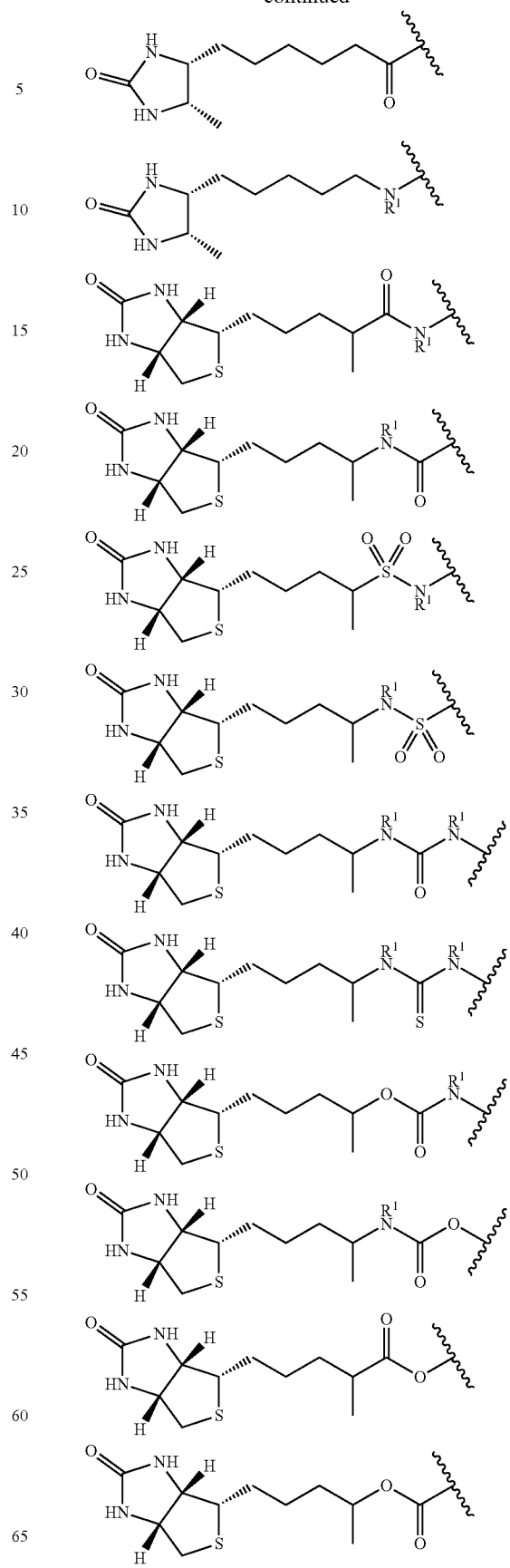

-continued

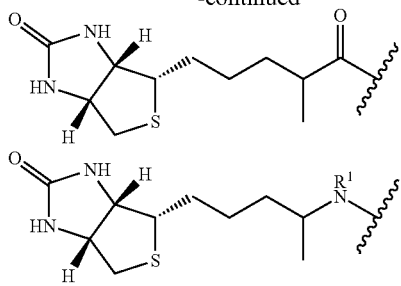

wherein $R^1$ is hydrogen or $C_{1-4}$ alkyl, and preferably $R^1$ is H.

It is even more preferred that in a compound of formula (II), (IIa), (III) or (IIIa) P—$X_4$— is selected from the groups listed below:

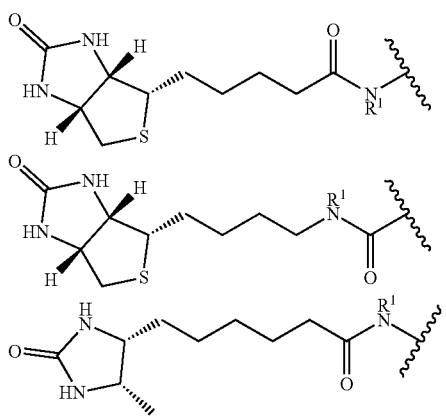

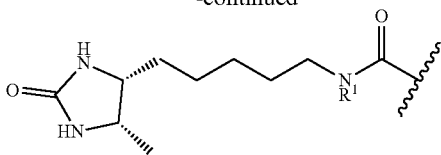

wherein $R^1$ is hydrogen or $C_{1-4}$ alkyl and preferably $R^1$ is H.

It is still even more preferred that in a compound of formula (II), (IIa), (III) or (IIIa) P—$X_4$— is

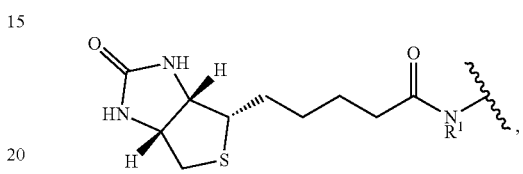

wherein $R^1$ is hydrogen or $C_{1-4}$ alkyl, and preferably $R^1$ is H (as, e.g., in the Examples 1.1 to 1.6).

It is to be understood that the present invention specifically relates to each and every combination of features or embodiments described above, including any combination of general and/or preferred features/embodiments. In particular, the invention specifically relates to all combinations of preferred features/embodiments (including all degrees of preference) of the compounds disclosed herein.

Particularly preferred compounds of the invention for use as chemoprobes are the compounds listed below, and salts thereof

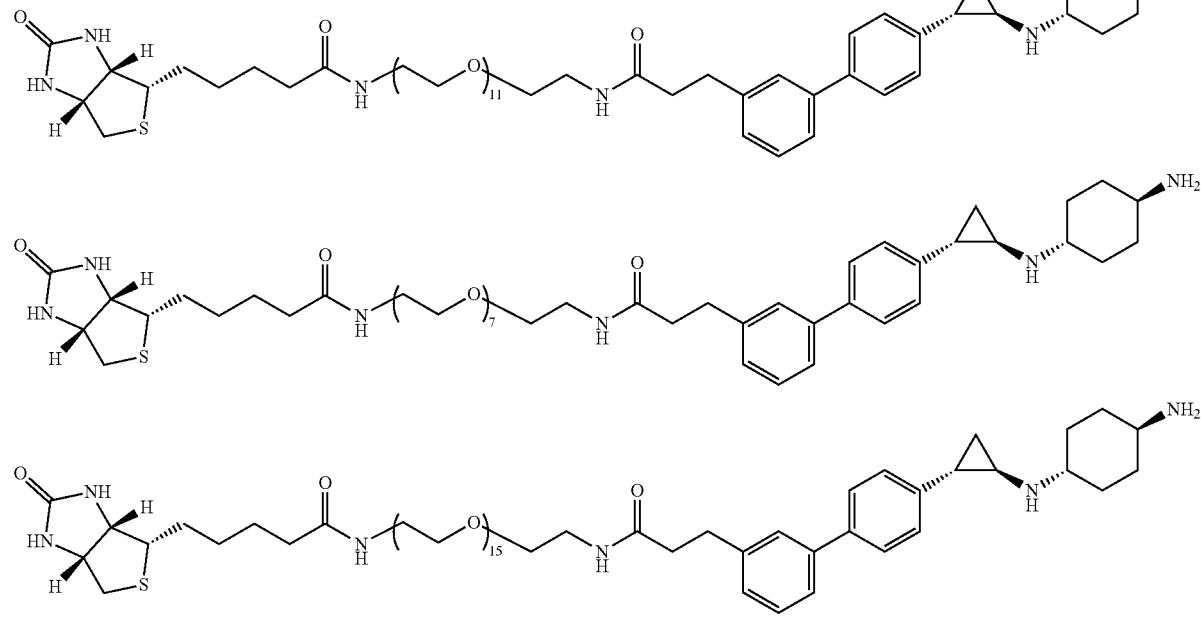

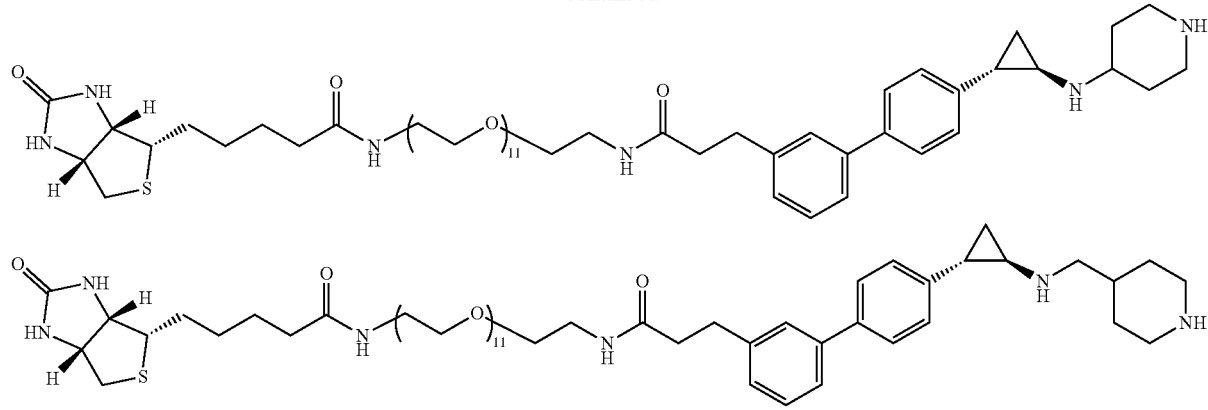

Preferably, the compounds of formula (I) (where Z is Z1, Z2, Z3a, Z3b), (II) and (III), including the compounds listed above, have the (S) configuration on the C atom in the cyclopropyl to which the phenyl ring is linked and the (R) configuration in the C atom in the cyclopropyl to which the N atom is linked.

Most preferred compounds for use as chemoprobes in the methods of the invention are the compounds listed below, and salts thereof:

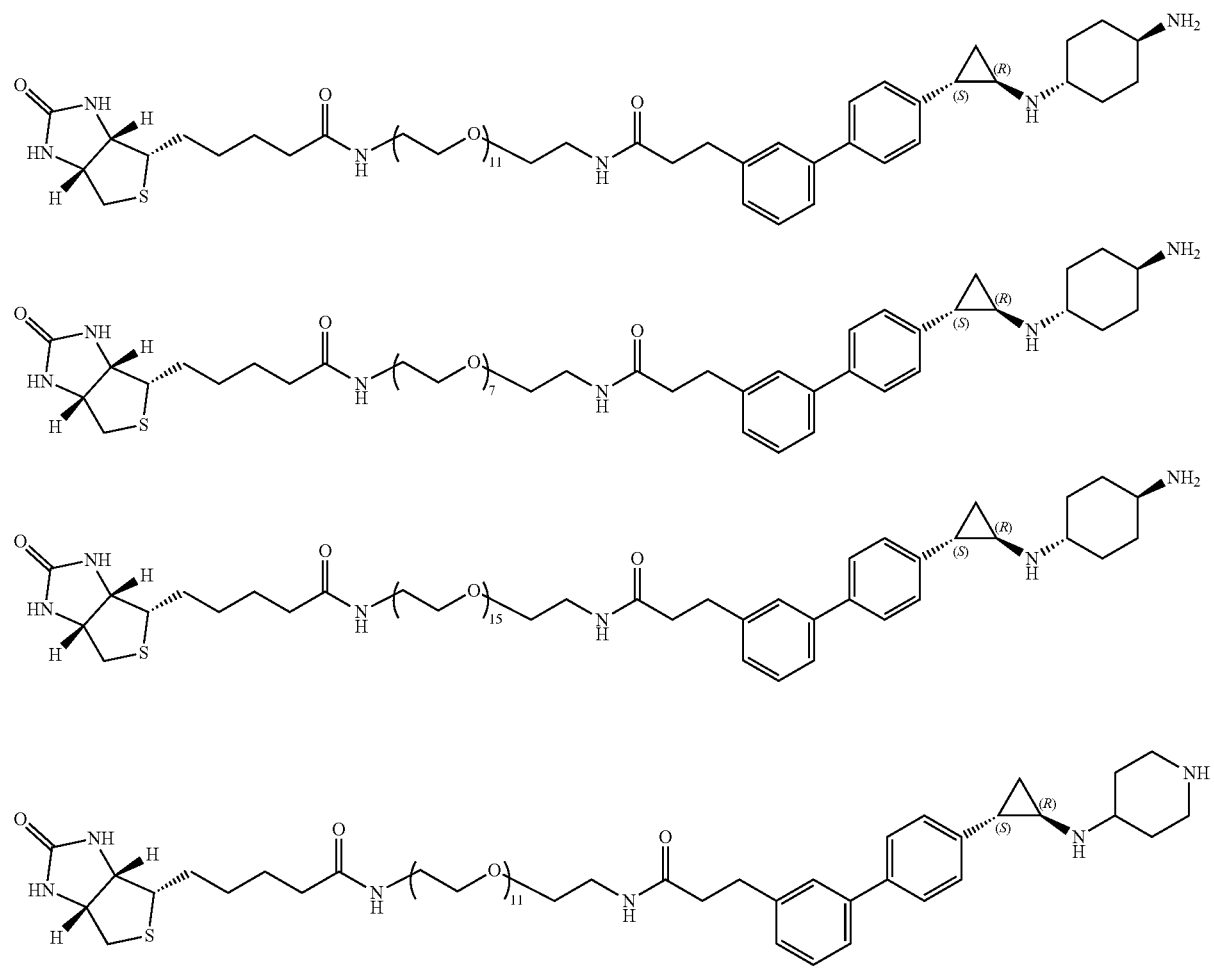

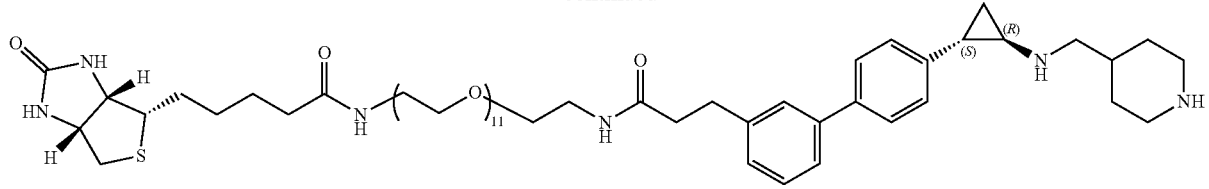

A particularly preferred compound is the compound of formula

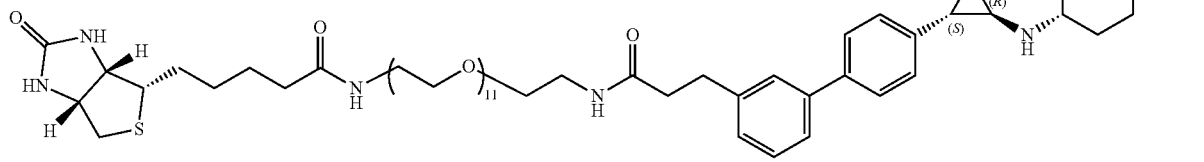

and salts thereof. This compound is named as N-(39-(4'-((1S,2R)-2-(((trans)-4-aminocyclohexyl)amino)cyclopropyl)-[1,1'-biphenyl]-3-yl)-37-oxo-3,6,9,12,15,18,21,24,27,30,33-undecaoxa-36-azanonatriacontyl)-5-((3aS,4S,6aR)-2-oxohexahydro-1H-thieno[3,4-d]imidazol-4-yl)pentanamide, and is described in example 1.6.

Unless defined for a specific term otherwise, in the definitions of the compounds of the invention of formula (I), (II), (IIa), (III) and (IIIa), the following definitions apply, when applicable:

As used herein, the term "cyclyl" refers any kind of ring regardless fuseness, aromaticity and hetero-carbo nature.

Examples of cyclyl include aryl, heterocyclyl (including heteroaryl and heterocycloalkyl), benzocycloalkyl and cycloalkyl group as defined herein.

As used herein, the term "aryl" refers to a carbocyclic aromatic system containing one ring, or two or three rings fused together wherein the ring atoms are all carbon. The term "aryl" includes, but is not limited to groups such as phenyl, naphthyl, or anthracenyl. The term "monocyclic aryl" refers to phenyl. An aryl group is preferably phenyl.

As used herein, the term "cycloalkyl", unless otherwise specified, refers to a saturated monocyclic, bicyclic or tricyclic group wherein the ring atoms of the cyclic system are all carbon and wherein each cyclic moiety contains from 3 to 12 carbon atom ring members. Examples of cycloalkyl groups include, but are not limited to cyclopropyl, cyclobutyl, cyclopentyl, cyclohexyl, cycloheptyl, or adamantyl. A preferred group of cycloalkyls is monocyclic $C_3$-7 cycloalkyl.

As used herein, the term "heteroaryl" refers to a 5- to 6-membered unsaturated monocyclic ring, or a fused bicyclic or tricyclic ring system in which the rings are aromatic and in which at least one ring contains at least one heteroatom selected from the group consisting of O, S, and N. Preferred heteroaryl groups are 5- to 6-membered monocyclic or 9- to 10-membered bicyclic heteroaryl groups. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocyclyl" or "heterocycle" each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitrogen or sulfur atoms may be oxidized (e.g., —N=O, —S(=O)—, or —S(=O)$_2$—). Additionally, 1, 2, or 3 of the carbon atoms of the heterocyclyl may be optionally oxidized (e.g., to give an oxo group or =O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl. Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocycloalkyl" refers to a heterocyclyl group that is not fully unsaturated e.g., one or more of the rings systems of a heterocycloalkyl is not aromatic. Preferably, the heterocyclyl group is fully saturated and contains from 1 to 4 heteroatoms selected from N, O and S, more preferably contains at least 1 N atom. In some embodiments, the heterocycloalkyl is a fully saturated 3- to 7-membered monocyclic or 7- to 15-membered polycyclic ring (which contains preferably two or three rings in the ring system, which can be fused, bridged and/or spiro rings), and wherein the heterocycloalkyl contains from 1 to 4 heteroatoms selected from N, O and S. Examples of heterocycloalkyls include azetidinyl, piperazinyl, morpholinyl, piperidinyl, or pyrrolidinyl. As used herein, the term "benzocycloalkyl" refers to a cycloalkyl as defined herein above, which cycloalkyl is fused to a phenyl ring (i.e., shares two adjacent ring carbon atoms with a phenyl ring). Non-limiting examples of benzocycloalkyls are indyl (i.e., 2,3-dihydro-1H-indenyl or benzocyclopentyl), 1,2,3,4-tetrahydronaphtyl (i.e., tetralinyl or benzocyclohexyl), or benzocycloheptyl. It is preferred that the benzocycloalkyl is attached to the remainder of the molecule via its cycloalkyl moiety (and not via its phenyl ring moiety).

The compounds of the present invention contain one or more basic nitrogens and may, therefore, form salts with organic or inorganic acids. Examples of these salts include: salts with inorganic acids such as hydrochloric acid, hydrobromic acid, hydroiodic acid, nitric acid, perchloric acid, sulfuric acid or phosphoric acid; and salts with organic acids such as methanesulfonic acid, thfluoromethanesulfonic acid, ethanesulfonic acid, benzenesulfonic acid, p-toluenesulfonic acid, fumaric acid, oxalic acid, acetic acid, maleic acid, ascorbic acid, citric acid, lactic acid, tartaric acid, malonic acid, glycolic acid, succinic acid and propionic acid, among others. The salts of a compound of the invention, for example a compound of formula I, II, IIa, III or IIIa, can be obtained during the final isolation and purification of the compounds of the invention or can be prepared by treating the compound with a sufficient amount of the desired acid to give the salt in a conventional manner. The salts of the compounds of the invention can be converted into other salts by ion exchange using ionic exchange resins.

The compounds of formula I, II, IIa, III or IIIa and their salts may differ in some physical properties but they are equivalent for the purposes of the present invention. All salts of the compounds of formula II, IIa, III or IIIa are included within the scope of the invention. The salts are preferably pharmaceutically acceptable salts. As used herein, a "pharmaceutically acceptable salt" is intended to mean a salt that retains the biological effectiveness and/or properties of the parent compound (i.e. the free acid or free base, as applicable) and that is not biologically or otherwise undesirable. Pharmaceutically acceptable salts include salts formed with inorganic or organic bases, and salts formed with inorganic and organic acids. Pharmaceutically acceptable salts are well known in the art. Exemplary pharmaceutically acceptable salts include those salts prepared by reaction of the compounds of the present invention with a mineral or organic acid, such as hydrochlorides, hydrobromides, sulfates, pyrosulfates, bisulfates, sulfites, bisulfites, phosphates, monohydrophosphates, dihydrophosphates, metaphosphates, pyrophosphates, chlorides, bromides, iodides, nitrates, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methanesulfonates, ethane-sulfonates, propanesulfonates, benzenesulfonates, toluenesulfonates, trifluoromethansulfonates, naphthalene-1-sulfonates, naphthalene-2-sulfonates, mandelates, pyruvates, stearates, ascorbates, or salicylates. When the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands such as ammonia, alkylamines, hydroxyalkylamines, lysine, arginine, N-methylglucamine, procaine and the like. The pharmaceutically acceptable salts of the present invention can be prepared from the parent compound which contains a basic or acidic moiety by conventional chemical methods. For example, such salts can be prepared by reacting the free acid or base forms of these compounds with a stoichiometric amount of the appropriate base or acid in a suitable solvent.

The compounds of the present invention may form complexes with solvents in which they are reacted or from which they are precipitated or crystallized. These complexes are known as solvates. As used herein, the term solvate refers to a complex of variable stoichiometry formed by a solute (a compound of formula I, II, IIa, III or IIIa, or a salt thereof) and a solvent. Examples of solvents include pharmaceutically acceptable solvents such as water, ethanol and the like. A complex with water is known as a hydrate. Solvates of compounds of the invention (or salts thereof), including hydrates, are included within the scope of the invention The compounds of formula I, II, IIa, III or IIIa may exist in different physical forms, i.e. amorphous and crystalline forms. Moreover, the compounds of the invention may have the ability to crystallize in more than one form, a characteristic which is known as polymorphism. Polymorphs can be distinguished by various physical properties well known in the art such as X-ray diffraction pattern, melting point or solubility. All physical forms of the compounds of formula I, II, IIa, III or IIIa, including all polymorphic forms ("polymorphs") thereof, are included within the scope of the invention.

Some of the compounds of the present invention may exist as several optical isomers. Optical isomers can be resolved by conventional techniques of optical resolution to give optically pure isomers. This resolution can be carried out on any chiral synthetic intermediate or on products of formula I, II, IIa, III or IIIa. Optically pure isomers can also be individually obtained using enantiospecific synthesis. The present invention covers all individual isomers as well as mixtures thereof (for example racemic mixtures), whether obtained by synthesis or by physically mixing them.

The KDM1A chemoprobes for use in the methods of the invention described below must exhibit high affinity to KDM1A and selectivity versus other FAD-dependent monoamine oxidases, such as MAO-A, MAO-B, SMOX, or IL4I1. Importantly, the KDM1A chemoprobes should exhibit high selectivity vs MAO-A and MAO-B, a likely off-target for cyclopropylamine-containing KDM1A inhibitors.

Preferably, the KDM1A chemoprobe has an IC50 against KDM1A below 1 mcM, more preferably below 500 nM. Preferably, KDM1A chemoprobes should exhibit a selectivity of at least 10-fold for KDM1A over other FAD-dependent monoamine oxidases, more preferably of at least 30-fold for KDM1A over other FAD-dependent monoamine oxidases, still more preferably of at least 50-fold for KDM1A over other FAD-dependent monoamine oxidases. Selectivity of at least X-fold means for example that the IC50 value for KDM1A is at least X-fold lower than the IC50 value for MAO-A, MAO-B and other FAD-dependent monoamine oxidases as determined for example using biochemical assays.

Different methods are described in the literature that permit to assess KDM1A, MAO-A, MAO-B, SMOX and IL4I1 inhibition. These methods include assessment of binding to the FAD cofactor by UV/VIS spectrometry, mass spectrometry, enzymatic assays to detect $H_2O_2$ or formaldehyde, byproducts of substrate demethylation, alphaLISA assays to measure H3K4me2/1 demethylation. For example, KDM1A inhibitory activity of the chemoprobes can be determined using the method disclosed in Example 2. The specificity of the chemoprobes for KDM1A over other FAD-dependent enzymes can be tested for example using the methods provided in Example 4. The data provided in Example 2 show that the chemoprobes of Examples 1.1, 1.2, 1.3, 1.4, 1.5 and 1.6 exhibit potent KDM1A-inhibitory activity, with IC50 values around or below 200 nM in all instances. Chemoprobe of example 1.6 (i.e. N-(39-(4'-((1S, 2R)-2-(((trans)-4-aminocyclohexyl)amino)cyclopropyl)-[1, 1'-biphenyl]-3-yl)-37-oxo-3,6,9,12,15,18,21,24,27,30,33-undecaoxa-36-azanonatriacontyl)-5-((3aS,4S,6aR)-2-oxohexahydro-1H-thieno[3,4-d]imidazol-4-yl)pentanamide, and salts thereof) was found to be very selective for KDM1A over other FAD-dependent enzymes as shown by the data provided in Example 4.

The inventors have identified chemoprobes as disclosed herein and in the appended examples, which exhibit potent and selective KDM1A inhibitory activity, as shown by the results in the appended Examples. This makes them particularly suitable for use as chemoprobes in the methods according to the invention, particularly in methods to determine target engagement of very potent KDM1A inhibitors like ORY-1001. Chemoprobes of Example 1.1 (i.e. N-(39-(4'-((trans)-2-(((trans)-4-aminocyclohexyl)amino)cyclopropyl)-[1,1'-biphenyl]-3-yl)-37-oxo-3,6,9,12,15,18,21,24,27, 30,33-undecaoxa-36-azanonatriacontyl)-5-((3aS,4S,6aR)-2-oxohexahydro-1H-thieno[3,4-d]imidazol-4-yl)pentanamide, and salts thereof) and specially Example 1.6 (i.e. N-(39-(4'-((1S,2R)-2-(((trans)-4-aminocyclohexyl)amino)cyclopropyl)-[1,1'-biphenyl]-3-yl)-37-oxo-3,6,9,12,15,18,21,24,27, 30,33-undecaoxa-36-azanonatriacontyl)-5-((3aS,4S,6aR)-2-oxohexahydro-1H-thieno[3,4-d]imidazol-4-yl)pentanamide, and salts thereof) are particularly preferred.

Tags and Labels

Tags: as defined above, herein tag will be used to describe a moiety that can be incorporated into a molecule, for example into a KDM1A chemoprobe, that can be recognized and used in capture, recovery, isolation, purification or detection procedure of that molecule or of complexes involving that molecule.

Preferentially, tags are small compounds that minimally disturb the functionalities, including the binding affinity and selectivity, of the molecule they are incorporated in.

Examples of suitable tags are

Biotin derivatives, which may be recognized by avidin, streptavidin or streptacin; and Digoxigenin derivatives, which may be recognized by an anti-digoxigenin antibody.

Examples include:

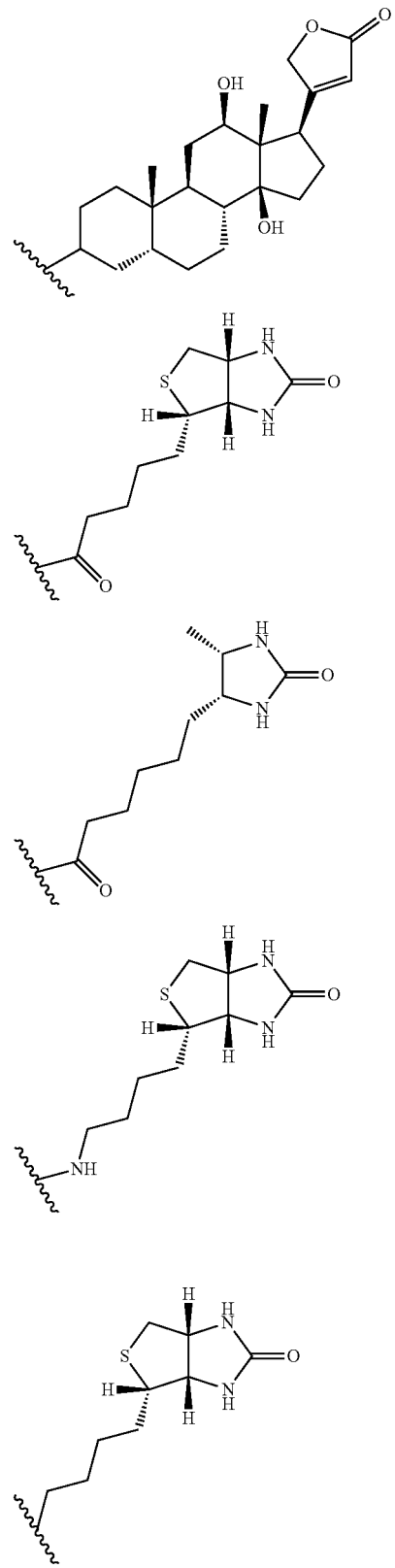

-continued

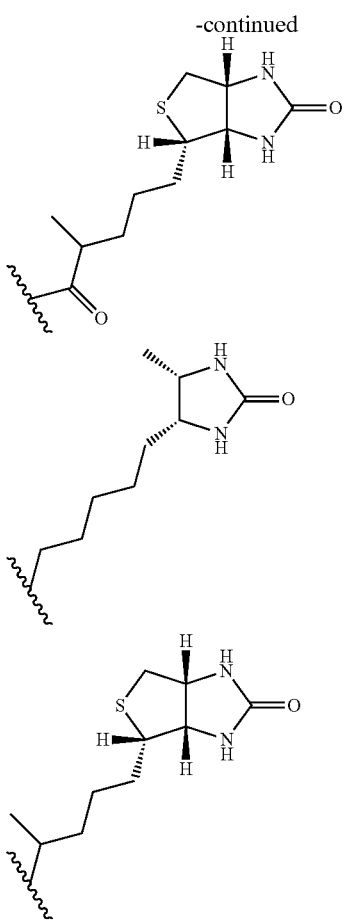

Haloalkanes tags, that can be recognized by Halo Tag® technology, are also suitable tags.

Tags may also be peptidic in nature, examples of peptide tags that can be incorporated into the chemoprobe/corresponding capture agents include, but are not limited to
AviTag, SBP, Strep-tag/avidin, streptavidin, streptacin
Calmodulin-tag/calmodulin
polyglutamate tag/anion-exchange resin such as Mono-Q (EEEEEE)
E-tag/anti E-tag antibody
FLAG-tag/anti FLAG antibody
HA-tag/anti HA antibody
polyhistidine tag e.g. 5-10 histidines such as His-tag (HHHHHH) bound by a nickel or cobalt chelate
Myc-tag/anti-Myc antibody
TC tag/FlAsH and ReAsH biarsenical compounds (CCPGCC)
V5 tag/V5 tag antibody
VSV-tag/VSV-tag antibody
Myc tags/antiMyc tag antibody
(poly) histidine tags/nickel and cobalt sepharose or agarose functionalised with a chelator, such as iminodiacetic acid (Ni-IDA) and nitrilotriacetic acid (Ni-NTA) for nickel and carboxylmethylaspartate (Co-CMA)
Tags may also be
synthetic oligonucleotides including PNA (protein nucleic acid), (modified) DNA, (modified) RNA tags/complementary natural or synthetic PNA, (modified) DNA, (modified) RNA oligonucleotides. Oligonucleotide tags may be recognized by other oligonucleotides with complementary (base paring) sequence.

Label: as defined above, herein label will be used to describe a moiety that can be incorporated into a molecule, for example into a KDM1A chemoprobe or detection agent, and that directly gives rise to a signal, for example a fluorescent, bioluminescent, isotope, mass spectrometry label. Preferentially, labels will be small (MW<1000), and should minimally disturb the functionalities, including the binding affinity and selectivity of the molecule they are incorporated in.

Examples of Fluorescent labels include Alexa Fluor, BODIPY®, Fluorescein, Oregon Green®, Rhodamine Green™, Long wavelength Rhodamines, Texas Red®, Coumarins, Pyrenes, Pyridioxazoles, naphtalenes, Dapoxyl® or Bimane, such as the groups listed below:

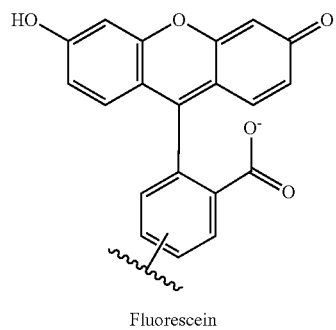

Fluorescein

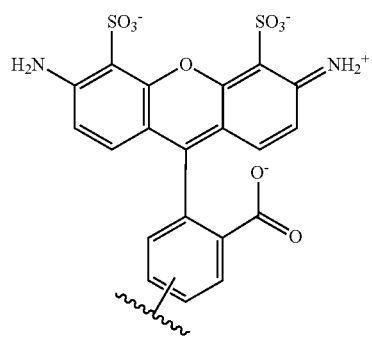

Alexa Fluor 488

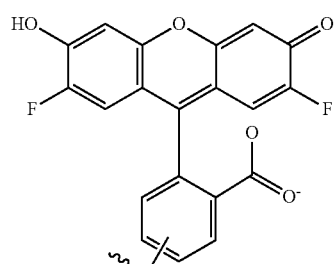

Oregon Green

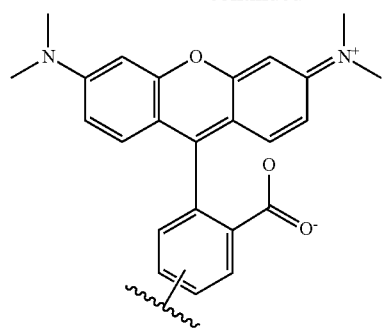
TAMRA
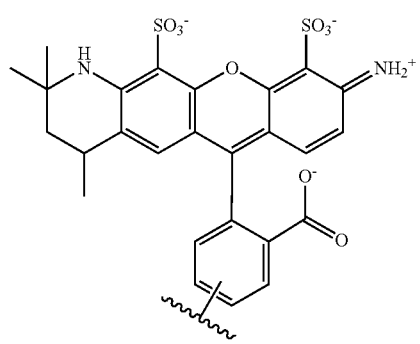
Alexa Fluor 514
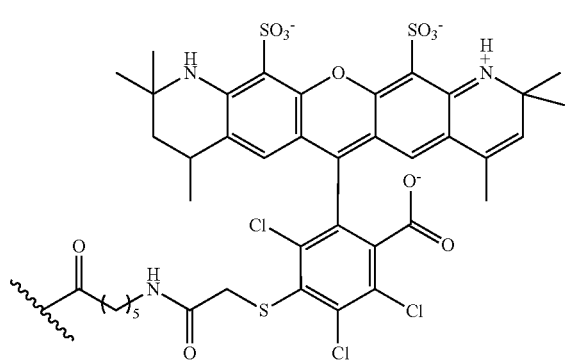
Alexa Fluor 546
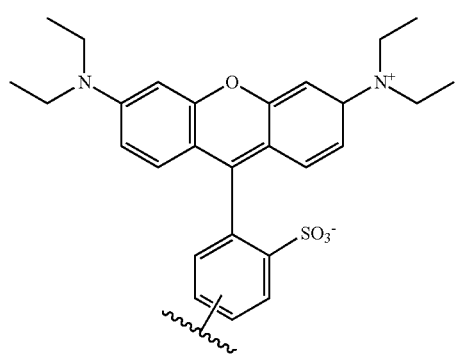
Rhodamine Red
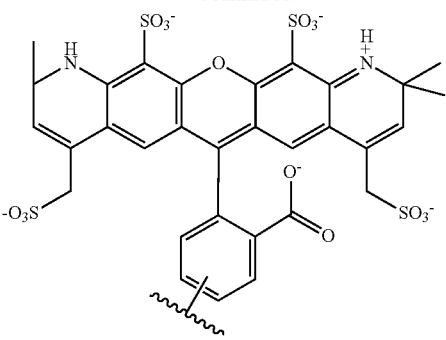
Alexa Fluor 568
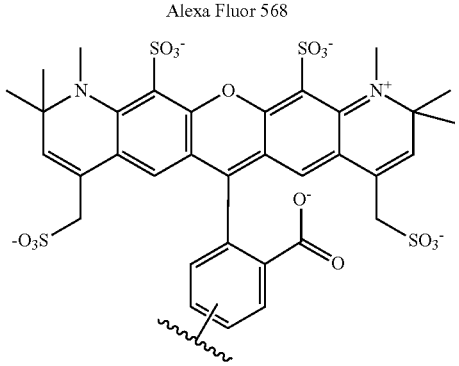
Alexa Fluor 594
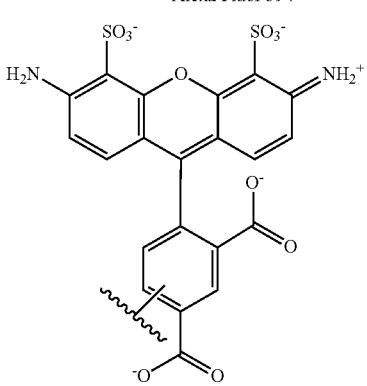
Alexa Fluor 555
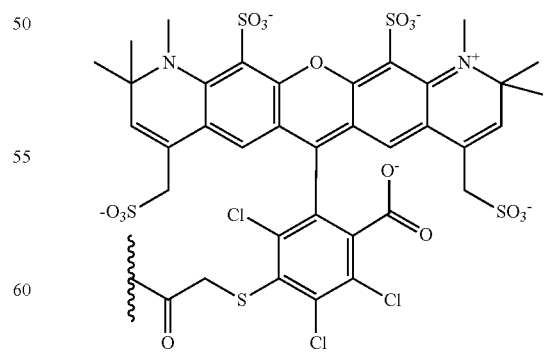
Alexa Fluor 610

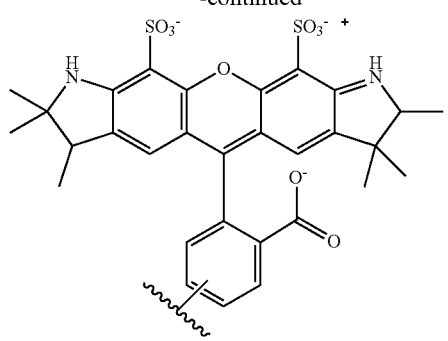
Alexa Fluor 532
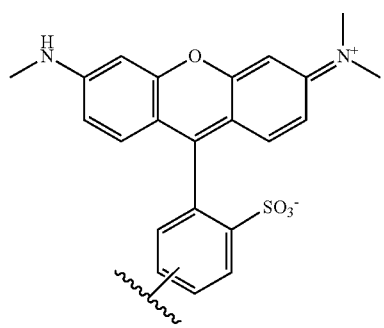
Tetramethyl Rhodamine
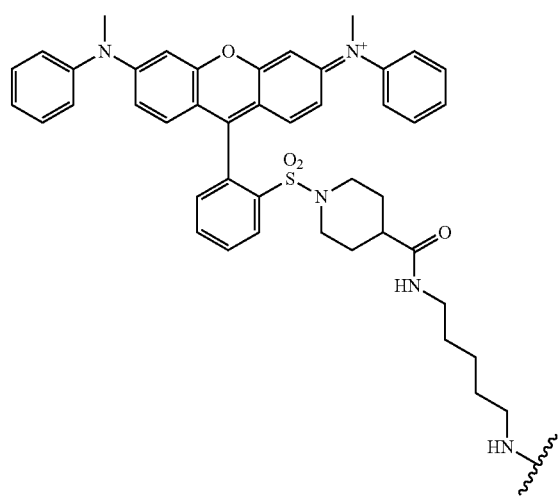
QSY 7 amine
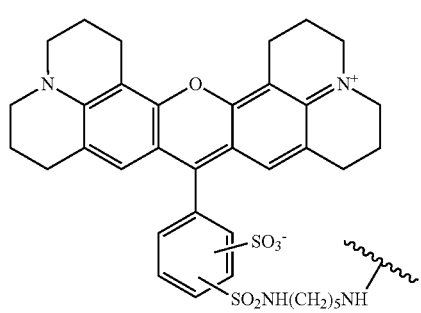
Texas Red
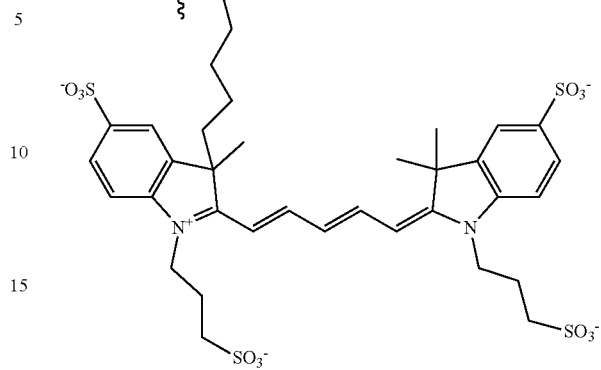
Alexa Fluor 647
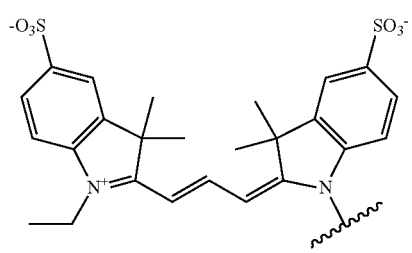
Cyanine
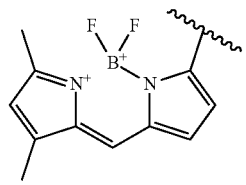
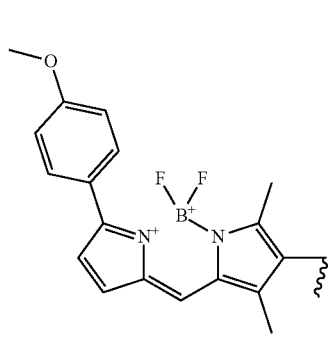
BODIPY
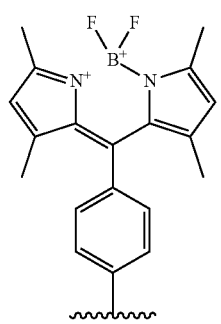

-continued

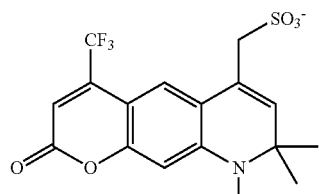

Alexa Fluor 430

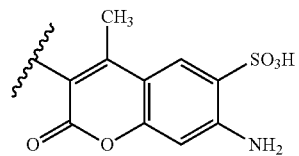

Alexa Fluor 350

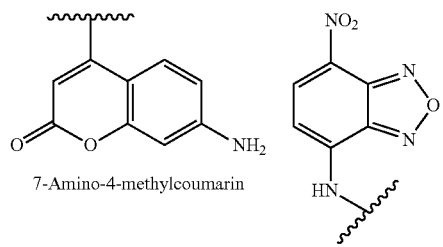

7-Amino-4-methylcoumarin    NBD

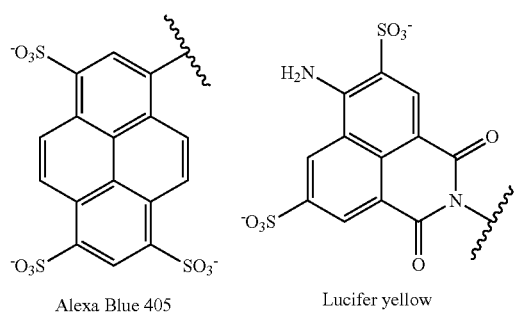

Alexa Blue 405    Lucifer yellow

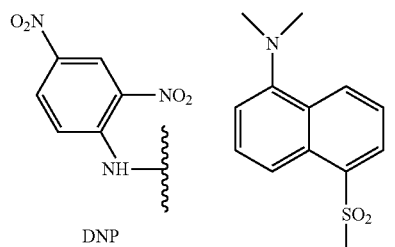

DNP    DNS

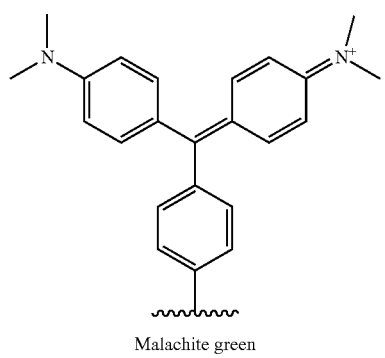

Malachite green

-continued

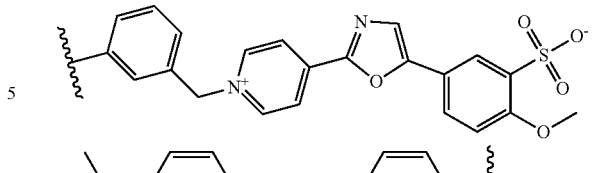

Dabcyl

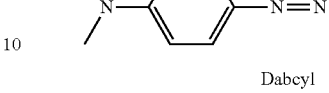

Bimane

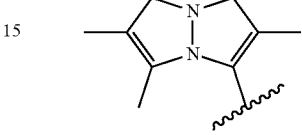

Badan

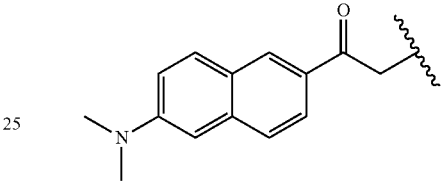

Dapoxyl

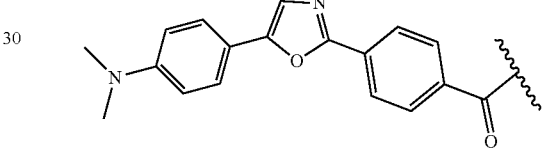

PDAM

A label can also be used as a tag if a suitable capture or detection agent is available, for example a fluorescein moiety can be recognized and captured by an anti-fluorescein antibody.

Capture agent: as defined above, this term is used to refer to an agent that recognizes and binds the tag and that can be used to capture the chemoprobe or chemoprobe complexes from their crude biological source. In this invention, the capture agent can also capture KDM1A or KDM1A containing complexes from their crude biological source. The capture reagent can be coupled to a surface. The capturing process can be direct or indirect, i.e. the recognition p.e. tag included in the chemoprobe can be captured by a primary capture agent coupled to a surface, recognized by a secondary capture agent that recognizes the first capture agent and that is bound to a surface. Suitable capture agents include antibodies or proteins with a high selectivity and affinity for the tag in KDM1A chemoprobe and for the KDM1A chemoprobe bound complexes, or with a high selectivity and affinity for KDM1A or KDM1A containing complexes.

Examples of suitable capture agents for a specific tag incorporated into the KDM1A chemoprobe are listed above.

Suitable capture agents to capture KDM1A or KDM1A containing complexes preferentially include high specificity/high affinity antibodies or antibody fragments to KDM1A or to KDM1A containing complexes. Antibodies can be commercially available or can be produced or synthesized by any known method.

A specially suitable tag for the KDM1A chemoprobe is biotin and the corresponding capture agent is streptavidin.

Surface: as mentioned above, the capture agent can be coupled to a surface. This can be any suitable surface or solid support including micro or nanobeads, microtiter plates, nanostrings, nanowires, biofilms, polymers or any other suitable matrix.

Detection agent: as defined above, herein a detection agent is an agent that recognizes and binds a tag and can be used to detect a tag incorporated in the KDM1A chemoprobe and can be used to detect KDM1A chemoprobe bound complexes. Alternatively, it can be an agent that can be used to detect KDM1A or KDM1A containing complexes in a sample.

Detection can be direct or indirect, amplified or non-amplified, mediated by a single molecule or a mix of molecules, but invariably includes a moiety that generates a signal that can be visualized or measured.

The detection agent may be used for direct detection of the KDM1A chemoprobe and chemoprobe bound complexes; or KDM1A or KDM1A containing complexes, and directly include the signal generating moiety.

Alternatively a primary detection agent may bind the KDM1A chemoprobe and chemoprobe bound complexes; or KDM1A or KDM1A containing complexes, the primary detection agent may be detected by a secondary detection agent which includes the signal generating moiety.

Said detection agent may include a fluorescent, luminescent, colorimetric, isotope or mass spectrometry label.

Alternatively, said detection agent may include a synthetic oligo nucleotide, that can be used to generate a signal using proximity ligation assay technology.

Alternatively, said detection agent may include an enzyme, for example horse radish peroxidase or alkaline phosphatase, that transforms a substrate in a colored, fluorescent or luminescent compound. Examples of such enzymes include Horseradish Peroxydase (HRP), Alkaline phosphatase (AP), Glucose oxidase and β-galactosidase enzyme. Colorimetric detection is based on conjugation with the Horseradish Peroxydase (HRP), Alkaline phosphatase (AP), Glucose oxidase or β-galactosidase enzyme, followed by incubation with the appropriate chromogenic reporter (respectively, 3,3'-diaminobenzidine, combination of nitro blue tetrazolium chloride and 5-bromo-4-chloro-3-indolyl phosphate, Nitro blue tetrazolium chloride or 5-bromo-4-chloro-3-indoyl-β-D-galactopyranoside). Chemiluminescent detection systems are based on the conversion, catalyzed by the HRP enzyme, of luminol to 3-aminophthalate, a luminescent moiety. Examples of substrates for Horseradish Peroxydase (HRP) include:

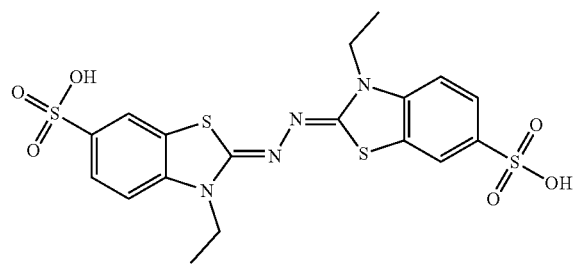

ABTS

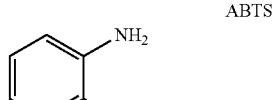

OPD

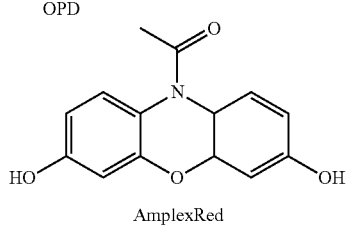

AmplexRed

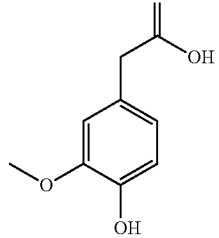

Homovanillic acid

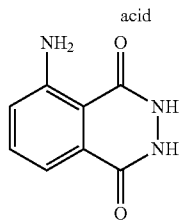

Luminol

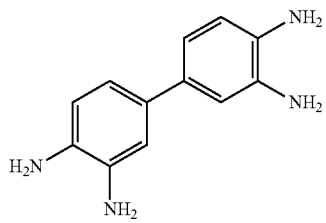

DAB

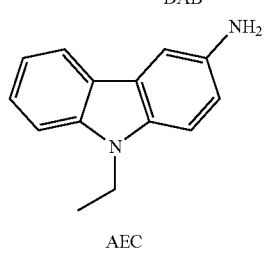

AEC

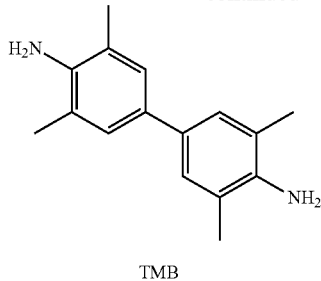

TMB

Said enzyme may be coupled directly to the agent that recognizes a tag incorporated in a KDM1A chemoprobe or KDM1A chemoprobe bound complexes, or it may be coupled to a secondary agent that recognizes said primary agent. Likewise, said enzyme can be coupled directly to an agent that recognizes KDM1A or KDM1A containing complexes, or it may be coupled to a secondary agent that recognizes said primary agent.

Alternatively, said primary detection agent can also incorporate a tag, detected by a secondary detection agent that incorporates a label or a moiety that generates a signal that can be visualized or measured.

Said (primary) detection agent has a high selectivity and affinity for the tag in KDM1A chemoprobe and for the KDM1A chemoprobe bound complexes, or for KDM1A or KDM1A containing complexes. Preferably, said (primary) detection agent comprises a binding molecule like an antibody or binding protein or other macro (molecule) (e.g. aptamer, affimer, etc) that recognizes the tag incorporated into the KDM1A chemoprobe, or KDM1A or KDM1A containing complex; with high specificity and high affinity. Herein, an antibody is preferentially a monoclonal antibody, or a single chain construct like a recombinant ScFv, Fabs or fusions proteins thereof. The antibody or protein antibody used to detect KDM1A or the KDM1A containing complex should be directed against an epitope which is readily accessible. Accessibility of the epitope can be modeled in silico, and tested in vitro using immunoprecipitation (IP) as described in the examples. Suitable KDM1A antibodies are disclosed in the examples; alternative antibodies can also be identified, following the strategy disclosed in the examples to identify said suitable antibodies. Alternative antibodies can also be raised against accessible epitopes from KDM1A-interacting factors that are part of the KDM1A complex. RCOR1, HDAC1 and HDAC2 are examples of such factors closely interacting with KDM1A.

Preferably, the detection or capture of the KDM1A bound chemoprobe or KDM1A bound chemoprobe containing complexes by a first detection or capture agent does not interfere with the detection of KDM1A or KDM1A containing complexes by a second detection agent, nor does the detection or capture of KDM1A or KDM1A containing complexes by a first detection or capture agent interfere with the detection of KDM1A or KDM1A containing complexes by a second detection agent.

The detection system: herein we will refer to a detection system when multiple detection agents are required to act in trans and in close proximity to generate a signal; p.e. the Förster/Resonance Energy Transfer (FRET), AlphaLISA, DELFIA, and proximity ligation assay technologies (protein PCR). In FRET, AlphaLISA and DELFIA a first detection agent will function as a donor that absorbs energy and generates an energy transfer (FRET) or oxygen singlet transfer (AlphaLISA, DELFIA) to an acceptor and provoke it to emit a signal at a specific, lower wavelength. In one embodiment of the invention described herein, a first detection agent is designed to recognize and bind to the KDM1A chemoprobe containing complexes, and a second detection agent to bind the KDM1A enzyme or to the KDM1A containing complex, to detect free KDM1A. In another embodiment, in addition to detect free KDM1A, two different detection agents that bind to different sites on KDM1A or the KDM1A containing complex are used to detect total KDM1A. Still alternatively, two KDM1A detection agents that bind to KDM1A or the KDM1A containing complexes and a third detection agent that binds to the KDM1A chemoprobe can be used. One KDM1A detection agent functions as a donor, and the other KDM1A detection agents and the KDM1A chemoprobe detection agent function as acceptors emitting at different wavelengths, allowing for simultaneous detection of free and total KDM1A. In the proximity ligation assay technology, the different detection agents carry nucleic acids that will anneal with a connector nucleic acid, be ligated and form an amplifyable fragment that can be detected using real time quantitative PCR. Again, the detection agents can detect the KDM1A chemoprobe containing complexes and the KDM1A protein, and can be used to detect free and total KDM1A independently or in a multiplex reaction in homogeneous or heterogeneous assays.

The tags, labels, capture and detection agents, enzymes, substrates and other tools and techniques described above are just to illustrate ways to carry out the invention and are not intended to be limiting the methods of the invention in any way.

Target Engagement Assays

The chemoprobes of the invention can be used in methods to determine target engagement of a KDM1A inhibitor, as described in more detail herein. The methods according to the invention allow for a direct assessment of target occupation by KDM1A inhibitors, as opposed to methods generally used so far, which are based on indirect determinations of KDM1A engagement, typically through the analysis of changes caused by said KDM1A inhibitors in the level of histone marks targeted by KDM1A or in gene expression.

The methods of the invention are, inter alia, based on the direct quantification of target engagement via measuring free KDM1A levels by means of chemoprobe "tagging" of the free KDM1A enzyme. As previously defined herein, free KDM1A means enzymatically active KDM1A present in a sample not bound by a KDM1A inhibitor. "tagging" is used herein in a broad sense, covering the use of both tags and labels as defined previously.

In cells, tissues, organs or subjects treated with a KDM1A inhibitor, a portion of the enzymatically active KDM1A enzyme pool will be bound (occupied) by the KDM1A inhibitor, which portion may change according to the (KDM1A inhibitory) potency of the compound and concentration/dose used. Free KDM1A levels can thus be used to determine how much KDM1A enzyme is bound by the KDM1A inhibitor, i.e. the target engagement by such inhibitor can be determined by the methods described herein. The chemoprobe-based methods for determining free KDM1A levels according to the invention are thus useful to assess target engagement and to assess the pharmacodynamics of KDM1A inhibitors, for example in clinical trials or in clinical practice.

Accordingly, in one aspect, the invention provides a
   method for determining a level of free KDM1A in a
   sample
   or subject, wherein said method comprises
   (i) contacting or exposing KDM1A to a chemoprobe,
      wherein said chemoprobe is a compound as defined
      above and in the appended claims; and
   (ii) determining said level of free KDM1A employing said
      chemoprobe in said sample or subject.

Methods for determining free KDM1A levels are provided below and in the appended examples.

In another aspect, the invention provides a method for in vitro determining a level of free KDM1A in a sample,
   wherein said method comprises
   (i) contacting or exposing KDM1A to a chemoprobe,
      wherein said chemoprobe is a compound as defined
      above or in the appended claims; and
   (ii) determining said level of free KDM1A employing said
      chemoprobe in said sample.

In vitro, when used in relation to the methods of the invention to determine free KDM1A level and to determine target engagement, means, as defined previously, outside a living organism (which can be for example a human), i.e. the method is not directly performed on said living organism. It thus includes for example methods implemented using samples taken from a living organism (for example a human) that has received in vivo treatment with a KDM1A inhibitor, which samples are referred to as "ex vivo" samples in the examples section. As illustrated in the Examples, methods to determine free KDM1A levels using chemoprobes of the invention may be performed in a variety of settings and sample types, including human samples.

Figure 6A:
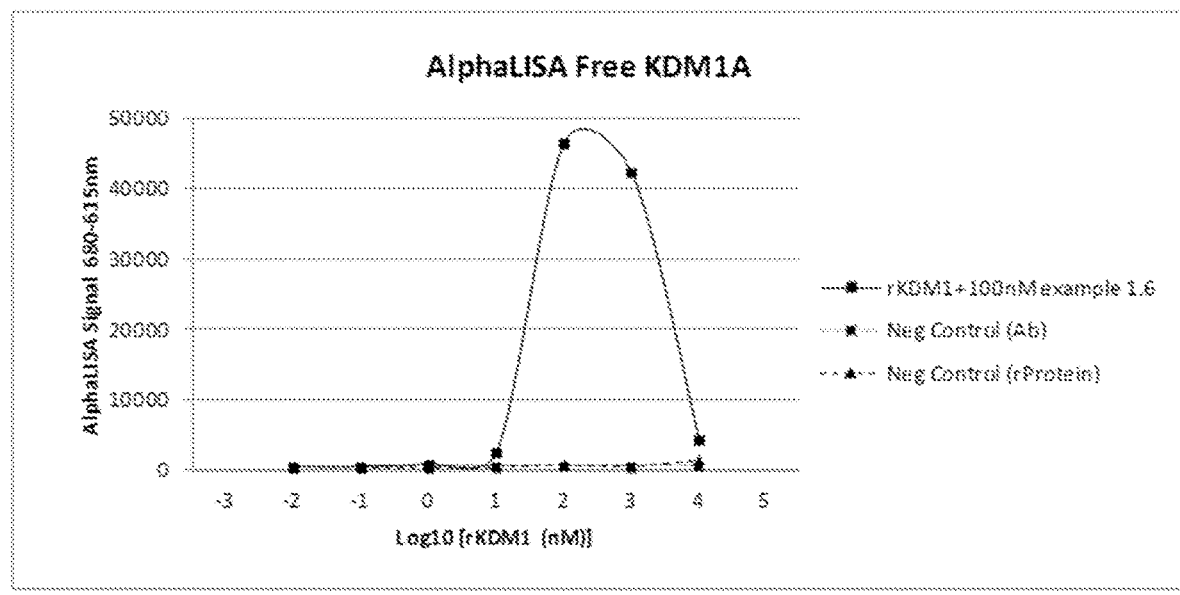
FIGS. 6A, 6B and 6C: Detection of free (FIG. 6A) and total (FIG. 6B) KDM1A by AlphaLISA as explained in example 6.

As illustrated in the appended examples, free KDM1A levels may be determined as shown in Example 5 using a KDM1A chemoprobe-based ELISA assay employing a chemoprobe of formula (I) which contains a biotin tag (as P group) to capture free KDM1A, and using different detection techniques, like luminescence or colorimetric (see Example 5.2 and 5.3). This method to determine free KDM1A may also be successfully implemented to determine free KDM1A levels in an homogeneous assay format using AlphaLISA technology, as shown for instance in Example 6 and FIG. 6A.

Figure 5A:
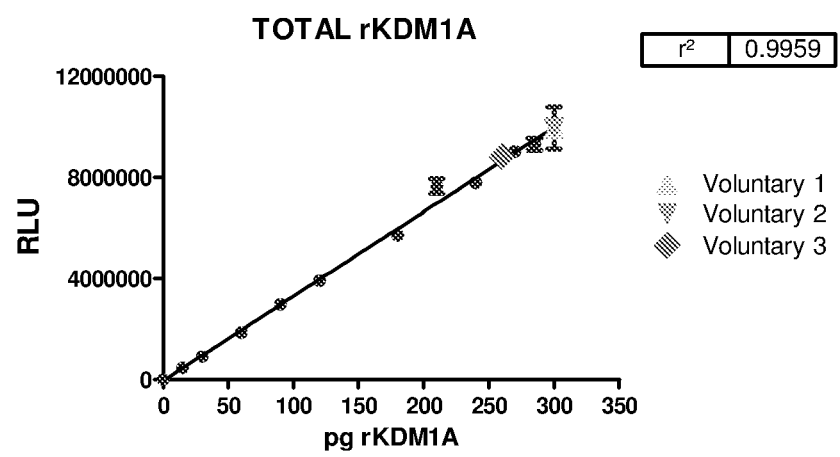
FIGS. 5A and 5B: Total (FIG. 5A) and free (FIG. 5B) KDM1A in human PBMCs from healthy donors according to example 5.
Figure 5B:
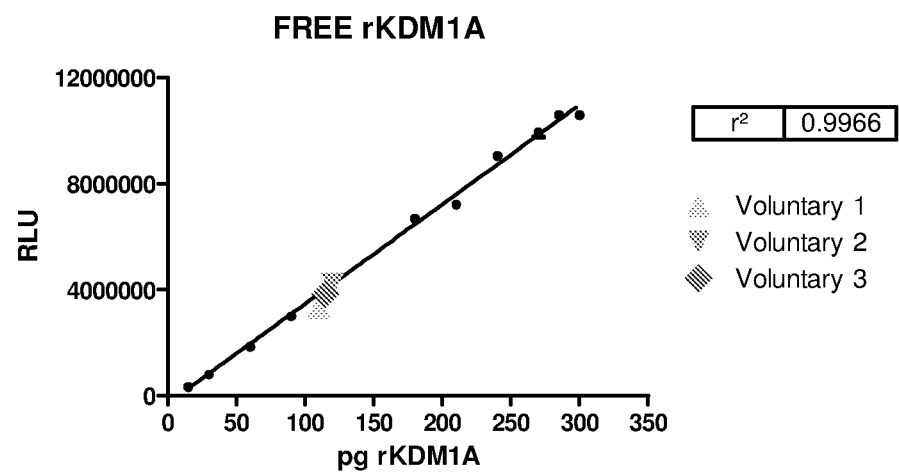

The chemoprobe-based method described in Example 5.2 was further used to determine free KDM1A levels in PBMCs isolated from human blood from healthy volunteers, as described in Example 5.2 and FIG. 5B. This shows that the chemoprobes and chemoprobe-based methods of the invention can successfully be used in human samples to determine free KDM1A levels, and accordingly to determine target engagement of KDM1A inhibitors in humans, as also described in more detail below.

As illustrated in Example 7, free KDM1A levels may be determined using the chemoprobe-based methods of the invention in cells treated with KDM1A inhibitors. In particular, in example 7, free KDM1A levels were determined in MV(4;11) human leukemia cells treated with several KDM1A inhibitors (or vehicle), as described in more detail in Example 7.3 and FIGS. 7 and 8A, as well as in other cell lines, including THP-1 human leukemia cells (see Example 7.3 and FIG. 8B), as well as in solid tumor cell lines like LNCap human prostate cancer cells (see Example 7.3 and FIG. 8C). The free KDM1A levels as determined therein may then be used to determine target engagement, following the methods described in more detail below. The results obtained in Example 7 showed a dose-response cellular target engagement in accordance with the in vitro KDM1A inhibitory activity of the tested KDM1A inhibitors, further showing that the chemoprobes and chemoprobe-based methods according to the invention can be used to provide reliable determinations of free KDM1A levels and of KDM1A target engagement by KDM1A inhibitors.

Figure 9A:
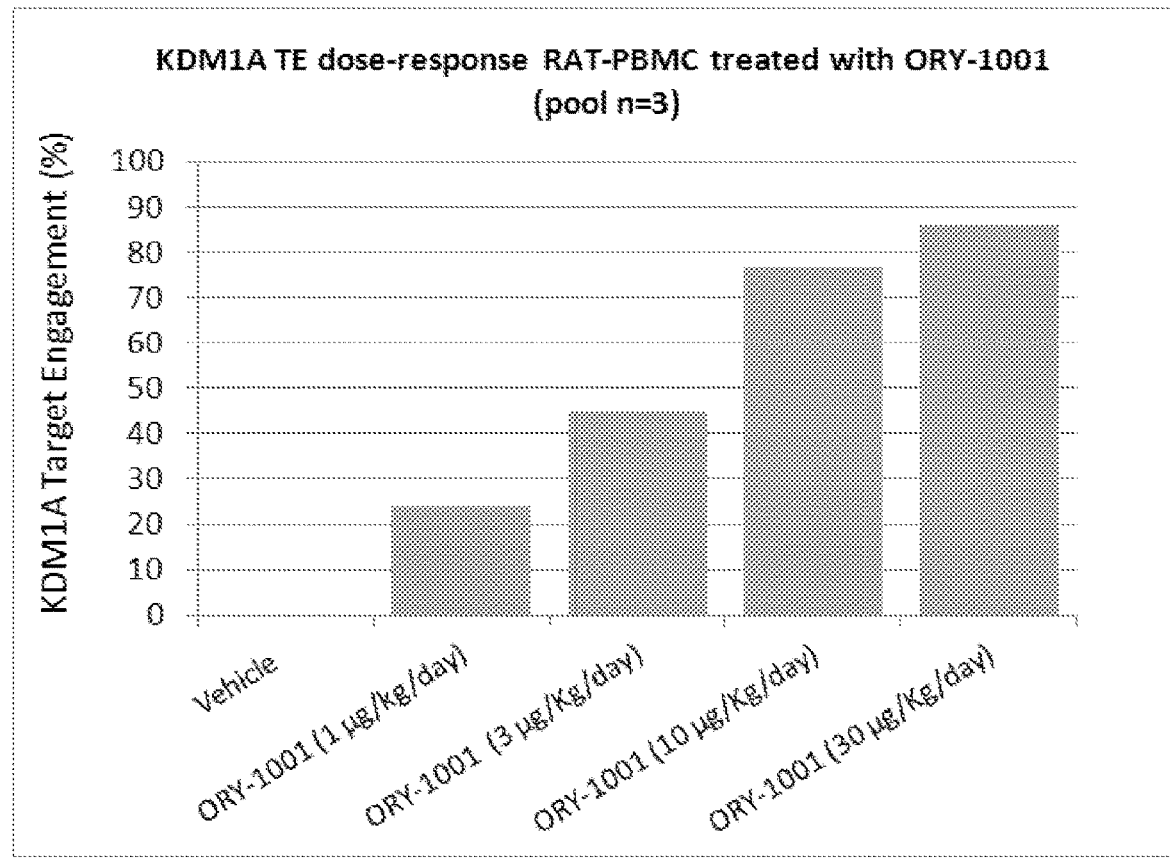
FIGS. 9A, 9B and 9C: KDM1A Target engagement in rat PBMCs (FIG. 9A) or rat lung (FIG. 9B) treated with ORY-1001 at different doses according to the conditions described in example 8.
Figure 9B:
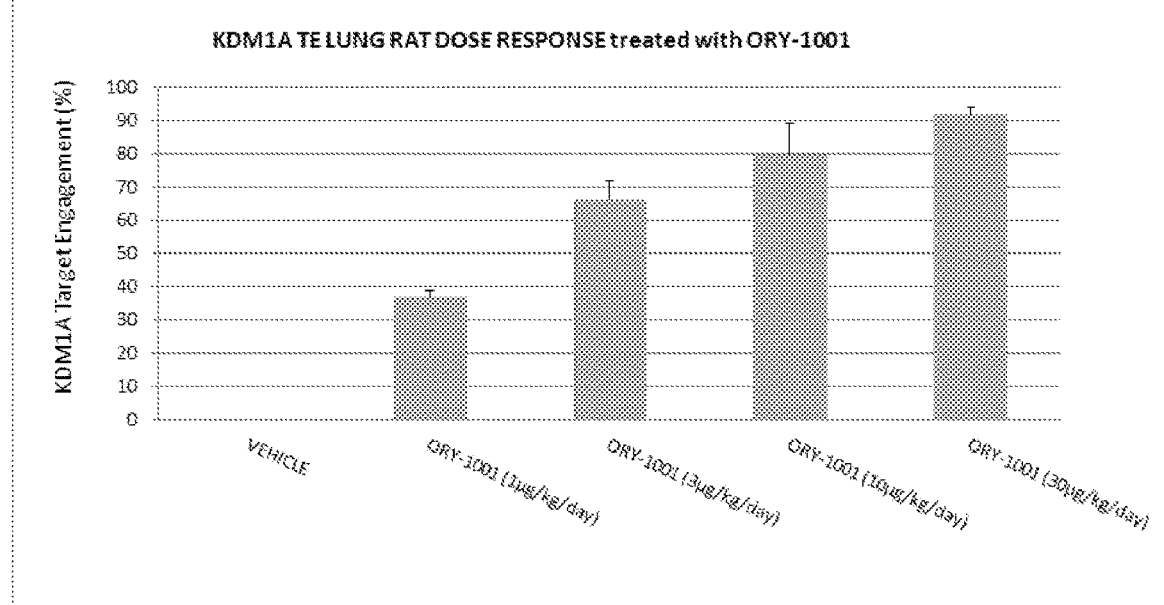

In particular, Example 8 and 9 further illustrate that free KDM1A levels may be determined using the chemoprobe-based methods of the invention in samples taken from animals that had been administered in vivo with single or repeated doses of a KDM1A inhibitor. For example, as described in Example 8, free KDM1A levels were determined in PBMCs and lung samples from rats treated with increasing doses of ORY-1001 or vehicle, and these levels were used to determine target engagement (as described below); the corresponding results are shown in FIGS. 9A and 9B. Additional examples showing the measurement of free KDM1A levels in animals treated with single or multiple doses of ORY-1001 are disclosed in Example 9. Free KDM1A levels were further determined in brain samples from mice from an experimental Alzheimer's disease model treated with another KDM1A inhibitor, Compound C (as further described in Example 8), or vehicle, which were used to determine target engagement of Compound C in the brain (see results in FIG. 9C); the free KDM1A level determinations and target engagement measurements using the methods of the invention confirmed that this compound enters the brain and inhibits KDM1A in the brain.

As illustrated in Example 9, the chemoprobes and methods of the invention may be used to determine free KDM1A levels in PBMC samples from human subjects which have been administered a KDM1A inhibitor in the context of a clinical trial. In particular, as described in Example 9, in a Phase I clinical trial to determine the safety, tolerability and pharmacokinetics of the KDM1A inhibitor designated as Compound C (as described in the Examples), samples were taken from each volunteer before and at different time points after administration of a single dose of the KDM1A inhibitor, and free KDM1A levels were determined in said samples, and used to determine target engagement, as described below.

The methods to determine free KDM1A levels according to the invention using a KDM1A chemoprobe to "tag" free KDM1A are not limited to the particular embodiments described in the examples. While the methods have been implemented using ELISA (or AlphaLISA) platforms, as particularly ELISA is a technology widely implemented in research labs and clinical analysis laboratories, the skilled person will readily recognize that the chemoprobe-based methods to determine free KDM1A protein levels may be implemented using other technologies, as outlined for example in the sections Detection agents and Detection systems above.

For example, other differently tagged/labeled KDM1A chemoprobes of formula (I) (or of formula II or III) may be used, where biotin is replaced with another tag or label P as defined above in relation to a compound of formula (I). In the section entitled Tags and Labels above, other examples of tags and labels that can be used in the chemoprobes of the invention instead of biotin are mentioned, as well as corresponding suitable methods to capture/detect said tags/labels in the chemoprobe and KDM1A-chemoprobe bound complexes, e.g. to determine free KDM1A levels. Likewise, other chemoprobes containing a different KDM1A inhibitor radical Z may be used. Chemoprobes as described in Examples 1.1, 1.2, 1.3 and 1.6, which correspond to a compound of both formula (I), (II) and (III), are based on the KDM1A inhibitor known as ORY-1001, whereas chemoprobes of examples 1.4 and 1.5, which correspond to a compound of both formula (I) and (II), are based on two other KDM1A inhibitor Z radicals. Alternative suitable chemoprobes may be prepared and used based on other KDM1A inhibitors, i.e. containing other Z radicals, preferably wherein Z is a radical of an irreversible KDM1A inhibitor. Examples of KDM1A inhibitors that may be used to prepare KDM1A chemoprobes are disclosed in the section KDM1A chemoprobes, above. Additional examples of KDM1A inhibitors are discussed in the section KDM1A inhibitors below, and they may also be used to generate KDM1A chemoprobes. The resulting KDM1A chemoprobe should be exhibiting appropriate KDM1A inhibitory potency and selectivity versus other targets for use in the methods of the invention, as discussed above under the KDM1A chemoprobe section.

In some embodiments, the above methods further comprises to determine a level of total KDM1A in said sample. For example, total KDM1A levels may be used for sample normalization, in order to correct for differences in the amount of KDM1A enzyme present in a sample, when comparing results obtained in different samples.

Figure 3A:
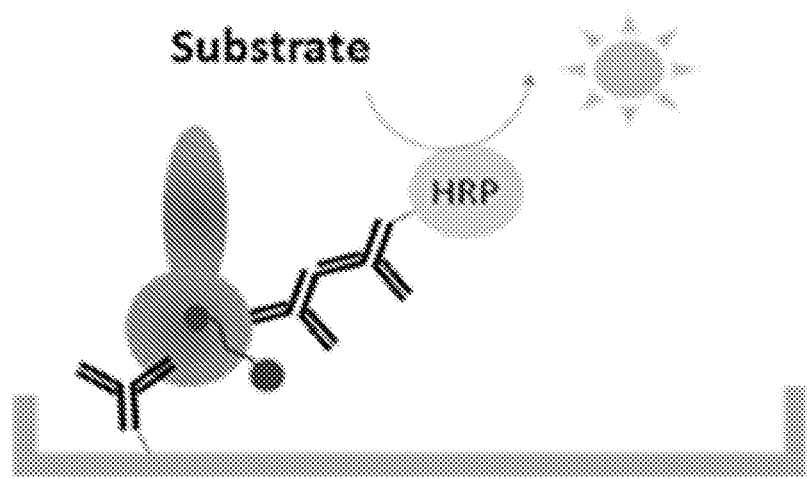
FIGS. 3A and 3B: Scheme of sandwich ELISA for determination of total KDM1A (FIG. 3A) and KDM1A chemoprobe capture ELISA based determination of free KDM1A (FIG. 3B) as described in Example 5.

For example, total KDM1A levels may be determined as illustrated in the Examples. For example, as described in Examples 5 and 6, total KDM1A levels may be determined using a sandwich ELISA (see Example 5 and FIG. 3A, showing a schematic representation of the sandwich ELISA) or in a corresponding AlphaLISA format (see Example 6) using two different antiKDM1A antibodies, which were selected using the criteria described in more detail in Example 5.1 and in the section Antibodies below. Other alternative antiKDM1A antibodies may be used, which may be selected as described in said Antibodies section. While an ELISA-based method such as for example the one described in the Examples is advantageous, as ELISA technology platforms are widely implemented in research and clinical analysis labs, alternative methods to determine the total amount of KDM1A protein present in a sample may be used, for example the methods outlined above under the sections Detection agent and Detection system, as will be apparent to those skilled in the art.

A level can be expressed as needed in different units (p.e. Relative Luminescence Units or RLU, Absorbance Units or AU, Fluorescence Units or FU, etc) in function of the technology used to obtain a signal, as long as there is a linear relationship between the amount of signal and the amount of free or total KDM1A in a sample (i.e. a dilution curve shows detection is in the linear range). The level can also be expressed as a concentration (amount), if a calibration curve was established from samples containing known amounts of total or free KDM1A protein and the concentration (amount) can be determined through interpolation.

The raw signals obtained from the measuring equipment can be subject to data processing. Data processing that is generally applied is subtraction of background signal, outlier elimination using established criteria like the Grubbs' test, Chauvenet's criterion, the MMS-test for outliers in linear regression, Peirce's criterion and business rules. The mean or median signal can be calculated, as well as the error on the measurement.

In some embodiments, the above methods further comprise determining target engagement of a KDM1A inhibitor in said sample.

In some embodiments, the determination of said target engagement comprises calculating the ratio between free KDM1A level in the sample and the free KDM1A level in a reference sample.

In some embodiments, the determination of said target engagement comprises calculating the ratio between free KDM1A level and total KDM1A level in the sample.

In some embodiments, the determination of said target engagement comprises calculating the ratio A/B, wherein A is the ratio of the free KDM1A level and the total KDM1A level in the sample and B is the ratio of the free KDM1A level and total KDM1A level in the reference sample.

Target engagement (TE) of a KDM1A inhibitor can be determined in various ways.

In a first method, TE in a sample X (TEx) can be calculated as $TE_X = 1 - LEVEL_{Free,X}/LEVEL_{Total,X}$; wherein $LEVEL_{Free,X}$ is the level of free KDM1A in sample X and $LEVEL_{Total,X}$ is the level of total KDM1A in sample X. This method of calculation can be used on the condition that the detection efficiency of free and total KDM1A are equal.

Accordingly, the invention provides a method to determine target engagement of a KDM1A inhibitor in a sample, wherein said target engagement is determined as 1 minus the ratio between free KDM1A level and total KDM1A level in the sample, wherein 1 corresponds to full target engagement and 0 corresponds to absence of target engagement.

In a second method, TE in a sample X (TEx) can also be calculated as $TE_X = 1 - LEVEL_{Free,X}/LEVEL_{Free,REF}$; wherein $LEVEL_{Free,X}$ is the level of free KDM1A in sample X and $LEVEL_{Free,REF}$ is the level of free KDM1A in a reference sample. This method can be used on the condition that the amount of total KDM1A present in sample X and in the reference sample is the same and on the condition that the detection efficiency of free KDM1A in sample X and in the reference sample is the same.

Accordingly, the invention provides a method to determine target engagement of a KDM1A inhibitor in a sample, wherein said target engagement is determined as 1 minus the ratio between free KDM1A level in the sample and the free KDM1A level in a reference sample, wherein 1 corresponds to full target engagement and 0 corresponds to absence of target engagement.

In a third method, TE in sample X can also be calculated as $TE_X = 1 - (R_X/R_{REF})$; where $R_X = LEVEL_{Free,X}/LEVEL_{Total,X}$ and
$R_{REF} = LEVEL_{Free,REF}/LEVEL_{Total,REF}$;

wherein $LEVEL_{Free,X}$ is the level of free KDM1A in sample X, $LEVEL_{Total,X}$ is the level of total KDM1A in sample X, $LEVEL_{Free,REF}$ is the level of free KDM1A in a reference sample and $LEVEL_{Total,REF}$ is the level of total KDM1A in the reference sample.

This is equivalent to calculating TE using $TE_X = 1 - (R_{Free}/R_{Total})$; where $R_{Free} = LEVEL_{Free,X}/LEVEL_{Free,REF}$ and
$R_{Total} = LEVEL_{Total,X}/LEVEL_{Total,REF}$ The advantage of this calculation method is that it does not require the detection efficiency of free and total KDM1A to be equal, nor does it require that the same amount of total KDM1A is used in every assay, which speeds up the procedure. The formula can be applied when it can be assumed that the detection efficiency of free KDM1A in sample X and the reference sample will be the same, and that the detection efficiency of total KDM1A will be the same in sample X and the reference sample. This is usually the case when both samples are of the same nature; p.e. extracts of a specific tissue or cell type.

Accordingly, the invention provides a method to determine target engagement of a KDM1A inhibitor in a sample, wherein said target engagement is determined as 1 minus the ratio $R_X/R_{REF}$, wherein $R_X$ is the ratio of the free KDM1A level and the total KDM1A level in the sample and $R_{REF}$ is the ratio of the free KDM1A level and total KDM1A level in the reference sample, wherein 1 corresponds to full target engagement and 0 corresponds to absence of target engagement.

In any case, target engagement calculated according to the above methods can be expressed as a fraction of 1 or in %, for example:

$TE_X(\%)=100-((R_X(\%)/R_{REF}(\%))\times 100)$; where
$R_X(\%)=(LEVEL_{Free,X}/LEVEL_{Total,X})\times 100$ and
$R_{REF}(\%)=(LEVEL_{Free,REF}/LEVEL_{Total,REF})\times 100$.

Accordingly, the invention provides a method for in vitro determining target engagement of an inhibitor of KDM1A in a sample, wherein said method comprises
- (i) contacting or exposing KDM1A to a chemoprobe of the invention;
- (ii) determining a level of free KDM1A employing said chemoprobe in said sample;
- (iii) determining a level of free KDM1A in a reference sample;
- (iv) calculating the ratio between the free KDM1A level in the sample and the free KDM1A level in the reference sample; and
- (v) determining target engagement as 1 minus the ratio calculated in step (iv).

In some embodiments, the method comprises contacting or exposing the sample to said chemoprobe.

In another aspect, the invention provides a method for in vitro determining target engagement of an inhibitor of KDM1A in a sample, wherein said method comprises
- (i) contacting or exposing KDM1A to a chemoprobe of the invention;
- (ii) determining a level of free KDM1A employing said chemoprobe in said sample;
- (iii) determining a level of total KDM1A in said sample;
- (iv) calculating the ratio between free KDM1A level and total KDM1A level in the sample; and
- (v) determining target engagement as 1 minus the ratio calculated in step (iv).

In some embodiments, the method comprises contacting or exposing the sample to said chemoprobe.

In another aspect, the invention provides a method for in vitro determining target engagement of an inhibitor of KDM1A in a sample, wherein said method comprises
- (i) contacting or exposing KDM1A to a chemoprobe of the invention;
- (ii) determining a level of free KDM1A employing said chemoprobe in said sample;
- (iii) determining a level of total KDM1A in said sample;
- (iv) determining a level of free KDM1A employing said chemoprobe in a reference sample;
- (v) determining a level of total KDM1A in said reference sample;
- (vi) calculating the ratio A/B, wherein A is the ratio of the free KDM1A level and the total KDM1A level in the sample and B is the ratio of the free KDM1A level and the total KDM1A level in the reference sample; and
- (vii) determining target engagement as 1 minus the ratio calculated in step (vi).

In some embodiments, the method comprises contacting or exposing the sample to said chemoprobe.

In some embodiments, the sample has been exposed or contacted to a KDM1A inhibitor in vitro.

In some embodiments, the sample is obtained from a subject that has been administered a KDM1A inhibitor.

In step (i) in the above methods, KDM1A is contacted or exposed to a chemoprobe of the invention. Any compound of formula (I), (II), (IIa), (III) or (IIIa) as described herein may be used as chemoprobe in the above methods. In the appended examples, chemoprobes of formula (I), (II), (IIa), (III) or (IIIa) wherein P is biotin have been used, but other differently tagged/labeled KDM1A chemoprobes of formula (I) (or of formula II, IIa, III or IIIa) may be used, where biotin is replaced with another tag or label P as defined above in relation to a compound of formula (I). In the section entitled Tags and Labels above, examples of tags and labels that can be used in the chemoprobes of the invention instead of biotin are mentioned. Likewise, other chemoprobes containing a different KDM1A inhibitor radical Z other than the ones shown in the chemoprobes as described in the Examples may be used. Preferably Z should be a radical of an irreversible KDM1A inhibitor. Examples of KDM1A inhibitors that may be used to prepare KDM1A chemoprobes are disclosed in the section KDM1A chemoprobes, above.

Additional examples of KDM1A inhibitors are discussed in the section KDM1A inhibitors below, and they may also be used to generate KDM1A chemoprobes. The resulting KDM1A chemoprobe should exhibit appropriate KDM1A inhibitory potency and selectivity versus other targets for use in the methods of the invention, as discussed above.

Said contacting or exposing KDM1A to the chemoprobe may be performed by contacting or exposing the sample (containing KDM1A) in vitro to the chemoprobe, such as by lysing the sample in the presence of the chemoprobe.

Said sample as used in step (i) in the above methods may be a sample that has been contacted or exposed to a KDM1A inhibitor in vitro, for example a cell culture like a human cell culture is contacted or exposed to said KDM1A inhibitor in vitro, or a tissue, organ or blood sample obtained from a subject is contacted or exposed to said KDM1A inhibitor in vitro. The sample may also be a sample that is obtained from a subject (for example a human or animal) that has been administered a KDM1A inhibitor. The sample may be for example a peripheral sample (e.g. PBMCs isolated from blood), biopsy, extracted tissues, extracted tumor and the like.

In step (ii) in the above methods, free KDM1A level in said sample is determined using said chemoprobe of the invention. As illustrated in the examples, free KDM1A level may be determined using a KDM1A chemoprobe-based ELISA assay employing a chemoprobe of formula (I) (or II, IIa, III or IIIa) which contains a biotin tag (as P group) to capture free KDM1A, and using different detection techniques, like luminescence or colorimetric. The method used to determine free KDM1A levels according to the invention using a KDM1A chemoprobe is not limited however to the particular embodiments described in the examples and other methods to determine free KDM1A levels may be used, as will be apparent to those skilled in the art. For example, it is possible to use other P tags or labels in the chemoprobe and/or other suitable capture agents (as described for example in the section Capture agents above) and/or other detection methods (as described for example in the sections Detection agent and Detection system above).

Some of the above methods comprise a step of determining a level of total KDM1A in the sample. As illustrated in the examples, total KDM1A levels may be determined using a sandwich ELISA (or corresponding AlphaLISA assay) using two different antiKDM1A antibodies. While an ELISA-based method such as for example the one described in the Examples is advantageous, as ELISA technology platforms are widely implemented in research and clinical analysis labs, alternative methods to determine the total amount of KDM1A protein present in a sample may be used, as will be apparent to those skilled in the art, for example the methods outlined above under the sections Detection agent and Detection system.

Some of the above methods comprise a step of determining a level of free KDM1A or total KDM1A in a reference sample. As defined above, the reference sample may be any tissue, cells, protein extract, recombinant protein that is chosen to serve as a reference to the sample under study. A reference sample, or the subject from which the reference sample has been obtained, may have been treated with a vehicle, or may have been obtained from the same subject prior to treatment with a KDM1A inhibitor, or may have been obtained from the same subject when the effect of the KDM1A inhibitor has ceased completely. Free KDM1A levels and total KDM1A levels in said reference sample may be determined using the same methods to determine free KDM1A levels and total KDM1A levels, respectively, in the sample under study.

The thus determined free and/or total KDM1A levels in a sample and/or in a reference sample may then be used to calculate the ratios as defined above, which are then used to determine target engagement as described above. Target engagement calculated according to the above methods may then be expressed as a fraction of 1 or in %.

For example, as illustrated in Example 7, target engagement of a KDM1A inhibitor may be determined as follows: a sample of cells (e.g. MV(4;11)) treated with a KDM1A inhibitor (e.g. ORY-1001) or with vehicle (used as reference sample) is lysed in the presence of a chemoprobe of the invention (e.g. example 1.6) and protein extracts are obtained such as described in Example 7.1, thereby contacting or exposing KDM1A (present in said cell sample) to said chemoprobe, as recited in step (i) above; the level of free KDM1A may be measured in said protein extract containing chemoprobe bound to KDM1A using the chemoprobe-based ELISA assay described in Example 5.2, as explained in Example 7.3, thus determining a level of free KDM1A employing said chemoprobe in said sample as recited in step (ii) above; the level of total KDM1A may be measured in the same protein extract using the sandwich ELISA assay described in Example 5.2, as explained in Example 7.3, thus determining a level of total KDM1A in said sample as recited in step (iii) above; same procedure may be followed using the sample of cells treated with vehicle described above as reference sample to measure free and total KDM1A level in said reference sample, thus determining a level of free KDM1A employing said chemoprobe in said reference sample as recited in step (iv) above, and determining a level of total KDM1A in said reference sample as recited in step (v); and the obtained values of free and total KDM1A level in the sample of cells treated with ORY-1001 and in the reference sample (treated with vehicle only) may be then used as described in Example 7.2 and 7.3 to calculate the ratio of free KDM1A/total KDM1A level in the sample (indicated as sample X in Example 7.2), corresponding to A above in step (vi) and the ratio of free KDM1A/total KDM1A level in the reference sample (indicated as sample REF in Example 7.2), corresponding to B above in step (vi) above and finally to calculate the ratio A/B, as recited in step (vi) above, and then target engagement may be calculated as outlined in Example 7.2, where target engagement in the sample (indicated as TEx in Example 7.2) corresponds to 1-A/B, thus determining target engagement as 1 minus the ratio calculated in step (vi), as recited in step (vii) above.

Target engagement may be expressed as a fraction of 1 or in %, as explained in more detail above.

As illustrated in the Examples, target engagement of KDM1A inhibitors may be determined according to the above methods in a range of sample types, including human samples. For example, target engagement for KDM1A inhibitors, may be determined in cell lines treated with KDM1A inhibitors, as shown in Example 7, in particular in MV(4;11) leukemia cells (see Example 7.3 and FIGS. 7 and 8A), as well as in other cell lines, including THP-1 leukemia cells (see Example 7.3 and FIG. 8B), and LNCap prostate cancer cells (see Example 7.3 and FIG. 8C).

As illustrated in the Examples, the methods of the invention may also be used to determine target engagement in samples taken from animals that have been administered in vivo with single or repeated doses of a KDM1A inhibitor. As illustrated in Example 8, target engagement for a KDM1A inhibitor (for example ORY-1001) may be determined in peripheral samples (for example PBMCs) and tissue (for example lung) samples from subjects (for example rats) treated with increasing doses of the KDM1A inhibitor or vehicle, as described in more detail in Example 8.3 and FIGS. 9A and 9B. Example 8 further illustrates that target engagement may be determined in further tissue samples, like brain samples; in particular, target engagement was determined in brain samples from SAMP8 mice (an experimental Alzheimer's disease model) treated with the KDM1A inhibitor designated as Compound C (a compound that crosses the blood-brain barrier in the brain, further described in Example 8), as described in Example 8.3 and in FIG. 9C.

As illustrated in the appended Examples, the methods of the invention may also be used to determine target engagement for a KDM1A inhibitor in human samples. In particular, Example 9 illustrates that target engagement for a KDM1A inhibitor may be determined in peripheral samples (PBMCs) from humans participating in a clinical trial. As described in Example 9 in more detail, as part of a Phase I clinical trial with the KDM1A inhibitor designated Compound C, whose main objective is to determine the safety, tolerability and pharmacokinetics of Compound C, cohorts of healthy volunteers have received a single dose of Compound C, or placebo. Samples have been taken from each volunteer at different time points and free and total KDM1A levels have been determined in said samples and have been used to calculate target engagement for Compound C, following the method described in Example 7.2.

The herein described KDM1A chemoprobes and methods have been applied to assess target engagement by ORY-1001 and other KDM1A inhibitors, as described in more detail in the Examples, and can be readily used to assess target engagement by other KDM1A inhibitors, such as the compounds disclosed in the "KDM1A inhibitors" section below. To ensure that the KDM1A chemoprobe and not residual unbound KDM1A inhibitor occupies the free KDM1A enzyme, preferentially the IC50 of the chemoprobe should be maximum 10× the IC50 of the KDM1A inhibitor and the chemoprobe should be added in excess.

In some embodiments, the KDM1A inhibitor is an irreversible KDM1A inhibitor. In some embodiments, the irreversible KDM1A inhibitor inhibits KDM1A through covalent binding to the FAD cofactor. In some embodiments, the KDM1A inhibitor is (trans)-N1-((1R,2S)-2-phenylcyclopropyl)cyclohexane-1,4-diamine, or (−) 5-(((((trans)-2-(4-(benzyloxy)phenyl)cyclopropyl)amino)methyl)-1,3,4-oxadiazol-2-amine. In some other embodiments, the KDM1A inhibitor is 4-((4-(((((1R,2S)-2-phenylcyclopropyl)amino)methyl)piperidin-1-yl)methyl)benzoic acid, or a salt thereof.

KDM1A target engagement by reversible KDM1A inhibitors that block the enzymatic activity of KDM1A can also be assessed. In this case, a less potent KDM1A chemoprobe with appropriate binding kinetics may be preferred to avoid that the chemoprobe displaces the reversible KDM1A inhibitor during the analysis procedure. Alternatively or combined with this approach, the chemoprobe binding reaction during the analysis procedure may be stopped by addition of an excess of a potent irreversible KDM1A inhibitor like ORY-1001 at selected timepoints.

In some embodiments, in the above methods the chemoprobe is used to capture or detect free KDM1A.

In some embodiments, in the chemoprobes of the invention P is a tag and the chemoprobe is captured or detected by a suitable capture or detection agent directed against the tag. The nature of the capture and/or detection agent will depend on the tag used. Examples of tags and corresponding capture or detection agents are explained in more detail under the section "Tags and labels".

In some embodiments, the determination of the level of free KDM1A comprises the use of an antibody specific to an epitope of KDM1A.

In some embodiments, the determination of the level of total KDM1A comprises the use of a first antibody specific to an epitope of KDM1A to capture or detect total KDM1A. In some embodiments, the determination of the level of total KDM1A comprises the use of a second antibody specific to an epitope of KDM1A to capture or detect total KDM1A, wherein said epitope of said second antibody is different from said epitope of the first antibody.

In some embodiments, the above methods comprise the use of a protein to capture or detect the tag in the chemoprobe and to determine said level of free KDM1A. Proteins that can be used are described in detail in the "Tags and labels" section. In one embodiment, such protein is streptavidin.

When selecting the detection and capture agents for use in the above methods, it is desirable that the binding of any of the antibodies to the target epitopes on KDM1A or the binding of the protein to the tag in the KDM1A-bound chemoprobe does not interfere with the ability of the remaining antibody(ies) to bind its target epitope on KDM1A or of the protein to bind the KDM1A-bound chemoprobe.

Antibodies

The criteria for selection of the antibodies to be used in the above methods of the invention will depend on the detection technology chosen for use with the methods of the invention. Factors to be considered include specificity, affinity, proximity and sterical hindrance, including the likeliness of mutual interference of binding of antibodies or probe, and the probability of the antibody to recognize the native enzyme within the protein complexes that contain it.

A suitable pair of antibodies for use in combination with the above methods includes an antibody directed against an epitope located at the N-terminal region of KDM1A and an antibody directed against an epitope located at the C-terminal region of KDM1A. In one embodiment, the pair of antibodies is mAb-825 and mAb-844, as defined below.

One of the antibodies is directed to epitope EP1, as defined below, and the other antibody binds to epitope EP2, as defined below.

mAb-825:

Rabbit N-terminal mAb-KDM1A (cell Signaling, #2184) that targets an epitope, designated herein EP1, located in the N terminal region proximate to proline 60 (P60) of the human KDM1A sequence (UNIPROT ID O60341-1) and blocked by peptide #LSD1 Blocking Peptide-2184 specific (Cell Signaling).

mAb-844:

mouse C-terminal mAb-KDM1A (Abcam #ab53269). This antibody targets an epitope, herein designated EP2, located on the C-terminal region and which comprises AMYTLPRQATPGVPAQ, corresponding to AA 832-847 of human KDM1A.

Both antibodies recognize at least human, rat and mouse KDM1A protein.

Further antibodies to KDM1A recognizing epitopes EP1 and EP2 can be readily developed by methods known in the art. In particular, antibodies that bind these epitopes can be identified by their ability to compete with the antibodies described herein or to be blocked by the peptide described above. The sequences comprised in the epitopes EP1 and EP2 above correspond to highly conserved regions in the KDM1A protein in the different species, including human, rat and mice.

In some embodiments, in the methods of the invention one of said antibodies targets epitope EP1, wherein EP1 is located in the N terminal region proximate to proline 60 (P60) of the human KDM1A sequence (UNIPROT ID O60341-1) and is blocked by peptide #LSD1 Blocking Peptide-2184 specific (Cell Signaling). In some embodiments, the other of said antibodies targets epitope EP2, wherein EP2 is located on the C-terminal region and comprises AMYTLPRQATPGVPAQ, corresponding to AA 832-847 of human KDM1A.

The KDM1A to be used in the herein disclosed test methods and target engagement assays is preferably a human KDM1A as, inter alia, provided in SEQ ID NO: 1 and the corresponding UNIPROT No. Also KDM1A isoforms or differential splice forms and natural or artificial variants of the human KDM1A sequence as provided herein and shown in SEQ ID NO:1, in particular functional homologs, as well as orthologs thereof in other species (e.g. rat, mice, as shown in the appended Examples) may be used in the test methods and target engagement assays of the invention. The KDM1A to be contacted with or to be exposed is an expressed protein, which may be naturally expressed, e.g. in a biological sample, or may also be recombinantly expressed.

In some embodiments, in the methods of the invention the antibodies are mAb-844 and mAb-825, the tag P in the KDM1A chemoprobe is biotin and the protein used to capture the chemoprobe is streptavidin.

In some embodiments, in the methods of the invention the level of total KDM1A is determined by sandwich ELISA and the level of free KDM1A is determined by a KDM1A chemoprobe capture ELISA. A schematic depiction of this method is shown in FIG. 3. Alternatively, the level of total KDM1A can be determined by AlphaLISA and the level of free KDM1A can be determined by a KDM1A chemoprobe capture AlphaLISA. In some embodiments, the determination of the level of free and total KDM1A is performed is multiplexed in the same sample.

In some embodiments, the ELISA uses chemoluminescent detection.

It is to be understood that the present invention specifically relates to each and every combination of features or embodiments described above, including any combination of general and/or preferred features/embodiments. In particular, the invention specifically relates to all combinations of preferred features/embodiments (including all degrees of preference) of the methods disclosed above.

Other Applications of the Chemoprobes of the Invention

The KDM1A chemoprobes described herein can also be used for the analysis of the spatial distribution of free KDM1A, for example using chemohistochemistry (CHC), chemofluorescence or flow cytometry on fixed-permeabilized cells or tissues. The concept is similar to immunohistochemistry (IHC), and comprises contacting a chemoprobe with (a) cell or tissue sample(s), and visualizing the spatial distribution of the chemoprobe through the incorporated tag or label.

Accordingly, the invention provides a method for in vitro determining a spatial distribution of free KDM1A in a sample, wherein said method comprises
  (i) contacting or exposing KDM1A to a chemoprobe of the invention, and
  (ii) visualizing the spatial distribution of said free KDM1A in said sample by detection of the chemoprobe.

Detection of KDM1A using a chemoprobe does not only provide information about where the protein is, but also on whether the protein is active.

The analysis of the spatial distribution of free KDM1A in a sample through detection of the KDM1A bound chemoprobe can be direct, when a label (as described above) is incorporated into the chemoprobe, or indirect, when a tag (as described above) is incorporated that, in its turn, can be detected by an agent incorporating a label or any other entity generating a signal, that can be detected using detection agents or detection systems, as previously described.

The cells, tissues or organism from which the sample derives may be untreated or may have been exposed to a KDM1A inhibitor, and in this case the KDM1A chemoprobe based method described herein can be used to assess the spatial distribution of free KDM1A, and consequently, the spatial distribution of target engagement. The spatial distribution of free KDM1A using a KDM1A chemoprobe can be assessed in cells sorted using Fluorescence Assisted Cell Sorting (FACS) with cell type specific markers. The cell type specific markers may include cell surface markers known to be induced by inhibition of KDM1A, p.e. induction of CD11b in THP-1 AML cells, and inform about the correlation of the degree of target inhibition and induction of differentiation at the individual cellular level.

The subcellular localization of free KDM1A can be analyzed using samples submitted to fractionation to achieve separation of cell components.

The spatial distribution can also be assessed in samples that conserve the structural integrity of the samples, p.e the KDM1A CHC method can be performed on tissue sections and in addition it can further be combined with traditional IHC, which allows for an assessment of the spatial distribution of free and total KDM1A protein in (a) cell or tissue sample(s). The KDM1A CHC method can also be combined with IHC directed to other proteins, for example to detect proteins which are expected to become up-regulated after KDM1A target engagement, allowing for a simultaneous detection of the target engagement and its down-stream effects.

In addition, the chemoprobes described herein are suitable for the isolation of KDM1A-containing complexes.

The invention therefore also relates to a method for in vitro determining interaction factors of KDM1A, wherein said method comprises
  (i) contacting or exposing a sample to a chemoprobe according to the invention (e.g. a chemoprobe of the appended claims);
  (ii) isolating chemoprobe-bound KDM1A-containing complexes;
  (iii) identifying said interaction factors of KDM1A, wherein said interaction factors are nucleic acid(s) and/or polypeptide(s).

To identify the protein partners in KDM1A containing complexes, cell are lyzed in "soft" conditions that don't destroy the protein complexes and contacted with a KDM1A chemoprobe that contains a tag that can be bound by a capture agent and used to "chemoprecipitate" the KDM1A containing complex. The thus obtained "chemoprecipitate" is submitted to protein analysis methods known in the art, including the identification of interacting proteins by Western blot analysis, microarray analysis using Antibody-Arrays or mass spectrometry.

To minimize false positives, produced by unspecific binding of proteins to the capture agent, a negative control sample can be included that has been exposed to an excess KDM1A inhibitor, thus blocking the possibility of the chemoprobe to bind the KDM1A complex.

Similarly, the KDM1A chemoprobes described herein can be used to isolate KDM1A target regions in the genome. KDM1A is recruited by transcription repressors to specific sites in the genome (sites vary in different cell types and under different conditions). The DNA-Protein complexes including nucleosomes can be isolated from the nuclei of target cells by cross-linking and digestion of chromatin. DNA associated to KDM1A can be isolated by chemoprecipitation with a KDM1A chemoprobe as described herein, and selected KDM1A target regions in the genome can be identified using quantitative PCR (qPCR), or KDM1A target regions can be analyzed genome wide by Chromatin Chemoprobe precipitation coupled to next generation sequencing (NGS) or using tiling DNA microarrays. An advantage of the KDM1A chemoprobes to the Chromatin Chemoprobe precipitation technique described herein is the irreversible nature of their binding, allowing for stringent washing procedures and high specificity.

Preparation of the KDM1A chemoprobes

The chemoprobes of the invention may be made by a variety of methods, including standard chemistry. Illustrative general synthetic methods are set out below and then the preparation of specific compounds of the invention is described in more detail in the Experimental Section.

As it will be obvious to one skilled in the art, the exact method used to prepare a given compound may vary depending on its chemical structure. Moreover, in some of the processes described below it may be necessary or advisable to protect the reactive or labile groups by conventional protecting groups. Both the nature of these protecting groups and the procedures for their introduction or removal are well known in the art (see for example Greene T. W. and Wuts P. G. M, "Protective Groups in Organic Synthesis", John Wiley & Sons, $3^{rd}$ edition, 1999). As an example, as protecting groups of an amino function the tert-butoxycarbonyl (Boc) group can be used. Whenever a protecting group is present, a later deprotection step will be required, which can be performed under standard conditions in organic synthesis, such as those described in the above-mentioned reference. Unless otherwise stated, in the methods described below the meanings of the different substituents are the meanings described above with regard to a compound of formula I.

$$P\text{-}L\text{-}Z \quad (I)$$

For instance, compounds of formula I can be prepared by coupling of P to L-Z or alternatively Z to P-L, with both parts conveniently functionalized. Examples of coupling reactions include, but are not limited to, formation of esters, amides, from activated acids or acyl halides optionally in the presence of a base under standard conditions; formation of sulfonamide by reaction of an amine with a sulfonyl halide, optionally in the presence of a base, under standard conditions; formation of amines by substitution of a primary or secondary amine with an alkylating agent under standard conditions, or by reductive amination, i.e. by treatment with an aldehyde or a ketone in the presence of a reducing agent such as sodium cyanoborohydride or sodium triacetoxyborohydride; formation of carbamates, ureas or thioureas from isocyanates, thioisocyanates and chloroformates, under standard conditions; formation of ethers and thioethers by alkylation of alcohols and thiols by reaction with alkylating agent under standard conditions.

Examples of reagents that can be used for the attachment of P include among others: Alexa Fluor® 405 carboxylic acid, succinimidyl ester; Alexa Fluor® 405 carboxylic acid, succinimidyl ester; Alexa Fluor® 488 carboxylic acid, succinimidyl ester; Alexa Fluor® 488 carboxylic acid, 2,3,5,6-tetrafluorophenyl ester; Alexa Fluor® 488 5-SDP ester; 3-amino-3-deoxydigoxigenin hemisuccinamide, succinimidyl ester; N-(2-aminoethyl)biotinamide, hydrobromide; Alexa Fluor® 405 cadaverine, trisodium salt; Alexa Fluor® 488 cadaverine, sodium salt; Alexa Fluor®555 cadaverine, disodium salt; Alexa Fluor®568 cadaverine, diammonium salt; Alexa Fluor® 594 cadaverine; 5-(aminoacetamido) fluoresceine (fluoresceinyl glycine amide); 5-((2-aminoethyl)amino)naphthalene-1-sulfonic acid, sodium salt; 7-amino-4-methylcoumarine; 4'-(aminomethyl)fluoresceine, hydrochloride; 5-(aminomethyl)fluoresceine, hydrochloride; 5-(and -6)-((N-(5-aminopentyl)amino)carbonyl)tetramethylrhodamine; N-(5-aminopentyl)-4-amino-3,6-disulfo-1,8-naphthalimide, dipotassium salt; 5-((5-aminopentyl)thioureidyl)fluoresceine, dihydrobromide salt; N-(5-aminopentyl)biotinamide, trifluoroacetic acid salt; bimane amine; 8-bromomethyl-4,4-difluoro-1,3,5,7-tetramethyl-4-bora-3a,4a-diaza-s-indacene; 6-bromoacetyl-2-dimethylaminonaphthalene; 5-(bromomethyl)fluoresceine; Biocytine; biocytine hydrazide; 6-((biotinoyl)amino)hexanoic acid, succinimidyl ester; 6-((biotinoyl)amino)hexanoic acid, sulfosuccinimidyl ester, sodium salt; 6-((6-((biotinoyl) amino)hexanoyl)amino)hexanoic acid, succinimidyl ester; 6-((6-((biotinoyl)amino)hexanoyl)amino)hexanoic acid, sulfosuccinimidyl ester, sodium salt; N-(biotinoyl)-N'-(iodoacetyl)ethylenediamine; D-biotin, succinimidyl ester; 5-(((N-(biotinoyl)amino)hexanoyl)amino)pentylamine, trifluoroacetic acid salt; biotin-X 2,4-dinitrophenyl-X-L-lysine, succinimidyl ester; BODIPY® FL, STP ester, sodium salt; Cascade Blue® acetyl azide, trisodium salt; 6-((4,4-difluoro-5,7-dimethyl-4-bora-3a,4a-diaza-s-indacene-3-propionyl)amino)hexanoic acid, succinimidyl ester; 6-((5-dimethylaminonaphthalene-1-sulfonyl)amino)hexanoic acid, succinimidyl ester; 6-(2,4-dinitrophenyl)aminohexanoic acid, succinimidyl ester; desthiobiotin-X C2-iodoacetamide; 5-dimethylaminonaphthalene-1-(N-(2-aminoethyl))sulfonamide; 5-dimethylaminonaphthalene-1-(N-(5-aminopentyl)) sulfonamide; 6-(fluorescein-5-(and -6)-carboxamido) hexanoic acid, succinimidyl ester; fluorescein-5-EX, succinimidyl ester; lucifer yellow iodoacetamide, dipotassium salt; Lissamine rhodamine B ethylenediamine; Na-(3-maleimidylpropionyl)biocyn; norbiotinamine, hydrochloride; 2-(2,3-naphthalimino)ethyl trifluoromethanesulfonate; 06185 Oregon Green® 488-X, succinimidyl ester *6-isomer*; QSY® 7 amine, hydrochloride; Rhodamine Red™-X, succinimidyl ester *5-isomer*; 6-(tetramethylrhodamine-5- (and -6)-carboxamido)hexanoic acid, succinimidyl ester; Texas Red®-X, succinimidyl ester; TS-Link™ desthiobiotin-X C5-thiosulfate, sodium salt; Texas Red® cadaverine;

In general, the compounds of formula II can be obtained in two steps by the method described in Scheme 1:

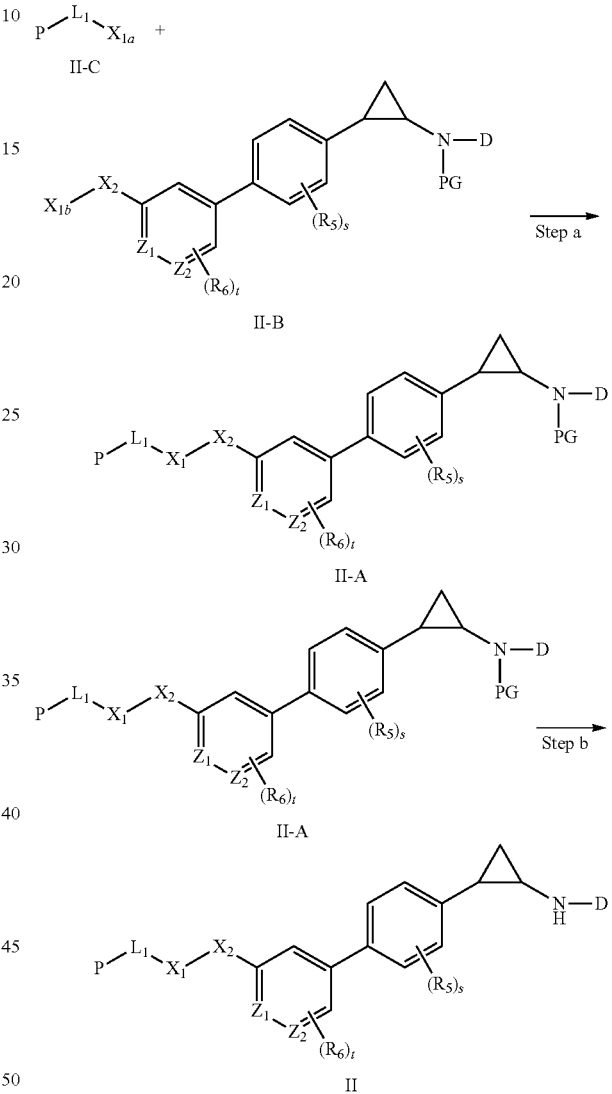

wherein P, $L_1$, $X_1$, X, $Z_1$, $Z_2$, $R_5$, $R_6$ and D have the meaning previously described in relation with a compound of formula II; PG represents an amine protecting group, such as for example tert-butoxycarbonyl (Boc); and $X_{1a}$ and $X_{1b}$ represent functional groups as —C(=O)OH, —C(=O)Cl, -halogen, —C(=O)H, —NH$_2$, —NHR$_1$, —N=C=O, —N=C=S, —OH, —SO$_2$Cl, —SH, —O(C=O)Cl, that by appropriate conversion reactions can generate $X_1$.

In a first step (step a), a compound of formula II-A can be prepared by coupling of compound of formula II-B to II-C with both parts bearing convenient reactive functions as $X_{1a}$ and $X_{1b}$ than can generate —$X_1$—.

For example, when $X_1$ is —NR$_1$—C(=O)— or —C(=O)—NR$_1$—, $X_{1a}$ is a carboxylic acid (—C(=O)OH)

and $X_{1b}$ is an amino group (—$NHR_1$) and vice versa, compounds of formula II-A can be obtained by means of activating agents.

Examples of said activating agents are among others: dicyclohexyl carbodiimide (DCC), 1-hydroxybenzotriazole (HOBT), N-hydroxysuccinimide (HOSu), 1-ethyl-3-(3'-dimethylamino)carbodiimide (EDC), diisopropyl carbodiimide (DIC), carbonyl diimidazole (CDI), Benzotriazol-1-yl-oxytris-(dimethylamino)-phosphonium hexafluorophosphate (BOP), Benzotriazol-1-yl-oxytris-pyrrolidinophosphonium hexafluorophosphate (PyBop), 0-(1Hbenzotriazol-1-yl)-N,N,N',N'-tetramethyluronium hexafluorophosphate (HBTU), 1-[Bis(dimethylamino)methylene]-1H-1,2,3-triazolo[4,5-b]pyridinium 3-oxid hexafluorophosphate (HATU). Reaction can be carried out in the presence of a base, such as, disopropylethylamine, pyridine, thriethylamine, or N-methylmorpholine, in a solvent, such as dimethoxyethane, N,N-dimethylformamide, tetrahydrofuran, dichloromethane or dioxane. Alternatively, carboxylic acids (C(=O)OH) are activated as mixed anhydrides or acid chlorides and then coupled with amides (—$NHR_1$) in the presence of a suitable base such as sodium hydride, triethylamine, diisopropylethylamine, pyridine or the like.

For example, when $X_1$ is —$NR_1$—, $X_{1a}$ is a ketone or an aldehyde (—C(=O) or —C(=O)H) and $X_1$ is an amino group (—$NHR_1$) and vice versa, compounds of formula II-A can be obtained by means of reductive amination or alkylation in the presence of a reducing agent such as sodium cyanoborohydride or sodium thacetoxyborohydride in a suitable solvent such as dioxane, THF, dichloromethane or diethyl ether. Alternatively, when $X_1$ is —$NR_1$—, $X_{1a}$ is a alkyl halide (—X) and $X_{1b}$ is an amino group (—$NHR_1$) and vice versa, compounds of formula II-A can be obtained by means of amine alkylation in the presence of a bases such as sodium carbonate, potassium carbonate, cesium carbonate, potassium phosphate or the like. Other preferred solvents include dioxane, tetrahydrofuran and pyridine. Temperature can be varied from room temperature to 100° C.

For example, when $X_1$ is —$SO_2$—$NR_1$— or —$SO_2$—$NR_1$—, $X_{1a}$ is a sulfonyl chloride (—$SO_2Cl$)—) and $X_{1a}$ is an amino group (—$NHR_1$—) and vice versa, compounds of formula II-A can be obtained by means of direct reaction of both compounds optionally in the presence of a base such as 4-dimethylaminopyhdine, in a suitable solvent such as dioxane, chloroform, dichloromethane or pyridine.

For example, when $X_1$ is —O—C(=O)—$NR^1$— or —$NR^1$—C(=O)—O—, $X_{1a}$ is a chloroformate (—O(C=O)Cl) and $X_{1b}$ is an amino group (—$NHR_1$) and vice versa, compounds of formula II-A can be obtained by means of direct reaction of both compounds optionally in the presence of a base such as 4-dimethylaminopyhdine, in a suitable solvent such as dioxane, chloroform, dichloromethane or pyridine.

For example, when $X_1$ is —C(=O)—O— or —O—C(=O)—, $X_{1a}$ is a carboxylic acid (—(C=O)—OH) and $X_1$ is an alcohol group (—OH) and vice versa, compounds of formula II-A can be obtained by means of activating agents. Examples of said activating agents are among others: dicyclohexyl carbodiimide (DCC), 1-hydroxybenzotriazole (HOBT), N-hydroxysuccinimide (HOSu), 1-ethyl-3-(3'-dimethylamino)carbodiimide (EDC), diisopropyl carbodiimide (DIC), carbonyl diimidazole (CDI), Benzotriazol-1-yl-oxytris-(dimethylamino)-phosphonium hexafluorophosphate (BOP), Benzotriazol-1-yl-oxytris-pyrrolidinophosphonium hexafluorophosphate (PyBop), O-(1Hbenzotriazol-1-yl)-N,N,N',N'-tetramethyluronium hexafluorophosphate (HBTU), 1-[Bis(dimethylamino)methylene]-1H-1,2,3-triazolo[4,5-b]pyridinium 3-oxide hexafluorophosphate (HATU). Reaction can be carried out in the presence of a base, such as, disopropylethylamine, pyridine, thriethylamine, or N-methylmorpholine, in a solvent, such as dimethoxyethane, N,N-dimethylformamide, tetrahydrofuran, dichloromethane or dioxane. Alternatively, when $X_1$ is —C(=O)—O— or —O—C(=O)—, $X_{1a}$ is a carboxylic acid (—(C=O)—OH) and $X_{1b}$ is an alcohol group (—OH) and vice versa, compounds of formula II-A can be obtained by Fisher esterification of both compounds in the presence of catalytic amounts of an acid as sulfuric acid, thionyl chloride, TMSCl, pTSOH, HCl, or oxallyl chloride.

For example, when X is —O—, $X_{1a}$ is a alkyl halide (—X) and $X_{1b}$ is an alcohol group (—OH) and vice versa, compounds of formula II-A can be obtained by Williamson ether synthesis in presence of a base such us sodium hydride, potassium tert-butoxide, sodium tert-butoxide, sodium hydroxide, potassium hydroxide, or a phase transfer catalyst such us benzyltrimethylammonium chloride, benzyltriethylammonium chloride, methyltricaprylammonium chloride, methyltributylammonium chloride, methyltrioctylammonium chloride, or hexadecvltributylphosphonium bromide.

For example, when $X_1$ is —NR1-C(=O)—NR1-, $X_{1a}$ is a alkyl isocyanate (—N=C=O) and $X_{1b}$ is an amino group (—NHR—) and vice versa, compounds of formula II-A can be obtained by means of direct reaction of both compounds, in a suitable solvent such as dioxane, toluene, or N,N-dimethylformamide.

For example, when $X_1$ is —NR1-C(=S)—NR1-, $X_{1a}$ is a alkyl isothiocyanate (—N=C=S) and $X_{1b}$ is an amino group (—$NHR_1$) and vice versa, compounds of formula II-A can be obtained by means of direct reaction of both compounds, in a suitable solvent such as dioxane, toluene, or N,N-dimethylformamide.

In the last step (step b), the protecting group of a compound of formula II-A is cleavaged under the standard conditions described in the literature to give a compound II. For example, in case Boo is used as PG, the cleavage is typically performed by treating compound II-A with a 4M dioxane/HCl $(_g)$ mixture at room temperature Scheme 2

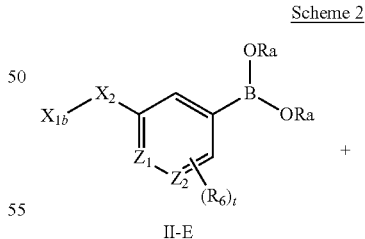

II-E

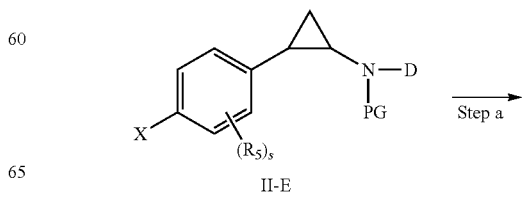

II-E

-continued

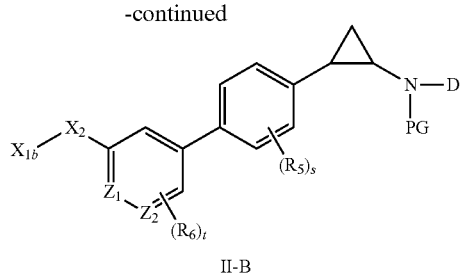

II-B

A compound of formula II-B can be obtained by reaction of a compound of formula II-E with a compound of formula II-D, as shown in Scheme 2, under the conditions reported in the literature for Suzuki couplings. For example, the reaction can be carried out in the presence of a base, such as $Na_2CO_3$, NaOH, $Cs_2CO_3$, CsF or $Ba(OH)_2$, and a palladium catalyst, such as $Pd(PPh_3)_4$, $Pd_2(dba)_3$ or $Pd(OAc)_2$, in a solvent, such as dimethoxyethane, toluene, N,N-dimethylformamide, tetrahydrofuran or dioxane, optionally in the presence of water, and heating, preferably at around 90° C.,

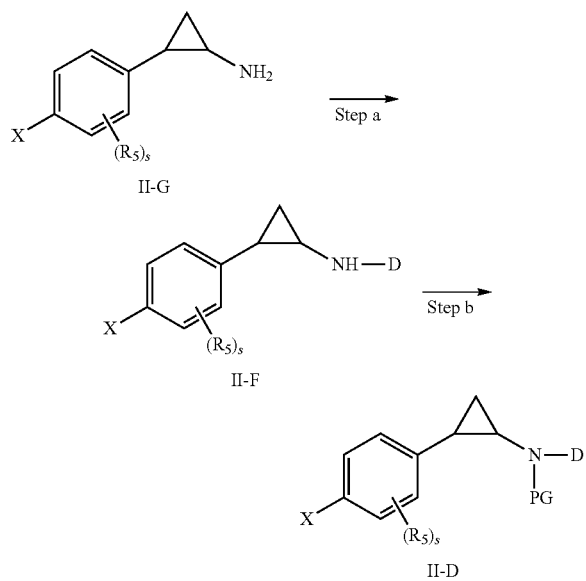

The compound of formula II-D can be prepared in two steps, as shown in Scheme 3. In a first step (step a), a compound of formula II-G is reacted with a commercially available aldehyde or ketone under reductive alkylation standard conditions, for example using sodium triacetoxyborohydride or sodium borohydride as reducing agent in a suitable solvent such as dichloroethane or methanol leading to the formation of (trans)-cyclopropylamino derivatives of formula 1-F. In a second step, the amino group is protected with a Boc protecting group (Boc: tert-butoxycarbonyl), under standard conditions, for example using Boc anhydride and a base, preferably triethylamine in a suitable solvent such as THF or ACN to give a compound of formula II-D.

Alternatively, compounds of formula II can be prepared by coupling of P to $L_1$ in the final steps with both parts conveniently functionalized. Examples of coupling reactions include, but are not limited to, formation of —C(=O)—, —$NR^1$—, —$NR^1$—C(=O)—, —C(=O)—$NR^1$—, —$NR^1$—C(=O)—$NR^1$—, —$NR^1$—C(=S)—$NR^1$—, —O—C(=O)—$NR^1$—, —$NR^1$—C(=O)—O—, —C(=O)—O—, —O—C(=O)—, —$SO_2$—$NR^1$—, —$NR^1$—$SO_2$— or —O— groups. The synthetic methods described for the preparation of $X_1$ groups in compounds of formula II can be applied to coupling of P to $L_1$.

Compounds of formula IIa, III and IIIa can be prepared likewise.

Furthermore, some compounds of the present invention can also be obtained from other compounds of formula I by appropriate conversion reactions of functional groups in one or several steps, using well-known reactions in organic chemistry under the standard experimental conditions.

Said transformations include, for example: the reduction of a nitro group to give an amino group, for example by treatment with hydrogen, hydrazine or formic acid in the presence of a suitable catalyst such as Pd/C; or by treatment with sodium borohydride in the presence of $NiCl_2$, Or $SnCl_2$; the substitution of a primary or secondary amine by treatment with an alkylating agent under standard conditions, or by reductive amination, i.e. by treatment with an aldehyde or a ketone in the presence of a reducing agent such as sodium cyanoborohydride or sodium thacetoxyborohydride; the conversion of an amine into a sulfonamide by reaction with a sulfonyl halide, such as sulfonyl chloride, optionally in the presence of a base such as 4-dimethylaminopyhdine, in a suitable solvent such as dioxane, chloroform, dichloromethane or pyridine, optionally in the presence of a base such as triethylamine or pyridine; the conversion of an amine into an amide, carbamate or urea under standard conditions; the alkylation of an amide by treatment with an alkylating agent under basic conditions; the conversion of an alcohol into an ether, ester or carbamate under standard conditions; the alkylation of a thiol to give a thioeter under standard conditions; the partial or total oxidation of an alcohol to give ketones, aldehydes or carboxylic acids under standard oxidizing conditions; the reduction of an aldehyde or ketone by treatment with a reducing agent such as sodium borohydride; the reduction of a carboxylic acid or a carboxylic acid derivative to an alcohol by treatment with a reducing agent such as diisobutylaluminium hydride or $LiAlH_4$; the oxidation of a thioeter to a sulfoxide or sulfone under standard conditions; the conversion of an alcohol into a halogen by reaction with $SOCl_2$, $PBr_3$, tetrabutylammonium bromide in the presence of $P_2O_5$, or $PCl_3$; the conversion of halogen into an amine by reaction with an amine, optionally in the presence of a suitable solvent, and preferably heating; and the conversion of a primary amide into a —CN group under standard conditions.

Likewise, any of the aromatic rings of the compounds of the present invention can undergo electrophilic aromatic substitution reactions or nucleophilic aromatic substitution reactions, widely described in the literature.

Some of these interconversion reactions are explained in greater detail in the examples. As it will be obvious to those skilled in the art, these interconversion reactions can be carried out upon the compounds of formula I as well as upon any suitable synthesis intermediate thereof.

Any reference in the synthetic methods described above to a compound of formula I apply likewise to a compound of formula II, IIa, III and IIIa.

KDM1A Inhibitors

The methods, assays and chemoprobes of the invention can be used to determine target engagement of KDM1A inhibitors.

Both irreversible and reversible KDM1A inhibitors have been reported. Irreversible KDM1A inhibitors exert their inhibitory activity by becoming covalently bound to the FAD cofactor within the KDM1A active site and are generally based on a 2-cyclyl-cyclopropylamino moiety such as a 2-(hetero)arylcyclopropylamino moiety.

Reversible inhibitors of KDM1A have also been disclosed.

Non-limiting examples of KDM1A inhibitors are disclosed e.g. in: WO2010/043721, WO2010/084160, WO2011/035941, WO2011/042217, WO2011/131697, WO2012/013727, WO2012/013728, WO2012/045883, WO2013/057320, WO2013/057322, WO2010/143582, US2010-0324147, WO2011/022489, WO2011/131576, WO2012/034116, WO2012/135113, WO2013/022047, WO2013/025805, WO2014/058071, WO2014/084298, WO2014/086790, WO2014/164867, WO2014/205213, WO2015/021128, WO2015/031564, US2015-0065434, WO2007/021839, WO2008/127734, WO2015/089192, CN104119280, CN103961340, CN103893163, CN103319466, CN103054869, WO2015/123408, WO2015/123424, WO2015/123437, WO2015/123465, WO2015/156417, WO2015/181380, WO2016/123387, WO2016/130952, WO2016/172496, WO2016/177656, WO2017/027678, CN106045862, WO2012/071469, WO2013/033688, WO2014/085613, WO2015/120281, WO2015/134973, WO2015/168466, WO2015/200843, WO2016/003917, WO2016/004105, WO2016/007722, WO2016/007727, WO2016/007731, WO2016/007736, WO2016/034946, WO2016/037005, WO2016/161282, and WO2017/004519 K Taeko et al, Bioorg Med Chem Lett 2015, 25(9):1925-8. doi: 10.1016/j.bmcl.2015.03.030. Epub 2015 Mar. 20, PMID: 25827526; S Valente et al, Eur J Med Chem. 2015, 94:163-74. doi: 10.1016/j.ejmech.2015.02.060. Epub 2015 Mar. 3, PMID:25768700; MN Ahmed Khan et al Med. Chem. Commun., 2015, 6, 407-412, DOI: 10.1039/C$_4$MD00330F epub 29 Sep. 2014; M Pieroni et al, Eur J Med Chem. 2015; 92:377-386. doi: 10.1016/j.ejmech.2014.12.032. Epub 2015 Jan. 7. PMID:25585008; V Rodriguez et al, Med. Chem. Commun., 2015, 6, 665-670 DOI: 10.1039/C$_4$MD00507D, Epub 23 Dec. 2014; P Vianello et al, Eur J Med Chem. 2014, 86:352-63. doi: 10.1016/j.ejmech.2014.08.068. Epub 2014 Aug. 27; DP Mould et al, Med. Res. Rev., 2015, 35:586-618. doi: 10.1002/med.21334, epub 24 Nov. 2014; LY Ma et al, 2015, 58(4):1705-16. doi: 10.1021/acs.jmedchem.5b00037. Epub 2015 Feb. 6; S L Nowotarski et al, 2015, 23(7):1601-12. doi: 10.1016/j.bmc.2015.01.049. Epub 2015 Feb. 7. PMID: 25725609; C J Kutz et al Medchemcomm. 2014, 5(12): 1863-1870 PMID: 25580204; C Zhou et al, Chemical Biology & Drug Design, 2015, 85(6):659-671. doi:10.1111/cbdd.12461, epub 22 Dec. 2014; P Prusevich et al, ACS Chem Biol. 2014, 9(6):1284-93. doi: 10.1021/cb500018s. Epub 2014 Apr. 7; B Dulla et al, Org Biomol Chem 2013, 11, 3103-3107, doi: 10.1039/c3ob40217g; J R Hitchin et al, Med Chem Commun, 2013, 4, 1513-1522 DOI: 10.1039/c3md00226h; and Y Zhou et al, Biorg Med Chem Lett, 2015, online publication 20 Jun. 2015, doi:10.1016/j.bmcl.2015.06.054.

Irreversible KDM1A inhibitors (which are nonpeptidic) that can be studied using the chemoprobes and methods of the invention include, without limitation, the compounds disclosed in: WO2010/043721, WO2010/084160, WO2011/035941, WO2011/042217, WO2011/131697, WO2012/013727, WO2012/013728, WO2012/045883, WO2013/057320, WO2013/057322, WO2010/143582, US2010-0324147, WO2011/131576, WO2012/135113, WO2013/022047, WO2014/058071, WO2014/084298, WO2014/086790, WO2014/164867, WO2015/021128; WO2015/123408, WO2015/123424, WO2015/123437, WO2015/123465, WO2015/156417, WO2015/181380, WO2016/123387, WO2016/130952, WO2016/172496, WO2016/177656, WO2017/027678, CN106045862, K Taeko et al, Bioorg Med Chem Lett. 2015, 25(9):1925-8. doi: 10.1016/j.bmcl.2015.03.030. Epub 2015 Mar. 20, PMID: 25827526; S Valente et al, Eur J Med Chem. 2015, 94:163-74. doi: 10.1016/j.ejmech.2015.02.060. Epub 2015 Mar. 3, PMID: 25768700; MN Ahmed Khan et al Med. Chem. Commun., 2015, 6, 407-412, DOI: 10.1039/C$_4$MD00330F epub 29 Sep. 2014; M Pieroni et al, Eur J Med Chem. 2015; 92:377-386. doi: 10.1016/j.ejmech.2014.12.032. Epub 2015 Jan. 7. PMID:25585008; V Rodriguez et al, Med. Chem. Commun., 2015, 6, 665-670 DOI: 10.1039/C$_4$MD00507D, Epub 23 Dec. 2014; P Vianello et al, Eur J Med Chem. 2014, 86:352-63. doi: 10.1016/j.ejmech.2014.08.068. Epub 2014 Aug. 27.

Reversible KDM1A inhibitors (which are nonpeptidic) that can be studied using the chemoprobes and methods of the invention include, without limitation, the compounds disclosed in WO2007/021839, WO2008/127734, WO2011/022489, WO2012/034116, WO2012/071469, WO2013/025805, US2015/0065434, WO2013/033688, CN103054869, CN103319466, WO2014/085613, CN103893163A, CN103961340, WO2014/205213, WO2015/031564, WO2015/089192, WO2015/120281, WO2015/134973, WO2015/168466, WO2015/200843, WO2016/003917, WO2016/004105, WO2016/007722, WO2016/007727, WO2016/007731, WO2016/007736, WO2016/034946, WO2016/037005, WO2016/161282, and WO2017/004519.

In the methods and uses according to the invention, the KDM1A inhibitor is preferably an irreversible KDM1A inhibitor, preferably a 2-(hetero)arylcyclopropylamino KDM1A inhibitor. As used herein, a "2-(hetero)arylcyclopropylamino KDM1A inhibitor" or a "2-(hetero)arylcyclopropylamino compound" means a KDM1A inhibitor whose chemical structure comprises a cyclopropyl ring substituted at position 1 with an amino group, which is optionally substituted, and substituted at position 2 with an aryl or heteroaryl group (wherein the aryl or heteroaryl group is optionally substituted).

The ability of a compound to inhibit KDM1A can be tested in vitro using any method to determine KDM1A inhibition known in the art, for example the method disclosed in Example 2.

In the methods and uses according to the invention, the KDM1A inhibitor can be a compound of formula (A) or an enantiomer, a diastereomer or a mixture of stereoisomers (such as a racemic mixture or a diastereomer mixture) thereof, or a pharmaceutically acceptable salt or solvate thereof:

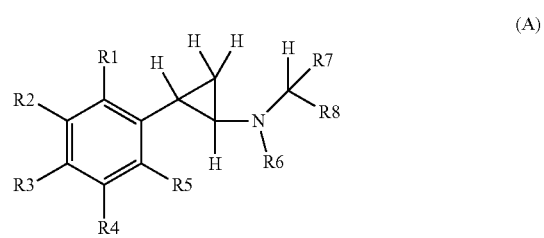

(A)

In formula (I), each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocycle, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;
R7 is chosen from —H, alkyl, and cycloalkyl;
R8 is chosen from —C(=O)NR$_x$R$_y$ and —C(=O)R$_z$;
R$_x$ when present is chosen from —H, alkyl, alkynyl, alkenyl, -L-carbocycle, -L-aryl, -L-heterocyclyl, all of which are optionally substituted;
R$_y$ when present is chosen from —H, alkyl, alkynyl, alkenyl, -L-carbocycle, -L-aryl, -L-heterocyclyl, all of which are optionally substituted;
R$_z$ when present is chosen from —H, alkoxy, -L-carbocyclic, -L-heterocyclic, -L-aryl, wherein the aryl, heterocyclyl, or carbocycle is optionally substituted;
each L can be saturated, partially saturated, or unsaturated, and is independently chosen from —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)NH(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$O(CH$_2$)$_n$—, —(CH$_2$)$_n$S(CH$_2$)$_n$—, and —(CH$_2$)$_n$NHC(=S)NH(CH$_2$)$_n$—, where each n is independently chosen from 0, 1, 2, 3, 4, 5, 6, 7, and 8, wherein optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

Compounds of formula (A) having a (trans) disposition on the substituents on the cyclopropyl ring are preferred.

Preferably, the compound of formula (A) is a compound from the list below:

N-cyclopropyl-2-{[(trans)-2-phenylcyclopropyl]amino}acetamide;
2-{[(trans)-2-phenylcyclopropyl]amino}acetamide;
N-cyclopropyl-2-{[(trans)-2-phenylcyclopropyl]amino}propanamide;
2-{[(trans)-2-phenylcyclopropyl]amino}-N-prop-2-ynylacetamide;
N-isopropyl-2-{[(trans)-2-phenylcyclopropyl]amino}acetamide;
N-(tert-butyl)-2-{[(trans)-2-phenylcyclopropyl]amino}acetamide;
N-(2-morpholin-4-yl-2-oxoethyl)-N-[(trans)-2-phenylcyclopropyl]amine;
2-{[(trans)-2-phenylcyclopropyl]amino}propanamide;
Methyl 2-{[(trans)-2-phenylcyclopropyl]amino}propanoate;
N-cyclopropyl-2-{methyl[(trans)-2-phenylcyclopropyl]amino}acetamide;
2-{methyl[(trans)-2-phenylcyclopropyl]amino}acetamide;
N-methyl-trans-2-(Phenylcyclopropylamino)propanamide;
1-(4-methylpiperazin-1-yl)-2-((trans)-2-phenylcyclopropylamino)ethanone;
1-(4-ethylpiperazin-1-yl)-2-((trans)-2-phenylcyclopropylamino)ethanone;
1-(4-benzylpiperazin-1-yl)-2-((trans)-2-phenylcyclopropylamino)ethanone;
2-((trans)-2-phenylcyclopropylamino)-1-(4-phenylpiperazin-1-yl)ethanone;
2-((trans)-2-(4-(benzyloxy)phenyl)cyclopropylamino)-1-(4-methylpiperazin-1-yl)ethanone;
2-((trans)-2-(4-(benzyloxy)phenyl)cyclopropylamino)-N-cyclopropylacetamide;
2-((trans)-2-(4-(3-fluorobenzyloxy)phenyl)cyclopropylamino)-1-(4-methylpiperazin-1-yl)ethanone;
2-((trans)-2-(4-(3-chlorobenzyloxy)phenyl)cyclopropylamino)-1-(4-methylpiperazin-1-yl)ethanone;
2-((trans)-2-(biphenyl-4-yl)cyclopropylamino)-1-(4-methylpiperazin-1-yl)ethanone;
1-(4-methylpiperazin-1-yl)-2-((trans)-2-(4-phenethoxyphenyl)cyclopropylamino)ethanone;
2-((trans)-2-(4-(4-fluorobenzyloxy)phenyl)cyclopropylamino)-1-(4-methylpiperazin-1-yl)ethanone;
2-((trans)-2-(4-(biphenyl-4-ylmethoxy)phenyl)cyclopropylamino)-1-(4-methylpiperazin-1-yl)ethanone;
2-({(trans)-2-[4-(benzyloxy)phenyl]cyclopropyl}amino)-N-cyclopropylacetamide,
N-[(trans)-2-(4-benzyloxyphenyl)cyclopropyl]}-N-[2-(4-methylpiperazin-1-yl)-2-oxoethyl]amine,
N-[2-oxo-2-(4-phenylpiperazin-1-yl)ethyl]-N-[(trans)-2-phenylcyclopropyl]amine,
N-[2-(4-benzylpiperazin-1-yl)-2-oxoethyl]-N-[(trans)-2-phenylcyclopropyl]amine,
N-[2-(4-ethylpiperazin-1-yl)-2-oxoethyl]-N-[(trans)-2-phenylcyclopropyl]amine,
N-[2-(4-methylpiperazin-1-yl)-2-oxoethyl]-N-[(trans)-2-phenylcyclopropyl]amine,
2-((trans)-2-(4-pyridin-3-ylphenyl) cyclopropylamino)-1-(4-methylpiperazin-1-yl)ethanone, and
2-((trans)-2-(3'-methoxy-1,1'-biphenyl-4-yl) cyclopropylamino)-1-(4-methylpiperazin-1-yl)ethanone,
and pharmaceutically acceptable salts thereof.

Compounds of formula (A) can be prepared by the methods disclosed in WO2010/043721, the disclosure of which is incorporated by reference herein in its entirety.

In the methods and uses according to the invention, the KDM1A inhibitor can be a compound of formula (B) or an enantiomer, a diastereomer or a mixture of stereoisomers (such as a racemic mixture or a diastereomer mixture) thereof, or a pharmaceutically acceptable salt or solvate thereof:

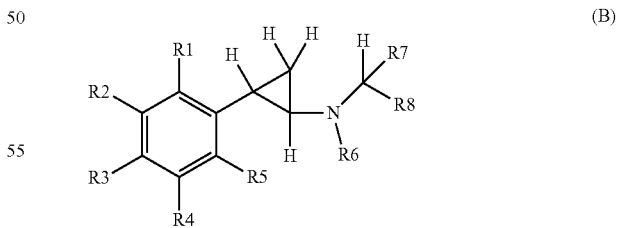

(B)

In formula (B), each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;

R7 is chosen from —H, alkyl, and cycloalkyl;

R8 is a -L-heterocyclyl wherein the ring or ring system of said -L-heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido; or R8 is -L-aryl wherein the ring or ring system of said -L-aryl has from 1-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

each L is independently chosen from $—(CH_2)_n—(CH_2)_n—$, $—(CH_2)_nNH(CH_2)_n—$, $—(CH_2)_nO(CH_2)_n—$, and $—(CH_2)_nS(CH_2)_n—$, and where each n is independently chosen from 0, 1, 2, and 3.

Compounds of formula (B) having a (trans) disposition on the substituents on the cyclopropyl ring are preferred.

Preferably the compound of formula (B) is a compound from the list below:

(trans)-N-(4-fluorobenzyl)-2-phenylcyclopropanamine;
(trans)-N-(4-fluorobenzyl)-2-phenylcyclopropanaminium;
4-(((trans)-2-phenylcyclopropylamino)methyl)benzonitrile;
(trans)-N-(4-cyanobenzyl)-2-phenylcyclopropanaminium;
(trans)-2-phenyl-N-(4-(trifluoromethyl)benzyl)cyclopropanamine;
(trans)-2-phenyl-N-(4-(trifluoromethyl)benzyl)cyclopropanaminium;
(trans)-2-phenyl-N-(pyridin-2-ylmethyl)cyclopropanamine;
(trans)-2-phenyl-N-(pyridin-3-ylmethyl)cyclopropanamine;
(trans)-2-phenyl-N-(pyridin-4-ylmethyl)cyclopropanamine;
(trans)-N-((6-methylpyridin-2-yl)methyl)-2-phenylcyclopropanamine;
(trans)-2-phenyl-N-(thiazol-2-ylmethyl)cyclopropanamine;
(trans)-2-phenyl-N-(thiophen-2-ylmethyl)cyclopropanamine;
(trans)-N-((3-bromothiophen-2-yl)methyl)-2-phenylcyclopropanamine;
(trans)-N-((4-bromothiophen-2-yl)methyl)-2-phenylcyclopropanamine;
(trans)-N-(3,4-dichlorobenzyl)-2-phenylcyclopropanamine;
(trans)-N-(3-fluorobenzyl)-2-phenylcyclopropanaminium;
(trans)-N-(2-fluorobenzyl)-2-phenylcyclopropanamine;
(trans)-2-phenyl-N-(quinolin-4-ylmethyl)cyclopropanamine;
(trans)-N-(3-methoxybenzyl)-2-phenylcyclopropanamine;
(trans)-2-phenyl-N-((6-(trifluoromethyl)pyridin-3-yl)methyl)cyclopropanamine;
(trans)-N-((6-chloropyridin-3-yl)methyl)-2-phenylcyclopropanamine;
(trans)-N-((4-methylpyridin-2-yl)methyl)-2-phenylcyclopropanamine;
(trans)-N-((6-methoxypyridin-2-yl)methyl)-2-phenylcyclopropanamine;
2-(((trans)-2-phenylcyclopropylamino)methyl)pyridin-3-ol;
(trans)-N-((6-bromopyridin-2-yl)methyl)-2-phenylcyclopropanamine;
4-(((trans)-2-(4-(benzyloxy)phenyl)cyclopropylamino)methyl)benzonitrile;
(trans)-N-(4-(benzyloxy)benzyl)-2-phenylcyclopropanamine;
(trans)-N-benzyl-2-(4-(benzyloxy)phenyl)cyclopropanamine;
(trans)-2-(4-(benzyloxy)phenyl)-N-(4-methoxybenzyl)cyclopropanamine;
(trans)-2-(4-(benzyloxy)phenyl)-N-(4-fluorobenzyl)cyclopropanamine;
(trans)-2-phenyl-N-(quinolin-2-ylmethyl)cyclopropanamine;
(trans)-2-phenyl-N-((5-(trifluoromethyl)pyridin-2-yl)methyl)cyclopropanamine;
(trans)-N-((3-fluoropyridin-2-yl)methyl)-2-phenylcyclopropanamine;
(trans)-2-phenyl-N-(quinolin-3-ylmethyl)cyclopropanamine;
(trans)-N-((6-methoxypyridin-3-yl)methyl)-2-phenylcyclopropanamine;
(trans)-N-((5-methoxypyridin-3-yl)methyl)-2-phenylcyclopropanamine;
(trans)-N-((2-methoxypyridin-3-yl)methyl)-2-phenylcyclopropanamine;
(trans)-N-((3H-indol-3-yl)methyl)-2-phenylcyclopropanamine;
3-(((trans)-2-phenylcyclopropylamino)methyl)benzonitrile;
(trans)-N-(2-methoxybenzyl)-2-phenylcyclopropanamine;
3-(((trans)-2-phenylcyclopropylamino)methyl)pyridin-2-amine;
(trans)-N-((2-chloropyridin-3-yl)methyl)-2-phenylcyclopropanamine;
(trans)-N-(3,4-dimethoxybenzyl)-2-phenylcyclopropanamine;
(trans)-N-((2,3-dihydrobenzofuran-5-yl)methyl)-2-phenylcyclopropanamine;
(trans)-N-(benzo[d][1,3]dioxol-5-ylmethyl)-2-phenylcyclopropanamine;
(trans)-N-((2,3-dihydrobenzo[b][1,4]dioxin-6-yl)methyl)-2-phenylcyclopropanamine;
(trans)-N-(2,6-difluoro-4-methoxybenzyl)-2-phenylcyclopropanamine;
(trans)-2-phenyl-N-(4-(trifluoromethoxy)benzyl)cyclopropanamine;
(trans)-N-(5-fluoro-2-methoxybenzyl)-2-phenylcyclopropanamine;
(trans)-N-(2-fluoro-4-methoxybenzyl)-2-phenylcyclopropanamine;
(trans)-N-((4-methoxynaphthalen-1-yl)methyl)-2-phenylcyclopropanamine;
(trans)-N-(2-fluoro-6-methoxybenzyl)-2-phenylcyclopropanamine;
(trans)-N-((2-methoxynaphthalen-1-yl)methyl)-2-phenylcyclopropanamine;
(trans)-N-((4,7-dimethoxynaphthalen-1-yl)methyl)-2-phenylcyclopropanamine;
(trans)-N-(4-methoxy-3-methylbenzyl)-2-phenylcyclopropanamine;
(trans)-N-(3-chloro-4-methoxybenzyl)-2-phenylcyclopropanamine;

(trans)-N-(3-fluoro-4-methoxybenzyl)-2-phenylcyclopropanamine;
(trans)-N-(4-methoxy-2-methylbenzyl)-2-phenylcyclopropanamine;
(trans)-N-((3,4-dihydro-2H-benzo[b][1,4]dioxepin-6-yl)methyl)-2-phenylcyclopropanamine;
(trans)-N-((3,4-dihydro-2H-benzo[b][1,4]dioxepin-7-yl)methyl)-2-phenylcyclopropanamine;
(trans)-N-((2,2-dimethylchroman-6-yl)methyl)-2-phenylcyclopropanamine;
(trans)-N-(4-methoxy-2,3-dimethylbenzyl)-2-phenylcyclopropanamine;
(trans)-N-(4-methoxy-2,5-dimethylbenzyl)-2-phenylcyclopropanamine;
(trans)-N-(2-fluoro-4,5-dimethoxybenzyl)-2-phenylcyclopropanamine;
(trans)-N-(3-chloro-4,5-dimethoxybenzyl)-2-phenylcyclopropanamine;
(trans)-N-(2-chloro-3,4-dimethoxybenzyl)-2-phenylcyclopropanamine;
(trans)-N-(2,4-dimethoxy-6-methylbenzyl)-2-phenylcyclopropanamine;
(trans)-N-(2,5-dimethoxybenzyl)-2-phenylcyclopropanamine;
(trans)-N-(2,3-dimethoxybenzyl)-2-phenylcyclopropanamine;
(trans)-N-(2-chloro-3-methoxybenzyl)-2-phenylcyclopropanamine;
(trans)-N-((1H-indol-5-yl)methyl)-2-phenylcyclopropanamine;
(trans)-2-(4-(benzyloxy)phenyl)-N-(pyridin-2-ylmethyl)cyclopropanamine;
(trans)-2-(4-(benzyloxy)phenyl)-N-(2-methoxybenzyl)cyclopropanamine;
(trans)-N-(1-(4-methoxyphenyl)ethyl)-2-phenylcyclopropanamine;
(trans)-N-(1-(3,4-dimethoxyphenyl)ethyl)-2-phenylcyclopropanamine;
(trans)-N-(1-(2,3-dihydrobenzo[b][1,4]dioxin-6-yl)ethyl)-2-phenylcyclopropanamine;
(trans)-N-(1-(5-fluoro-2-methoxyphenyl)ethyl)-2-phenylcyclopropanamine;
(trans)-N-(1-(3,4-dimethoxyphenyl)propan-2-yl)-2-phenylcyclopropanamine;
(trans)-N-((3-methyl-1,2,4-oxadiazol-5-yl)methyl)-2-phenylcyclopropanamine; and
pharmaceutically acceptable salts thereof.

Compounds of formula (B) can be prepared by the methods disclosed in WO2010/084160, the disclosure of which is incorporated by reference herein in its entirety.

In the methods and uses according to the invention, the KDM1A inhibitor can be a compound of formula (C) or an enantiomer, a diastereomer or a mixture of stereoisomers (such as a racemic mixture or a diastereomer mixture) thereof, or a pharmaceutically acceptable salt or solvate thereof:

  (C)

In formula (C), (A) is heteroaryl or aryl;
each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, amido, and sulfinyl;
X is 0, 1, 2, or 3;

(B) is a cyclopropyl ring, wherein (A) and (Z) are covalently bonded to different carbon atoms of (B); (Z) is —NH—;
(L) is chosen from —CH$_2$CH$_2$—, —CH$_2$CH$_2$CH$_2$—, and —CH$_2$CH$_2$CH$_2$CH$_2$—; and
(D) is chosen from —N(—R1)-R2, —O—R3, and —S—R3, wherein:
R1 and R2 are mutually linked to form a heterocyclic ring together with the nitrogen atom that R1 and R2 are attached to, wherein said heterocyclic ring has 0, 1, 2, or 3 substituents independently chosen from —NH$_2$, —NH(C$_1$-C$_6$alkyl), —N(C$_1$-C$_6$ alkyl)(C$_1$-C$_6$ alkyl), alkyl, halo, cyano, alkoxy, haloalkyl, and haloalkoxy, or
R1 and R2 are independently chosen from —H, alkyl, cycloalkyl, haloalkyl, and heterocyclyl, wherein the sum of substituents on R1 and R2 together is 0, 1, 2, or 3, and the substituents are independently chosen from —NH$_2$, —NH(C$_1$-C$_6$ alkyl), —N(C$_1$-C$_6$ alkyl)(C$_1$-C$_6$ alkyl), and fluoro; and
R3 is chosen from —H, alkyl, cycloalkyl, haloalkyl, and heterocyclyl, wherein R3 has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), and fluoro.

Compounds of formula (C) having a (trans) disposition on the substituents on the cyclopropyl ring are preferred.

Preferably the compound of formula (C) is a compound from the list below:
N-[2-(4-methylpiperazin-1-yl)ethyl]-N-[(trans)-2-phenylcyclopropyl]amine;
N-cyclopropyl-N'-[(trans)-2-phenylcyclopropyl]ethane-1,2-diamine;
N,N-dimethyl-N'-(2-{[(trans)-2-phenylcyclopropyl]amino}ethyl)ethane-1,2-diamine;
(3R)-1-(2-{[(trans)-2-phenylcyclopropyl]amino}ethyl)pyrrolidin-3-amine;
(3S)—N,N-dimethyl-1-(2-{[(trans)-2-phenylcyclopropyl]amino}ethyl) pyrrolidin-3-amine;
(3R)—N,N-dimethyl-1-(2-{[(trans)-2-phenylcyclopropyl]amino}ethyl)pyrrolidin-3-amine;
N-[(trans)-2-phenylcyclopropyl]-N-(2-piperazin-1-ylethyl)amine;
N1,N1-diethyl-N2-((trans)-2-phenylcyclopropyl)ethane-1,2-diamine;
N-[(trans)-2-phenylcyclopropyl]-N-(2-piperidin-1-ylethyl)amine;
(trans)-2-(4-(benzyloxy)phenyl)-N-(2-(4-methylpiperazin-1-yl)ethyl) cyclopropanamine;
(trans)-N-(2-(4-methylpiperazin-1-yl)ethyl)-2-(3'-(trifluoromethyl) biphenyl-4-yl)cyclopropanamine;
(trans)-2-(3'-chlorobiphenyl-4-yl)-N-(2-(4-methylpiperazin-1-yl)ethyl) cyclopropanamine;
(R)-1-(2-((trans)-2-(3'-(trifluoromethyl)biphenyl-4-yl)cyclopropylamino)ethyl)pyrrolidin-3-amine; and
N$^1$-cyclopropyl-N$^2$-((trans)-2-(3'-(trifluoromethyl)biphenyl-4-yl) cyclopropyl)ethane-1,2-diamine;
N1-((trans)-2-(4-(3-bromobenzyloxy)phenyl)cyclopropyl)-N2-cyclopropylethane-1,2-diamine;
N1-((trans)-2-(3'-chlorobiphenyl-4-yl)cyclopropyl)-N2-cyclopropylethane-1,2-diamine;
N1-cyclopropyl-N2-((trans)-2-(4-phenethoxyphenyl)cyclopropyl)ethane-1,2-diamine;

N1,N1-diethyl-N2-((trans)-2-(4-(3-fluorobenzyloxy)phenyl)cyclopropyl)ethane-1,2-diamine;
(trans)-2-(4-bromophenyl)-N-(2-(4-methylpiperazin-1-yl)ethyl)cyclopropanamine;
N1-((trans)-2-(terphenyl-4-yl)cyclopropyl)-N2-cyclopropylethane-1,2-diamine;
(trans)-N-(2-(piperidin-1-yl)ethyl)-2-(3'-(trifluoromethyl)biphenyl-4-yl)cyclopropanamine;
N1,N1-diethyl-N2-((trans)-2-(3'-(trifluoromethyl)biphenyl-4-yl)cyclopropyl)ethane-1,2-diamine;
(trans)-N-(2-(piperazin-1-yl)ethyl)-2-(3'-(trifluoromethyl)biphenyl-4-yl)cyclopropanamine;
(S)-1-(2-((trans)-2-(3'-(trifluoromethyl)biphenyl-4-yl)cyclopropylamino)ethyl)pyrrolidin-3-amine;
(R)-1-(2-((trans)-2-(3'-chlorobiphenyl-4-yl)cyclopropylamino)ethyl)pyrrolidin-3-amine;
(R)-1-(2-((trans)-2-(4'-chlorobiphenyl-4-yl)cyclopropylamino)ethyl)pyrrolidin-3-amine;
(R)-1-(2-((trans)-2-(3'-methoxybiphenyl-4-yl)cyclopropylamino)ethyl)pyrrolidin-3-amine;
(R)-1-(2-((trans)-2-(4-(3-bromobenzyloxy)phenyl)cyclopropylamino)ethyl)pyrrolidin-3-amine; and
(R)-1-(2-((trans)-2-(6-(3-(trifluoromethyl)phenyl)pyridin-3-yl)cyclopropylamino)ethyl)pyrrolidin-3-amine;
N-(trans)-2-(isobutylthio)-ethyl-2-phenylcyclopropanamine,
N-trans-(2-ethoxyethyl)-2-phenylcyclopropanamine, and
N-trans-(2-methoxyethyl)-2-phenylcyclopropanamine,
(R)-1-(2-((trans)-2-(4-(4-bromobenzyloxy)phenyl)cyclopropylamino)ethyl)pyrrolidin-3-amine;
(R)-1-(2-((trans)-2-(4-(4-chlorobenzyloxy)phenyl)cyclopropylamino)ethyl)pyrrolidin-3-amine;
(R)-1-(2-((trans)-2-(4-(biphenyl-4-ylmethoxy)phenyl)cyclopropylamino)ethyl)pyrrolidin-3-amine;
(R)-1-(2-((trans)-2-(3',5'-dichlorobiphenyl-4-yl)cyclopropylamino)ethyl)pyrrolidin-3-amine;
N1-((trans)2-(2-[1,1';4',1" ]terphenyl-4"-yl-cyclopropyl)-N2-cyclopropylethane-1,2-diamine;
(R)-1-(2-((trans)-2-(6-(benzyloxy)-4'-(trifluoromethyl)biphenyl-3-yl)cyclopropylamino)ethyl)pyrrolidin-3-amine; and
(R)-1-(2-((trans)-2-(6-(benzyloxy)biphenyl-3-yl)cyclopropylamino)ethyl)pyrrolidin-3-amine;
(R)-1-(2-((trans)-2-(4-phenethoxyphenyl)cyclopropylamino)ethyl)pyrrolidin-3-amine;
(R)-1-(2-((trans)-2-(6-(3-methoxyphenyl)pyridin-3-yl)cyclopropylamino)ethyl)pyrrolidin-3-amine;
(R)-1-(2-((trans)-2-(6-(4-chlorophenyl)pyridin-3-yl)cyclopropylamino)ethyl)pyrrolidin-3-amine; and
4-((4-((trans)-2-(2-((R)-3-aminopyrrolidin-1-yl)ethylamino)cyclopropyl)phenoxy)methyl)benzonitrile;
and pharmaceutically acceptable salts thereof.

Compounds of formula (C) can be prepared by the methods disclosed in WO2011/035941, the disclosure of which is incorporated by reference herein in its entirety.

In the methods and uses according to the invention, the KDM1A inhibitor can be a compound of formula (D) or an enantiomer, a diastereomer or a mixture of stereoisomers (such as a racemic mixture or a diastereomer mixture) thereof, or a pharmaceutically acceptable salt or solvate thereof:

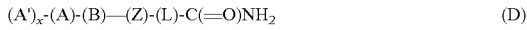

(A')$_x$-(A)-(B)—(Z)-(L)-C(=O)NH$_2$   (D)

In formula (D), (A) is heteroaryl or aryl;
each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2 or 3 substituents independently chosen from halo, haloalkyl, aryl, arylalkoxy, alkyl, alkoxy, cyano, sulfonyl, sulfinyl, and carboxamide;
X is 0, 1, 2, or 3;
(B) is a cyclopropyl ring, wherein (A) and (Z) are covalently bonded to different carbon atoms of (B);
(Z) is —NH—; and
(L) is —(CH$_2$)$_m$CR$_1$R$_2$—, wherein m is 0, 1, 2, 3, 4, 5, or 6, and wherein R$_1$ and R$_2$ are each independently hydrogen or C$_1$-C$_6$ alkyl;
provided that, if (L) is —CH$_2$— or —CH(CH$_3$)—, then X is not 0.

Compounds of formula (D) having a (trans) disposition on the substituents on the cyclopropyl ring are preferred.

Preferably, the compound of formula (D) is a compound from the list below:
2-((trans)-2-(4-(4-cyanobenzyloxy)phenyl)cyclopropylamino)acetamide,
2-((trans)-2-(4-(3-cyanobenzyloxy)phenyl)cyclopropylamino)acetamide,
2-((trans)-2-(4-(benzyloxy)phenyl)cyclopropylamino)acetamide,
2-((trans)-2-(4-(4-fluorobenzyloxy)phenyl)cyclopropylamino)acetamide,
2-((trans)-2-(4-(3-fluorobenzyloxy)phenyl)cyclopropylamino)acetamide,
2-((trans)-2-(4-(3-chlorobenzyloxy)phenyl)cyclopropylamino)acetamide,
2-((trans)-2-(4-(4-chlorobenzyloxy)phenyl)cyclopropylamino)acetamide,
2-((trans)-2-(4-(3-bromobenzyloxy)phenyl)cyclopropylamino)acetamide,
2-((trans)-2-(4-(3,5-difluorobenzyloxy)phenyl)cyclopropylamino)acetamide,
2-((trans)-2-(4-phenethoxyphenyl)cyclopropylamino)acetamide,
2-((trans)-2-(3'-(trifluoromethyl)biphenyl-4-yl)cyclopropylamino)acetamide,
2-((trans)-2-(3'-chlorobiphenyl-4-yl)cyclopropylamino)acetamide,
2-((trans)-2-(6-(4-chlorophenyl)pyridin-3-yl)cyclopropylamino)acetamide,
(R)-2-((trans)-2-(4-(3-fluorobenzyloxy)phenyl)cyclopropylamino)propanamide,
(S)-2-((trans)-2-(4-(4-fluorobenzyloxy)phenyl)cyclopropylamino)propanamide,
(R)-2-((trans)-2-(4-(4-fluorobenzyloxy)phenyl)cyclopropylamino)propanamide,
(S)-2-((trans)-2-(4-(4-fluorobenzyloxy)phenyl)cyclopropylamino)propanamide,
(R)-2-((trans)-2-(4-(benzyloxy)phenyl)cyclopropylamino)propanamide,
(S)-2-((trans)-2-(4-(benzyloxy)phenyl) cyclopropylamino)propanamide,
2-(2-[1,1';4',1"]Terphenyl-4"-yl-cyclopropylamino)acetamide,
5'-((trans)-2-(2-amino-2-oxoethylamino)cyclopropyl)-2'-(benzyloxy)biphenyl-3-carboxamide,
5-((trans)-2-(4'-chlorobiphenyl-4-yl)cyclopropylamino)pentanamide,
3-((trans)-2-(4-(3-bromobenzyloxy)phenyl)cyclopropylamino)propanamide,
4-((trans)-2-phenylcyclopropylamino)butanamide,
5-((trans)-2-phenylcyclopropylamino)pentanamide,
5-((trans)-2-(4'-chlorobiphenyl-4-yl)cyclopropylamino)-2-methylpentanamide, 4-((trans)-2-(4'-chlorobiphenyl-4-yl)cyclopropylamino)-2-methylbutanamide,
3-((trans)-2-(4-(3-fluorobenzyloxy)phenyl)cyclopropylamino)-2,2-dimethylpropanamide,
3-((trans)-2-(4'-chlorobiphenyl-4-yl)cyclopropylamino)propanamide,
4-((trans)-2-(4'-chlorobiphenyl-4-yl)cyclopropylamino)butanamide,
4-((trans)-2-(4-(3-bromobenzyloxy)phenyl)cyclopropylamino)butanamide,
5-((trans)-2-(4-(3-bromobenzyloxy)phenyl)cyclopropylamino)pentanamide,
5-((trans)-2-(6-(benzyloxy)biphenyl-3-yl)cyclopropylamino)pentanamide, and
4-((trans)-2-(6-(benzyloxy)biphenyl-3-yl)cyclopropylamino)butanamide,
and pharmaceutically acceptable salts thereof.

Compounds of formula (D) can be prepared by the methods disclosed in WO2011/042217, the disclosure of which is incorporated by reference herein in its entirety.

In the methods and uses according to the invention, the KDM1A inhibitor can be a compound of formula (E) or an enantiomer, a diastereomer or a mixture of stereoisomers (such as a racemic mixture or a diastereomer mixture) thereof, or a pharmaceutically acceptable salt or solvate thereof:

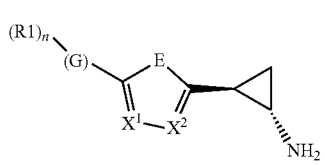

(E)

In formula (E), E is —N(R3)—, —O—, or —S—, or is —$X^3$═$X^4$—;
$X^1$ and $X^2$ are independently C(R2) or N;
$X^3$ and $X_4$, when present, are independently C(R2) or N;
(G) is a cyclyl group;
each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;
each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;
R3 is —H or a ($C_1$-$C_6$)alkyl group;
each L1 is independently alkylene or heteroalkylene; and
n is 0, 1, 2, 3, 4 or 5.

Compounds of formula (E) having a (trans) disposition on the substituents on the cyclopropyl ring are preferred.

Preferably, the compound of formula (E) is a compound from the list below:
(trans)-2-(3'-(trifluoromethyl)biphenyl-4-yl)cyclopropanamine;
(trans)-2-(terphenyl-4-yl)cyclopropanamine;
4'-((trans)-2-aminocyclopropyl)biphenyl-4-ol;
4'-((trans)-2-aminocyclopropyl)biphenyl-3-ol;
(trans)-2-(6-(3-(trifluoromethyl)phenyl)pyridin-3-yl)cyclopropanamine;
(Trans)-2-(6-(3,5-dichlorophenyl)pyridin-3-yl)cyclopropanamine;
(trans)-2-(6-(4-chlorophenyl)pyridin-3-yl)cyclopropanamine;
(trans)-2-(6-(3-chlorophenyl)pyridin-3-yl)cyclopropanamine;
(trans)-2-(6-(4-(trifluoromethyl)phenyl)pyridin-3-yl)cyclopropanamine;
(trans)-2-(6-(4-methoxyphenyl)pyridin-3-yl)cyclopropanamine;
(trans)-2-(6-(3-methoxyphenyl)pyridin-3-yl)cyclopropanamine;
4-(5-((trans)-2-aminocyclopropyl)pyridin-2-yl)benzonitrile;
3-(5-((trans)-2-aminocyclopropyl)pyridin-2-yl)benzonitrile;
(Trans)-2-(6-p-tolylpyridin-3-yl)cyclopropanamine;
(Trans)-2-(6-m-tolylpyridin-3-yl)cyclopropanamine;
4-(5-((trans)-2-aminocyclopropyl)pyridin-2-yl)phenol;
3-(5-((trans)-2-aminocyclopropyl)pyridin-2-yl)phenol;
4-(5-((trans)-2-aminocyclopropyl)pyridin-2-yl)benzamide;
3-(5-((trans)-2-aminocyclopropyl)pyridin-2-yl)benzamide;
2-(5-((trans)-2-aminocyclopropyl)pyridin-2-yl)phenol;
3-(5-((trans)-2-aminocyclopropyl)pyridin-2-yl)phenol;
(Trans)-2-(6-(3-methoxy-4-methylphenyl)pyridin-3-yl)cyclopropanamine;
5-(5-((trans)-2-aminocyclopropyl)pyridin-2-yl)-2-fluorophenol;
3-(5-((trans)-2-aminocyclopropyl)pyridin-2-yl)-5-fluorophenol;
3-(5-((trans)-2-aminocyclopropyl)pyridin-2-yl)-4-fluorophenol;
3-(5-((trans)-2-aminocyclopropyl)pyridin-2-yl)-2-fluorophenol;
3-(5-((trans)-2-aminocyclopropyl)pyridin-2-yl)-2,4-difluorophenol;
3-(5-((trans)-2-aminocyclopropyl)pyridin-2-yl)-2,4,6-trifluorophenol;
3-(5-((trans)-2-aminocyclopropyl)pyridin-2-yl)-5-chlorophenol;
(Trans)-2-(6-(2-fluoro-3-(trifluoromethyl)phenyl)pyridin-3-yl)cyclopropanamine;
(Trans)-2-(6-(5-chlorothiophen-2-yl)pyridin-3-yl)cyclopropanamine;
(Trans)-2-(6-(5-methylthiophen-2-yl)pyridin-3-yl)cyclopropanamine;
(Trans)-2-(6-(1H-indol-6-yl)pyridin-3-yl)cyclopropanamine;
(Trans)-2-(6-(benzo[b]thiophen-5-yl)pyridin-3-yl)cyclopropanamine;
3-(5-((trans)-2-aminocyclopropyl)-3-methylpyridin-2-yl)phenol;
(trans)-2-(6-(3-chlorophenyl)-5-methylpyridin-3-yl)cyclopropanamine;
(trans)-2-(5-methyl-6-(3-(trifluoromethyl)phenyl)pyridin-3-yl)cyclopropanamine;
(trans)-2-(6-(4-fluoro-3-methoxyphenyl)pyridin-3-yl)cyclopropanamine;

(trans)-2-(6-(3-fluoro-5-methoxyphenyl)pyridin-3-yl)cyclopropanamine;
(trans)-2-(6-(2-fluoro-5-methoxyphenyl)pyridin-3-yl)cyclopropanamine;
(trans)-2-(6-(2-fluoro-3-methoxyphenyl)pyridin-3-yl)cyclopropanamine;
(trans)-2-(6-(3-chloro-5-methoxyphenyl)pyridin-3-yl)cyclopropanamine;
(trans)-2-(6-(2-chloro-5-methoxyphenyl)pyridin-3-yl)cyclopropanamine;
(trans)-2-(6-(3-methoxy-5-(trifluoromethyl)phenyl)pyridin-3-yl)cyclopropanamine;
3-(5-((trans)-2-aminocyclopropyl)pyridin-2-yl)-5-methoxybenzonitrile;
5-(5-((trans)-2-aminocyclopropyl)pyridin-2-yl)-2-methylphenol;
3-(5-((trans)-2-aminocyclopropyl)pyridin-2-yl)-4-chlorophenol;
3-(5-((trans)-2-aminocyclopropyl)pyridin-2-yl)-5-(trifluoromethyl)phenol;
(trans)-2-(6-(2-fluoro-5-(trifluoromethyl)phenyl)pyridin-3-yl)cyclopropanamine;
(trans)-2-(6-(2-chloro-5-(trifluoromethyl)phenyl)pyridin-3-yl)cyclopropanamine;
(trans)-2-(6-(3,5-bis(trifluoromethyl)phenyl)pyridin-3-yl)cyclopropanamine;
N-(3-(5-((trans)-2-aminocyclopropyl)pyridin-2-yl)phenyl)acetamide;
N-(3-(5-((trans)-2-aminocyclopropyl)pyridin-2-yl)phenyl)methanesulfonamide;
(trans)-2-(6-(benzo[b]thiophen-2-yl)pyridin-3-yl)cyclopropanamine;
(trans)-2-(6-(benzo[b]thiophen-3-yl)pyridin-3-yl)cyclopropanamine;
5-(5-((trans)-2-aminocyclopropyl)pyridin-2-yl)thiophene-2-carbonitrile;
(trans)-2-(6-(4-methylthiophen-3-yl)pyridin-3-yl)cyclopropanamine;
(trans)-2-(2-chloro-6-(3-(trifluoromethyl)phenyl)pyridin-3-yl)cyclopropanamine;
(trans)-2-(2-(4-chlorophenyl)-6-(3-(trifluoromethyl)phenyl)pyridin-3-yl)cyclopropanamine;
4-(3-((trans)-2-aminocyclopropyl)-6-(3-(trifluoromethyl)phenyl)pyridin-2-yl)phenol;
4-(3-((trans)-2-aminocyclopropyl)-6-(3-(trifluoromethyl)phenyl)pyridin-2-yl)benzamide;
(trans)-2-(2-methyl-6-(3-(trifluoromethyl)phenyl)pyridin-3-yl)cyclopropanamine;
3-(5-((trans)-2-aminocyclopropyl)pyridin-2-yl)-5-hydroxybenzonitrile;
(trans)-2-(6-(3,4-difluoro-5-methoxyphenyl)pyridin-3-yl)cyclopropanamine;
5-(5-((trans)-2-aminocyclopropyl)pyridin-2-yl)-2,3-difluorophenol;
(trans)-2-(6-(3-chloro-4-fluoro-5-methoxyphenyl)pyridin-3-yl)cyclopropanamine;
5-(5-((trans)-2-aminocyclopropyl)pyridin-2-yl)-3-chloro-2-fluorophenol;
(trans)-2-(6-(1H-indazol-6-yl)pyridin-3-yl)cyclopropanamine;
(trans)-2-(6-(9H-carbazol-2-yl)pyridin-3-yl)cyclopropanamine;
6-(5-((trans)-2-aminocyclopropyl)pyridin-2-yl)indolin-2-one;
6-(5-((trans)-2-aminocyclopropyl)pyridin-2-yl)benzofuran-2(3H)-one;
4-(5-((trans)-2-aminocyclopropyl)pyridin-2-yl)pyridin-2(1H)-one;
N-(3-(5-((trans)-2-aminocyclopropyl)pyridin-2-yl)phenyl)benzenesulfonamide;
N-(3-(5-((trans)-2-aminocyclopropyl)pyridin-2-yl)phenyl)propane-2-sulfonamide;
4'-((trans)-2-aminocyclopropyl)-4-fluorobiphenyl-3-ol;
4'-((trans)-2-aminocyclopropyl)-5-chlorobiphenyl-3-ol;
4'-((trans)-2-aminocyclopropyl)-5-chloro-4-fluorobiphenyl-3-ol;
N-(4'-((trans)-2-aminocyclopropyl)biphenyl-3-yl)benzenesulfonamide;
N-(4'-((trans)-2-aminocyclopropyl)biphenyl-3-yl)propane-2-sulfonamide;
N-(4'-((trans)-2-aminocyclopropyl)biphenyl-3-yl)methanesulfonamide;
N-(2-(5-((trans)-2-aminocyclopropyl)pyridin-2-yl)phenyl)methanesulfonamide;
3-(5-((trans)-2-aminocyclopropyl)pyridin-2-yl)-4-methoxybenzonitrile;
N-(4'-((trans)-2-aminocyclopropyl)biphenyl-2-yl)methanesulfonamide;
4'-((trans)-2-aminocyclopropyl)-6-methoxybiphenyl-3-carbonitrile;
N-(4'-((trans)-2-aminocyclopropyl)-6-methoxybiphenyl-3-yl)methanesulfonamide;
4'-((trans)-2-aminocyclopropyl)-6-hydroxybiphenyl-3-carbonitrile;
N-(4'-((trans)-2-aminocyclopropyl)-6-hydroxybiphenyl-3-yl)methanesulfonamide;
3-(5-((trans)-2-aminocyclopropyl)pyridin-2-yl)-4-hydroxybenzonitrile;
N-(3-(5-((trans)-2-aminocyclopropyl)pyridin-2-yl)-4-hydroxyphenyl)methanesulfonamide;
N-(3-(5-((trans)-2-aminocyclopropyl)pyridin-2-yl)-5-(trifluoromethyl)phenyl)ethanesulfonamide;
N-(3-(5-((trans)-2-aminocyclopropyl)pyridin-2-yl)-5-(trifluoromethyl)phenyl)methanesulfonamide;
3-(6-((trans)-2-aminocyclopropyl)pyridin-3-yl)phenol;
(Trans)-2-(5-(3-methoxyphenyl)pyridin-2-yl)cyclopropanamine;
4-(6-((trans)-2-aminocyclopropyl)pyridin-3-yl)phenol;
2-(6-((trans)-2-aminocyclopropyl)pyridin-3-yl)phenol;
2-(5-((trans)-2-aminocyclopropyl)thiophen-2-yl)phenol;
3-(5-((trans)-2-aminocyclopropyl)thiophen-2-yl)phenol;
4-(5-((trans)-2-aminocyclopropyl)thiophen-2-yl)phenol;
2-(5-((trans)-2-aminocyclopropyl)thiazol-2-yl)phenol;
3-(5-((trans)-2-aminocyclopropyl)thiazol-2-yl)phenol;
4-(5-((trans)-2-aminocyclopropyl)thiazol-2-yl)phenol;
2-(2-((trans)-2-aminocyclopropyl)thiazol-5-yl)phenol;
3-(2-((trans)-2-aminocyclopropyl)thiazol-5-yl)phenol;
2-(2-((trans)-2-aminocyclopropyl)thiazol-5-yl)phenol;
3-(2-((trans)-2-aminocyclopropyl)thiazol-5-yl)phenol;
3-(5-((trans)-2-aminocyclopropyl)pyrimidin-2-yl)phenol;
4-(5-((trans)-2-aminocyclopropyl)pyrimidin-2-yl)phenol;
N-(3-(5-((trans)-2-aminocyclopropyl)pyridin-2-yl)-4-methoxyphenyl)methanesulfonamide;
N-(4'-((trans)-2-aminocyclopropyl)-5-chloro-[1,1'-biphenyl]-3-yl)methanesulfonamide;
N-(3-(5-((trans)-2-aminocyclopropyl)pyridin-2-yl)-5-chlorophenyl)methanesulfonamide;
N-(4'-((trans)-2-aminocyclopropyl)-4-fluoro-[1,1'-biphenyl]-3-yl)methanesulfonamide;
N-(5-(5-((trans)-2-aminocyclopropyl)pyridin-2-yl)-2-fluorophenyl)methanesulfonamide;
N-(3-(5-((trans)-2-aminocyclopropyl)pyridin-2-yl)phenyl)ethanesulfonamide;

N-(3-(5-((trans)-2-aminocyclopropyl)pyridin-2-yl)phenyl)-4-cyanobenzenesulfonamide;
N-(3-(5-((trans)-2-aminocyclopropyl)pyridin-2-yl)phenyl)-3-cyanobenzenesulfonamide;
N-(3-(5-((trans)-2-aminocyclopropyl)pyridin-2-yl)phenyl)-2-cyanobenzenesulfonamide;
N-(3-(5-((trans)-2-aminocyclopropyl)pyridin-2-yl)-5-(trifluoromethyl)phenyl)-4-cyanobenzenesulfonamide
N-(4'-((trans)-2-aminocyclopropyl)-[1,1'-biphenyl]-3-yl)-1,1,1-trifluoromethanesulfonamide;
4'-((trans)-2-aminocyclopropyl)-6-hydroxy-[1,1'-biphenyl]-3-carbonitrile;
4'-((trans)-2-aminocyclopropyl)-[1,1'-biphenyl]-2-ol;
4'-((trans)-2-aminocyclopropyl)-3'-methoxy-[1,1'-biphenyl]-3-ol;
N-(3-(5-((trans)-2-aminocyclopropyl)thiazol-2-yl)phenyl)-2-cyanobenzenesulfonamide;
and pharmaceutically acceptable salts thereof.

Compounds of formula (E) can be prepared by the methods disclosed in WO2012/013727, the disclosure of which is incorporated by reference herein in its entirety.

In the methods and uses according to the invention, the KDM1A inhibitor can be a compound of formula (F) or an enantiomer, a diastereomer or a mixture of stereoisomers (such as a racemic mixture or a diastereomer mixture) thereof, or a pharmaceutically acceptable salt or solvate thereof:

$(A')_x-(A)-(B)-(Z)-(L)-(D)$  (F)

In formula (F), (A) is heteroaryl or aryl;
each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;
X is 0, 1, 2, or 3;
(B) is a cyclopropyl ring, wherein (A) and (Z) are covalently bonded to different carbon atoms of (B); (Z) is —NH—;
(L) is chosen from a single bond, —CH$_2$—, —CH$_2$CH$_2$—, —CH$_2$CH$_2$CH$_2$—, and —CH$_2$CH$_2$CH$_2$CH$_2$—; and
(D) is an aliphatic carbocyclic group or benzocycloalkyl, wherein said aliphatic carbocyclic group or said benzocycloalkyl has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy.

Preferably in formula (VI),
(A) is aryl or heteroaryl. Said aryl is preferably phenyl. Said heteroaryl is preferably pyridinyl, pyrimidinyl, or thiophenyl; and/or
(A'), if present, is aryl or arylalkoxy. Said aryl is preferably phenyl. Said arylalkoxy is preferably benzyloxy, all of which can be optionally substituted as provided above; and/or
(L) is a single bond.

Compounds of formula (F) having a (trans) disposition on the substituents on the cyclopropyl ring are preferred.

Preferably, the compound of formula (F) is a compound from the list below:
N-((trans)-2-(4-(benzyloxy)phenyl)cyclopropyl)-6-methoxy-2,3-dihydro-1H-inden-1-amine;
N-((trans)-2-(4-(benzyloxy)phenyl)cyclopropyl)-5,6-dimethoxy-2,3-dihydro-1H-inden-1-amine;
N-((trans)-2-(4-(benzyloxy)phenyl)cyclopropyl)-4,5-dimethoxy-2,3-dihydro-1H-inden-1-amine;
N-((trans)-2-phenylcyclopropyl)-2,3-dihydro-1H-inden-1-amine;
6-methoxy-N-((trans)-2-phenylcyclopropyl)-2,3-dihydro-1H-inden-1-amine;
6-chloro-N-((trans)-2-phenylcyclopropyl)-2,3-dihydro-1H-inden-1-amine;
N-((trans)-2-phenylcyclopropyl)-6-(trifluoromethyl)-2,3-dihydro-1H-inden-1-amine;
7-methoxy-N-((trans)-2-phenylcyclopropyl)-1,2,3,4-tetrahydronaphthalen-1-amine;
N-((trans)-2-(3'-chlorobiphenyl-4-yl)cyclopropyl)-6-methoxy-2,3-dihydro-1H-inden-1-amine;
N-((trans)-2-(4'-chlorobiphenyl-4-yl)cyclopropyl)-6-methoxy-2,3-dihydro-1H-inden-1-amine;
6-methoxy-N-((trans)-2-(3'-methoxybiphenyl-4-yl)cyclopropyl)-2,3-dihydro-1H-inden-1-amine;
N-trans-(2-cyclohexylethyl)-2-phenylcyclopropanamine;
(Trans)-N-(3-cyclohexylpropyl)-2-phenylcyclopropanamine;
(Trans)-N-(2-cycloheptylethyl)-2-phenylcyclopropanamine;
(Trans)-2-(4-(3-bromobenzyloxy)phenyl)-N-(2-cyclohexylethyl) cyclopropanamine;
N-((trans)-2-(4-(3-bromobenzyloxy)phenyl)cyclopropyl)-6-methoxy-2,3-dihydro-1H-inden-1-amine;
(Trans)-2-(3'-chlorobiphenyl-4-yl)-N-(2-cyclohexylethyl) cyclopropanamine;
(Trans)-2-(4'-chlorobiphenyl-4-yl)-N-(2-cyclohexylethyl) cyclopropanamine;
(Trans)-N-(2-cyclohexylethyl)-2-(3'-methoxybiphenyl-4-yl) cyclopropanamine;
N-((trans)-2-(4-(benzyloxy)phenyl)cyclopropyl)-7-methoxy-1,2,3,4-tetrahydronaphthalen-1-amine; and
1-((trans)-2-(4-(benzyloxy)phenyl)cyclopropylamino)cyclopropanecarboxamide;
and pharmaceutically acceptable salts thereof.

Compounds of formula (F) can be prepared by the methods disclosed in WO2011/131697, the disclosure of which is incorporated by reference herein in its entirety.

In the methods and uses according to the invention, the KDM1A inhibitor can be a compound of formula (G) or an enantiomer, a diastereomer or a mixture of stereoisomers (such as a racemic mixture or a diastereomer mixture) thereof, or a pharmaceutically acceptable salt or solvate thereof:

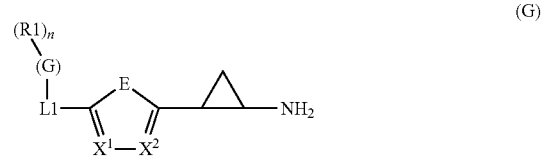

In formula (G), E is —X$^3$=X$^4$—,—N(R3)-, —S—, or —O—;
X$^1$ and X$^2$ are each independently C(R2) or N;
X$^3$ and X$^4$, when present, are each independently C(R2) or N;
L1 is —NH— or —NH—CH$_2$—;
G is a cyclyl group;

each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each R2 group has 1, 2, or 3 independently chosen optional substituents, and further wherein two R2 groups bound to adjacent carbon atoms can be taken together to form a heterocyclyl or aryl group having 1, 2, or 3 independently chosen optional substituents; wherein said optional substituents are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate;

R3 is —H or an ($C_1$-$C_6$)alkyl group;

each L2 is independently chosen from alkylene or heteroalkylene; and n is 0, 1, 2, 3, 4 or 5.

Compounds of formula (G) having a (trans) disposition on the substituents on the cyclopropyl ring are preferred.

Preferably, the compound of formula (G) is a compound from the list below:

5-((trans)-2-aminocyclopropyl)-N-(3-chlorophenyl)pyridin-2-amine;
5-((trans)-2-aminocyclopropyl)-N-(4-chlorophenyl)pyridin-2-amine;
5-((trans)-2-aminocyclopropyl)-N-(4-(trifluoromethyl)phenyl)pyridin-2-amine;
5-((trans)-2-aminocyclopropyl)-N-(3-methoxyphenyl)pyridin-2-amine;
5-((trans)-2-aminocyclopropyl)-N-(4-methoxyphenyl)pyridin-2-amine;
5-((trans)-2-aminocyclopropyl)-N-p-tolylpyridin-2-amine;
5-((trans)-2-aminocyclopropyl)-N-m-tolylpyridin-2-amine;
4-(5-((trans)-2-aminocyclopropyl)pyridin-2-ylamino)benzonitrile;
3-(5-((trans)-2-aminocyclopropyl)pyridin-2-ylamino)benzonitrile;
3-(5-((trans)-2-aminocyclopropyl)pyridin-2-ylamino)benzamide;
4-(5-((trans)-2-aminocyclopropyl)pyridin-2-ylamino)benzamide;
5-((trans)-2-aminocyclopropyl)-N-(3-chlorobenzyl)pyridin-2-amine;
5-((trans)-2-aminocyclopropyl)-N-(4-chlorobenzyl)pyridin-2-amine;
5-((trans)-2-aminocyclopropyl)-N-(3-(trifluoromethyl)benzyl)pyridin-2-amine;
5-((trans)-2-aminocyclopropyl)-N-(4-(trifluoromethyl)benzyl)pyridin-2-amine;
5-((trans)-2-aminocyclopropyl)-N-(3-methylbenzyl)pyridin-2-amine;
5-((trans)-2-aminocyclopropyl)-N-(4-methylbenzyl)pyridin-2-amine;
3-((5-((trans)-2-aminocyclopropyl)pyridin-2-ylamino)methyl)benzonitrile;
4-((5-((trans)-2-aminocyclopropyl)pyridin-2-ylamino)methyl)benzonitrile;
5-((trans)-2-aminocyclopropyl)-N-(3-methoxybenzyl)pyridin-2-amine;
5-((trans)-2-aminocyclopropyl)-N-(4-methoxybenzyl)pyridin-2-amine;
4-(5-((trans)-2-aminocyclopropyl)pyridin-2-ylamino)phenol;
3-((5-((trans)-2-aminocyclopropyl)pyridin-2-ylamino)methyl)benzamide;
4-((5-((trans)-2-aminocyclopropyl)pyridin-2-ylamino)methyl)benzamide;
4-((5-((trans)-2-aminocyclopropyl)pyridin-2-ylamino)methyl)phenol;
5-((trans)-2-aminocyclopropyl)-N-(3-ethynylphenyl)pyridin-2-amine;
N-(5-((trans)-2-aminocyclopropyl)pyridin-2-yl)-1H-indol-7-amine;
N-(5-((trans)-2-aminocyclopropyl)pyridin-2-yl)-1H-indazol-7-amine;
3-(5-((trans)-2-aminocyclopropyl)pyridin-2-ylamino)phenol;
4-((trans)-2-aminocyclopropyl)-N-(4-methylbenzyl)aniline;
4-((trans)-2-aminocyclopropyl)-N-(4-(trifluoromethyl)benzyl)aniline;
4-((trans)-2-aminocyclopropyl)-N-(3-chlorobenzyl)aniline;
3-(((4-((trans)-2-aminocyclopropyl)phenyl)amino)methyl)benzonitrile;
4-((trans)-2-aminocyclopropyl)-N-(p-tolyl)aniline;
4-((trans)-2-aminocyclopropyl)-N-(4-chlorophenyl)aniline;
3-((4-((trans)-2-aminocyclopropyl)phenyl)amino)benzonitrile;
N-(4-((trans)-2-aminocyclopropyl)phenyl)-3-methoxyaniline;
3-((4-((trans)-2-aminocyclopropyl)phenyl)amino)benzamide;

and pharmaceutically acceptable salts thereof.

Compounds of formula (G) can be prepared by the methods disclosed in WO2012/045883, the disclosure of which is incorporated by reference herein in its entirety.

In the methods and uses according to the invention, the KDM1A inhibitor can be a compound of formula (H) or an enantiomer, a diastereomer or a mixture of stereoisomers (such as a racemic mixture or a diastereomer mixture) thereof, or a pharmaceutically acceptable salt or solvate thereof:

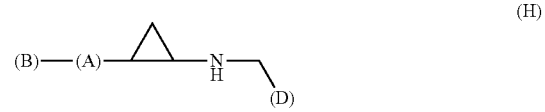

(H)

In formula (H), (A) is a cyclyl group having n substituents (R3);

(B) is a cyclyl group or an -(L1)-cyclyl group, wherein said cyclyl group or the cyclyl moiety comprised in said -(L1)-cyclyl group has n substituents (R2);

(L1) is —O—, —NH—, —N(alkyl)-, alkylene or heteroalkylene;

(D) is a heteroaryl group or an -(L2)-heteroaryl group, wherein said heteroaryl group or the heteroaryl moiety comprised in said -(L2)-heteroaryl group has one substituent (R1), and further wherein said heteroaryl group is covalently bonded to the remainder of the molecule through a ring carbon atom or the heteroaryl moiety comprised in said -(L2)-heteroaryl group is covalently bonded to the (L2) moiety through a ring carbon atom;

(L2) is —O—, —NH—, —N(alkyl)-, alkylene or heteroalkylene;

(R1) is a hydrogen bonding group, including but not limited to —OH, —NH$_2$, amido, —S(O)$_2$NH$_2$, —C(=O)NH$_2$, —CH$_2$—C(=O)NH$_2$, —NH—C(=O)CH$_3$, —NHCH$_3$, —N(CH$_3$)$_2$ or —CH$_2$—NH$_2$;

each (R$^2$) is independently selected from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea;

each (R3) is independently selected from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate, or urea; and n is independently 0, 1, 2, 3 or 4.

Preferably in formula (H), (A) is aryl or heteroaryl. Said aryl is preferably phenyl. Said heteroaryl is preferably pyridinyl, and/or;

(B) is —O—CH$_2$-phenyl or phenyl, each of which can be optionally substituted with n substituents R2, and/or;

(D) is a monocyclic heteroaryl, preferably thiazolyl, oxadiazolyl or pyrimidinyl, and more preferably oxadiazolyl; and/or;

(R1) is —NH$_2$ or —NHCH$_3$ and more preferably —NH$_2$.

Compounds of formula (H) having a (trans) disposition on the substituents on the cyclopropyl ring are preferred.

Preferably, the compound of formula (H) is a compound from the list below:

5-(((trans)-2-(4-(benzyloxy)phenyl)cyclopropylamino)methyl)pyrimidin-2-amine;
5-(((trans)-2-(4-(benzyloxy)phenyl)cyclopropylamino)methyl)thiazol-2-amine;
5-(((trans)-2-(6-(3-(trifluoromethyl)phenyl)pyridin-3-yl)cyclopropylamino)methyl)pyrimidin-2-amine;
5-(((trans)-2-(6-(3-(trifluoromethyl)phenyl)pyridin-3-yl)cyclopropylamino)methyl)thiazol-2-amine;
3-(5-((trans)-2-((2-aminopyrimidin-5-yl)methylamino)cyclopropyl)pyridin-2-yl)phenol;
3-(5-((trans)-2-((2-aminothiazol-5-yl)methylamino)cyclopropyl)pyridin-2-yl)phenol;
4'-((trans)-2-((2-aminopyrimidin-5-yl)methylamino)cyclopropyl)biphenyl-3-ol;
4'-((trans)-2-((2-aminothiazol-5-yl)methylamino)cyclopropyl)biphenyl-3-ol;
5-(((trans)-2-(4-(benzyloxy)phenyl)cyclopropylamino)methyl)-1,2,4-oxadiazol-3-amine;
5-(((trans)-2-(4-(benzyloxy)phenyl)cyclopropylamino)methyl)-1,3,4-oxadiazol-2-amine;
5-((((trans)-2-(4-((4-fluorobenzyl)oxy)phenyl)cyclopropyl)amino)methyl)-1,3,4-oxadiazol-2-amine;
5-((((trans)-2-(4-((3-fluorobenzyl)oxy)phenyl)cyclopropyl)amino)methyl)-1,3,4-oxadiazol-2-amine;
5-((((trans)-2-(4-((3,5-difluorobenzyl)oxy)phenyl)cyclopropyl)amino)methyl)-1,3,4-oxadiazol-2-amine;
5-((((trans)-2-(4-((4-chlorobenzyl)oxy)phenyl)cyclopropyl)amino)methyl)-1,3,4-oxadiazol-2-amine;
5-((((trans)-2-(4-((3-chlorobenzyl)oxy)phenyl)cyclopropyl)amino)methyl)-1,3,4-oxadiazol-2-amine;
5-((((trans)-2-(4-((2-fluorobenzyl)oxy)phenyl)cyclopropyl)amino)methyl)-1,3,4-oxadiazol-2-amine;
5-((((trans)-2-(4-(benzyloxy)phenyl)cyclopropyl)amino)methyl)-N-methyl-1,3,4-oxadiazol-2-amine;
N-(5-((((trans)-2-(4-(benzyloxy)phenyl)cyclopropyl)amino)methyl)-1,3,4-oxadiazol-2-yl)acetamide;
4'-((trans)-2-(((5-amino-1,3,4-oxadiazol-2-yl)methyl)amino)cyclopropyl)-[1,1'-biphenyl]-3-ol;
5-(((((trans)-2-(6-(3-(trifluoromethyl)phenyl)pyridin-3-yl)cyclopropyl)amino)methyl)-1,3,4-oxadiazol-2-amine;
5-((((trans)-2-(4-(benzyloxy)phenyl)cyclopropyl)amino)methyl)-1,3,4-thiadiazol-2-amine;
2-((((trans)-2-(4-(benzyloxy)phenyl)cyclopropyl)amino)methyl)thiazol-5-amine;
4-((((trans)-2-(3'-(trifluoromethyl)-[1,1'-biphenyl]-4-yl)cyclopropyl)amino)methyl)thiazol-2-amine;
2-((((trans)-2-(4-(benzyloxy)phenyl)cyclopropyl)amino)methyl)oxazol-5-amine;
3-((((trans)-2-(4-(benzyloxy)phenyl)cyclopropyl)amino)methyl)isoxazol-5-amine;
5-((((trans)-2-(4-(benzyloxy)phenyl)cyclopropyl)amino)methyl)-N,N-dimethyl-1,3,4-oxadiazol-3-amine;
3-((((trans)-2-(4-(benzyloxy)phenyl)cyclopropyl)amino)methyl)-1,2,4-oxadiazol-5-amine;
5-((((trans)-2-(4-(benzyloxy)phenyl)cyclopropyl)amino)methyl)-1,2,4-thiadiazol-3-amine;
5-((((trans)-2-(4-(benzyloxy)phenyl)cyclopropyl)amino)methyl)pyridin-2-amine;
6-((((trans)-2-(4-(benzyloxy)phenyl)cyclopropyl)amino)methyl)pyridazin-3-amine;
5-((((trans)-2-(4-(benzyloxy)phenyl)cyclopropyl)amino)methyl)pyrazin-2-amine;
2-((((trans)-2-(4-(benzyloxy)phenyl)cyclopropyl)amino)methyl)pyrimidin-5-amine;
6-((((trans)-2-(4-(benzyloxy)phenyl)cyclopropyl)amino)methyl)-1,2,4-triazin-3-amine;
3-((((trans)-2-(4-(benzyloxy)phenyl)cyclopropyl)amino)methyl)-1,2,4-triazin-6-amine;
4'-((trans)-2-((2-aminothiazol-5-yl)methylamino)cyclopropyl)biphenyl-3-ol;
5-(((trans)-2-(4-(benzyloxy)phenyl)cyclopropylamino)methyl)-1,2,4-oxadiazol-3-amine;
5-(((trans)-2-(4-(benzyloxy)phenyl)cyclopropylamino)methyl)-1,3,4-oxadiazol-2-amine;
5-((((trans)-2-(4-((4-fluorobenzyl)oxy)phenyl)cyclopropyl)amino)methyl)-1,3,4-oxadiazol-2-amine;
5-((((trans)-2-(4-((3-fluorobenzyl)oxy)phenyl)cyclopropyl)amino)methyl)-1,3,4-oxadiazol-2-amine;
(−) 5-((((trans)-2-(4-(benzyloxy)phenyl)cyclopropyl)amino)methyl)-1,3,4-oxadiazol-2-amine;
(−) 5-((((trans)-2-(4-((3-fluorobenzyl)oxy)phenyl)cyclopropyl)amino)methyl)-1,3,4-oxadiazol-2-amine;
(−) 5-((((trans)-2-(4-(benzyloxy)phenyl)cyclopropyl)amino)methyl)-N-methyl-1,3,4-oxadiazol-2-amine;
(−)N-(5-((((trans)-2-(4-(benzyloxy)phenyl)cyclopropyl)amino)methyl)-1,3,4-oxadiazol-2-yl)acetamide;
(−) 5-((((trans)-2-(4-(benzyloxy)phenyl)cyclopropyl)amino)methyl)pyrimidin-2-amine;
(−) 5-((((trans)-2-(4-(benzyloxy)phenyl)cyclopropyl)amino)methyl)-1,3,4-thiadiazol-2-amine;
(−) 5-((((trans)-2-(4-((2-fluorobenzyl)oxy)phenyl)cyclopropyl)amino)methyl)-1,3,4-oxadiazol-2-amine;
4'-((trans)-2-((2-aminothiazol-5-yl)methylamino)cyclopropyl)biphenyl-3-ol;
5-(((trans)-2-(4-(benzyloxy)phenyl)cyclopropylamino)methyl)-1,2,4-oxadiazol-3-amine;
5-(((trans)-2-(4-(benzyloxy)phenyl)cyclopropylamino)methyl)-1,3,4-oxadiazol-2-amine;
5-((((trans)-2-(4-((4-fluorobenzyl)oxy)phenyl)cyclopropyl)amino)methyl)-1,3,4-oxadiazol-2-amine;

5-((((trans)-2-(4-((3-fluorobenzyl)oxy)phenyl)cyclopropyl)amino)methyl)-1,3,4-oxadiazol-2-amine;

(−) 5-((((trans)-2-(4-(benzyloxy)phenyl)cyclopropyl)amino)methyl)-1,3,4-oxadiazol-2-amine;

(−) 5-((((trans)-2-(4-((3-fluorobenzyl)oxy)phenyl)cyclopropyl)amino)methyl)-1,3,4-oxadiazol-2-amine;

(−) 5-((((trans)-2-(4-(benzyloxy)phenyl)cyclopropyl)amino)methyl)-N-methyl-1,3,4-oxadiazol-2-amine;

(−)N-(5-((((trans)-2-(4-(benzyloxy)phenyl)cyclopropyl)amino)methyl)-1,3,4-oxadiazol-2-yl)acetamide;

(−) 5-((((trans)-2-(4-(benzyloxy)phenyl)cyclopropyl)amino)methyl)pyrimidin-2-amine;

(−) 5-((((trans)-2-(4-(benzyloxy)phenyl)cyclopropyl)amino)methyl)-1,3,4-thiadiazol-2-amine;

(−) 5-((((trans)-2-(4-((2-fluorobenzyl)oxy)phenyl)cyclopropyl)amino)methyl)-1,3,4-oxadiazol-2-amine;

and pharmaceutically acceptable salts thereof.

Still more preferably, the compound of formula (H) is (−) 5-((((trans)-2-(4-(benzyloxy)phenyl)cyclopropyl)amino)methyl)-1,3,4-oxadiazol-2-amine, or a pharmaceutically acceptable salt thereof.

Compounds of formula (H) can be prepared by the methods disclosed in WO2012/013728, the disclosure of which is incorporated by reference herein in its entirety.

In the methods and uses according to the invention, the KDM1A inhibitor can be a compound of formula (J) or an enantiomer, a diastereomer or a mixture of stereoisomers (such as a racemic mixture or a diastereomer mixture) thereof, or a pharmaceutically acceptable salt or solvate thereof:

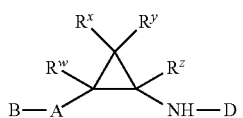

(J)

wherein:

A is aryl or heteroaryl, wherein said aryl or said heteroaryl is optionally substituted with one or more $R^1$;

B is hydrogen, $R^1$ or -L-E;

E is aryl or heteroaryl, wherein said aryl or said heteroaryl is optionally substituted with one or more $R^2$;

L is a bond, —O—, —NH—, —N($C_{1-4}$ alkyl)-, $C_{1-4}$ alkylene or hetero$C_{1-4}$ alkylene;

D is a cycloalkyl group having from 4 to 7 C atoms, wherein said cycloalkyl group has one or two substituents $R^3$ and is further optionally substituted with one or more $R^4$, and wherein the cycloalkyl group optionally:

(a) is fused to a phenyl or a 5- or 6-membered aromatic heterocyclic ring containing from 1 to 3 heteroatoms independently selected from N, O and S, wherein said fused phenyl or said fused aromatic heterocyclic ring is optionally substituted with one or more $R^5$; or (b) is bonded to a linker group —$(C(R^a)_2)_p$— linking together any two non-adjacent ring carbon atoms of the cycloalkyl group, wherein p is 1 or 2 and each $R^a$ independently is hydrogen or $C_{1-4}$ alkyl; or (c) is linked to a second ring that is either a 3- to 7-membered saturated carbocyclic ring or a 3- to 7-membered saturated heterocyclic ring containing from 1 to 3 heteroatoms independently selected from N, O and S, wherein said second ring is linked together with the cycloalkyl group via a single carbon atom common to both rings, and wherein said second ring is optionally substituted with one or more $R^6$;

each $R^1$ is independently selected from $C_1$s alkyl, $C_{2-8}$ alkenyl, $C_{2-8}$ alkynyl, cyclyl, amino, amido, hydroxyl, nitro, halo, halo$C_{1-8}$ alkyl, halo$C_{1-8}$alkoxy, cyano, sulfinyl, sulfonyl, sulfonamide, $C_{1-8}$alkoxy, acyl, carboxyl, O-carboxy, C-carboxy, carbamate and urea;

each $R^2$ is independently selected from $C_1$s alkyl, $C_{2-8}$ alkenyl, $C_{2-8}$ alkynyl, cyclyl, amino, amido, hydroxyl, nitro, halo, halo$C_{1-8}$ alkyl, halo$C_{1-8}$ alkoxy, cyano, sulfinyl, sulfonyl, sulfonamide, $C_{1-8}$ alkoxy, acyl, carboxyl, O-carboxy, C-carboxy, carbamate and urea;

each $R^3$ is independently selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$alkylene-$NR^7R^8$, —$C_{1-4}$alkylene-NHOH, —$C_{1-4}$alkyene-$NR^9COR^{10}$, —$C_{1-4}$ alkylene-$NR^9SO_2R^{10}$, —$C_{1-4}$ alkylene-$NR^9COOR^{10}$, —$C_{1-4}$ alkylene-$NR^9CONR^7R^8$, —$C_{1-4}$ alkylene-$NR^9SO_2NR^7R^8$, —$C_{1-4}$alkylene-OH and —$C_{1-4}$ alkylene-$CONR^7R^8$;

each $R^4$ and each $R^6$ is independently selected from $C_{1-8}$ alkyl, halo, halo$C_{1-8}$ alkyl, halo$C_{1-8}$ alkoxy and $C_{1-8}$ alkoxy;

each $R^5$ is independently selected from $C_{1-8}$ alkyl, $C_{2-3}$ alkenyl, $C_{2-3}$ alkynyl, cyclyl, amino, amido, hydroxyl, nitro, halo, halo$C_{1-8}$alkyl, halo$C_{1-8}$alkoxy, cyano, sulfinyl, sulfonyl, sulfonamide, $C_{1-8}$ alkoxy, acyl, carboxyl, O-carboxy, C-carboxy, carbamate and urea;

each $R^7$ and each $R^8$ is independently selected from hydrogen, $C_{1-8}$ alkyl, $R^{12}R^{13}N$—$C_{1-8}$ alkyl and hydroxy$C_{1-8}$ alkyl, or $R^7$ and $R^8$ are linked together to form, along with the N atom to which they are bound, a saturated 3- to 7-membered heterocyclic ring which optionally contains one further heteroatom selected from N, O and S, wherein one or more C atoms in said heterocyclic ring are optionally oxidized to form CO groups, wherein one or more S atoms in said heterocyclic ring, if present, are optionally oxidized to form independently SO groups or $SO_2$ groups, and wherein said heterocyclic ring is optionally substituted with one or more $R^{11}$;

each $R^9$ is independently selected from hydrogen and $C_{1-4}$ alkyl;

each $R^{10}$ is independently selected from $C_{1-8}$ alkyl, halo$C_{1-8}$ alkyl, cyclyl and cyclyl$C_{1-8}$ alkyl, wherein said cyclyl or the cyclyl moiety comprised in said cyclyl$C_{1-8}$ alkyl is optionally substituted with one or more $R^{14}$—;

each $R^{11}$ is independently selected from $C_{1-8}$ alkyl, halo, $C_{1-8}$ alkoxy, hydroxyl and —$NR^{12}R^{13}$;

each $R^{12}$ and each $R^{13}$ is independently selected from hydrogen and $C_{1-4}$ alkyl;

each $R^{14}$ is independently selected from $C_{1-8}$ alkyl, $C_{2-8}$ alkenyl, $C_{2-8}$ alkynyl, amino, amido, hydroxyl, nitro, halo, halo$C_{1-8}$ alkyl, halo$C_{1-8}$ alkoxy, cyano, sulfinyl, sulfonyl, sulfonamide, $C_{1-8}$ alkoxy, acyl, carboxyl, O-carboxy, C-carboxy, carbamate and urea; and each $R^w$, $R^x$, $R^y$ and $R^z$ is independently selected from hydrogen, halo and $C_{1-4}$ alkyl.

Preferably in formula (J), (A) is phenyl, thiazolyl or pyridyl, preferably phenyl, which rings can be optionally substituted with one or more R1, and/or (B) is H, and/or (R1) is $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea, and more preferably halo, $C_{1-4}$ alkyl, halo$C_{1-4}$ alkyl, $C_{1-4}$ alkoxy and $C_{3-6}$ cycloalkyl; and/or (D) is selected from D1, D2, D3 and D4;

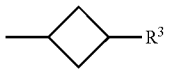 D1

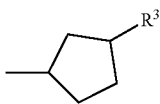 D2

 D3

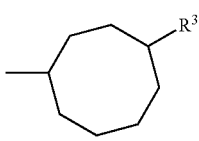 D4 and more preferably D3; and/or (R3) is selected from —$NR^7R^8$, —NHOH, —$NR^9COR^{10}$, —$NR^9SO_2R^{10}$, —$NR^9COOR^{10}$, —$NR^9CONR^7R^8$, —$NR^9SO_2NR^7R^8$, —OH, —$CONR^7R^8$, oxo, —$C_{1-4}$alkylene-$NR^7R^8$, —$C_{1-4}$ alkylene-OH and —$C_{1-4}$alkylene-$CONR^7R^8$, more preferably from —$NR^7R^8$, —OH, —$C_{1-4}$ alkylene-$NR^7R^8$, and —$C_{1-4}$ alkylene-OH, still more preferably —$NR^7R^8$ (such as —$NH_2$); and/or each $R^w$, $R^x$, $R^y$ and $R^z$ is hydrogen.

Compounds of formula (J) having a (trans) disposition on the substituents on the cyclopropyl ring are preferred.

Preferably, the compound of formula (J) is a compound from the list below:

N1-((trans)-2-phenylcyclopropyl)cyclohexane-1,4-diamine;
(cis)-N1-((1S,2R)-2-phenylcyclopropyl)cyclohexane-1,4-diamine;
(trans)-N1-((1S,2R)-2-phenylcyclopropyl)cyclohexane-1,4-diamine;
(cis)-N1-((1R,2S)-2-phenylcyclopropyl)cyclohexane-1,4-diamine;
(trans)-N1-((1R,2S)-2-phenylcyclopropyl)cyclohexane-1,4-diamine;
N1-((trans)-2-(thiazol-5-yl)cyclopropyl)cyclohexane-1,4-diamine;
N1-((trans)-2-(pyridin-3-yl)cyclopropyl)cyclohexane-1,4-diamine;
N1-((trans)-2-(6-(3-(trifluoromethyl)phenyl)pyridin-3-yl)cyclopropyl)cyclohexane-1,4-diamine;
N1-((trans)-2-(3'-(trifluoromethyl)-[1,1'-biphenyl]-4-yl)cyclopropyl)cyclohexane-1,4-diamine;
N1-((trans)-2-(4-(benzyloxy)phenyl)cyclopropyl)cyclohexane-1,4-diamine;
4-(((trans)-2-(6-(3-(trifluoromethyl)phenyl)pyridin-3-yl)cyclopropyl)amino)cyclohexanol;
4-(((trans)-2-(6-(3-(trifluoromethyl)phenyl)pyridin-3-yl)cyclopropyl)amino)cyclohexanecarboxamide;
N-(4-(((trans)-2-(6-(3-(trifluoromethyl)phenyl)pyridin-3-yl)cyclopropyl)amino)cyclohexyl)acetamide;
N-(4-(((trans)-2-(6-(3-(trifluoromethyl)phenyl)pyridin-3-yl)cyclopropyl)amino)cyclohexyl)methanesulfonamide;
(R)-1-(4-(((trans)-2-phenylcyclopropyl)amino)cyclohexyl)pyrrolidin-3-amine;
N1-((trans)-2-(4'-chloro-[1,1'-biphenyl]-4-yl)cyclopropyl)cyclohexane-1,4-diamine;
N1-((trans)-2-(3'-chloro-[1,1'-biphenyl]-4-yl)cyclopropyl)cyclohexane-1,4-diamine;
4'-((trans)-2-((4-aminocyclohexyl)amino)cyclopropyl)-[1,1'-biphenyl]-3-ol;
N-(4'-((trans)-2-((4-aminocyclohexyl)amino)cyclopropyl)-[1,1'-biphenyl]-3-yl)methanesulfonamide;
N1-((trans)-2-(4-((2-fluorobenzyl)oxy)phenyl)cyclopropyl)cyclohexane-1,4-diamine;
N1-((trans)-2-(4-((3-fluorobenzyl)oxy)phenyl)cyclopropyl)cyclohexane-1,4-diamine;
N1-((trans)-2-(4-((4-fluorobenzyl)oxy)phenyl)cyclopropyl)cyclohexane-1,4-diamine;
N1-methyl-N4-((trans)-2-phenylcyclopropyl)cyclohexane-1,4-diamine;
N1-methyl-N4-((trans)-2-(3'-(trifluoromethyl)-[1,1'-biphenyl]-4-yl)cyclopropyl)cyclohexane-1,4-diamine;
N1-((trans)-2-(4-(benzyloxy)phenyl)cyclopropyl)-N4-methylcyclohexane-1,4-diamine;
N1-((trans)-2-phenylcyclopropyl)cyclobutane-1,3-diamine;
N1-((trans)-2-(3'-(trifluoromethyl)-[1,1'-biphenyl]-4-yl)cyclopropyl)cyclobutane-1,3-diamine;
N1-((trans)-2-(4-(benzyloxy)phenyl)cyclopropyl)cyclobutane-1,3-diamine;
N1-((trans)-2-phenylcyclopropyl)-2,3-dihydro-1H-indene-1,3-diamine;
N1-((trans)-2-(3'-(trifluoromethyl)-[1,1'-biphenyl]-4-yl)cyclopropyl)-2,3-dihydro-1H-indene-1,3-diamine;
N1-((trans)-2-(4-(benzyloxy)phenyl)cyclopropyl)-2,3-dihydro-1H-indene-1,3-diamine;
N1-((trans)-2-fluoro-2-phenylcyclopropyl)cyclohexane-1,4-diamine;
N1-((1S,2S)-2-fluoro-2-phenylcyclopropyl)cyclohexane-1,4-diamine;
N1-((1R,2R)-2-fluoro-2-phenylcyclopropyl)cyclohexane-1,4-diamine;
1-methyl-N4-((trans)-2-phenylcyclopropyl)cyclohexane-1,4-diamine;
4-(aminomethyl)-N-((trans)-2-phenylcyclopropyl)cyclohexanamine;
N1-((trans)-2-phenylcyclopropyl)cyclohexane-1,3-diamine;
N1-((cis)-2-phenylcyclopropyl)cyclohexane-1,4-diamine;
Tert-butyl (4-(((trans)-2-phenylcyclopropyl)amino)cyclohexyl)carbamate;
1-ethyl-3-(4-(((trans)-2-phenylcyclopropyl)amino)cyclohexyl)urea;
4-morpholino-N-((trans)-2-phenylcyclopropyl)cyclohexanamine;
N1-((trans)-2-(4-bromophenyl)cyclopropyl)cyclohexane-1,4-diamine;
N1-(2-(o-tolyl)cyclopropyl)cyclohexane-1,4-diamine;
N1-(2-(4-(trifluoromethyl)phenyl)cyclopropyl)cyclohexane-1,4-diamine;
N1-(2-(4-methoxyphenyl)cyclopropyl)cyclohexane-1,4-diamine;
4-(2-((4-aminocyclohexyl)amino)cyclopropyl)phenol;
N1-(2-(2-fluorophenyl)cyclopropyl)cyclohexane-1,4-diamine;
N1-(2-(3,4-difluorophenyl)cyclopropyl)cyclohexane-1,4-diamine;
N1-(2-(naphthalen-2-yl)cyclopropyl)cyclohexane-1,4-diamine;

N1-(2-methyl-2-phenylcyclopropyl)cyclohexane-1,4-diamine;
(R)-1-(4-(((trans)-2-(3'-(trifluoromethyl)-[1,1'-biphenyl]-4-yl)cyclopropyl) amino)cyclohexyl)pyrrolidin-3-amine;
(Cis)-N1-((1S,2R)-2-(3'-(trifluoromethyl)-[1,1'-biphenyl]-4-yl)cyclopropyl)cyclohexane-1,4-diamine;
(Trans)-N1-((1S,2R)-2-(3'-(trifluoromethyl)-[1,1'-biphenyl]-4-yl)cyclo-propyl)cyclohexane-1,4-diamine;
(Cis)-N1-((1R,2S)-2-(3'-(trifluoromethyl)-[1,1'-biphenyl]-4-yl)cyclo-propyl)cyclohexane-1,4-diamine;
(Trans)-N1-((1R,2S)-2-(3'-(trifluoromethyl)-[1,1'-biphenyl]-4-yl)cyclo-propyl)cyclohexane-1,4-diamine;
N1-((trans)-2-(4-cyclopropylphenyl)cyclopropyl)cyclohexane-1,4-diamine;
N1-((trans)-2-(4-(pyridin-3-yl)phenyl)cyclopropyl)cyclohexane-1,4-diamine;
N1-((trans)-2-(4-(1H-indazol-6-yl)phenyl)cyclopropyl)cyclohexane-1,4-diamine;
N1-((trans)-2-(4-(1H-pyrazol-5-yl)phenyl)cyclopropyl)cyclohexane-1,4-diamine;
3-(5-((trans)-2-((4-aminocyclohexyl)amino)cyclopropyl)thiophen-2-yl)phenol;
3-(5-((trans)-2-((4-aminocyclohexyl)amino)cyclopropyl)thiazol-2-yl)phenol;
3-(5-((trans)-2-((4-aminocyclohexyl)amino)cyclopropyl)pyridin-2-yl)-5-methoxybenzonitrile;
5-(5-((trans)-2-((4-aminocyclohexyl)amino)cyclopropyl)pyridin-2-yl)-2-methylphenol;
N-(4'-((trans)-2-((4-aminocyclohexyl)amino)cyclopropyl)-6-methoxy-[1,1'-biphenyl]-3-yl)methanesulfonamide;
N-(3-(5-((trans)-2-((4-aminocyclohexyl)amino)cyclopropyl)thiazol-2-yl)phenyl)-2-cyanobenzenesulfonamide;
N-(4'-((trans)-2-((4-aminocyclohexyl)amino)cyclopropyl)-[1,1'-biphenyl]-3-yl)-2-cyanobenzenesulfonamide;
6-amino-N-(4'-((trans)-2-((4-aminocyclohexyl)amino)cyclopropyl)-[1,1'-biphenyl]-3-yl)pyridine-3-sulfonamide;
N-(4'-((trans)-2-((4-aminocyclohexyl)amino)cyclopropyl)-[1,1'-biphenyl]-3-yl)piperazine-1-sulfonamide;
N1-((cis)-2-fluoro-2-phenylcyclopropyl)cyclohexane-1,4-diamine;
N1-((trans)-2-(4-((3-(piperazin-1-yl)benzyl)oxy)phenyl)cyclopropyl)cyclohexane-1,4-diamine;
N1-((trans)-2-(4-(pyridin-3-ylmethoxy)phenyl)cyclopropyl)cyclohexane-1,4-diamine;
N1-((trans)-2-(6-((3-methylbenzyl)amino)pyridin-3-yl)cyclopropyl)cyclohexane-1,4-diamine;
3-((5-((trans)-2-((4-aminocyclohexyl)amino)cyclopropyl)pyridin-2-yl) amino)benzonitrile;
N1-((trans)-2-(naphthalen-2-yl)cyclopropyl)cyclohexane-1,4-diamine;
N1-((trans)-2-(o-tolyl)cyclopropyl)cyclohexane-1,4-diamine;
N1-((trans)-2-(4-(trifluoromethyl)phenyl)cyclopropyl)cyclohexane-1,4-diamine;
N1-((trans)-2-(4-methoxyphenyl)cyclopropyl)cyclohexane-1,4-diamine;
N1-((trans)-2-(2-fluorophenyl)cyclopropyl)cyclohexane-1,4-diamine;
N1-((trans)-2-(3,4-difluorophenyl)cyclopropyl)cyclohexane-1,4-diamine;
N1-((trans)-2-methyl-2-phenylcyclopropyl)cyclohexane-1,4-diamine;
(cis)-N1-((1S,2R)-2-(pyridin-3-yl)cyclopropyl)cyclohexane-1,4-diamine;
(trans)-N1-((1R,2S)-2-(pyridin-3-yl)cyclopropyl)cyclohexane-1,4-diamine;
(cis)-N1-((1R,2S)-2-(pyridin-3-yl)cyclopropyl)cyclohexane-1,4-diamine;
(trans)-N1-((1S,2R)-2-(pyridin-3-yl)cyclopropyl)cyclohexane-1,4-diamine;
(cis)-N1-((1S,2R)-2-phenylcyclopropyl)cyclobutane-1,3-diamine;
(trans)-N1-((1R,2S)-2-phenylcyclopropyl)cyclobutane-1,3-diamine;
(cis)-N1-((1R,2S)-2-phenylcyclopropyl)cyclobutane-1,3-diamine;
(trans)-N1-((1S,2R)-2-phenylcyclopropyl)cyclobutane-1,3-diamine;
(cis)-N1-((1S,2R)-2-(3,4-difluorophenyl)cyclopropyl)cyclohexane-1,4-diamine;
(trans)-N1-((1R,2S)-2-(3,4-difluorophenyl)cyclopropyl)cyclohexane-1,4-diamine;
(cis)-N1-((1R,2S)-2-(3,4-difluorophenyl)cyclopropyl)cyclohexane-1,4-diamine;
(trans)-N1-((1S,2R)-2-(3,4-difluorophenyl)cyclopropyl)cyclohexane-1,4-diamine;
(cis)-N1-((1S,2R)-2-(naphthalen-2-yl)cyclopropyl)cyclohexane-1,4-diamine;
(trans)-N1-((1R,2S)-2-(naphthalen-2-yl)cyclopropyl)cyclohexane-1,4-diamine;
(cis)-N1-((1R,2S)-2-(naphthalen-2-yl)cyclopropyl)cyclohexane-1,4-diamine;
(trans)-N1-((1S,2R)-2-(naphthalen-2-yl)cyclopropyl)cyclohexane-1,4-diamine;
(cis)-N1-((1S,2R)-2-(4-(1H-pyrazol-5-yl)phenyl)cyclopropyl)cyclohexane-1,4-diamine;
(trans)-N1-((1R,2S)-2-(4-(1H-pyrazol-5-yl)phenyl)cyclopropyl)cyclohexane-1,4-diamine;
(cis)-N1-((1R,2S)-2-(4-(1H-pyrazol-5-yl)phenyl)cyclopropyl)cyclohexane-1,4-diamine;
(trans)-N1-((1S,2R)-2-(4-(1H-pyrazol-5-yl)phenyl)cyclopropyl)cyclohexane-1,4-diamine;
N-(4'-((1R,2S)-2-(((cis)-4-aminocyclohexyl)amino)cyclopropyl)-[1,1'-biphenyl]-3-yl)piperazine-1-sulfonamide;
N-(4'-((1S,2R)-2-(((trans)-4-aminocyclohexyl)amino)cyclopropyl)-[1,1'-biphenyl]-3-yl)piperazine-1-sulfonamide;
N-(4'-((1S,2R)-2-(((cis)-4-aminocyclohexyl)amino)cyclopropyl)-[1,1'-biphenyl]-3-yl)piperazine-1-sulfonamide;
N-(4'-((1R,2S)-2-(((trans)-4-aminocyclohexyl)amino)cyclopropyl)-[1,1'-biphenyl]-3-yl)piperazine-1-sulfonamide;
(cis)-N1-((1S,2R)-2-(4-((2-fluorobenzyl)oxy)phenyl)cyclopropyl)cyclohexane-1,4-diamine;
(trans)-N1-((1R,2S)-2-(4-((2-fluorobenzyl)oxy)phenyl)cyclopropyl)cyclohexane-1,4-diamine;
(cis)-N1-((1R,2S)-2-(4-((2-fluorobenzyl)oxy)phenyl)cyclopropyl)cyclohexane-1,4-diamine;
(trans)-N1-((1S,2R)-2-(4-((2-fluorobenzyl)oxy)phenyl)cyclopropyl)cyclohexane-1,4-diamine;
and pharmaceutically acceptable salts thereof.

Still more preferably, the compound of formula (J) is (trans)-N1-((1R,2S)-2-phenylcyclopropyl)cyclohexane-1,4-diamine; or a pharmaceutically acceptable salt thereof.

Compounds of formula (J) can be prepared by the methods disclosed in WO2013/057322, the disclosure of which is incorporated by reference herein in its entirety.

In the methods and uses according to the invention, the KDM1A inhibitor can be a compound of formula (K) or an enantiomer, a diastereomer or a mixture of stereoisomers (such as a racemic mixture or a diastereomer mixture) thereof, or a pharmaceutically acceptable salt or solvate thereof:

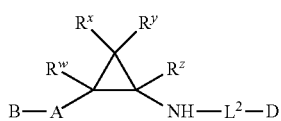
(K)

wherein:
A is aryl or heteroaryl, wherein said aryl or heteroaryl is optionally substituted with one or more $R^1$;
B is H, $R^1$ or -$L^1$-E;
E is aryl or heteroaryl, wherein said aryl or said heteroaryl is optionally substituted with one or more $R^2$
$L^1$ is a bond, —O—, —NH—, —N($C_{1-4}$ alkyl)-, $C_{1-4}$ alkylene or hetero$C_{1-4}$alkylene;
$L^2$ is a bond and D is a cyclic group selected from:
  (i) a 3- to 7-membered monocyclic saturated heterocyclic ring containing 1 or 2 heteroatoms independently selected from N, O and S, and
  (ii) a 7- to 15-membered polycyclic ring system which comprises at least one saturated heterocyclic ring, wherein the polycyclic ring system contains from 1 to 4 heteroatoms independently selected from N, O and S,
wherein the cyclic group (i) or (ii) is linked to the remainder of the compound of Formula I through a ring C atom, wherein one or more ring C atoms in the cyclic group (i) or (ii) are optionally oxidized to form CO groups, wherein one or more S atoms in the cyclic group (i) or (ii), if present, are optionally oxidized to form independently SO groups or $SO_2$ groups, and
wherein the cyclic group (i) or (ii) is optionally substituted with one or more $R^3$;
or $L^2$ is $C_{1-4}$ alkylene and D is a cyclic group selected from:
  (iii) a 3- to 7-membered monocyclic saturated heterocyclic ring containing 1 or 2 heteroatoms independently selected from N, O and S, and
  (iv) a 7- to 15-membered polycyclic saturated ring system which comprises at least one heterocyclic ring, wherein the polycyclic saturated ring system contains from 1 to 4 heteroatoms independently selected from N, O and S,
wherein the cyclic group (iii) or (iv) is linked to the remainder of the compound of Formula I through a ring C atom, wherein one or more ring C atoms in the cyclic group (iii) or (iv) are optionally oxidized to form CO groups, wherein one or more S atoms in the cyclic group (iii) or (iv), if present, are optionally oxidized to form independently SO groups or $SO_2$ groups, and
wherein the cyclic group (iii) or (iv) is optionally substituted with one or more $R^3$; each $R^1$ is independently selected from $C_{1-8}$ alkyl, $C_{2-8}$ alkenyl, $C_{2-8}$ alkynyl, cyclyl, amino, amido, hydroxyl, nitro, halo, halo$C_{1-8}$ alkyl, halo$C_{1-8}$ alkoxy, cyano, sulfinyl, sulfonyl, sulfonamide, $C_{1-8}$ alkoxy, acyl, carboxyl, O-carboxy, C-carboxy, carbamate and urea;
each $R^2$ is independently selected from $C_{1-4}$ alkyl, $C_{2-8}$ alkenyl, $C_{2-8}$ alkynyl, cyclyl, amino, amido, hydroxyl, nitro, halo, halo$C_{1-8}$ alkyl, halo$C_{1-8}$ alkoxy, cyano, sulfinyl, sulfonyl, sulfonamide, $C_{1-8}$ alkoxy, acyl, carboxyl, O-carboxy, C-carboxy, carbamate and urea;
each $R^3$ is independently selected from $C_{1-8}$ alkyl, $C_{2-8}$ alkenyl, $C_{2-8}$ alkynyl, cyclyl, amino, amido, hydroxyl, nitro, halo, halo$C_{1-8}$ alkyl, halo$C_{1-8}$ alkoxy, cyano, sulfinyl, sulfonyl, sulfonamide, $C_{1-8}$ alkoxy, acyl, carboxyl, O-carboxy, C-carboxy, carbamate and urea; and
each $R^w$, $R^x$, $R^y$ and $R^z$ is Independently Selected from Hydrogen, Halo and $C_{1-4}$ Alkyl.

Preferably in formula (K),
(A) is phenyl, thiazolyl or pyridyl, preferably phenyl, which rings can be optionally substituted with one or more R1, and/or
(B) is H, and/or
($R^1$) is $C_{1-8}$ alkyl, amino, amido, hydroxyl, halo, halo$C_{1-8}$ alkyl, halo$C_{1-8}$ alkoxy, cyano, sulfonamide, $C_{1-8}$ alkoxy, acyl, carboxyl, carbamate, and urea and more preferably halo, $C_{1-4}$ alkyl, halo$C_{1-4}$ alkyl, $C_{1-4}$ alkoxy and $C_{3-6}$ cycloalkyl; and/or
L2 is a bond and (D) is a 3- to 7-membered monocyclic saturated heterocyclic ring containing 1 heteroatom selected from N, O and S wherein D is linked to the remainder of the compound of formula (X) through a C, more preferably a 3- to 7-membered monocyclic saturated heterocyclic ring containing 1 N atom wherein D is linked to the remainder of the compound of formula (X) through a C, and even more preferably D is 4-piperidinyl, or L2 is a bond and (D) is a ring system selected from (a), (b), (c) and (d)

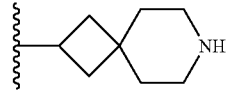
(a)

(b)

(c)

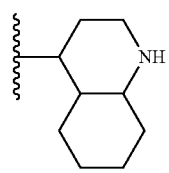
(d)

wherein any D is optionally substituted with one or more R3; and/or
each $R^w$, $R^x$, $R^y$ and $R^z$ is hydrogen.

Compounds of formula (K) having a (trans) disposition on the substituents on the cyclopropyl ring are preferred.

Preferably, the compound of formula (K) is a compound from the list below:
N-((trans)-2-phenylcyclopropyl)piperidin-4-amine;
N-((1S,2R)-2-phenylcyclopropyl)piperidin-4-amine;
N-((1R,2S)-2-phenylcyclopropyl)piperidin-4-amine;
N-((trans)-2-(4-(benzyloxy)phenyl)cyclopropyl)piperidin-4-amine;
N-((trans)-2-(6-(3-(trifluoromethyl)phenyl)pyridin-3-yl)cyclopropyl)tetrahydro-2H-pyran-4-amine;
N-((trans)-2-(pyridin-3-yl)cyclopropyl)piperidin-4-amine;
N-((trans)-2-(thiazol-5-yl)cyclopropyl)piperidin-4-amine;
N-((trans)-2-(3'-(trifluoromethyl)-[1,1'-biphenyl]-4-yl)cyclopropyl)piperidin-4-amine;
N-((trans)-2-phenylcyclopropyl)piperidin-3-amine;

N-((trans)-2-(3'-(trifluoromethyl)-[1,1'-biphenyl]-4-yl)cyclopropyl)piperidin-3-amine;
N-((trans)-2-(4-(benzyloxy)phenyl)cyclopropyl)piperidin-3-amine;
N-((trans)-2-phenylcyclopropyl)pyrrolidin-3-amine;
N-((trans)-2-(3'-(trifluoromethyl)-[1,1'-biphenyl]-4-yl)cyclopropyl)pyrrolidin-3-amine;
N-((trans)-2-(4-(benzyloxy)phenyl)cyclopropyl)pyrrolidin-3-amine;
N-((trans)-2-phenylcyclopropyl)azetidin-3-amine;
N-((trans)-2-(3'-(trifluoromethyl)-[1,1'-biphenyl]-4-yl)cyclopropyl)azetidin-3-amine;
N-((trans)-2-(4-(benzyloxy)phenyl)cyclopropyl)azetidin-3-amine;
N-((trans)-2-phenylcyclopropyl)azepan-3-amine;
N-((trans)-2-phenylcyclopropyl)-8-azabicyclo[3.2.1]octan-3-amine;
N-((trans)-2-phenylcyclopropyl)-3-azabicyclo[3.2.1]octan-8-amine;
N-((trans)-2-phenylcyclopropyl)decahydroquinolin-4-amine;
N-((trans)-2-phenylcyclopropyl)-1,2,3,4-tetrahydroquinolin-4-amine;
N-((trans)-2-phenylcyclopropyl)-3-azaspiro[5.5]undecan-9-amine;
N-((trans)-2-phenylcyclopropyl)-2-azaspiro[4.5]decan-8-amine;
N-((trans)-2-phenylcyclopropyl)-2,3-dihydrospiro[indene-1,4'-piperidin]-3-amine;
N-((1S,2R)-2-(4-(benzyloxy)phenyl)cyclopropyl)piperidin-4-amine;
N-((1R,2S)-2-(4-(benzyloxy)phenyl)cyclopropyl)piperidin-4-amine;
N-((1S,2R)-2-(pyridin-3-yl)cyclopropyl)piperidin-4-amine;
N-((1R,2S)-2-(pyridin-3-yl)cyclopropyl)piperidin-4-amine;
N-((1S,2S)-2-(thiazol-5-yl)cyclopropyl)piperidin-4-amine;
N-((1R,2R)-2-(thiazol-5-yl)cyclopropyl)piperidin-4-amine;
N-((1S,2R)-2-(3'-(trifluoromethyl)-[1,1'-biphenyl]-4-yl)cyclopropyl)piperidin-4-amine;
N-((1R,2S)-2-(3'-(trifluoromethyl)-[1,1'-biphenyl]-4-yl)cyclopropyl)piperidin-4-amine;
N-((trans)-2-phenylcyclopropyl)-7-azaspiro[3.5]nonan-2-amine;
N-(2-(o-tolyl)cyclopropyl)piperidin-4-amine;
N-(2-(2-fluorophenyl)cyclopropyl)piperidin-4-amine;
N-(2-(3,4-difluorophenyl)cyclopropyl)piperidin-4-amine;
N-(2-(4-methoxyphenyl)cyclopropyl)piperidin-4-amine;
N-(2-(naphthalen-2-yl)cyclopropyl)piperidin-4-amine;
N-(2-methyl-2-phenylcyclopropyl)piperidin-4-amine;
N-(6-methoxy-4'-((trans)-2-(piperidin-4-ylamino)cyclopropyl)-[1,1'-biphenyl]-3-yl)methanesulfonamide;
N-(4'-((trans)-2-(piperidin-4-ylamino)cyclopropyl)-[1,1'-biphenyl]-3-yl)propane-2-sulfonamide;
1-(methylsulfonyl)-N-((trans)-2-phenylcyclopropyl)piperidin-4-amine;
1-(4-(((trans)-2-(4-bromophenyl)cyclopropyl)amino)piperidin-1-yl)ethanone;
4-(((trans)-2-(4-bromophenyl)cyclopropyl)amino)piperidine-1-carboxamide;
N-((trans)-2-(4-bromophenyl)cyclopropyl)tetrahydro-2H-pyran-4-amine;
2,2,6,6-tetramethyl-N-((trans)-2-phenylcyclopropyl)piperidin-4-amine;
1-methyl-N-((trans)-2-phenylcyclopropyl)piperidin-4-amine;
1-isopropyl-N-((trans)-2-phenylcyclopropyl)piperidin-4-amine;
N-((trans)-2-phenylcyclopropyl)-1-(2,2,2-trifluoroethyl)piperidin-4-amine;
N-((trans)-2-phenylcyclopropyl)-1-(pyridin-4-yl)piperidin-4-amine;
4-(((trans)-2-(4-bromophenyl)cyclopropyl)amino)tetrahydro-2H-thiopyran 1,1-dioxide;
N-((trans)-2-fluoro-2-phenylcyclopropyl)piperidin-4-amine;
N-((1S,2S)-2-fluoro-2-phenylcyclopropyl)piperidin-4-amine;
N-((1R,2R)-2-fluoro-2-phenylcyclopropyl)piperidin-4-amine;
N-((trans)-2-(naphthalen-2-yl)cyclopropyl)piperidin-4-amine;
N-((trans)-2-methyl-2-phenylcyclopropyl)piperidin-4-amine;
N-((trans)-2-(o-tolyl)cyclopropyl)piperidin-4-amine;
N-((trans)-2-(2-fluorophenyl)cyclopropyl)piperidin-4-amine;
N-((trans)-2-(3,4-difluorophenyl)cyclopropyl)piperidin-4-amine;
N-((trans)-2-(4-methoxyphenyl)cyclopropyl)piperidin-4-amine;
(Trans)-2-phenyl-N-(piperidin-4-ylmethyl)cyclopropanamine;
(Trans)-2-phenyl-N-(2-(piperidin-4-yl)ethyl)cyclopropanamine;
(Trans)-2-phenyl-N-(2-(tetrahydro-2H-pyran-4-yl)ethyl)cyclopropanamine;
(Trans)-2-(4'-chloro-[1,1'-biphenyl]-4-yl)-N-(2-(tetrahydro-2H-pyran-4-yl)ethyl)cyclopropanamine;
(Trans)-N-(piperidin-4-ylmethyl)-2-(pyridin-3-yl)cyclopropanamine;
(Trans)-N-(piperidin-4-ylmethyl)-2-(thiazol-5-yl)cyclopropanamine;
(Trans)-N-(piperidin-4-ylmethyl)-2-(3'-(trifluoromethyl)-[1,1'-biphenyl]-4-yl)cyclopropanamine;
(Trans)-2-(4-(benzyloxy)phenyl)-N-(piperidin-4-ylmethyl)cyclopropanamine;
(Trans)-N-(2-(piperidin-4-yl)ethyl)-2-(pyridin-3-yl)cyclopropanamine;
(Trans)-N-(2-(piperidin-4-yl)ethyl)-2-(thiazol-5-yl)cyclopropanamine;
(Trans)-N-(2-(piperidin-4-yl)ethyl)-2-(3'-(trifluoromethyl)-[1,1'-biphenyl]-4-yl)cyclopropanamine;
(Trans)-2-(4-(benzyloxy)phenyl)-N-(2-(piperidin-4-yl)ethyl)cyclopropanamine;
(1S,2R)-2-phenyl-N-(piperidin-4-ylmethyl)cyclopropanamine;
(1R,2S)-2-phenyl-N-(piperidin-4-ylmethyl)cyclopropanamine;
(1S,2R)-2-phenyl-N-(2-(piperidin-4-yl)ethyl)cyclopropanamine;
(1R,2S)-2-phenyl-N-(2-(piperidin-4-yl)ethyl)cyclopropanamine;
(1S,2R)—N-(piperidin-4-ylmethyl)-2-(pyridin-3-yl)cyclopropanamine;
(1R,2S)—N-(piperidin-4-ylmethyl)-2-(pyridin-3-yl)cyclopropanamine;
(1S,2S)—N-(piperidin-4-ylmethyl)-2-(thiazol-5-yl)cyclopropanamine;
(1R,2R)—N-(piperidin-4-ylmethyl)-2-(thiazol-5-yl)cyclopropanamine;
(1S,2R)—N-(piperidin-4-ylmethyl)-2-(3'-(trifluoromethyl)-[1,1'-biphenyl]-4-yl)cyclopropanamine;
(1R,2S)—N-(piperidin-4-ylmethyl)-2-(3'-(trifluoromethyl)-[1,1'-biphenyl]-4-yl)cyclopropanamine;

(1S,2R)-2-(4-(benzyloxy)phenyl)-N-(piperidin-4-ylmethyl)cyclopropanamine;
(1R,2S)-2-(4-(benzyloxy)phenyl)-N-(piperidin-4-ylmethyl)cyclopropanamine;
(1S,2R)—N-(2-(piperidin-4-yl)ethyl)-2-(pyridin-3-yl)cyclopropanamine;
(1R,2S)—N-(2-(piperidin-4-yl)ethyl)-2-(pyridin-3-yl)cyclopropanamine;
(1S,2S)—N-(2-(piperidin-4-yl)ethyl)-2-(thiazol-5-yl)cyclopropanamine;
(1R,2R)—N-(2-(piperidin-4-yl)ethyl)-2-(thiazol-5-yl)cyclopropanamine;
(1S,2R)—N-(2-(piperidin-4-yl)ethyl)-2-(3'-(trifluoromethyl)-[1,1'-biphenyl]-4-yl)cyclopropanamine;
(1R,2S)—N-(2-(piperidin-4-yl)ethyl)-2-(3'-(trifluoromethyl)-[1,1'-biphenyl]-4-yl)cyclopropanamine;
(1S,2R)-2-(4-(benzyloxy)phenyl)-N-(2-(piperidin-4-yl)ethyl)cyclopropanamine;
(1R,2S)-2-(4-(benzyloxy)phenyl)-N-(2-(piperidin-4-yl)ethyl)cyclopropanamine;
(Trans)-2-phenyl-N-(pyrrolidin-3-ylmethyl)cyclopropanamine;
(Trans)-2-(4-((2-fluorobenzyl)oxy)phenyl)-N-(piperidin-4-ylmethyl)cyclopropanamine;
(Trans)-N-(azetidin-3-ylmethyl)-2-phenylcyclopropanamine;
(Trans)-2-(4-cyclopropylphenyl)-N-(piperidin-4-ylmethyl)cyclopropanamine;
(Trans)-N-(piperidin-4-ylmethyl)-2-(4-(pyridin-3-yl)phenyl)cyclopropanamine;
(Trans)-2-(4-(1H-pyrazol-5-yl)phenyl)-N-(piperidin-4-ylmethyl)cyclopropanamine;
(Trans)-2-(naphthalen-2-yl)-N-(piperidin-4-ylmethyl)cyclopropanamine;
2-methyl-2-phenyl-N-(piperidin-4-ylmethyl)cyclopropanamine;
(trans)-2-methyl-2-phenyl-N-(piperidin-4-ylmethyl)cyclopropanamine;
(trans)-2-(4-(benzyloxy)phenyl)-N-((1-methylpiperidin-4-yl)methyl)cyclopropanamine;
and pharmaceutically acceptable salts thereof.
Still more preferably, the compound of formula (K) is a compound from the list below:
N-((trans)-2-phenylcyclopropyl)piperidin-4-amine;
N-((1S,2R)-2-phenylcyclopropyl)piperidin-4-amine;
N-((1R,2S)-2-phenylcyclopropyl)piperidin-4-amine;
N-((trans)-2-(4-(benzyloxy)phenyl)cyclopropyl)piperidin-4-amine;
N-((trans)-2-(6-(3-(trifluoromethyl)phenyl)pyridin-3-yl)cyclopropyl)tetrahydro-2H-pyran-4-amine;
N-((trans)-2-(pyridin-3-yl)cyclopropyl)piperidin-4-amine;
N-((trans)-2-(thiazol-5-yl)cyclopropyl)piperidin-4-amine;
N-((trans)-2-(3'-(trifluoromethyl)-[1,1'-biphenyl]-4-yl)cyclopropyl)piperidin-4-amine;
N-((trans)-2-phenylcyclopropyl)piperidin-3-amine;
N-((trans)-2-(3'-(trifluoromethyl)-[1,1'-biphenyl]-4-yl)cyclopropyl)piperidin-3-amine;
N-((trans)-2-(4-(benzyloxy)phenyl)cyclopropyl)piperidin-3-amine;
N-((trans)-2-phenylcyclopropyl)pyrrolidin-3-amine;
N-((trans)-2-(3'-(trifluoromethyl)-[1,1'-biphenyl]-4-yl)cyclopropyl)pyrrolidin-3-amine;
N-((trans)-2-(4-(benzyloxy)phenyl)cyclopropyl)pyrrolidin-3-amine;
N-((trans)-2-phenylcyclopropyl)azetidin-3-amine;
N-((trans)-2-(3'-(trifluoromethyl)-[1,1'-biphenyl]-4-yl)cyclopropyl)azetidin-3-amine;
N-((trans)-2-(4-(benzyloxy)phenyl)cyclopropyl)azetidin-3-amine;
N-((trans)-2-phenylcyclopropyl)azepan-3-amine;
N-((trans)-2-phenylcyclopropyl)-8-azabicyclo[3.2.1]octan-3-amine;
N-((trans)-2-phenylcyclopropyl)-3-azabicyclo[3.2.1]octan-8-amine;
N-((trans)-2-phenylcyclopropyl)decahydroquinolin-4-amine;
N-((trans)-2-phenylcyclopropyl)-1,2,3,4-tetrahydroquinolin-4-amine;
N-((trans)-2-phenylcyclopropyl)-3-azaspiro[5.5]undecan-9-amine;
N-((trans)-2-phenylcyclopropyl)-2-azaspiro[4.5]decan-8-amine;
N-((trans)-2-phenylcyclopropyl)-2,3-dihydrospiro[indene-1,4'-piperidin]-3-amine;
N-((1S,2R)-2-(4-(benzyloxy)phenyl)cyclopropyl)piperidin-4-amine;
N-((1R,2S)-2-(4-(benzyloxy)phenyl)cyclopropyl)piperidin-4-amine;
N-((1S,2R)-2-(pyridin-3-yl)cyclopropyl)piperidin-4-amine;
N-((1R,2S)-2-(pyridin-3-yl)cyclopropyl)piperidin-4-amine;
N-((1S,2S)-2-(thiazol-5-yl)cyclopropyl)piperidin-4-amine;
N-((1R,2R)-2-(thiazol-5-yl)cyclopropyl)piperidin-4-amine;
N-((1S,2R)-2-(3'-(trifluoromethyl)-[1,1'-biphenyl]-4-yl)cyclopropyl)piperidin-4-amine;
N-((1R,2S)-2-(3'-(trifluoromethyl)-[1,1'-biphenyl]-4-yl)cyclopropyl)piperidin-4-amine;
N-((trans)-2-phenylcyclopropyl)-7-azaspiro[3.5]nonan-2-amine;
N-(2-(o-tolyl)cyclopropyl)piperidin-4-amine;
N-(2-(2-fluorophenyl)cyclopropyl)piperidin-4-amine;
N-(2-(3,4-difluorophenyl)cyclopropyl)piperidin-4-amine;
N-(2-(4-methoxyphenyl)cyclopropyl)piperidin-4-amine;
N-(2-(naphthalen-2-yl)cyclopropyl)piperidin-4-amine;
N-(2-methyl-2-phenylcyclopropyl)piperidin-4-amine;
N-(6-methoxy-4'-((trans)-2-(piperidin-4-ylamino)cyclopropyl)-[1,1'-biphenyl]-3-yl)methanesulfonamide;
N-(4'-((trans)-2-(piperidin-4-ylamino)cyclopropyl)-[1,1'-biphenyl]-3-yl)propane-2-sulfonamide;
1-(methylsulfonyl)-N-((trans)-2-phenylcyclopropyl)piperidin-4-amine;
1-(4-(((trans)-2-(4-bromophenyl)cyclopropyl)amino)piperidin-1-yl)ethanone;
4-(((trans)-2-(4-bromophenyl)cyclopropyl)amino)piperidine-1-carboxamide;
N-((trans)-2-(4-bromophenyl)cyclopropyl)tetrahydro-2H-pyran-4-amine;
2,2,6,6-tetramethyl-N-((trans)-2-phenylcyclopropyl)piperidin-4-amine;
1-methyl-N-((trans)-2-phenylcyclopropyl)piperidin-4-amine;
1-isopropyl-N-((trans)-2-phenylcyclopropyl)piperidin-4-amine;
N-((trans)-2-phenylcyclopropyl)-1-(2,2,2-trifluoroethyl)piperidin-4-amine;
N-((trans)-2-phenylcyclopropyl)-1-(pyridin-4-yl)piperidin-4-amine;
4-(((trans)-2-(4-bromophenyl)cyclopropyl)amino)tetrahydro-2H-thiopyran 1,1-dioxide;
N-((trans)-2-fluoro-2-phenylcyclopropyl)piperidin-4-amine;
N-((1S,2S)-2-fluoro-2-phenylcyclopropyl)piperidin-4-amine;
N-((1R,2R)-2-fluoro-2-phenylcyclopropyl)piperidin-4-amine;

N-((trans)-2-(naphthalen-2-yl)cyclopropyl)piperidin-4-amine;
N-((trans)-2-methyl-2-phenylcyclopropyl)piperidin-4-amine;
N-((trans)-2-(o-tolyl)cyclopropyl)piperidin-4-amine;
N-((trans)-2-(2-fluorophenyl)cyclopropyl)piperidin-4-amine;
N-((trans)-2-(3,4-difluorophenyl)cyclopropyl)piperidin-4-amine;
N-((trans)-2-(4-methoxyphenyl)cyclopropyl)piperidin-4-amine;
or a pharmaceutically acceptable salt thereof.

Compounds of formula (K) can be prepared by the methods disclosed in WO2013/057320, the disclosure of which is incorporated by reference herein in its entirety.

In the methods and uses according to the invention, the KDM1A inhibitor can be a compound of formula (L) or an enantiomer, a diastereomer or a mixture of stereoisomers (such as a racemic mixture or a diastereomer mixture) thereof, or a pharmaceutically acceptable salt or solvate thereof:

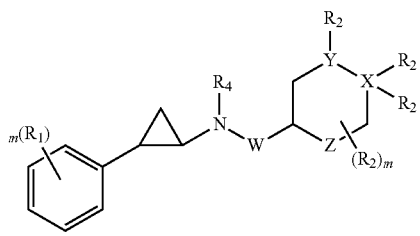

(L)

wherein
$R_1$ is selected from the group consisting of: $C_1$-$C_6$alkyl, —$NSO_2Me$, —$NSO_2Ph$, arylalkoxy, $C_3$-$C_7$cycloalkyl, —$NC(O)R_a$, 1-methyl-1H-pyrazol-4-yl, hydroxyl, $C_1$-$C_4$alkoxy, halogen, amide, amino, substituted amino, and —$C(O)OR_a$;
$R_2$ is hydrogen or COOH;
each $R_3$ is independently selected from the group consisting of: aryl, heteroaryl, hydrogen, $C_1$-$C_6$alkyl, —$SO_2R_a$, —$NC(O)R_a$, —$CH_2C(O)OR_a$, —$C(O)OR_a$, —$C(O)R_a$, —$C(O)NR_aR_b$, substituted amino, amino, urea, amide, sulfonamide, arylalkyl, and heteroarylalkyl;
each $R_a$ is independently hydrogen, phenyl, phenylmethyl, 3,5-dimethylisoxazol-4-yl, 1,2-dimethyl-1H-imidazol-4-yl, $C_3$-$C_7$cycloalkyl, $C_1$-$C_6$alkyl, $C_1$-$C_4$alkoxy, $C_1$-$C_3$alkylamino, or —NHPh;
$R_b$ is hydrogen or $C_1$-$C_3$alkyl, or when attached to the same atom; or
$R_a$ and $R_b$ together form a 5- or 6-membered heterocycloalkyl ring;
$R_4$ is $C_1$-$C_4$alkyl, acyl, —$C(O)CF_3$ or hydrogen;
W is —$(CH_2)_{1-4}$, or —$CH(R_c)(CH_2)_{0-3}$, in which $R_c$ is CN or $C_1$-$C_4$alkyl;
Y is N or C;
X is N or C;
Z is 0 or $(CH_2)_q$, wherein q is 0-2, when q is 0, Z represents a bond;
m is 0-3, n is 0-3;
provided that when Z is 0, Y is N and X is C;
also provided that when X is C, at least one of the $R_3$ groups attached to X is not hydrogen.

Compounds of formula (L) can be prepared by the methods disclosed in WO2012/135113, the disclosure of which is incorporated by reference herein in its entirety.

Preferably, the compound of formula (L) is a compound from examples 1 to 150 in WO2012/135113 or a pharmaceutically acceptable salt thereof. Still more preferably, the compound of formula (L) is 4-((4-((((1R,2S)-2-phenylcyclopropyl)amino)methyl)piperidin-1-yl)methyl)benzoic acid or a pharmaceutically acceptable salt thereof.

In the methods and uses according to the invention, the KDM1A inhibitor can be a compound of formula (M) or an enantiomer, a diastereomer or a mixture of stereoisomers (such as a racemic mixture or a diastereomer mixture) thereof, or a pharmaceutically acceptable salt or solvate thereof:

A compound represented by the formula (M):

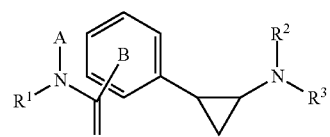

(M)

wherein A is a hydrocarbon group optionally having substituent(s), or a heterocyclic group optionally having substituent(s);
B is a benzene ring optionally having further substituent(s);
$R^1$, $R^2$ and $R^3$ are each independently a hydrogen atom, a hydrocarbon group optionally having substituent(s), or
a heterocyclic group optionally having substituent(s);
A and $R^1$ are optionally bonded to each other to form, together with the adjacent nitrogen atom, a cyclic group optionally having substituent(s); and
$R^2$ and $R^3$ are optionally bonded to each other to form, together with the adjacent nitrogen atom, a cyclic group optionally having substituent(s).

Compounds of formula (M) can be prepared by the methods disclosed in WO2014/058071, the disclosure of which is incorporated by reference herein in its entirety.

Preferably, the compound of formula (M) is a compound from examples 1 to 273 in WO2014/058071 or a pharmaceutically acceptable salt thereof. More preferably, the compound of formula (M) is 3-(trans-2-((cyclopropylmethyl)amino)cyclopropyl)-N-(5-methyl-1,2-oxazol-3-yl)benzamide, 3-(trans-2-((1-cyclopropylpiperidin-4-yl)amino)cyclopropyl)-N-(5-methyl-1,3,4-thiadiazol-2-yl)benzamide, 3-(trans-2-((cyclobutylamino)cyclopropyl)-N-(tetrahydro-2H-pyran-4-yl)benzamide, or a salt thereof.

In the methods and uses according to the invention, the KDM1A inhibitor can be a compound of formula (N) or an enantiomer, a diastereomer or a mixture of stereoisomers (such as a racemic mixture or a diastereomer mixture) thereof, or a pharmaceutically acceptable salt or solvate thereof:

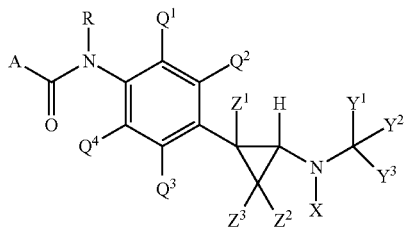

wherein A is a hydrocarbon group optionally having substituent(s), or a heterocyclic group optionally having substituent(s);

R is a hydrogen atom, a hydrocarbon group optionally having substituent(s), or a heterocyclic group optionally having substituent(s); or A and R are optionally bonded to each other to form a ring optionally having substituent(s);

$Q^1$, $Q^2$, $Q^3$ and $Q^4$ are each independently a hydrogen atom or a substituent; $Q^1$ and $Q^2$, and $Q^3$ and $Q^4$, are each optionally bonded to each other to form a ring optionally having substituent(s);

X is a hydrogen atom, an acyclic hydrocarbon group optionally having substituent(s), or a saturated cyclic group optionally having substituent(s);

$Y^1$, $Y^2$ and $Y^3$ are each independently a hydrogen atom, a hydrocarbon group optionally having substituent(s), or a heterocyclic group optionally having substituent(s);

X and $Y^1$, and $Y^1$ and $Y^2$, are each optionally bonded to each other to form a ring optionally having substituent(s); and $Z^1$, $Z^2$ and $Z^3$ are each independently a hydrogen atom or a substituent, Compounds of formula (N) can be prepared by the methods disclosed in WO2013/022047, the disclosure of which is incorporated by reference herein in its entirety.

Preferably, the compound of formula (N) is a compound from examples 1 to 166 in WO2013/022047, or a pharmaceutically acceptable salt thereof. More preferably, the compound of formula (N) is N-(4-(trans-2-[(cyclopropylmethyl)amino]cyclopropyl)phenyl)biphenyl-4-carboxamide, N-(4-(trans-2-[(1-methylpiperidin-4-yl)amino]cyclopropyl)phenyl)-3-(trifluoromethyl)benzamide, N-(4-(trans-2-[(cyclopropylmethyl)amino]cyclopropyl)phenyl)-1H-pyrazole-4-carboxamide, or a salt thereof. A particularly preferred compound of formula (N) is N-[4-[2-[(cyclopropylmethylamino)methyl]cyclopropyl]phenyl]-1-methylpyrazole-4-carboxamide (Ex. 163), or a salt thereof.

The KDM1A inhibitor can also be the compound 1-((4-(methoxymethyl)-4-(((1R,2S)-2-phenylcyclopropylamino)methyl)piperidin-1-yl)methyl)cyclobutanecarboxylic acid or a salt thereof, such as the p-toluenesulfonic acid salt. This compound is disclosed in WO2017/27678.

A particularly preferred KDM1A inhibitor for use in the methods of the invention is (trans)-N1-((1R,2S)-2-phenylcyclopropyl)cyclohexane-1,4-diamine, or a salt thereof.

Other preferred LSD1 inhibitors for use in the methods of the invention are:

(−) 5-((((trans)-2-(4-(benzyloxy)phenyl)cyclopropyl)amino)methyl)-1,3,4-oxadiazol-2-amine;

4-((4-((((1R,2S)-2-phenylcyclopropyl)amino)methyl)piperidin-1-yl)methyl)benzoic acid;

and salts thereof.

Preferably, the salts of KDM1A inhibitors as disclosed above are pharmaceutically acceptable salts. As used herein, a "pharmaceutically acceptable salt" is intended to mean a salt that retains the biological effectiveness and/or properties of the parent compound (i.e. the free acid or free base, as applicable) and that is not biologically or otherwise undesirable. Pharmaceutically acceptable salts include salts formed with inorganic or organic bases, and salts formed with inorganic and organic acids. Pharmaceutically acceptable salts are well known in the art.

Exemplary pharmaceutically acceptable salts include those salts prepared by reaction of the compounds of the present invention with a mineral or organic acid, such as hydrochlorides, hydrobromides, sulfates, pyrosulfates, bisulfates, sulfites, bisulfites, phosphates, monohydrophosphates, dihydrophosphates, metaphosphates, pyrophosphates, chlorides, bromides, iodides, nitrates, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, ethane-sulfonates, propanesulfonates, benzenesulfonates, toluenesulfonates, trifluoromethansulfonates, naphthalene-1-sulfonates, naphthalene-2-sulfonates, mandelates, pyruvates, stearates, ascorbates, or salicylates. When the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands such as ammonia, alkylamines, hydroxyalkylamines, lysine, arginine, N-methylglucamine, procaine and the like. The pharmaceutically acceptable salts of the present invention can be prepared from the parent compound which contains a basic or acidic moiety by conventional chemical methods. For example, such salts can be prepared by reacting the free acid or base forms of these compounds with a stoichiometric amount of the appropriate base or acid in a suitable solvent.

It is to be understood that the present invention specifically relates to each and every combination of features or embodiments described herein, including any combination of general and/or preferred features/embodiments. In particular, the invention specifically relates to all combinations of preferred features/embodiments (including all degrees of preference) of the methods and uses provided herein.

Unless otherwise stated, in the definitions of KDM1A inhibitors provided above, particularly in the definitions of compounds of formula (A) to (N), the following definitions apply, when applicable:

Any definition herein may be used in combination with any other definition to describe a composite structural group. By convention, the trailing element of any such definition is that which attaches to the parent moiety. For example, the composite group cyclylC$_{1-8}$ alkyl would represent a cyclyl group attached to the parent molecule through a C$_{1-8}$ alkyl group.

As used herein, the term "acyl" refers to a carbonyl attached to an alkenyl, alkyl, aryl, cycloalkyl, heteroaryl, heterocyclyl, or any other moiety where the atom attached to the carbonyl is carbon. Preferably, the term "acyl" refers to a group of formula —C(=O)R", wherein R" represents alkenyl, alkyl, aryl, cycloalkyl, heteroaryl or heterocyclyl. An "acetyl" group refers to a —C(=O)CH$_3$ group. An "alkylcarbonyl" or "alkanoyl" group refers to an alkyl group attached to the parent molecular moiety through a carbonyl group. Examples of such groups include, but are not limited to, methylcarbonyl or ethylcarbonyl. Examples of acyl groups include, but are not limited to, formyl, alkanoyl or aroyl.

As used herein, the term "alkenyl" refers to a straight-chain or branched-chain hydrocarbon group having one or more double bonds and containing from 2 to 20 carbon atoms. A $C_{2-8}$ alkenyl is an alkenyl group having from 2 to 8 carbon atoms.

As used herein, the term "alkoxy" refers to an alkyl ether group (i.e. a group of formula alkyl-O—), wherein the term alkyl is as defined below. Examples of suitable alkyl ether groups include, but are not limited to, methoxy, ethoxy, n-propoxy, isopropoxy, n-butoxy, iso-butoxy, sec-butoxy, tert-butoxy, or n-pentoxy. The term $C_{1-z}$ alkoxy refers to an alkoxy group wherein the alkyl moiety has from 1 to z carbon atoms; for example a $C_{1-8}$ alkoxy is an alkoxy group wherein the alkyl moiety is $C_{1-8}$ alkyl, i.e. a group of formula $C_{1-8}$ alkyl-O—.

As used herein, the term "alkyl" refers to a straight-chain or branched-chain alkyl group containing from 1 to 20 carbon atoms. A $C_{1-z}$ alkyl is an alkyl from 1 to z carbon atoms; thus, a $C_{1-8}$ alkyl has from 1 to 8 carbon atoms, a $C_{1-4}$ alkyl has from 1 to 4 carbon atoms and a $C_{1-2}$ alkyl has from 1 to 2 carbon atoms. Examples of alkyl groups include, but are not limited to, methyl, ethyl, n-propyl, isopropyl, n-butyl, isobutyl, sec-butyl, tert-butyl, pentyl, isopentyl, neo-pentyl, iso-amyl, hexyl, heptyl, octyl, or nonyl.

As used herein, the term "$C_{1-4}$ alkylene" refers to a $C_{1-4}$ alkyl group attached at two positions, i.e. an alkanediyl group. Examples include, but are not limited to, methylene (i.e. a group of formula —$CH_2$—), ethylene (including ethane-1,2-diyl and ethane-1,1-diyl), propylene (e.g. propane-1,3-diyl, propane-1,2-diyl and propane-1,1-diyl) and butylene (e.g. butane-1,4-diyl, butane-1,3-diyl or butane-1,1-diyl). Accordingly, the term "$C_{1-4}$ alkylene" may refer to a straight-chain or branched-chain alkylene group having from 1 to 4 carbon atoms. A "linear $C_{1-4}$ alkylene" refers to a straight chain alkylene group having from 1 to 4 carbon atoms, i.e. a —$(CH_2)_y$— group wherein y is 1, 2, 3 or 4.

As used herein, the term "alkylamino," refers to an alkyl group attached to the parent molecular moiety through an amino group. Suitable alkylamino groups may be mono- or dialkylated, forming groups including, but not limited to N-methylamino, N-ethylamino, N,N-dimethylamino, N,N-ethylmethylamino, N,N-diethylamino, N-propylamino, and N,N-methylpropylamino.

As used herein, the term "alkynyl" refers to a straight-chain or branched-chain hydrocarbon group having one or more triple bonds and containing from 2 to 20 carbon atoms. A $C_{2-8}$ alkynyl has from 2 to 8 carbon atoms.

Examples of alkynyl groups include, but are not limited to, ethynyl, propynyl, hydroxypropynyl, butyn-1-yl, butyn-2-yl, pentyn-1-yl, 3-methylbutyn-1-yl, or hexyn-2-yl.

As used herein, the term "amido" and "carbamoyl" refers to an amino group as described below attached to the parent molecular moiety through a carbonyl group (e.g., —C(=O)NRR'), or vice versa (—N(R)C(=O)R'). "Amido" and "carbamoyl" encompasses "C-amido" and "N-amido" as defined herein. R and R' are as defined herein.

As used herein, the term "C-amido" refers to a —C(=O)NRR' group with R and R' as defined herein.

As used herein, the term "N-amido" refers to a —N(R)C(=O)R' group with R and R' as defined herein.

As used herein, the term "amino" refers to —NRR', wherein R and R' are independently selected from the group consisting of hydrogen, alkyl, heteroalkyl, aryl, carbocyclyl, and heterocyclyl. Additionally, R and R' may be combined to form a heterocyclyl. Exemplary "amino" groups include, without being limited thereto, —$NH_2$, —$NH(C_{1-4}$ alkyl) and —$N(C_{1-4}$ alkyl)($C_{1-4}$ alkyl).

As used herein, the term "aryl" refers to a carbocyclic aromatic system containing one ring, or two or three rings fused together where in the ring atoms are all carbon. The term "aryl" includes, but is not limited to groups such as phenyl, naphthyl, or anthracenyl. The term "monocyclic aryl" refers to phenyl.

As used herein, the term "arylalkoxy" or "aralkoxy," refers to an aryl group attached to the parent molecular moiety through an alkoxy group. Examples of arylalkoxy groups include, but are not limited to, benzyloxy or phenethoxy.

As used herein, the term "arylalkyl" or "aralkyl," refers to an aryl group attached to the parent molecular moiety through an alkyl group.

As used herein, the term "aryloxy" refers to an aryl group attached to the parent molecular moiety through an oxy (—O—).

As used herein, the term "carbamate" refers to an O-carbamyl or N-carbamyl group as defined herein. An N-carbamyl group refers to —NR—COOR', wherein R and R' are as defined herein. An O-carbamyl group refers to —OCO—NRR', wherein R and R' are as defined herein.

As used herein, the term "carbonyl" when alone includes formyl —C(=O)H and in combination is a —C(=O)— group.

As used herein, the term "carboxyl" or "carboxy" refers to —C(=O)OH or the corresponding "carboxylate" anion, such as is in a carboxylic acid salt.

An "O-carboxy" group refers to a RC(=O)O— group, where R is as defined herein.

A "C-carboxy" group refers to a —C(=O)OR groups where R is as defined herein.

As used herein, the term "cyano" refers to —CN.

As used herein, the term "carbocyclyl" refers to a saturated or partially saturated monocyclic or a fused bicyclic or tricyclic group wherein the ring atoms of the cyclic system are all carbon and wherein each cyclic moiety contains from 3 to 12 carbon atom ring members. "Carbocyclyl" encompasses benzo fused to a carbocyclyl ring system. One group of carbocyclyls have from 5 to 7 carbon atoms. Examples of carbocyclyl groups include, but are not limited to, cyclopropyl, cyclobutyl, cyclopentyl, cyclohexyl, cycloheptyl, tetrahydronaphthyl, indanyl, octahydronaphthyl, 2,3-dihydro-1H-indenyl, or adamantyl.

As used herein, the term "cycloalkyl", unless otherwise specified, refers to a saturated monocyclic, bicyclic or tricyclic group wherein the ring atoms of the cyclic system are all carbon and wherein each cyclic moiety contains from 3 to 12 carbon atom ring members. A $C_{3-6}$ cycloalkyl is a cycloalkyl that has from 3 to 6 carbon atoms, i.e. cyclopropyl, cyclobutyl, cyclopentyl and cyclohexyl. A cycloalkyl containing from 4 to 7 C atoms includes cyclobutyl, cyclopentyl, cyclohexyl and cycloheptyl. Examples of cycloalkyl groups include, but are not limited to, cyclopropyl, cyclobutyl, cyclopentyl, cyclohexyl, cycloheptyl, or adamantyl.

As used herein, the term "cycloalkenyl" refers to a partially saturated monocyclic, bicyclic or tricyclic group wherein the ring atoms of the cyclic system are all carbon and wherein each cyclic moiety contains from 3 to 12 carbon atom ring members. One group of carboalkenyls has from 5 to 7 carbon atoms. Examples of cycloalkenyl groups include, but are not limited to, cyclobutenyl, cyclopentenyl, or cyclohexenyl.

As used herein, the term "cyclyl" refers to an aryl, heterocyclyl, or carbocyclyl group as defined herein.

As used herein, the term "cyclyl$C_{1-8}$ alkyl" refers to a $C_{1-8}$ alkyl as defined above wherein one hydrogen atom in the $C_{1-8}$ alkyl group has been replaced with one cyclyl group as defined above.

As used herein, the term "halo" or "halogen" refers to fluorine, chlorine, bromine, or iodine.

As used herein, the term "haloalkoxy" refers to a haloalkyl group (as defined below) attached to the parent molecular moiety through an oxygen atom. A halo$C_{1-8}$ alkoxy group refers to a haloalkoxy group wherein the haloalkyl moiety has from 1 to 8 C atoms. Examples of haloalkoxy groups include, but are not limited to, trifluoromethoxy, 2-fluoroethoxy, pentafluoroethoxy, or 3-chloropropoxy.

As used herein, the term "haloalkyl" refers to an alkyl group having the meaning as defined above wherein one or more hydrogens are replaced with a halogen. A halo$C_{1-8}$ alkyl group refers to a haloalkyl group wherein the alkyl moiety has from 1 to 8 C atoms. Specifically embraced are monohaloalkyl, dihaloalkyl or polyhaloalkyl groups. A monohaloalkyl group, for one example, may have an iodo, bromo, chloro or fluoro atom within the group. Dihalo or polyhaloalkyl groups may have two or more of the same halo atoms or a combination of different halo groups. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl or dichloropropyl.

As used herein, the term "heteroalkyl" refers to a straight or branched alkyl chain, wherein one, two, or three carbons forming the alkyl chain are each replaced by a heteroatom independently selected from the group consisting of O, N, and S, and wherein the nitrogen and/or sulfur heteroatom(s) (if present) may optionally be oxidized and the nitrogen heteroatom(s) (if present) may optionally be quaternized. The heteroatom(s) O, N and S may, for example, be placed at the end(s) or at an interior position of the heteroalkyl group, i.e., the heteroalkyl may be bound to the remainder of the molecule via a heteroatom or a carbon atom. Up to two heteroatoms may be consecutive, such as, for example, —CH$_2$—NH—OCH$_3$. Accordingly, a further example for a "heteroalkyl" group is a straight or branched alkyl group, in which two consecutive carbon atoms are replaced by the heteroatoms S and N, respectively, and the sulfur heteroatom is furthermore oxidized, resulting in moieties such as, e.g., —S(=O)$_2$—NH$_2$, —S(=O)$_2$—NH(alkyl) or —S(=O)$_2$—N(alkyl)(alkyl).

As used herein, the term "heteroalkylene" refers to a heteroalkyl group attached at two positions. Examples include, but are not limited to, —CH$_2$OCH$_2$—, —CH$_2$SCH$_2$—, and —CH$_2$NHCH$_2$—, —CH$_2$S—, or —CH$_2$NHCH(CH$_3$)CH$_2$—.

Accordingly, the term "heteroalkylene" may, e.g., refer to a straight or branched alkylene group (i.e., a straight or branched alkanediyl group) having from 1 to 6 carbon atoms, wherein 1,2 (if present) or 3 (if present) of said carbon atoms are each replaced by a heteroatom independently selected from O, N or S. It is to be understood that the presence of hydrogen atoms will depend on the valence of the heteroatom replacing the respective carbon atom. If, for example, the carbon atom in a —CH$_2$— group is replaced by O or S, the resulting group will be —O— or —S—, respectively, while it will be —N(H)— when the carbon atom replaced by N. Likewise, if the central carbon atom in a group —CH$_2$—CH(—CH$_3$)—CH$_2$— is replaced by N, the resulting group will be —CH$_2$—N(—CH$_3$)—CH$_2$—. An example for a "heteroalkylene" group is a straight or branched alkylene group, in which two consecutive carbon atoms are replaced by the heteroatoms S and N, respectively, and the sulfur heteroatom is furthermore oxidized, resulting in moieties such as, e.g., —S(=O)$_2$—N(H)— or —S(=O)$_2$—N(alkyl)-. Accordingly, the groups —S(=O)$_2$—N(H)— and —S(=O)$_2$—N(alkyl)- (e.g., —S(=O)$_2$—N($C_1$-$C_6$ alkyl)-) are exemplary "heteroalkylene" groups.

As used herein, the term "hetero$C_{1-4}$ alkylene" refers to a straight or branched $C_{1-4}$ alkylene group (i.e., a straight or branched $C_{1-4}$ alkanediyl group) linked to one heteroatom selected from O, N and S and also refers to a straight or branched $C_{1-4}$ alkylene group wherein one or more (e.g., 1, 2 (if present) or 3 (if present)) of the carbon atoms of said alkylene group are each replaced by a heteroatom independently selected from O, N or S. The nitrogen and/or sulfur heteroatom(s) (if present) may optionally be oxidized and the nitrogen heteroatom(s) (if present) may optionally be quaternized. The heteroatom(s) O, N and S may be placed at the end(s) and/or at an interior position of the hetero$C_{1-4}$ alkylene group. It is to be understood that the presence of hydrogen atoms will depend on the valence of the heteroatom replacing the respective carbon atom. If, for example, the carbon atom in a —CH$_2$— group is replaced by O or S, the resulting group will be —O— or —S—, respectively, while it will be —N(H)— when the carbon atom is replaced by N. Likewise, if the central carbon atom in a group —CH$_2$—CH(—CH$_3$)—CH$_2$— is replaced by N, the resulting group will be —CH$_2$—N(—CH$_3$)—CH$_2$—. An example for a "hetero$C_{1-4}$ alkylene" group is a straight or branched $C_{1-4}$ alkylene group, in which two consecutive carbon atoms are replaced by the heteroatoms S and N, respectively, and the sulfur heteroatom is furthermore oxidized, resulting in moieties such as, e.g., —S(=O)$_2$—N(H)— or —S(=O)$_2$—N(CH$_3$)—.

As used herein, the term "heteroaryl" refers to a 5 to 6 membered unsaturated monocyclic ring, or a fused bicyclic or tricyclic ring system in which the rings are aromatic and in which at least one ring contains at least one heteroatom selected from the group consisting of O, S, and N. Preferred heteroaryl groups are 5- to 6-membered monocyclic or 9- to 10-membered bicyclic heteroaryl groups. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocyclyl" or "heterocycle" each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitrogen or sulfur atoms may be oxidized (e.g., —N=O, —S(=O)—, or —S(=O)$_2$—).

Additionally, 1, 2, or 3 of the carbon atoms of the heterocyclyl may be optionally oxidized (e.g., to give an oxo group or =O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl.

Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocycloalkyl" refers to a heterocyclyl group that is not fully unsaturated e.g., one or more of the rings systems of a heterocycloalkyl is not aromatic. Examples of heterocycloalkyls include piperazinyl, morpholinyl, piperidinyl, or pyrrolidinyl.

As used herein, the term "hydroxyl" or "hydroxy" refers to —OH.

As used herein, the term "hydroxyalkyl," as used herein, refers to a hydroxyl group attached to the parent molecular moiety through an alkyl group.

As used herein, the term "hydroxy$C_{1-3}$ alkyl" refers to a $C_{1-8}$ alkyl group, wherein one or more hydrogen atoms (preferably one or two) have been replaced by hydroxy groups.

As used herein, the term "$R^{12}R^{13}N$—$C_{1-3}$ alkyl" refers to a $C_{1-8}$ alkyl group, wherein one or more hydrogen atoms (preferably one or two, more preferably one) have been replaced by —$NR^{12}R^{13}$.

As used herein, the phrase "in the main chain," refers to the longest contiguous or adjacent chain of carbon atoms starting at the point of attachment of a group to the compounds of any one of the formulas disclosed herein.

As used herein, the term phrase "linear chain of atoms" refers to the longest straight chain of atoms independently selected from carbon, nitrogen, oxygen and sulfur.

As used herein, the term "lower" where not otherwise specifically defined, means containing from 1 to and including 6 carbon atoms.

As used herein, the term "lower aryl," means phenyl or naphthyl.

As used herein, the term "nitro" refers to —$NO_2$.

As used herein, the term "saturated" in relation to a ring means that the ring does not contain any unsaturation.

As used herein, the terms "sulfonate" "sulfonic acid" and "sulfonic" refer to the —$SO_3H$ group and its anion as the sulfonic acid is used in salt formation.

As used herein, the term "sulfanyl," to —S—.

As used herein, the term "sulfinyl" refers to —S(=O)(R), with R as defined herein.

As used herein, the term "sulfonyl" refers to —S(=O)$_2$R, with R as defined herein.

As used herein, the term "sulfonamide" refers to an N-sulfonamido or S-sulfonamido group as defined herein.

As used herein, the term "N-sulfonamido" refers to a RS(=O)$_2$N(R')— group with R and R' as defined herein.

Preferred N-sulfonamido groups are —NHSO$_2$R, wherein R is as defined herein, preferably R is alkyl, cycloalkyl, heteroalkyl, aryl, heteroaryl or heterocycloalkyl, more preferably R is alkyl, aryl, heteroaryl or heterocycloalkyl, wherein said alkyl, said cycloalkyl, said heteroalkyl, said aryl, said heteroaryl and said heterocycloalkyl are each optionally substituted. The optional substituents on said alkyl, said cycloalkyl, said heteroalkyl, said aryl, said heteroaryl and said heterocycloalkyl may be selected independently from lower alkyl, lower alkenyl, lower alkynyl, lower alkanoyl, lower heteroalkyl, lower heterocycloalkyl, lower haloalkyl, lower cycloalkyl, phenyl, aryl, heteroaryl, pyridyl, aryloxy, lower alkoxy, lower haloalkoxy, oxo, lower acyloxy, carbonyl, carboxyl, lower alkylcarbonyl, lower carboxyester, lower carboxamido, cyano, halogen, hydroxyl, amino, amido, nitro, thiol, lower alkylthio, lower haloalkylthio, lower perhaloalkylthio, arylthio, sulfonate, sulfonic acid, trisubstituted silyl, $N_3$, SH, SCH$_3$, C(O)CH$_3$, CO$_2$CH$_3$, CO$_2$H, carbamate, and urea. Preferably, the optional substituents are independently selected from hydroxyl, halo, alkyl, alkoxy, haloalkyl, haloalkoxy, —N(C$_{1-3}$ alkyl)$_2$, —NH(C$_{1-3}$ alkyl), —NHC(=O)(C$_{1-3}$ alkyl), —C(=O)OH, —C(=O)O(C$_{1-3}$ alkyl), —C(=O)(C$_{1-3}$ alkyl), —C(=O)NH$_2$, —C(=O)NH(C$_{1-3}$ alkyl), —C(=O)NH(cycloalkyl), —C(=O)N(C$_{1-3}$ alkyl)$_2$, —S(=O)$_2$(C$_{1-3}$ alkyl), —S(=O)$_2$NH$_2$, —S(=O)$_2$N(C$_{1-3}$ alkyl)$_2$, —S(=O)$_2$NH(C$_{1-3}$ alkyl), —CHF$_2$, —OCF$_3$, —OCHF$_2$, —SCF$_3$, —CF$_3$, —CN, —NH$_2$, —NO$_2$, or tetrazolyl. Particularly preferred N-sulfonamido groups are —NHSO$_2$R, wherein R is alkyl, cycloalkyl, heteroalkyl, aryl, heteroaryl or heterocycloalkyl, and preferably R is alkyl, aryl, heteroaryl or heterocycloalkyl, and —NHSO$_2$ (optionally substituted aryl). Still more preferred N-sulfonamido groups are —NHSO$_2$alkyl and —NHSO$_2$ (optionally substituted aryl).

Exemplary, non-limiting N-sulfonamido groups are —NHSO$_2$alkyl such as —NHSO$_2$CH$_3$, —NHSO$_2$CH$_2$CH$_3$ or —NHSO$_2$ (isopropyl), and —NHSO$_2$ (optionally substituted aryl) such as —NHSO$_2$-phenyl, —NHSO$_2$-(2-cyanophenyl), —NHSO$_2$-(3-cyanophenyl), —NHSO$_2$-(4-cyanophenyl), —NHSO$_2$-(2-aminophenyl), —NHSO$_2$-(3-aminophenyl) or —NHSO$_2$-(4-aminophenyl). Other exemplary N-sulfonamido groups are —NHSO$_2$ (optionally substituted heterocycloalkyl) such as —NHSO$_2$-(piperazin-1-yl) and —NHSO$_2$ (optionally substituted heteroaryl) such as —NHSO$_2$-(optionally substituted pyridyl) like —NHSO$_2$-(3-pyridyl) or —NHSO$_2$-(6-amino-3-pyridyl).

As used herein, the term "S-sulfonamido" refers to a —S(=O)$_2$NRR', group, with R and R' as defined herein.

As used herein, the term "urea" refers to a —N(R)C(=O)N(R)(R') group wherein R and R' are as defined herein.

As used herein, "hydrogen bonding group" refers to a substituent group, which is capable of taking part in a non-covalent bonding between hydrogen and another atom (usually nitrogen or oxygen). Examples include, but are not limited to, —NH$_2$, —OH, amido, —S(O)$_2$NH$_2$, —C(=O)NH$_2$, —CH$_2$—C(=O)NH$_2$,— and —CH$_2$—NH$_2$. Other non-limiting examples include NHC(=O)CH$_3$ or —NHCH$_3$.

As used herein, the term "amide isostere" refers to a monocyclic or bicyclic ring system that is isosteric or bioisosteric with an amide moiety. Examples of amide isosteres include but are not limited to those disclosed in, e.g., Meanwell (2011) J. Med. Chem. PMID: 21413808, The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl. Both unsubstituted and substituted forms of the above groups are encompassed.

Whether an R group has a number designation or not, every R group, including R, R' and $R^z$ where z=(1, 2, 3, . . . z), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(=O)N(R)— may be attached to the parent moiety at either the carbon or the nitrogen.

As used herein, the term "optionally substituted" means the preceding or anteceding group may be substituted or unsubstituted. When substituted and unless otherwise specified, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower cycloalkyl, phenyl, aryl, heteroaryl, pyridyl, aryloxy, lower alkoxy, lower haloalkoxy, oxo, lower acyloxy, carbonyl, carboxyl, lower alkylcarbonyl, lower carboxyester, lower carboxamido, cyano, halogen, hydroxyl, amino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, carbamate, and urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." In one specific definition, the optional substituents are chosen from hydroxyl, halo, alkyl, alkoxy, haloalkyl, haloalkoxy, —N($C_{1-3}$ alkyl)$_2$, —NH($C_{1-3}$ alkyl), —NHC(=O)($C_{1-3}$ alkyl), —C(=O)OH, —C(=O)O($C_{1-3}$ alkyl), —C(=O)($C_{1-3}$ alkyl), —C(=O)$NH_2$, —C(=O)NH($C_{1-3}$ alkyl), —C(=O)NH(cycloalkyl), —C(=O)N($C_{1-3}$alkyl)$_2$, —S(=O)$_2$($C_{1-3}$ alkyl), —S(=O)$_2NH_2$, —S(=O)$_2$N($C_{1-3}$alkyl)$_2$, —S(=O)$_2$NH($C_{1-3}$ alkyl), —$CHF_2$, —$OCF_3$, —$OCHF_2$, —$SCF_3$, —$CF_3$, —CN, —$NH_2$, —$NO_2$, or tetrazolyl.

As used herein, the term "optional substituent" denotes that the corresponding substituent may be present or may be absent. Accordingly, a compound having 1, 2 or 3 optional substituents may be unsubstituted or may be substituted with 1, 2 or 3 substituents, which may be the same or different.

In accordance with the above, the present invention in particular relates to:

1. A compound of formula (I)

P-L-Z                        (I)

or a salt thereof,
wherein:
P is a tag or label;
L is a divalent $C_{6-100}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —$NR^1$—, —$NR^1$—C(=O)—, —C(=O)—$NR^1$—, —$NR^1$—C(=O)—$NR^1$—, —$NR^1$—C(=S)—$NR^1$—, —O—C(=O)—$NR^1$—, —$NR^1$—C(=O)—O—, —C(=O)—O—, —O—C(=O)—, —$SO_2$—$NR^1$— and —$NR^1$—$SO_2$—, and wherein L provides a distance of at least 6 atoms between P and Z;
$R^1$ is hydrogen or $C_{1-4}$ alkyl; and
Z is a radical of a KDM1A inhibitor.

2. The compound of item 1, wherein Z is a radical of an irreversible KDM1A inhibitor.

3. The compound of item 1 or 2, wherein Z is a radical of an irreversible KDM1A inhibitor comprising a 2-cyclyl-cyclopropylamino moiety.

4. The compound of any one of items 1 to 3, wherein Z is a radical of an irreversible KDM1A inhibitor disclosed in WO2010/043721, WO2010/084160, WO2011/035941, WO2011/042217, WO2011/131697, WO2012/013727, WO2012/013728, WO2012/045883, WO2013/057320, WO2013/057322, WO2012/135113, WO2013/022047, WO2014/058071, WO2010/143582, US2010/0324147, WO2011/131576, WO2014/084298, WO2014/086790, WO2014/164867, WO2015/021128, WO2015/123408, WO2015/123424, WO2015/123437, WO2015/123465, WO2015/156417 or WO2015/181380.

5. The compound of any one of items 1 to 3, wherein Z is a group of formula Z1

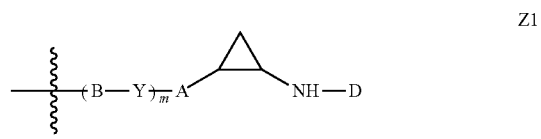

wherein:
A is aryl or heteroaryl, wherein said aryl or said heteroaryl is optionally substituted;
B is aryl, heteroaryl or heterocycloalkyl, wherein B is optionally substituted;
m is 0 or 1;
Y is a bond, —($C_{1-4}$ alkylene)-O—, —($C_{1-4}$ alkylene)-$NR^2$—, —($C_{0-4}$ alkylene)-C(=O)—$NR^2$—, or —($C_{0-4}$ alkylene)-$NR^2$—C(=O)—;
$R^2$ is hydrogen or $C_{1-4}$ alkyl;

D is hydrogen, —(C$_{1-4}$ alkylene)-CO—NR$^3$R$^4$, cyclyl or —(C$_{1-4}$ alkylene)-cyclyl, wherein cyclyl and the cyclyl moiety in the —(C$_{1-4}$ alkylene)-cyclyl are each optionally substituted;

R$^3$ and R$^4$ are each independently selected from hydrogen, C$_{1-4}$ alkyl and —(C$_{0-4}$ alkylene)-cyclyl, wherein the cyclyl moiety in the —(C$_{0-4}$ alkylene)-cyclyl is optionally substituted, or R$^3$ and R$^4$ are linked together to form together with the N atom to which they are bound a heterocyclic ring which may contain one or more additional heteroatoms selected from N, O and S and which is optionally substituted;

and the groups —(B—Y)$_m$-A- and —NH-D on the cyclopropyl ring are in trans configuration.

6. The compound of item 5, wherein D is —(C$_{1-4}$ alkylene)-CO—NR$^3$R$^4$, cyclyl or —(C$_{1-4}$ alkylene)-cyclyl, wherein cyclyl and the cyclyl moiety in the —(C$_{1-4}$ alkylene)-cyclyl are each optionally substituted.

7. The compound of item 5, wherein D is cyclyl or —(C$_{1-4}$ alkylene)-cyclyl, wherein cyclyl and the cyclyl moiety in the —(C$_{1-4}$ alkylene)-cyclyl are each optionally substituted.

8. The compound of item 5, wherein D is cycloalkyl, benzocycloalkyl, heterocycloalkyl or —(C$_{1-4}$ alkylene)-cyclyl, wherein the cycloalkyl, the benzocycloalkyl, the heterocycloalkyl and the cyclyl moiety in the —(C$_{1-4}$ alkylene)-cyclyl are each optionally substituted.

9. The compound of item 5, wherein D is optionally substituted cycloalkyl or optionally substituted benzocycloalkyl.

10. The compound of item 9, wherein D is a group of formula

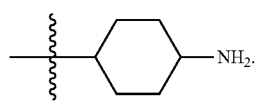 [SMILES: *C1CCC(N)CC1]

11. The compound of item 5, wherein D is optionally substituted heterocycloalkyl.

12. The compound of item 11, wherein D is optionally substituted piperidinyl.

13. The compound of item 11, wherein D is optionally substituted 4-piperidinyl.

14. The compound of item 5, wherein D is —(C$_{1-4}$ alkylene)-cyclyl wherein the cyclyl moiety in the —(C$_{1-4}$ alkylene)-cyclyl is optionally substituted.

15. The compound of item 14, wherein D is —(C$_{1-4}$alkylene)-cycloalkyl wherein the cycloalkyl in the —(C$_{1-4}$ alkylene)-cycloalkyl is optionally substituted.

16. The compound of item 14, wherein D is —(C$_{1-4}$ alkylene)-heterocycloalkyl, wherein the heterocycloalkyl in the —(C$_{1-4}$ alkylene)-heterocycloalkyl is optionally substituted.

17. The compound of item 16, wherein D is —CH$_2$-heterocycloalkyl, preferably —CH$_2$-(4-piperidinyl), wherein the heterocycloalkyl in the —CH$_2$-heterocycloalkyl and the 4-piperidinyl in the —CH$_2$-(4-piperidinyl) are each optionally substituted.

18. The compound of item 17, wherein D is a group of formula

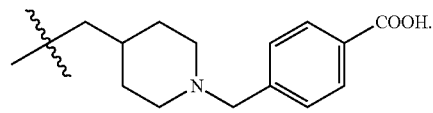 [SMILES: *CC1CCN(Cc2ccc(C(=O)O)cc2)CC1]

19. The compound of item 14, wherein D is —(C$_{1-4}$ alkylene)-heteroaryl, preferably-CH$_2$-heteroaryl, wherein the heteroaryl in the —(C$_{1-4}$ alkylene)-heteroaryl and the heteroaryl in the —CH$_2$-heteroaryl is optionally substituted.

20. The compound of item 19, wherein D is a group of formula

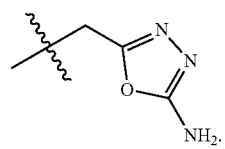 [SMILES: *Cc1nnc(N)o1]

21. The compound of any of items 5 to 20, wherein Y is a bond, —CH$_2$—O—, —C(=O)—NR$^2$—, or —NR$^2$—C(=O)—.

22. The compound of any of items 5 to 21, wherein R$^2$ is hydrogen.

23. The compound of any of items 5 to 22, wherein A is optionally substituted phenyl.

24. The compound of any of items 5 to 22, wherein A is phenyl.

25. The compound of any of items 5 to 24, wherein m is 0.

26. The compound of any of items 5 to 24, wherein m is 1.

27. The compound of item 26, wherein Y is a bond.

28. The compound of any of items 5 to 24 or 26 to 27, wherein B is aryl or heteroaryl, wherein B is optionally substituted.

29. The compound of any of items 5 to 24 or 26 to 28, wherein B is optionally substituted aryl, preferably optionally substituted phenyl.

30. The compound of item 29, wherein B is phenyl.

31. The compound of any one of items 1 to 3 or 5, wherein Z is a group of formula Z2

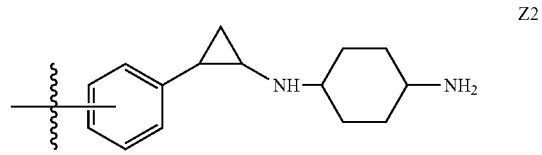

wherein the phenyl ring is optionally substituted, and wherein the substituents on the cyclopropyl ring are in trans configuration.

32. The compound of item 31, wherein Z is a group of formula Z3a or Z3b

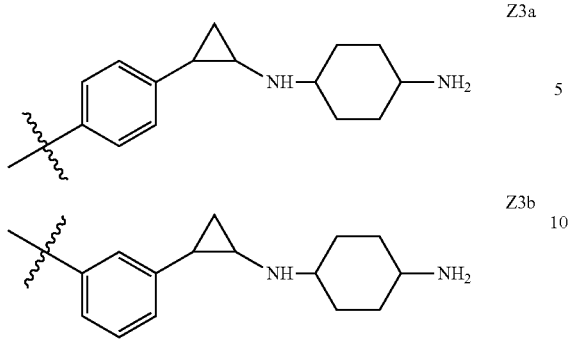

wherein in Z3a and Z3b the phenyl ring is optionally substituted and the substituents on the cyclopropyl ring are in trans configuration 33. The compound of item 31, wherein Z is a group of formula Z4:

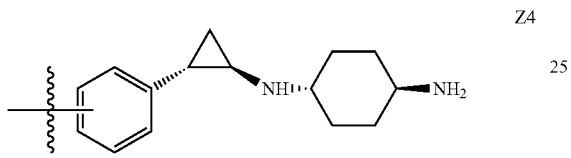

34. The compound of item 33, wherein Z is a group of formula Z5a or Z5b:

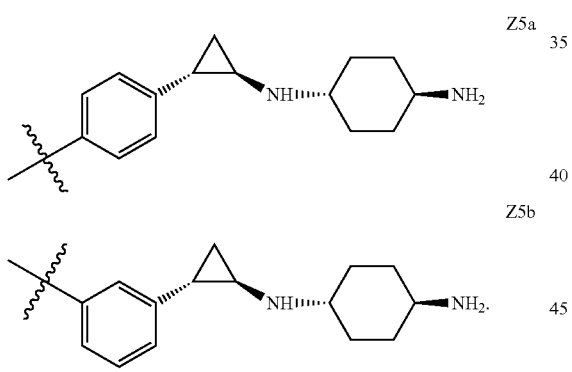

35. The compound of any one of items 1 to 25, wherein L provides a distance between P and Z of 6 to 90 atoms.
36. The compound of any one of items 1 to 35, wherein L is a divalent $C_{30}$-$C_{80}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— and —NR$^1$—SO$_2$—, and wherein L provides a distance between P and Z of 25 to 70 atoms.
37. The compound of any one of items 1 to 36, wherein L is a divalent $C_{40}$-$C_{70}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— and —NR$^1$—SO$_2$—, and wherein L provides a distance between P and Z of 35 to 65 atoms.
38. The compound of any one of items 1 to 35, wherein L comprises a heteroalkylene group of 6 to 70 atoms, preferably of 6 to 50 atoms.
39. The compound of any one of items 1 to 35 wherein L comprises a group of formula (i) or (ii):
   (i) —(CH$_2$CH$_2$O)$_n$—(CH$_2$)$_p$—, wherein n is an integer from 6 to 20, preferably from 8 to 18, and p is an integer from 1 to 5; or
   (ii) —(CH$_2$CH$_2$O)$_x$(CH$_2$)$_q$-G-(CH$_2$CH$_2$O)$_y$(CH$_2$)$_r$, wherein G is —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, or —O—C(=O)—, preferably G is —NR$^1$—C(=O)— or —C(=O)—NR$^1$—, one of x and y is an integer from 1 to 18 and the other from x and y is an integer from 0 to 17 provided that x+y is from 4 to 18, preferably x+y is from 6 to 16, and each of q and r is an integer independently selected from 1 to 5.
40. The compound of item 39, wherein L comprises a group of formula (i) or (ii):
   (i) —(CH$_2$CH$_2$O)$_n$—(CH$_2$)$_p$—, wherein n is an integer from 6 to 20, preferably from 8 to 18, and p is an integer from 1 to 5; or
   (ii) —(CH$_2$CH$_2$O)$_x$(CH$_2$)$_q$-G-(CH$_2$CH$_2$O)$_y$(CH$_2$)$_r$, wherein G is —NR$^1$—C(=O)— or —C(=O)—NR$^1$—, one of x and y is an integer from 1 to 18 and the other from x and y is an integer from 0 to 17 provided that x+y is from 4 to 18, preferably x+y is from 6 to 16, and each of q and r is an integer independently selected from 1 to 5.
41. The compound of any one of items 1 to 35 wherein L comprises a group of formula —(CH$_2$CH$_2$O)$_n$—(CH$_2$)$_p$—, wherein n is an integer from 6 to 20, preferably from 8 to 18, and p is an integer from 1 to 5.
42. The compound of any of items 1 to 41, wherein L comprises a group of formula X$_1$—X$_2$—X$_3$, wherein X$_1$ is linked to the remainder of L and X$_3$ is linked to Z, and wherein:
   X$_1$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$—, —NR$^1$—SO$_2$— or —O—;
   X$_2$ is $C_{0-5}$ alkylene;
   X$_3$ is arylene or heteroarylene, wherein said arylene and said heteroarylene are each optionally substituted.
43. The compound of item 42, wherein X$_1$ is —NHC(=O)—, —C(=O)NH—, —SO$_2$—NH— or —NH—SO$_2$—.

44. The compound of item 42 or 43, wherein $X_1$ is —NHC(=O)— or —C(=O)NH—, preferably —NHC(=O)—.

45. The compound of any of items 42 to 44, wherein $X_3$ is connected to $X_1$—$X_2$ and to Z in a 1,3 disposition.

46. The compound of item 45, wherein $X_3$ is a group of formula:

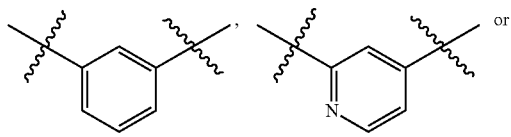

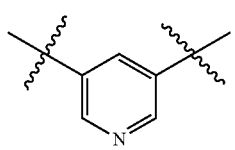

wherein each ring is optionally substituted.

47. The compound of item 46, wherein $X_3$ is a group of formula:

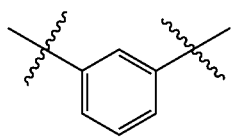

which is optionally substituted.

48. The compound of any one of items 42 to 47, wherein $X_2$ is $C_{1-5}$ alkylene, preferably —(CH$_2$)$_{1-5}$—.

49. The compound of item 42, wherein $X_1$ is —NHC(=O)— or —C(=O)NH—, $X_2$ is $C_{1-5}$ alkylene and $X_3$ is a group of formula:

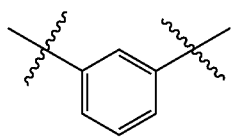

50. The compound of item 42, wherein $X_1$—$X_2$—$X_3$ is a group of formula:

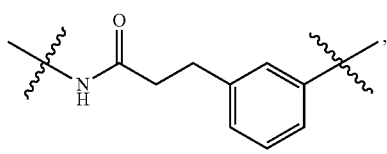 [SMILES: *NC(=O)CCc1cccc(*)c1]

wherein the group is linked to Z through the phenyl ring and to the remainder of L through the N atom.

51. A compound of formula (II)

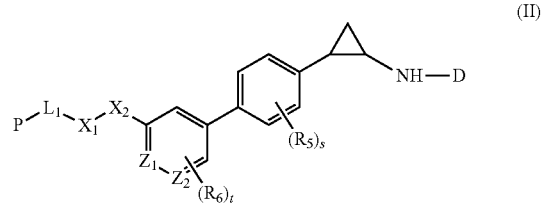

(II)

or a salt thereof,
wherein:
P is a tag or label;
D is cyclyl or —(C$_{1-4}$ alkylene)-cyclyl, wherein cyclyl and the cyclyl moiety in the —(C$_{1-4}$ alkylene)-cyclyl are each optionally substituted;
$L_1$ is a divalent C$_6$-90 hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— and —NR$^1$—SO$_2$—, and wherein $L_1$ provides a distance of at least 3 atoms between P and $X_1$; $R^1$ is hydrogen or C$_{1-4}$ alkyl;
$X_1$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$—, —NR$^1$—SO$_2$— or —O—;
$X_2$ is C$_{0-5}$ alkylene;
one of $Z_1$ and $Z_2$ is CH or N, and the other of $Z_1$ and $Z_2$ is CH;
s and t are each independently selected from 0, 1 and 2;
$R_5$ and $R_6$ are at each occurrence independently selected from C$_{1-4}$ alkyl, halo, —NH$_2$, —NR$^a$R$^c$, —CN, —OH, —OR$^c$, haloC$_{1-4}$ alkyl, cyclyl, cyclylC$_{1-4}$ alkyl-, C$_{1-4}$ alkyl-O—C$_{1-4}$ alkyl;
$R^a$ is selected from hydrogen, C$_{1-4}$ alkyl and haloC$_{1-4}$ alkyl;
$R^c$ is independently selected from C$_{1-4}$alkyl, haloC$_{1-4}$ alkyl, cyclyl, cyclylC$_{1-4}$ alkyl-, and C$_{1-4}$alkyl-O—C$_{1-4}$ alkyl-; and
wherein the phenyl and —NH-D groups on the cyclopropyl ring are in trans configuration.

52. The compound of item 51, which has formula (IIa), or a salt thereof

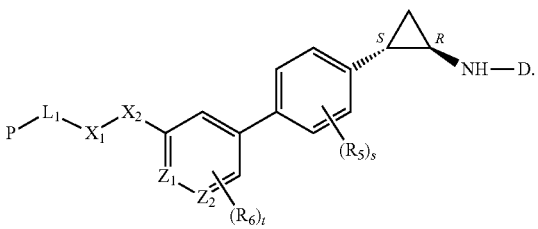

(IIa)

53. The compound of item 51 or 52 wherein D is cycloalkyl, benzocycloalkyl, heterocycloalkyl or —(C$_{1-4}$alkylene)-cyclyl, wherein the cycloalkyl, the benzocycloalkyl, the heterocycloalkyl and the cyclyl moiety in the —(C$_{1-4}$ alkylene)-cyclyl are each optionally substituted.

54. The compound of item 51 or 52 wherein D is optionally substituted cycloalkyl or optionally substituted benzocycloalkyl.

55. The compound of item 51 or 52 wherein D is optionally substituted heterocycloalkyl 56. The compound of item 51 or 52, wherein D is optionally substituted piperidinyl 57. The compound of item 51 or 52, wherein D is optionally substituted 4-piperidinyl 58. The compound of item 51 or 52 wherein D is —(C$_{1-4}$ alkylene)-cyclyl wherein the cyclyl moiety in the —(C$_{1-4}$ alkylene)-cyclyl is optionally substituted.

59. The compound of item 51 or 52 wherein D is —(C$_{1-4}$alkylene)-cycloalkyl wherein the cycloalkyl in the —(C$_{1-4}$ alkylene)-cycloalkyl is optionally substituted.

60. The compound of item 51 or 52 wherein D is —(C$_{1-4}$ alkylene)-heterocycloalkyl, wherein the heterocycloalkyl in the —(C$_{1-4}$ alkylene)-heterocycloalkyl is optionally substituted.

61. The compound of item 51 or 52 wherein D is —CH$_2$-heterocycloalkyl, preferably —CH$_2$-(4-piperidinyl), wherein the heterocycloalkyl in the —CH$_2$-heterocycloalkyl and the 4-piperidinyl in the —CH$_2$-(4-piperidinyl) are each optionally substituted.

62. The compound of item 51 or 52 wherein D is —(C$_{1-4}$ alkylene)-heteroaryl, preferably —CH$_2$-heteroaryl, wherein the heteroaryl in the —(C$_{1-4}$ alkylene)-heteroaryl and the heteroaryl in the —CH$_2$-heteroaryl is optionally substituted.

63. The compound of item 51 or 52 wherein D is a group of formula

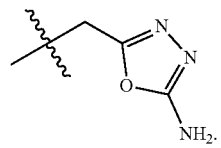 [SMILES: *Cc1nnc(N)o1]

64. The compound of item 51, which has formula (III), or a salt thereof

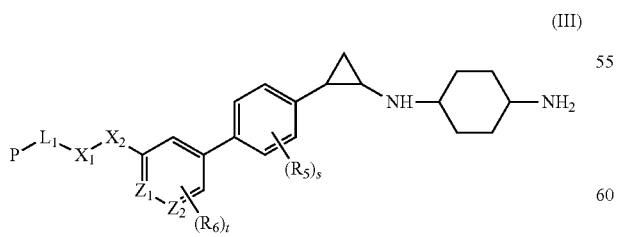

wherein the substituents on the cyclopropyl ring are in trans configuration.

65. The compound of item 64, which has formula (IIIa), or a salt thereof

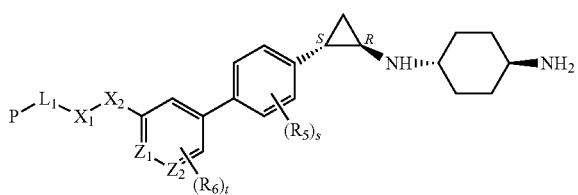

66. The compound of any of items 51 to 65, wherein X$_1$ is —NR$^1$—C(=O)—, —C(=O)—NR$^1$—, —SO$_2$—NR$^1$— or —NR$^1$—SO$_2$—.

67. The compound of item 66 wherein X$_1$ is —NHC(=O)—, —C(=O)NH—, —SO$_2$—NH— or —NH—SO$_2$—.

68. The compound of item 66 wherein X$_1$ is —NHC(=O)— or —C(=O)NH—.

69. The compound of item 66 wherein X$_1$ is —NHC(=O)—.

70. The compound of any of items 51 to 69, wherein X$_2$ is C$_{1-5}$ alkylene, preferably —(CH$_2$)$_{1-5}$—.

71. The compound of any one of items 51 to 65 wherein X$_1$—X$_2$ is a group of formula

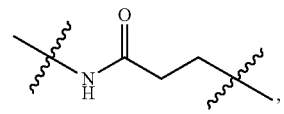 [SMILES: *CCC(=O)N*]

wherein the group is linked to the ring through the carbon atom and to L$_1$ through the N atom.

72. The compound of any of items 51 to 71, wherein each of Z$_1$ and Z$_2$ is CH.

73. The compound of any of items 51 to 72, wherein each of s and t is 0.

74. The compound of any of items 51 to 73, wherein L$_1$ is a group of formula X$_4$—X$_5$, wherein X$_4$ is linked to P and X$_5$ is linked to X$_1$ wherein:
X$_4$ is —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— or —NR$^1$—SO$_2$—; and
X$_5$ is a group of formula (i) or (ii):
(i) —(CH$_2$CH$_2$O)$_n$—(CH$_2$)$_p$—, wherein n is an integer from 6 to 20, preferably from 8 to 18, and p is an integer from 1 to 5; or
(ii) —(CH$_2$CH$_2$O)$_x$—(CH$_2$)$_q$-G-(CH$_2$CH$_2$O)$_y$-(CH$_2$)$_r$—, wherein G is —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, or —O—C(=O)—, preferably G is-NR$^1$—C(=O)— or —C(=O)—NR$^1$—, one of x and y is an integer from 1 to 18 and the other from x and y is an integer from 0 to 17 provided that x+y is from 4 to 18, preferably x+y is from 6 to 16, and each of q and r is an integer independently selected from 1 to 5.

75. The compound of item 74, wherein X$_5$ is a group of formula (i) or (ii):
(i) —(CH$_2$CH$_2$O)$_n$—(CH$_2$)$_p$—, wherein n is an integer from 6 to 20, preferably from 8 to 18, and p is an integer from 1 to 5; or (ii) —(CH$_2$CH$_2$O)$_x$—(CH$_2$)$_q$-G-(CH$_2$CH$_2$O)$_y$(CH$_2$)$_r$, wherein G is —NR$^1$—C(=O)— or —C(=O)—NR$^1$—, one of x and y is an integer from 1 to 18 and the other from x and y is an integer from 0 to 17 provided that x+y is from 4 to 18, preferably x+y is from 6 to 16, and each of q and r is an integer independently selected from 1 to 5.

76. The compound of item 74, wherein X$_5$ is a group of formula —(CH$_2$CH$_2$O)$_n$—(CH$_2$)$_p$—, wherein n is an integer from 6 to 20, preferably from 8 to 18, and p is an integer from 1 to 5.

77. The compound of any one of items 1 to 76, wherein P is a tag.

78. The compound of item 77, wherein P is biotin or a biotin derivative.

79. The compound of any one of items 1 to 76, wherein P is a label.

80. The compound of item 79, wherein P is a fluorescent label.

81. The chemoprobe of item 80, wherein P is fluorescein or a fluorescein derivative.

82. The compound of any one of items 1 to 81, wherein the compound has an IC50 against KDM1A below 1 mcM, more preferably below 500 nM.

83. The compound of any one of items 1 to 82, with a selectivity of at least 10-fold for KDM1A over other FAD-dependent monoamine oxidases.

84. The compound of any one of items 1 to 82, with a selectivity of at least 30-fold for KDM1A over other FAD-dependent monoamine oxidases.

85. The compound of any one of items 1 to 82 with a selectivity of at least 50-fold for KDM1A over other FAD-dependent monoamine oxidases.

86. The compound of item 1 or 51 selected from

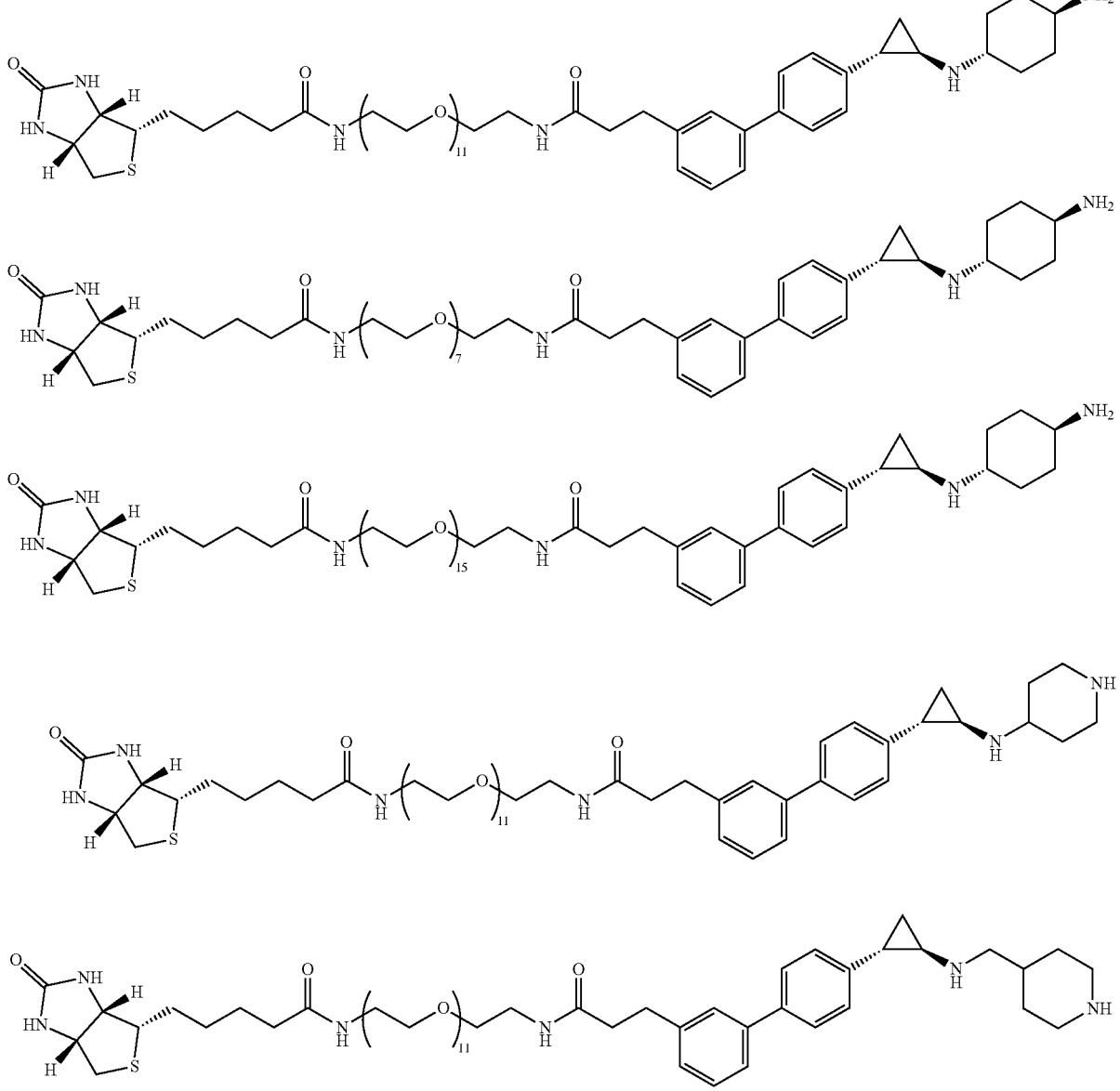

and salts thereof.

87. The compound of item 1 or 51 selected from

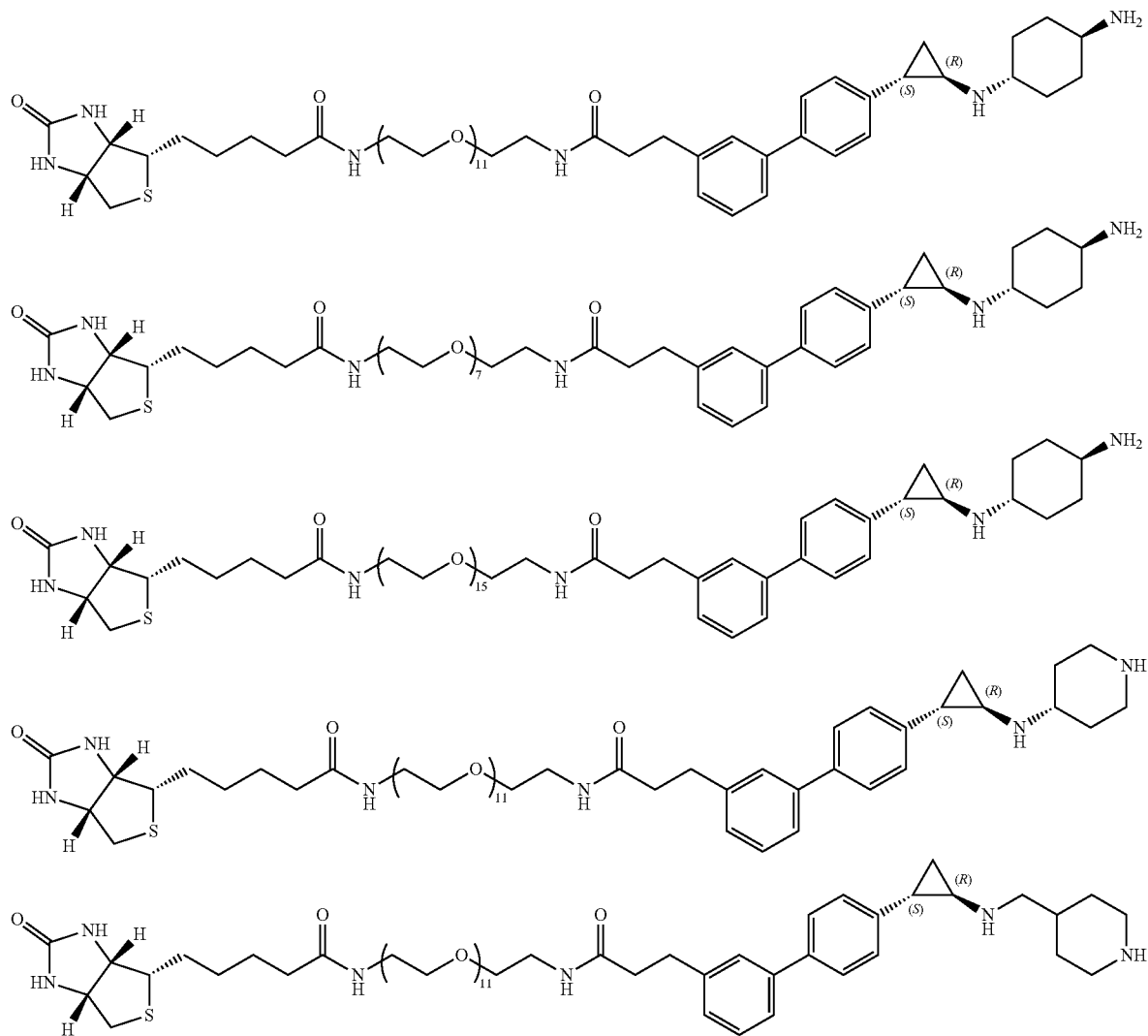

and salts thereof.

88. The compound of item 1 or 51, wherein the compound is

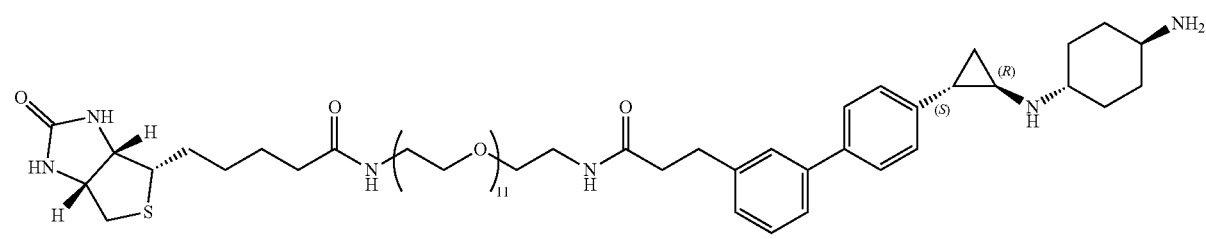

or a salt thereof.

89. A method for determining a level of free KDM1A in a sample or subject, wherein said method comprises
(i) contacting or exposing KDM1A to a chemoprobe, wherein said chemoprobe is a compound of any one of items 1 to 88; and
(ii) determining said level of free KDM1A employing said chemoprobe in said sample or subject.

90. A method for in vitro determining a level of free KDM1A in a sample, wherein said method comprises
(i) contacting or exposing KDM1A to a chemoprobe, wherein said chemoprobe is a compound of any one of items 1 to 88; and (ii) determining said level of free KDM1A employing said chemoprobe in said sample.
91. The method of item 89 or 90, wherein said method further comprises to determine a level of total KDM1A in said sample.
92. The method of any one of items 89 to 91, wherein said method further comprises determining target engagement of a KDM1A inhibitor in said sample.
93. The method of item 92, wherein the determination of said target engagement comprises calculating the ratio between free KDM1A level in the sample and the free KDM1A level in a reference sample.
94 The method of item 92, wherein the determination of said target engagement comprises calculating the ratio between free KDM1A level and total KDM1A level in the sample.
95. The method of item 92, wherein the determination of said target engagement comprises calculating the ratio $R_X/R_{REF}$, wherein $R_X$ is the ratio of the free KDM1A level and the total KDM1A level in the sample and $R_{REF}$ is the ratio of the free KDM1A level and total KDM1A level in the reference sample.
96. The method of item 92, wherein the target engagement is determined as 1 minus the ratio calculated according to any of items 93 to 95, wherein 1 corresponds to full target engagement and 0 corresponds to absence of target engagement.
97. A method for in vitro determining target engagement of an inhibitor of KDM1A in a sample,
wherein said method comprises
(i) contacting or exposing KDM1A to a chemoprobe, wherein said chemoprobe is a compound of any one of items 1 to 88;
(ii) determining a level of free KDM1A employing said chemoprobe in said sample;
(iii) determining a level of free KDM1A in a reference sample;
(iv) calculating the ratio between the free KDM1A level in the sample and the free KDM1A level in the reference sample; and
(v) determining target engagement as 1 minus the ratio calculated in step (iv).
98. A method for in vitro determining target engagement of an inhibitor of KDM1A in a sample,
wherein said method comprises
(i) contacting or exposing KDM1A to a chemoprobe, wherein said chemoprobe is a compound of any one of items 1 to 88;
(ii) determining a level of free KDM1A employing said chemoprobe in said sample;
(iii) determining a level of total KDM1A in said sample;
(iv) calculating the ratio between free KDM1A level and total KDM1A level in the sample; and
(v) determining target engagement as 1 minus the ratio calculated in step (iv).
99. A method for in vitro determining target engagement of an inhibitor of KDM1A in a sample,
wherein said method comprises
(i) contacting or exposing KDM1A to a chemoprobe, wherein said chemoprobe is a compound of any one of items 1 to 88;
(ii) determining a level of free KDM1A employing said chemoprobe in said sample;
(iii) determining a level of total KDM1A in said sample;
(iv) determining a level of free KDM1A employing said chemoprobe in a reference sample;
(v) determining a level of total KDM1A in said reference sample;
(vi) calculating the ratio A/B, wherein A is the ratio of the free KDM1A level and the total KDM1A level in the sample and B is the ratio of the free KDM1A level and the total KDM1A level in the reference sample; and
(vii) determining target engagement as 1 minus the ratio calculated in step (vi).
100. The method according to any one of items 97 to 99, wherein said method is used to assess pharmacodynamics of KDM1A target engagement.
101. A method for in vitro determining a spatial distribution of free KDM1A in a sample,
wherein said method comprises
(i) contacting or exposing KDM1A to a chemoprobe, wherein said chemoprobe is a compound of any one of items 1 to 88; and
(ii) visualizing the spatial distribution of said free KDM1A in said sample by detection of the chemoprobe.
102. The method of item 101, wherein said method further comprises determining the spatial distribution of total KDM1A in said sample.
103. A method for in vitro determining interaction factors of KDM1A,
wherein said method comprises
(i) contacting or exposing a sample to a chemoprobe, wherein said chemoprobe is a compound of any one of items 1 to 88;
(ii) isolating chemoprobe-bound KDM1A-containing complexes;
(iii) identifying said interaction factors of KDM1A, wherein said interaction factors are nucleic acid(s) and/or polypeptide(s).
104. The method of any one of items 89 to 103, wherein said sample is obtained from a subject.
105. The method of item 104, wherein said subject has been administered a KDM1A inhibitor.
106. The method of any one of items 89 to 103, wherein said sample has been exposed or contacted to a KDM1A inhibitor.
107. The method of any one of items 92 to 100, wherein said inhibitor of KDM1A is an irreversible inhibitor of KDM1A.
108. The method of item 107, wherein said irreversible KDM1A inhibitor is a compound disclosed in: WO2010/043721, WO2010/084160, WO2011/035941, WO2011/042217, WO2011/131697, WO2012/013727, WO2012/013728, WO2012/045883, WO2013/057320, WO2013/057322, WO2010/143582, US2010-0324147, WO2011/131576, WO2012/135113, WO2013/022047, WO2014/058071, WO2014/084298, WO2014/086790, WO2014/164867, WO2015/021128; WO2015/123408, WO2015/123424, WO2015/123437, WO2015/123465, WO2015/156417 or WO2015/181380
109. The method of item 108, wherein said irreversible KDM1A inhibitor is (trans)-N1-((1R,2S)-2-phenylcyclopropyl)cyclohexane-1,4-diamine, (−) 5-((((trans)-2-(4-(benzyloxy)phenyl)cyclopropyl)amino)methyl)-1,3,4-oxadiazol-2-amine, or 4-((4-((((1R,2S)-2-phenylcyclopropyl)amino)methyl)piperidin-1-yl) methyl)benzoic acid, or a salt thereof.

110. The method of any one of items 92 to 100, wherein said inhibitor of KDM1A is a reversible inhibitor of KDM1A.
111. The method of item 110, wherein said reversible inhibitor of KDM1A is a compound disclosed in WO2007/021839, WO2008/127734, WO2011/022489, WO2012/034116, WO2012/071469, WO2013/025805, US2015/0065434, WO2013/033688, CN103054869, CN103319466, WO2014/085613, CN103893163A, CN103961340, WO2014/205213, WO2015/031564, WO2015/089192, WO2015/120281, WO2015/134973, WO2015/168466, WO2015/200843, WO2016/003917, WO2016/004105, WO2016/007722, WO2016/007727, WO2016/007731, WO2016/007736, WO2016/034946 and WO2016/037005.
112. The method of any one of items 89 to 111, wherein the chemoprobe is used to capture or detect free KDM1A.
113. The method of 112, wherein P in the chemoprobe is a tag and the chemoprobe is captured or detected by a suitable capture or detection agent.
114. The method of item 112 or 113, wherein the determination of the level of free KDM1A comprises the use of an antibody specific to an epitope of KDM1A.
115. The method of any one of items 112 to 114, wherein the determination of the level of total KDM1A comprises the use of a first antibody specific to an epitope of KDM1A to capture or detect total KDM1A.
116. The method of item 115, wherein the determination of the level of total KDM1A comprises the use of a second antibody specific to an epitope of KDM1A to capture or detect total KDM1A, wherein said epitope of said second antibody is different from said epitope of the first antibody.
117. The method of any one of item 89 to 116 which comprises the use of a protein to capture or detect the tag in the chemoprobe and to determine said level of free KDM1A.
118. The method of item 116, wherein one of said antibodies is directed against an epitope located at the N-terminal region of KDM1A and the other antibody is directed against an epitope located at the the C-terminal region of KDM1A.
119. The method of item 116, wherein one of said antibodies targets epitope EP1, wherein EP1 is located in the N terminal region proximate to proline 60 (P60) of the human KDM1A sequence (UNIPROT ID 060341-1) and is blocked by peptide #LSD1 Blocking Peptide-2184 specific (Cell Signaling).
120. The method of item 119, wherein the other of said antibodies targets epitope EP2, wherein EP2 is located on the C-terminal region and comprises AMYTLPRQATPGVPAQ, corresponding to AA 832-847 of human KDM1A.
121. The method of item 120, wherein the antibodies are mAb-844 and mAb-825, the tag P in the KDM1A chemoprobe is biotin and the protein used to capture the chemoprobe is streptavidin.
122. The method of item 121, wherein the level of total KDM1A is determined by sandwich ELISA and the level of free KDM1A is determined by a KDM1A chemoprobe capture ELISA.
123. The method of item 122, where the ELISA uses chemiluminescent detection.
124. The method of item 101 or 102, where said method further comprises determining the spatial distribution of a downstream KDM1A target in said sample.
125. The method of item 103, wherein said interaction factors of KDM1A are identified by mass spectrometry, antibody microarray or Western Blot analysis.
126. The method of item 103, wherein said interaction factors of KDM1A are identified by qPCR, DNA microarray analysis or next generation sequencing.

The following examples illustrate various aspects of the invention. The examples should, of course, be understood to be merely illustrative of only certain embodiments of the invention and not to constitute limitations upon the scope of the invention.

EXAMPLES

Unless stated otherwise, in the compounds of all Examples of the present specification the stereochemical configuration is defined by the chemical name indicated for the respective compound, even though the drawn structure may represent a more specific configuration. Nevertheless, the invention relates to all stereoisomers of the compounds described and defined herein. Accordingly, the invention encompasses the compounds described in the Examples as defined by their chemical names and, in addition thereto, also the corresponding compounds having the absolute configuration shown in the respective drawn structures.

The following abbreviations have been used:

ACN: acetonitrile, AcOH: acetic acid, aq: aqueous, Boc: tert-butyloxycarbonyl, $(Boc)_2O$: di-tert-butyl dicarbonate, DCE: 1,2-dichloroethane, DCM: dichloromethane, DMF: N,N-dimethylformamide, DMSO: dimethylsulfoxide, DIPEA: N,N-Diisopropylethylamine, $Et_2O$: diethyl ether, EtOAc: ethyl acetate, HATU: 1-[Bis(dimethylamino)methylene]-1H-1,2,3-triazolo[4,5-b]pyridinium 3-oxid hexafluorophosphate, HPLC: high performance liquid chromatography, LC-MS: Liquid chromatography-mass spectrometry, m: multiplet, MeOH: methanol, NMR: nuclear magnetic resonance, $Pd(PPh_3)_4$: Tetrakis(triphenylphosphine)palladium(0), PEG: Polyethylene glycol, Pet ether: petroleum ether, q: quadruplet, Rt: retention time, RT: room temperature, sat.: saturated, TE: target engagement, TEA: triethylamine, THF: tetrahydrofuran, TLC: thin layer chromatography, um: micrometers, UPLC: Ultra Performance Liquid Chromatography.

As used herein, μ, u, mc have been used interchangeably to indicate micro, as in μM, uM, mcM: micromolar, μg, ug, mcg: microgram, μl, ul: microliter, μm, um: micrometer, etc.

Example 1: Synthesis of Chemoprobes

One of the following methods was used for the determination by LC-MS:

Method 1: Column: Xbridge C18 (100 mm×4.6 mm, 3.5 um); Mobile Phase: A: Acetonitrile, B: 0.01 M Ammonium Bicarbonate in Water; Gradient: Time/% A: 0/5, 3/5, 10/80, 12/90, 15/90, 15.1/5; Flow Rate: 1.0 mL/min; Diluent: Acetonitrile:Water (70:30)

Method 2: Column: Aquity UPLC BEH C18 (50 mm×2.1 mm, 1.7 um); Mobile Phase: A: 0.05% Formic Acid in Water B: 0.05% Formic Acid in Acetonitrile; Gradient: Time/% A: 0/97, 0.3/97, 3.2/2, 3.8/2, 4.3/97, 4.5/97; Column Temp: 35° C.; Flow Rate: 0.6 mL/min Method 3: Column: Aquity UPLC BEH C18 (50 mm×2.1 mm, 1.7 um); Mobile Phase: A: 0.1% Formic Acid in Water B: 0.1% Formic Acid in Acetonitrile; Gradient: Time/% B: 0/3, 0.4/3, 3.2/98, 3.8/98, 4.2/3, 4.5/3; Column Temp: 35° C.; Flow Rate: 0.6 mL/min Method 4: Column: Xbridge C18 (100 mm×4.6 mm, 3.5 um); Mobile Phase: A: Acetonitrile, B: 0.01 M Ammonium Bicarbonate in Water; Gradient: Time/% B: 0/90, 3/15, 5/2, 7/2, 8/90, 10/90; Flow Rate: 1.0 mL/min; Diluent: Water Method 5: Column: Xbridge C18 (100 mm×4.6 mm, 3.5 um); Mobile Phase: A: 100% Acetonitrile, B: Water; Gradient: Time/% B: 0/100, 5/100, 8/10, 10/10, 15/98; Flow Rate: 1.0 mL/min; Diluent: Water Method 6: Column: Gemini C18 (150 mm×4.6 mm, 5 um); Mobile Phase: A: 0.01 M Ammonium Acetate (aq), B: Acetonitrile; Gradient: Time/% B: 0/10, 1/10, 6/90, 8/98, 12/98, 12.01/10; Flow Rate: 1.0 mL/min; Diluent: Water Method 7: Column: Xbridge C18 (100 mm×4.6 mm, 3.5 um); Mobile Phase: A: Acetonitrile, B: 10 mM Ammonium Bicarbonate in Aq; Gradient: Time/% B: 0/95, 2/95, 4/5, 7/5, 8/95, 10/95; Flow Rate: 1.0 mL/min; Diluent: Acetonitrile: Water (1:1)

Method 8: Column: Aquity UPLC BEH C18 (50 mm×2.1 mm, 1.7 um); Mobile Phase: A: 0.1% Formic Acid in Acetonitrile, B: 0.1% Formic Acid in Water; Gradient: Time/% B: 0/97, 0.3/97, 3.2/2, 4/2, 4.01/97; Column Temp: 35° C.; Flow Rate: 0.6 mL/min Method 9: Column: Aquity UPLC BEH C18 (50 mm×2.1 mm, 1.7 um); Mobile Phase: A: 0.1% Formic Acid in Acetonitrile, B: 0.1% Formic Acid in Water; Gradient: Time/% B: 0/97, 0.3/97, 5.5/2, 6/2, 6.01/97; Column Temp: 35° C.; Flow Rate: 0.6 mL/min Method 10: Column: Aquity UPLC BEH C18 (50 mm×2.1 mm, 1.7 um); Mobile Phase: A: 0.05% Formic Acid in Water, B: 0.05% Formic Acid in Acetonitrile; Gradient: Time/% A: 0/97, 0.3/97, 3.2/2, 4.8/2, 5/97, 5.10/97; Column Temp: 35° C.; Flow Rate: 0.6 mL/min Method 11: Column: Aquity UPLC BEH C18 (50 mm×2.1 mm, 1.7 um); Mobile Phase: A: 0.05% Formic Acid in Water, B: 0.05% Formic Acid in Acetonitrile; Gradient: Time/% A: 0/97, 0.3/97, 3.5/2, 4.8/2, 5/97, 5.01/97; Column Temp: 35° C.; Flow Rate: 0.6 mL/min Method 12: Column: Aquity UPLC BEH C18 (50 mm×2.1 mm, 1.7 um); Mobile Phase: A: 0.05% Formic Acid in Water, B: 0.05% Formic Acid in Acetonitrile; Gradient: Time/% A: 0/95, 1.5/95, 3/85, 7/45, 10/5, 14/5, 17/95, 20/95; Column Temp: 35° C.; Flow Rate: 0.6 mL/min Reference Example 1: 3-(4'-((trans)-2-((tert-butoxycarbonyl)((trans)-4-((tert-butoxycarbonyl)amino) cyclohexyl)amino)cyclopropyl)-[1,1'-biphenyl]-3-yl) propanoic acid Step 1: Preparation of tert-butyl ((trans)-4-(((trans)-2-(4-bromophenyl)cyclopropyl)amino)cyclohexyl) carbamate Tert-butyl 4-oxocyclohexylcarbamate (22.1 g, 0.104 mol) was added to a solution of trans-2-(4-bromophenyl) cyclopropanamine (22 g, 0.104 mol) in DCE (400 mL) at 0° C., followed by the addition of AcOH (1.6 mL), and the mixture was stirred at the same temperature for 5 min. Sodium triacetoxy borohydride (40 g, 0.187 mol) was slowly added portions wise at 0° C. and the mixture was allowed to stir at RT for 16 h. The progress of the reaction was monitored by TLC. After completion, the reaction mixture was poured into saturated aq. $NaHCO_3$ solution (100 mL) and extracted with DCM (2×200 mL). The combined organic extracts were washed with water (100 mL), brine (100 mL), dried over anhydrous $Na_2SO_4$, filtered and filtrate was evaporated to get cis and trans mixture of tert-butyl (4-(((trans)-2-(4-bromophenyl)cyclopropyl)amino)cyclohexyl)carbamate (28 g crude). The crude compound was purified by flash column chromatography by using ($SiO_2$) EtOAc: pet ether (70:30), first the less polar tert-butyl ((cis)-4-(((trans)-2-(4-bromophenyl)cyclopropyl)amino)cyclohexyl)carbamate (3 g) was isolated followed by the more polar tert-butyl ((trans)-4-(((trans)-2-(4-bromophenyl)cyclopropyl)amino)cyclohexyl)carbamate (6 g, yield: 14.09%) obtained as a white solid, and also recovered 15 g of cis-trans mixture.

LC-MS (Method 1): Rt=4.87 min; m/z=409.3/411.4 $(M+H^+/M+2+H^+)$.

Step 2: Preparation of tert-butyl ((trans)-2-(4-bromophenyl)cyclopropyl)((trans)-4-((tert-butoxycarbonyl)amino)cyclohexyl)carbamate TEA (5.1 mL, 0.0367 mol) and $(Boc)_2O$ (6.41 g, 0.0294 mol) were added to a solution of tert-butyl ((trans)-4-(((trans)-2-(4-bromophenyl)cyclopropyl)amino)cyclohexyl) carbamate (Step 1 of Ref. example 1) (10 g, 0.0245 mol) in dry THF (100 mL) at 10° C. Then the reaction mixture was allowed to stir at RT for 16 h. Completion of the reaction was confirmed by TLC. The reaction mixture was poured into water (200 mL) and extracted with EtOAc (2×100 mL). The combined organic extracts were washed with brine (100 mL), dried over anhydrous $Na_2SO_4$, filtered and filtrate was evaporated under reduced pressure. The crude was purified by silica gel column chromatography using EtOAc: pet ether (2:8) to afford tert-butyl ((trans)-2-(4-bromophenyl)cyclopropyl)((trans)-4-((tert-butoxycarbonyl)amino)cyclohexyl) carbamate (10.4 g, yield: 83.3%) as an off-white solid.

LC-MS (Method 2): Rt=3.23 min; m/z=531.15/533.19 $(M+Na^+/M+2+Na^+)$.

Step 3: Preparation of 3-(4'-((trans)-2-((tert-butoxycarbonyl)((trans)-4-((tert-butoxycarbonyl)amino) cyclohexyl)amino)cyclopropyl)-[1,1'-biphenyl]-3-yl) propanoic acid Pd $(PPh_3)_4$ (39.82 mg, 0.034 mmol) was added to a degassed solution of tert-butyl ((trans)-2-(4-bromophenyl) cyclopropyl)((trans)-4-((tert-butoxycarbonyl)amino)cyclohexyl)carbamate (Step-2 of Ref. example 1) (350 mg, 0.688 mmol), $K_2CO_3$ (285.2 mg, 2.066 mmol) and 3-(2-carboxyethyl) phenyl boronic acid (0.826 mmol) in MeCN—$H_2O$ (40 mL, 8:2) at RT. The mixture was again degassed for 5 min and heated to 90° C. for 16 h. Completion of the reaction was confirmed by TLC. The reaction mixture was diluted with EtOAc and filtered through the pad of Celite, the filtrate was concentrated and the crude compound was purified by preparative HPLC to afford 3-(4'-((trans)-2-((tert-butoxycarbonyl)((trans)-4-((tert-butoxycarbonyl) amino)cyclohexyl)amino)cyclopropyl)-[1,1'-biphenyl]-3-yl)propanoic acid (250 mg, yield: 62.8%) as an off-white solid LC-MS (Method 4): Rt=4.63 min; m/z=577.0 $(M-H^+)$.

Reference Examples 2-4

The following compounds were obtained by following the procedure described in reference example 1, but using suitable starting materials.

| Ref Example | Name | Starting material | LC-MS method | Rt (min) | m/z |
|---|---|---|---|---|---|
| 2 | 3-(4'-((trans)-2-((tert-butoxycarbonyl)(1-(tert-butoxycarbonyl)piperidin-4-yl)amino)cyclopropyl)-[1,1'-biphenyl]-3-yl)propanoic acid | trans-2-(4-bromophenyl)cyclopropanamine and tert-butyl 4-oxopiperidine-1-carboxylate | 8 | 2.96 | 562.9 (M − H$^+$) |
| 3 | 3-(4'-((trans)-2-((tert-butoxycarbonyl)((1-(tert-butoxycarbonyl)piperidin-4-yl)methyl)amino)cyclopropyl)-[1,1'-biphenyl]-3-yl)propanoic acid | trans-2-(4-bromophenyl)cyclopropanamine and tert-butyl 4-formylpiperidine-1-carboxylate | 8 | 3.01 | 576.8 (M − H$^+$) |
| 4 | 3-(4'-((1S,2R)-2-((tert-butoxycarbonyl)((trans)-4-((tert-butoxycarbonyl)amino)cyclohexyl)amino)cyclopropyl)-[1,1'-biphenyl]-3-yl)propanoic acid | (1R,2S)-2-(4-bromophenyl)cyclopropan-1-amine and tert-butyl 4-oxocyclohexylcarbamate | 10 | 3.30 | 601.4 (M + Na$^+$) |

The reference examples 1, 2, and 3 are a mixture of 2 isomers, which correspond to the combination of the two different (trans) configuration regarding the cyclopropyl ring (which are (1R,2S) and (1S,2R), respectively) and the reference example 4 is a single (1S,2R) isomer regarding the cyclopropyl ring. The reference examples 1 and 4 contain a cyclohexane ring with TRANS configuration.

Reference Example 5: (+)-Biotin-PEG$_7$-CH2CH2NH2·HCl (N-(23-amino-3,6,9,12,15,18,21-heptaoxatricosyl)-5-((3aS,4S,6aR)-2-oxohexahydro-1H-thieno[3,4-d]imidazol-4-yl)pentanamide hydrochloride)

Step 1: Preparation of (tert-butyl (25-oxo-29-((3aS,4S,6aR)-2-oxohexahydro-1H-thieno[3,4-d]imidazol-4-yl)-3,6,9,12,15,18,21-heptaoxa-24-azanonacosyl)carbamate)

HATU (0.97 g, 2.56 mmol) and DIPEA (0.67 mL, 3.84 mmol) were added to a solution of Boc-NH-PEG$_7$-CH$_2$CH$_2$NH$_2$ (tert-butyl 23-amino-3,6,9,12,15,18,21-heptaoxatricosylcarbamate) (1.2 g, 2.56 mmol) and 5-((3aS,4S,6aR)-2-oxohexahydro-1H-thieno[3,4-d]imidazol-4-yl)pentanoic acid (0.7 g, 2.56 mmol) in DMF (12 mL). The reaction mixture was stirred at RT for 16 h. After completion, the reaction mixture was poured into ice water (50 mL) and extracted with 10% MeOH/DCM (2×40 mL). The combined organic extracts were washed with water (2×40 mL), brine (50 mL), dried over anhydrous Na$_2$SO$_4$, filtered and filtrate was evaporated to afford crude and it was purified by column chromatography (SiO$_2$) by eluting with 3% MeOH:DCM, to afford tert-butyl (25-oxo-29-((3aS,4S,6aR)-2-oxohexahydro-1H-thieno[3,4-d]imidazol-4-yl)-3,6,9,12,15,18,21-heptaoxa-24-azanonacosyl)carbamate (600 mg, yield: 33.7%) as an off-white semi solid LC-MS (Method 11): Rt=2.10 min; m/z=695.6 (M+H$^+$)

Step 2: Preparation of (+)-Biotin-PEG$_7$-CH$_2$CH$_2$NH$_2$·HCl (N-(23-amino-3,6,9,12,15,18,21-heptaoxatricosyl)-5-((3aS,4S,6aR)-2-oxohexahydro-1H-thieno[3,4-d]imidazol-4-yl)pentanamide hydrochloride)

HCl in 1,4-dioxane (4M) (2.0 mL) was added to a solution of tert-butyl (25-oxo-29-((3aS,4S,6aR)-2-oxohexahydro-1H-thieno[3,4-d]imidazol-4-yl)-3,6,9,12,15,18,21-heptaoxa-24-azanonacosyl)carbamate (Step-1 of Ref. example 5) (400 mg, 0.57 mmol) in 1,4-dioxane (1.0 mL) at 10° C. The reaction mixture was allowed to stir at RT for 2 h. After completion, the reaction mixture was evaporated and the residue was triturated with diethyl ether to afford (+)-Biotin-PEG$_7$-CH$_2$CH$_2$NH$_2$·HCl (N-(23-amino-3,6,9,12,15,18,21-heptaoxatricosyl)-5-((3aS,4S,6aR)-2-oxohexahydro-1H-thieno[3,4-d]imidazol-4-yl)pentanamide hydrochloride) (300 mg, 83.4%) as a light brown gummy liquid.

LC-MS (Method 12): Rt=3.64 min; m/z=596.1 (M+H+)

Reference Example 6: (+)-Biotin-PEG$_{15}$-CH$_2$CH$_2$NH$_2$·HCl (N-(47-amino-3,6,9,12,15,18,21,24,27,30,33,36,39,42,45-pentadecaoxaheptatetracontyl)-5-((3aS,4S,6aR)-2-oxohexahydro-1H-thieno[3,4-d]imidazol-4-yl)pentanamide hydrochloride)

This compound was obtained by following the procedure described in reference example 5, but using Boc-NH-PEG$_{15}$-CH$_2$CH$_2$NH$_2$ instead of Boc-NH-PEG$_7$-CH$_2$CH$_2$NH$_2$.

LC-MS (Method 3): Rt=3.59 min; m/z=947.6 (M+H$^+$)

Reference Example 7: Tert-Butyl ((Trans)-4-((Tert-Butoxycarbonyl)Amino)Cyclohexyl)((Trans)-2-(3'-(3,41-dioxo-45-((3aS,4S,6aR)-2-oxohexahydro-1H-thieno[3,4-d]imidazol-4-yl)-7,10,13,16,19,22,25,28,31,34,37-undecaoxa-4,40-diazapentatetracontyl)-[1,1'-biphenyl]-4-yl)cyclopropyl)carbamate A solution of (+)-Biotin-PEG$_{11}$-CH$_2$CH$_2$NH$_2$ (212.8 mg, 0.276 mmol) in DMF (0.5 mL) was added to a solution of 3-(4'-((trans)-2-((tert-butoxycarbonyl)((trans)-4-((tert-butoxycarbonyl)amino)cyclohexyl)amino)cyclopropyl)-[1,1'-biphenyl]-3-yl)propanoic acid (Ref. Example 1) (160 mg, 0.276 mmol), HATU (104 mg, 0.276 mmol) and DIPEA (56 mg, 0.414 mmol) in DMF (2.5 mL) at RT. The reaction mixture was stirred at RT for 16 h. Completion of the reaction was confirmed by TLC. The reaction mixture was poured into ice water (50 mL) and extracted with ethyl acetate (2×25 mL). The combined organic layer was washed with saturated aq. NaHCO$_3$ solution (20 mL), brine (20 mL), dried over anhydrous $Na_2SO_4$, filtered and the filtrate was concentrated under reduced pressure. The crude product was purified by preparative HPLC to afford tert-butyl ((trans)-4-((tert-butoxycarbonyl)amino)cyclohexyl)((trans)-2-(3'-(3,41-dioxo-45-((3aS,4S,6aR)-2-oxohexahydro-1H-thieno[3,4-d]imidazol-4-yl)-7,10,13,16,19,22,25,28,31,34,37-undecaoxa-4,40-diazapentatetracontyl)-[1,1'-biphenyl]-4-yl)cyclopropyl)carbamate (50 mg, yield: 13.6%) as an off-white gummy solid.

LC-MS (Method 11): Rt=3.17 min; m/z=1331.9 (M+H$^+$).

Reference Examples 8-12

The following compounds were obtained by following the procedure described in reference example 8, but using suitable starting materials.

| Ref Example | Name | Starting material | LC-MS method | Rt (min) | m/z (M + H$^+$) |
|---|---|---|---|---|---|
| 8 | tert-butyl ((trans)-4-((tert-butoxycarbonyl)amino)cyclohexyl)((trans)-2-(3'-(3,29-dioxo-33-((3aS,4S,6aR)-2-oxohexahydro-1H-thieno[3,4-d]imidazol-4-yl)-7,10,13,16,19,22,25-heptaoxa-4,28-diazatritriacontyl)-[1,1'-biphenyl]-4-yl)cyclopropyl)carbamate | Ref. Example 1 and Ref. example 5 | 11 | 3.19 | 1155.8 |
| 9 | tert-butyl ((trans)4-((tert-butoxycarbonyl)amino)cyclohexyl)((trans)-2-(3'-(3,53-dioxo-57-((3aS,4S,6aR)-2-oxohexahydro-1H-thieno[3,4-d]imidazol-4-yl)-7,10,13,16,19,22,25,28,31,34,37,40,43,46,49-pentadecaoxa-4,52-diazaheptapentacontyl)-[1,1'-biphenyl]-4-yl)cyclopropyl)carbamate | Ref. Example 1 and Ref. example 6 | 12 | 4.82 | 1508.0 |
| 10 | tert-butyl 4-((tert-butoxycarbonyl)((trans)-2-(3'-(3,41-dioxo-45-((3aS,4S,6aR)-2-oxohexahydro-1H-thieno[3,4-d]imidazol-4-yl)-7,10,13,16,19,22,25,28,31,34,37-undecaoxa-4,40-diazapentatetracontyl)-[1,1'-biphenyl]-4-yl)cyclopropyl)amino)piperidine-1-carboxylate | Ref. Example 2 and (+)-Biotin-PEG$_{11}$-CH$_2$CH$_2$NH$_2$ | 9 | 3.89 | 1317.5 |
| 11 | tert-butyl 4-(((tert-butoxycarbonyl)((trans)-2-(3'-(3,41-dioxo-45-((3aS,4S,6aR)-2-oxohexahydro-1H-thieno[3,4-d]imidazol-4-yl)-7,10,13,16,19,22,25,28,31,34,37-undecaoxa-4,40-diazapentatetracontyl)-[1,1'-biphenyl]-4-yl)cyclopropyl)amino)methyl)piperidine-1-carboxylate | Ref. Example 3 and (+)-Biotin-PEG$_{11}$-CH$_2$CH$_2$NH$_2$ | 8 | 2.58 | 1332.6 |
| 12 | tert-butyl ((trans)-4-((tert-butoxycarbonyl)amino)cyclohexyl)((1R,2S)-2-(3'-(3,41-dioxo-45-((3aS,4S,6aR)-2-oxohexahydro-1H-thieno[3,4-d]imidazol-4-yl)-7,10,13,16,19,22,25,28,31,34,37-undecaoxa-4,40-diazapentatetracontyl)-[1,1'-biphenyl]-4-yl)cyclopropyl)carbamate | Ref. Example 4 and (+)-Biotin-PEG$_{11}$-CH$_2$CH$_2$NH$_2$ | 10 | 2.97 | 1332.2 |

The reference examples 8, 9, 10, and 11 are a mixture of 2 isomers, which correspond to the combination of the two different (trans) configurations regarding the cyclopropyl ring (which are (1R,2S) and (1S,2R), respectively) and the reference example 12 is a single (1S,2R) isomer regarding the cyclopropyl ring. The reference examples 8, 9 and 12 contain a cyclohexane ring with TRANS configuration.

Example 1.1: N-(39-(4'-((trans)-2-(((trans)-4-amino-cyclohexyl)amino)cyclopropyl)-[1,1'-biphenyl]-3-yl)-37-oxo-3,6,9,12,15,18,21,24,27,30,33-undecaoxa-36-azanonatriacontyl)-5-((3aS,4S,6aR)-2-oxohexahydro-1H-thieno[3,4-d]imidazol-4-yl)pentanamide dihydrochloride HCl in 1,4-dioxane (4M) (0.5 mL) was added to a solution of tert-butyl ((trans)-4-((tert-butoxycarbonyl)amino)cyclohexyl)((trans)-2-(3'-(3,41-dioxo-45-((3aS,4S,6aR)-2-oxohexahydro-1H-thieno[3,4-d]imidazol-4-yl)-7,10,13,16,19,22,25,28,31,34,37-undecaoxa-4,40-diazapentatetracontyl)-[1,1'-biphenyl]-4-yl)cyclopropyl)carbamate (Ref. Example 7) (50 mg, 0.037 mmol) in 1,4-dioxane (0.3 mL) at 10° C. and the reaction mixture was stirred at 10° C. for 2 h. Completion of the reaction was confirmed by LCMS. The reaction mixture was concentrated under reduced pressure below 30° C., the residue was triturated with EtOAc/diethyl ether and the obtained compound was dissolved in deionized water and lyophilized to afford N-(39-(4'-((trans)-2-(((trans)-4-aminocyclohexyl)amino)cyclopropyl)-[1,1'-biphenyl]-3-yl)-37-oxo-3,6,9,12,15,18,21,24,27,30,33-undecaoxa-36-azanonatriacontyl)-5-((3aS,4S,6aR)-2-oxohexahydro-1H-thieno[3,4-d]imidazol-4-yl)pentanamide dihydrochloride (40 mg, yield: 89.8%) as an off-white solid LC-MS (Method 5): Rt=3.82 min; m/z=1132.8 (M+H$^+$).

Example 1.2-1.6

The following compounds were obtained by following the procedure described in example 1.1, but using suitable starting materials.

| Example | Name | Starting material | LC-MS method | Rt (min) | m/z (M + H$^+$) |
|---|---|---|---|---|---|
| 1.2 | N-(27-(4'-((trans)-2-(((trans)-4-aminocyclohexyl)amino)cyclopropyl)-[1,1'-biphenyl]-3-yl)-25-oxo-3,6,9,12,15,18,21-heptaoxa-24-azaheptacosyl)-5-((3aS,4S,6aR)-2-oxohexahydro-1H-thieno[3,4-d]imidazol-4-yl)pentanamide dihydrochloride | Ref. Example 8 | 11 | 1.81 | 955.7 |
| 1.3 | N-(51-(4'-((trans)-2-(((trans)-4-aminocyclohexyl)amino)cyclopropyl)-[1,1'-biphenyl]-3-yl)-49-oxo-3,6,9,12,15,18,21,24,27,30,33,36,39,42,45-pentadecaoxa-48-azahenpentacontyl)-5-((3aS,4S,6aR)-2-oxohexahydro-1H-thieno[3,4-d]imidazol-4-yl)pentanamide dihydrochloride | Ref. Example 9 | 11 | 1.42 | 1307.7 |
| 1.4 | N-(37-oxo-39-(4'-((trans)-2-(piperidin-4-ylamino)cyclopropyl)-[1,1'-biphenyl]-3-yl)-3,6,9,12,15,18,21,24,27,30,33-undecaoxa-36-azanonatriacontyl)-5-((3aS,4S,6aR)-2-oxohexahydro-1H-thieno[3,4-d]imidazol-4-yl)pentanamide dihydrochloride | Ref. Example 10 | 6 | 5.50 | 1117.8 |
| 1.5 | N-(37-oxo-39-(4'-((trans)-2-((piperidin-4-ylmethyl)amino)cyclopropyl)-[1,1'-biphenyl]-3-yl)-3,6,9,12,15,18,21,24,27,30,33-undecaoxa-36-azanonatriacontyl)-5-((3aS,4S,6aR)-2-oxohexahydro-1H-thieno[3,4-d]imidazol-4-yl)pentanamide dihydrochloride | Ref. Example 11 | 6 | 5.57 | 1131.8 |
| 1.6 | N-(39-(4'-((1S,2R)-2-(((trans)-4-aminocyclohexyl)amino)cyclopropyl)-[1,1'-biphenyl]-3-yl)-37-oxo-3,6,9,12,15,18,21,24,27,30,33-undecaoxa-36- | Ref. Example 12 | 7 | 4.58 | 1132.0 |

| Example | Name | Starting material | LC-MS method | Rt (min) | m/z (M + H+) |
|---|---|---|---|---|---|
| | azanonatriacontyl)-5-((3aS,4S,6aR)-2-oxohexahydro-1H-thieno[3,4-d]imidazol-4-yl)pentanamide dihydrochloride | | | | |
The chemical structures of the compounds of examples 1.1 to 1.6 are shown in the table below:
| Example # | STRUCTURE |
|---|---|
| Example 1.1 | 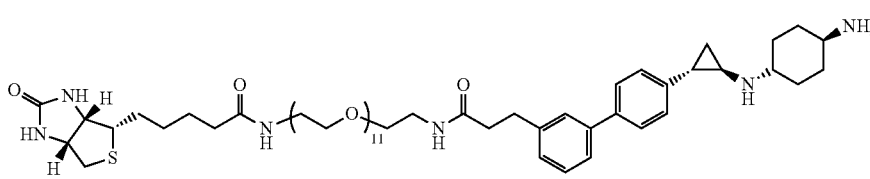 |
| Example 1.2 | 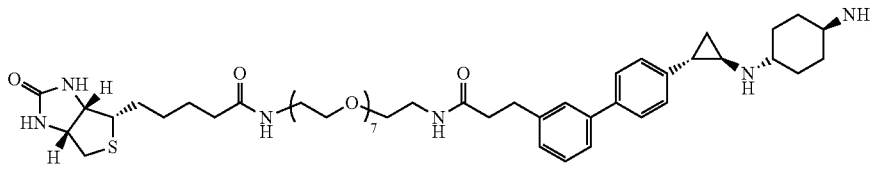 |
| Example 1.3 | 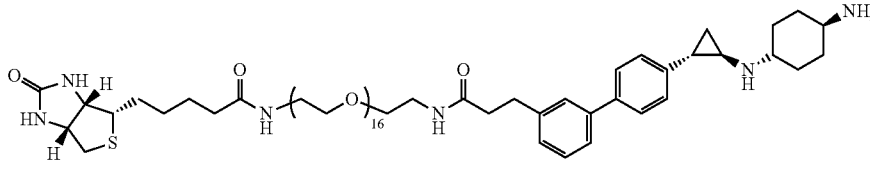 |
| Example 1.4 | 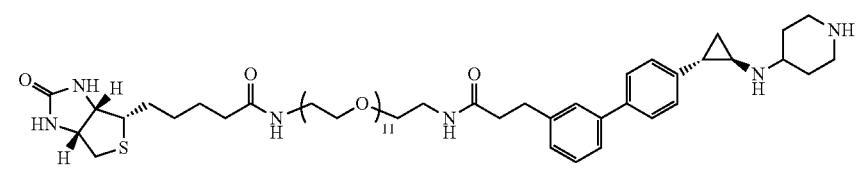 |
| Example 1.5 | 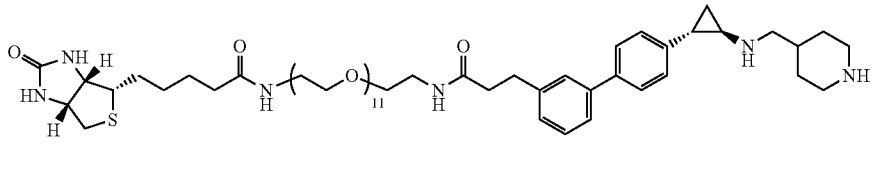 |
| Example 1.6 | 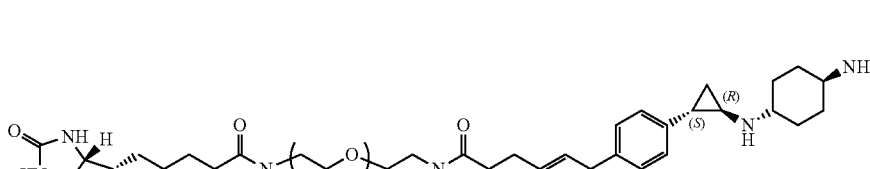 |

The examples 1.1, 1.2, 1.3, 1.4 and 1.5 are a mixture of 2 isomers, which correspond to the combination of the two different (trans) configurations regarding the cyclopropyl ring (which are (1R,2S) and (1S,2R), respectively) and the example 1.6 is a single (1S,2R) isomer regarding the cyclopropyl ring. The reference examples 1.1, 1.2, 1.3 and 1.6 contain a cyclohexane ring with TRANS configuration.

The corresponding single (1S,2R) isomers of examples 1.2, 1.3, 1.4 and 1.5 can be also prepared:

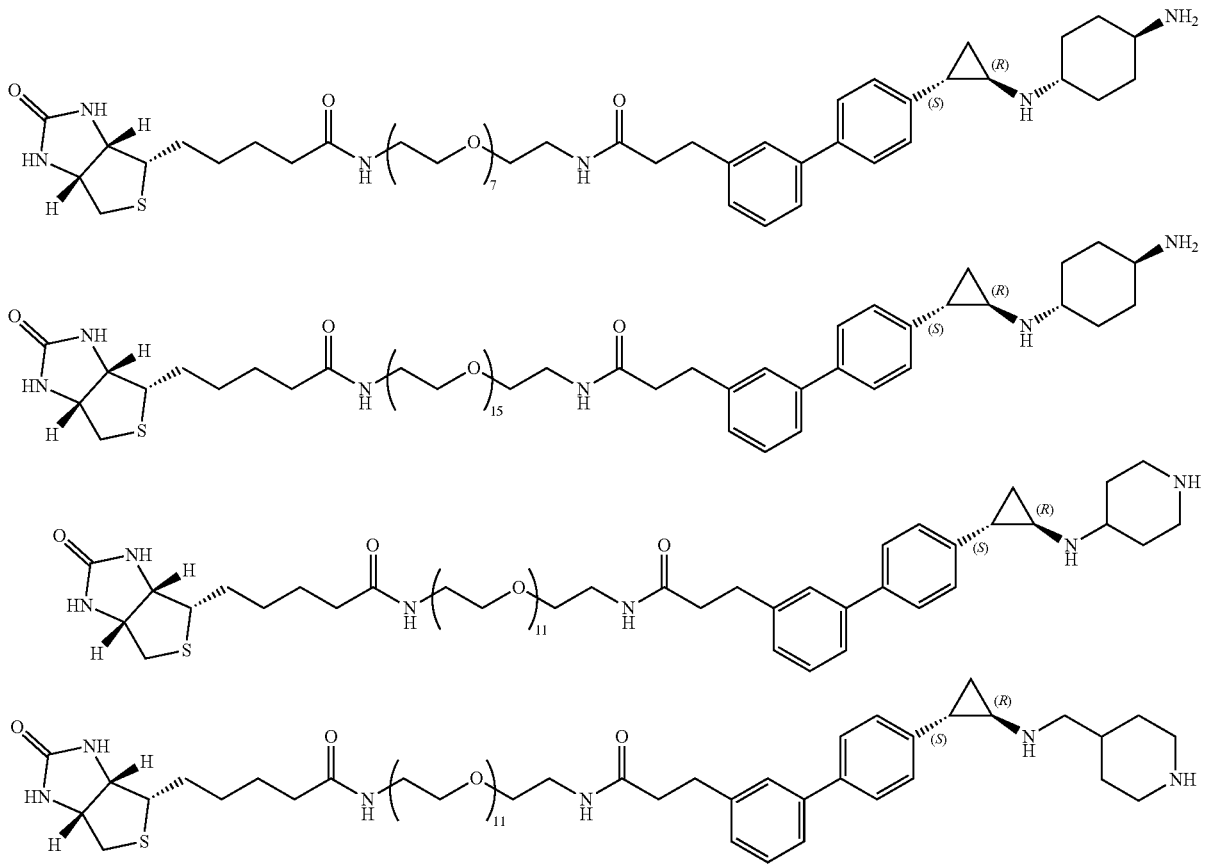

Other chemoprobes that can be prepared:

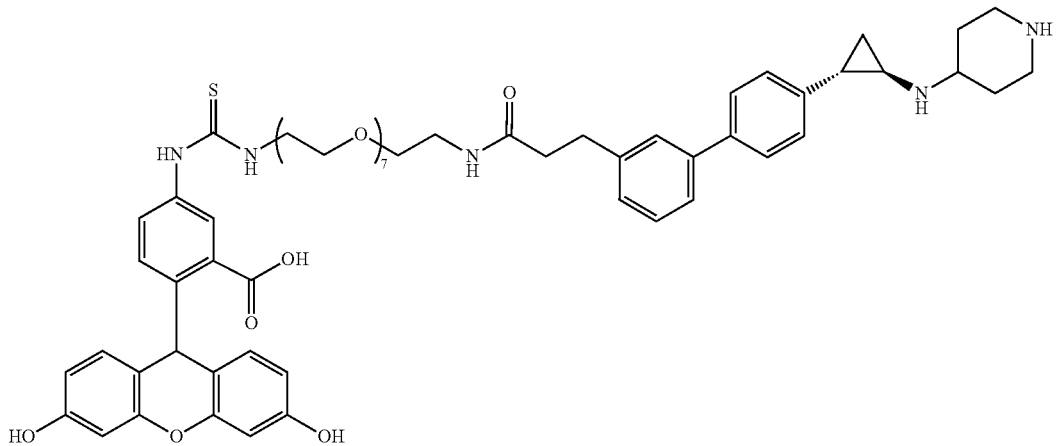

133
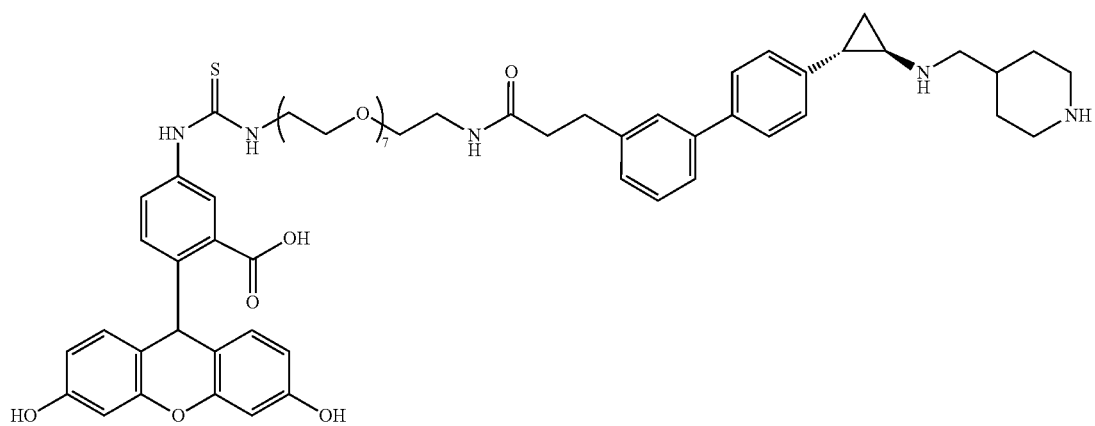
134
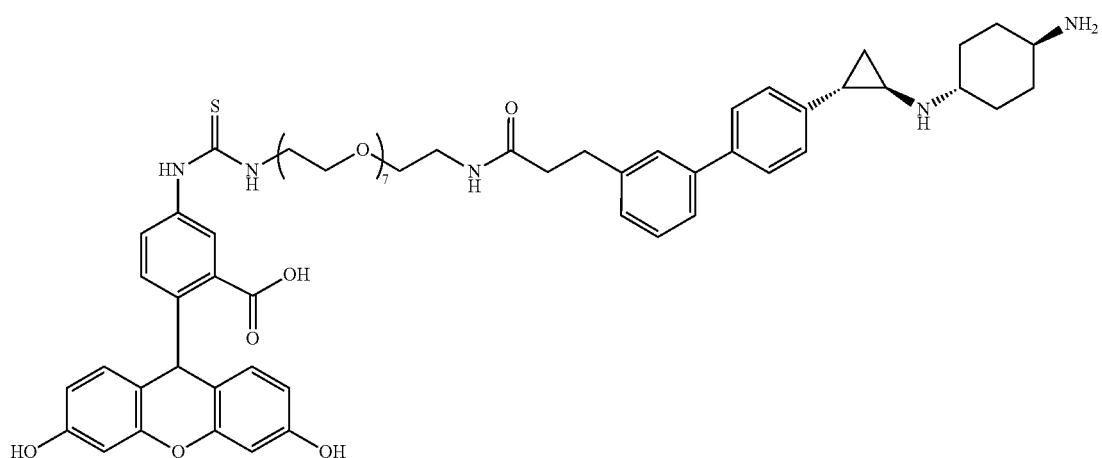
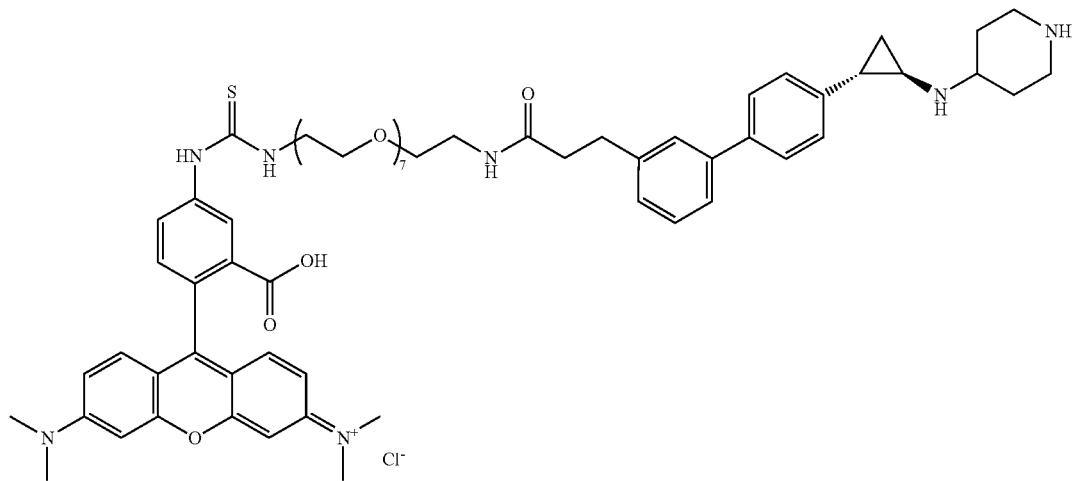

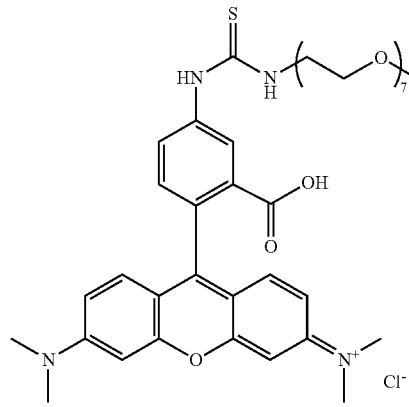
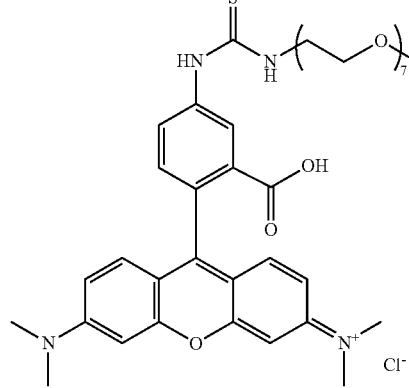
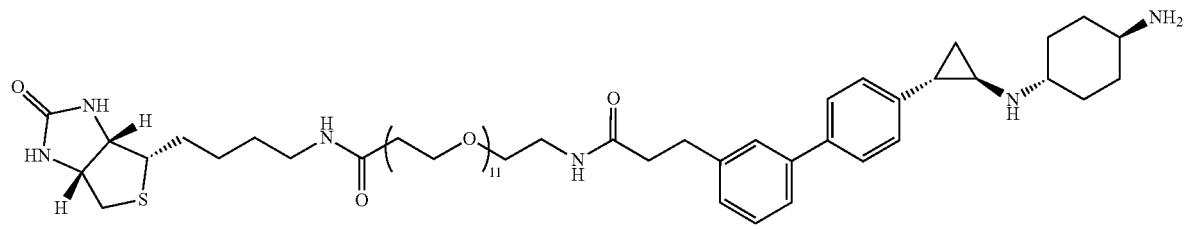
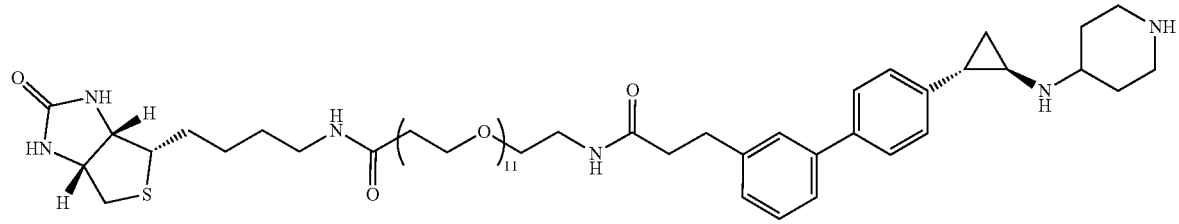
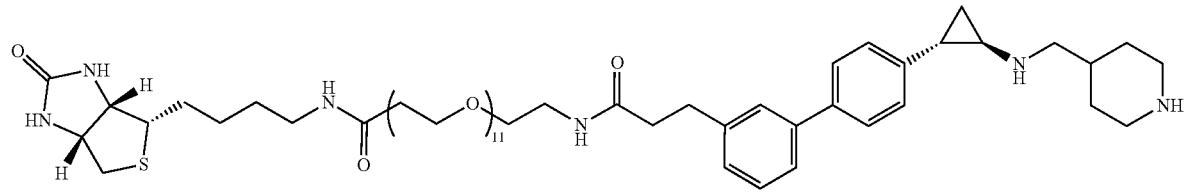

These chemoprobes can be prepared as a mixture of 2 isomers, which correspond to the combination of the two different (trans) configurations regarding the cyclopropyl ring (which are (1R,2S) and (1S,2R), respectively) or as single (1S,2R) isomers regarding the cyclopropyl ring.

Biological Assays

Example 2. Chemoprobe Inhibition of KDM1A Activity

The ability of the chemoprobes to inhibit KDM1A was tested in vitro using the assay described below. KDM1A inhibition assay: a multistep enzymatic reaction in which the enzyme first produces $H_2O_2$ during the demethylation of lysine 4 in a 21 AA H3K4me2 N-terminal peptide. KDM1A chemoprobes were pre-incubated for 15 min with human recombinant KDM1A enzyme (BPS Bioscience, Ref. 50100) on ice in the assay buffer (50 mM sodium phosphate pH 7.4). The enzymatic reaction was initiated by the addition of $K_M$ dimethylH3K4 peptide substrate (Anaspec, Ref. 63677). After 30 min of incubation at 37° C. Amplex Red reagent and the horseradish peroxidase (HRP) solution were added according to the recommendations of the supplier (Invitrogen) and left to incubate for 5 min at room temperature in the dark. Conversion of the Amplex Red reagent to resorufin, was monitored by fluorescence ($\lambda$ex=540 nm, $\lambda$em=590 nm) using a microplate reader (Infinite F200 Tecan). Signals were corrected for background and the $IC_{50}$ value was calculated with GraphPad Prism Software.

In Table 1 we summarize the KDM1A $IC_{50}$ value of the all compounds described in example 1.

| Example # | KDM1A $IC_{50}$ (uM) |
|---|---|
| 1.1 | 0.133 |
| 1.2 | 0.21 |
| 1.3 | 0.213 |
| 1.4 | 0.126 |
| 1.5 | 0.041 |
| 1.6 | 0.120 |

Example 3. Chemoprobe Mediated Precipitation of KDM1A

Preparation of Samples and Assay Conditions

Selected KDM1A chemoprobes (example 1.1 and 1.6) that have biotin tag incorporated were incubated with human recombinant KDM1A (Active Motif; #31334) or cell extracts obtained from KDM1A expressing THP-1 or MV(4; 11) (human AML cell lines from ATCC) at increasing concentrations of the chemoprobe. The capture agent used was streptavidin-coated paramagnetic beads (ThermoFisher Scientific; #11205D).

Cells were lysed in 1× Cell Lysis Buffer (Cell Signaling; #9803) containing 1× Complete Mini, Protease Inhibitor Cocktail Tablets (ROCHE; #11836153001) and chemoprobe (at the indicated concentrations, e.g. 5 M for pull down assays) was added to frozen cell pellets containing $1 \cdot 10^6$ cells. Tubes were incubated for 5 min on ice and briefly sonicated to achieve lysis. The resulting extracts were centrifuged 10 min at 14.000×g at 4° C. Supernatants were collected and quantified by Bradford assay (BIO—RAD; #500-0006) following manufacturer's instructions.

250 µL of Dynabeads M-280 Streptavidin (ThermoFisher Scientific; #11205D) were washed 3 times and resuspended in 250 µL PBS. 350 µg of protein extracts (containing the chemoprobe) was then added and incubated for 30 min at room temperature (RT) using gentle rotation. The chemoprobe-KDM1A complex bound to the streptavidin beads was separated using a magnet and washed 4 times in PBS. After the last wash, samples were resuspended in 25 µL of 3×SDS Sample Buffer and analyzed by western blot. Samples were separated on a 10% Bis-Tris NuPAGE® Novex® Precast gel (Invitrogen; #P0301BOX) following manufacturer's instructions. Gels were transferred onto nitrocellulose membrane (GE Healthcare; #RPN303D) for immunodetection by semi-dry transfer. N-specific binding sites were blocked by incubating membranes in blocking buffer (5% non-fat dry milk in PBS-Tween 0.1%) at RT for 1 h. Nitrocellulose membrane was then incubated in blocking buffer with an anti-KDM1A antibody (Cell Signaling; #2184) diluted 1:1000 overnight (O/N) at 4° C. as a primary detection reagent. After 5 washes in PBS-Tween 0.5%, the membrane was incubated with a peroxidase-conjugated secondary antibody (Jackson Immunoresearch; #711-035-152) diluted 1:5000 for 1 h at RT. Signal was detected by enhanced chemiluminescence (ECL, Amersham, GE Healthcare; #W9643350) using a GeneGnome HR System (Syngene).

Results:

Titration analysis was performed using chemoprobe (at concentrations 0.2-500 nM) to determine the probe concentration required to pull down the protein complexes. The results shown in FIG. 1A demonstrate that the chemoprobe example 1.6 efficiently binds to KDM1A from THP-1 cells in a dose-dependent manner and that its biotin group is readily accessible to the streptavidin on the surface of the paramagnetic beads.

Figure 1B:
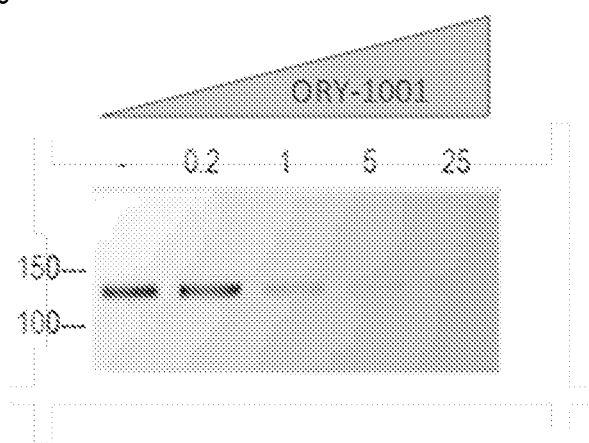

Four days of pretreatment of cells with increasing concentrations of ORY-1001 (0.2, 1, 5 and 25 nM) provoked a dose dependent reduction of the amount of KDM1A that could be pulled down using the chemoprobe 1.1 or 1.6. Cellular extracts were obtained in presence of excess (5 uM) chemoprobe and proteins pulled down using magnetic streptavidin Dynabeads analyzed by Western blot using KDM1A antibody. Pretreatment with 25 nM of ORY-1001 completely prevented pull-down of KDM1A with chemoprobe corresponding as example 1.1, indicating that KDM1A inhibition was complete at this dose. The FIG. 1B shows the effect of pretreatment of cells with different doses of ORY-1001 (nM) on chemoprobe mediated pull-down from THP-1 cells.

We also verified that other chemoprobes, such as Examples 1.4 and 1.5 at 5 uM efficiently pulled down KDM1A from 500 ug of MV(4;11) protein extracts. Pretreatment of the cells with 25 nM of ORY-1001 completely prevented pull-down of KDM1A with these chemoprobes.

Example 4. Chemoprobe Binding and Specificity

Example 4.1. Chemoprobe Specificity

Preferentially, the chemoprobes used for this invention selectively bind the KDM1A target and do not bind other proteins, and more specifically, the chemoprobes do not bind the FAD cofactor in other structurally related monoamine oxidases. The target selectivity of the chemoprobes for binding FAD in KDM1A relative to other FAD containing enzymes is evaluated by testing the chemoprobes in different biochemical assays to determine its MAO-A, MAO-B, IL4I1 and SMOX inhibitory activity in vitro. All IC50 values were calculated using Graph Prism Software.

Example 4.1.1. MAO Inhibition

Human recombinant MAO-A and MAO-B were purchased from Sigma Aldrich (#M7316 and #M7441 respectively). Enzymatic activities and inhibition rate were analyzed in a fluorescence based assay using kynuramine (Sigma Aldrich #K3250) as a substrate. Clorgiline and Deprenyl (Sigma Aldrich #M3778 and #M003) were used as controls for specific inhibition of MAO-A and MAO-B respectively. Compounds were pre-incubated with protein for 15 min on ice in 100 mM Hepes pH 7.5. The enzymatic reaction was initiated by the addition of specific $K_M$ Kynuramine and incubated 1h at 37° C. The reaction was stopped by adding NaOH 2N (v/v). The conversion of kynuramine to 4-hydroxyquinoline was monitored by fluorescence ($\lambda$ex=320 nm, $\lambda$em=360 nm) using a microplate reader. Chemoprobe (example 1.6) did not inhibit MAO-A or MAO-B activity in the tested dose range, its MAO-A and MAO-B IC50 is >100 uM.

Example 4.1.2. IL-4I1 Inhibition

Human recombinant IL-4I1 was purchased from RD Systems (#5684-AO-020). The biochemical activity was measured by its ability to oxidize phenylalanine and produce $H_2O_2$ in a horseradish peroxidase coupled assay using Amplex red as substrate. The assay buffer was 50 mM Sodium Phosphate pH 7; inhibition of IL-4I1 by compounds tested was monitored during 30 minutes in the presence of $K_M$ phenylalanine. Chemoprobe example 1.6 showed 31% of hIL-4I1 inhibition at 100 uM; its IC50 was >100 uM.

Example 4.1.3. SMOX Inhibition

Mouse recombinant SMOX enzyme was provided by Professor Paolo Mariottini (Rome University). The biochemical activity was measured by its ability to oxidize spermine in a horseradish peroxidase coupled assay using Amplex red as a substrate. The assay buffer for mSMOX reaction was 100 mM Sodium Phosphate pH 8.0. The inhibition by tested compounds was monitored during 10 minutes in the presence of $K_M$ spermine. The mSMOX IC50 value of chemoprobe example 1.6 was 13 uM.

Example 4.1.4. Cellular Binding

Figure 2:
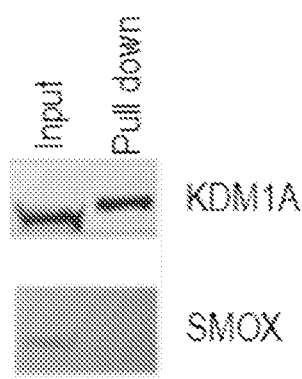
FIG. 2: Western blot using KDM1A or SMOX antibody, the pull-down product was mediated by chemoprobe example 1.6 (described in example 4).

To assess whether the chemoprobe binds selectively to KDM1A in cellular extracts, the KDM1A chemoprobe can be used to chemoprecipitate proteins from cells. Chemoprobe example 1.6 inhibited recombinant SMOX with an IC50 of 13 uM. Chemoprobe example 1.6 was used to pull down target protein from MV(4;11) cells using magnetic streptavidin beads as a capture agent and analysis by western blot were performed as described in example 3 using anti-SMOX antibody (Proteintec Europe; #15052-1-AP) diluted 1:200 or anti-KDM1A antibody as a primary detection reagent described. As shown in FIG. 2, KDM1A was quantitatively recuperated by the chemoprecipitation but SMOX was not detected, illustrating the selectivity of the probe for the KDM1A enzyme in cell extracts.

Example 5. Development of Chemoprobe Immunosorbent Assays to Detect Total and Free KDM1A We developed two independent KDM1A ELISA assays to determine both total and free KDM1A in recombinant KDM1A full length protein or in protein extracts from biological samples (e.g. cells or tissues) in a solid phase assay. In particular, to determine free KDM1A levels, a KDM1A chemoprobe-based immunosorbent assay was used. The assessment of the level of total and particularly free KDM1A is useful to evaluate the degree of occupation of KDM1A (target engagement) by a KDM1A inhibitor, as described in more detail in Example 7.

Example 5.1. Selection of Specific KDM1A Antibodies Useful for ELISA Applications To select a pair of antibodies with ability to bind KDM1A protein for use in our assays, the following parameters were evaluated: the anti-KDM1A antibodies could recognize non-overlapping epitopes that did not interfere with the streptavidin or other tag coupled to chemoprobe nor with the interaction between KDM1A and Co-REST. Commercial antibody lists were scanned for antibodies that were preferentially monoclonal and announced to be functional in IHC, IP and WB. Preliminary modeling of the antibodies' epitope recognition sites on the KDM1A protein was performed in order to evaluate the diversity and the likeliness of unwanted interactions, and candidate antibodies were selected for further functional evaluation. Said candidate antibodies were then verified for their capacity to immunoprecipitate KDM1A protein from fresh extracts from human cells. Two antibodies from different species were selected, mouse C-terminal mAb-KDM1A (Abcam #ab53269) herein designated as mAb-844, and rabbit N-terminal mAb-KDM1A (cell Signaling, #2184) herein designated as mAb-825, which can bind to KDM1A without interfering with each other binding and without affecting the binding of the KDM1A chemoprobe example 1.6. Vice versa, inhibition of KDM1A with KDM1A inhibitors (and also with the chemoprobe) does not interfere with the KDM1A recognition by the antibodies, and no steric hindrance was detected between antibody-antibody or antibody-probe and the capability to measure total KDM1A protein using cellular extracts.

mAb-825:
Rabbit N-terminal mAb-KDM1A (cell Signaling, #2184) that targets an epitope, designated herein EP1, located in the N terminal region proximate to proline 60 (P60) of the human KDM1A sequence (UNIPROT ID O60341-1) and blocked by peptide #LSD1 Blocking Peptide-2184 specific (Cell Signaling).

mAb-844:
mouse C-terminal mAb-KDM1A (Abcam #ab53269). This antibody targets an epitope, herein designated EP2, located on the C-terminal region and which comprises AMYTLPRQATPGVPAQ, corresponding to AA 832-847 of human KDM1A.

Both antibodies recognize at least human, rat and mouse KDM1A protein.

Example 5.2. Luminescent KDM1A ELISA

Figure 3B:
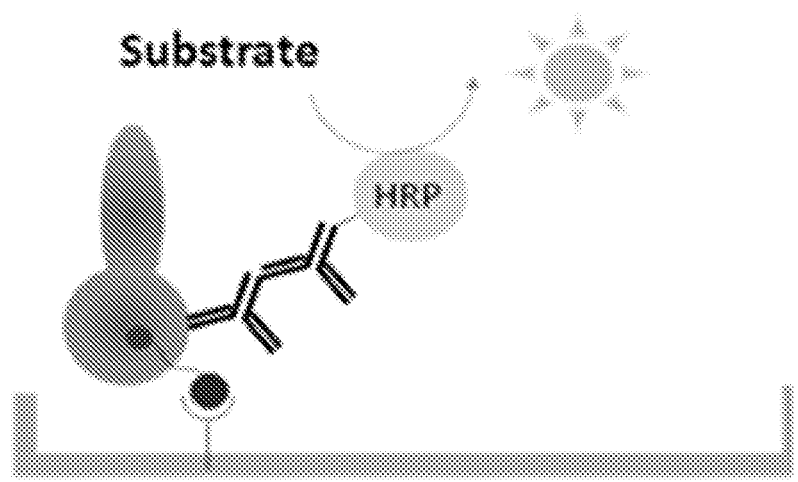

For quantification of total and free amount of KDM1A protein in tissue and cell samples luminescent KDM1A sandwich ELISA and KDM1A chemoprobe ELISA assays were established. To measure total KDM1A levels, a sandwich ELISA was employed using a surface-bound first anti-KDM1A antibody as a capture antibody (e.g. mAb-844) followed by a second antiKDM1A antibody (e.g. mAb-825) for detection. A horseradish peroxidase (HRP)-conjugated secondary antibody to the antiKDM1A antibody (mAb-825)

was employed to measure total KDM1A bound to the plate surface. A schematic representation of this sandwich ELISA assay to detect total KDM1A is depicted in FIG. 3A. To measure free KDM1A levels, a chemoprobe-linked immunosorbent assay was used that employs streptavidin-coated plates to capture a biotin tagged KDM1A chemoprobe bound to KDM1A and that uses an antiKDM1A antibody (e.g. mAb-825) as the detection antibody, using a HRP-conjugated secondary antibody as described before. A schematic representation of this KDM1A chemoprobe-based ELISA assay to detect free KDM1A is depicted in FIG. 3B.

Isolation of PBMCs from peripheral blood by density gradient centrifugation:

Peripheral blood mononuclear cells (PBMCs) from rat were isolated from peripheral fresh blood collected in anti-coagulant tubes for blood (K2- or K3-EDTA as the preferred anticoagulant tubes) and diluted with an equal volume of PBS, using Ficoll-Paque PLUS reagent (GE Healthcare; #17-1440-02) or Leucosep Tubes (Greiner bio-one; #227288) according to manufacturer's instructions. Cells were stained with tryptan blue and cell number and viability were determined using a Neubauer Chamber in an optical microscope. Pellets of $1\cdot10^6$ PBMCs were preserved at $-80°$ C. The same procedure can be used for isolation of PBMCs from other resources such as human or mouse blood. In the case of human samples, preferably Leucosep procedure is used, whereas for mouse PBMCs, Ficoll procedure is preferred.

Sample Preparation: Cells were lysed in presence of 25 nM KDM1A chemoprobe example 1.6 added to frozen cell pellets containing $1\cdot10^6$ cells following the conditions described in example 3. The same protein extracts is used in sandwich ELISA developed for determination of total KDM1A and in KDM1A chemoprobe capture ELISA developed for determination of free KDM1A.

ELISA:

To quantify total KDM1A, the surface of Luminunc Plates Maxisorp (NUNC; #436110) were coated with a monoclonal anti-KDM1A antibody (Abcam; #ab53269, referred to as mAb-844) at 2 Ng/mL in PBS as a capture agent. For quantification of free KDM1A, the surface of plates were coated with streptavidin (Promega Biotech Ibérica; #Z7041) at 10 g/mL in PBS as a capture agent. Coating was performed at 4° C. O/N. Wells were washed 3 times in PBS, 0.1% Tween-20 and blocked with PBS-BSA 1% (Sigma; #A3059) for 2 h.

A KDM1A calibration curve of full length rKDM1A (Active Motif; #31334) diluted in PBS was included in each plate. Plates were then incubated 1h at RT and washed 5 times. Afterwards, monoclonal anti-KDM1A antibody (Cell Signaling; #2184, referred to as mAb-825), used as a primary detection agent was diluted at 0.125 Ng/mL in PBS and plates were incubated 1h at RT. After 6 washes, a secondary detection agent; peroxidase-conjugated secondary antibody (Jackson Immunoresearch; #711-035-152) diluted 1:5000 was added to plates, incubated for 1 h at RT and plates were washed again. 100 µL/well of chemiluminescent substrate specific for horseradish peroxidase [HRP] in ELISA procedure (superSignal ELISA Femto Substrate, Invitrogen; #37074) was added. Plates were centrifuged during 30 sec to 1,500×g, shaken for 1 min at 100 rpm and incubated inside the microplate reader (Infinite 200, Tecan) for 3 min at 25° C. The level of total KDM1A were determined using relative luminescence units (RLU) read-outs that were acquired using a 1000 ms integration time and 150 ms settle time. FIG. 3 represents the KDM1A ELISA assays developed, sandwich ELISA for determination of total KDM1A (FIG. 3A) and KDM1A chemoprobe capture ELISA for determination of free KDM1A (FIG. 3B). The two determinations are run in two separate assays, HRP coupled secondary antibody directed against the anti-KDM1A antibody reacts with the appropriate substrate to generate a luminescent signal.

Figure 4:
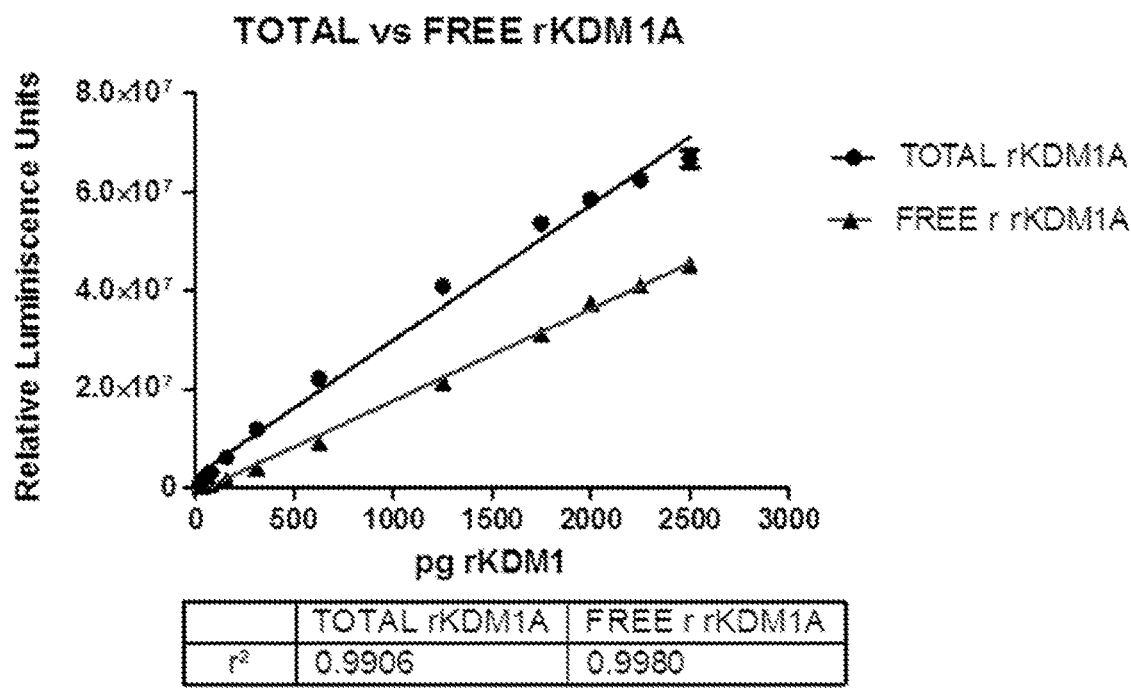
FIG. 4: Total and free rKDM1A calibration curves as described in example 5.

Results:

A dilution series of full length active recombinant rKDM1A was used to establish a standard curve and to assess the dynamic range and sensitivity of the luminescent assays for total and free KDM1A. FIG. 4 shows the standard curve of total and free human rKDM1A (Active Motif Ref 31334, batch #3303004), both the sandwich ELISA and the KDM1A chemoprobe capture ELISA are conducted in presence of chemoprobe example 1.6 (25 nM). As shown in FIG. 4, total and free KDM1A standard curves exhibited linear behavior ($r^2>0.99$). The ELISA LLOD (Lower Limit of Detection) is around 10 pg of KDM1A and the detection range 15-2500 pg.

This curve can be used directly to determine the concentration (amount) of total KDM1A and free KDM1A in a biological sample if the efficiency of detection of total and free recombinant KDM1A and of cellular total and free KDM1A and the specific activity of the recombinant and cellular KDM1A is the same, or after applying the appropriate correction function if efficiency of detection and specific activity of recombinant and cellular free KDM1A differ. The standard curve can be included in each ELISA assay as a positive control.

The above described KDM1A sandwich ELISA and KDM1A chemoprobe ELISA assays (both for total and free KDM1A), using the conditions and reagents described, can be used at least for the analysis of biological samples from different species, including human, rat and mouse. They can also be adapted to analyze samples from other animal species by selecting a suitable antibody for said species. Importantly, the method can be used to assess total and free KDM1A in clinically useful samples, p.e. in PBMCs obtained from human blood, using a PBMCs isolation protocol, for example one of the PBMC isolation protocols disclosed above. FIG. 5 shows the determination of the levels of total (FIG. 5A) and free (FIG. 5B) KDM1A in 7.5 ug of protein extract from PBMCs of three healthy donors (run in parallel with standard curve of rKDM1A of total and free KDM1A as a positive control). The data in FIGS. 5A and 5B show that free and total KMD1A levels can be determined in human PBMCs.

Example 5.3. Colorimetric KDM1A ELISA

The assay performed is similar to the assay disclosed above for the luminescent ELISA, but using Maxisorp plates (NUNC; #735-0013) as a surface and Tetramethylbenzidine (TMB) Liquid Substrate system (SIGMA-ALDRICH; #T0440) as substrate for the secondary detection agent. 100 µL TMB was added per well and plates were incubated for 10 min before stopping the reaction by addition of 100 uL/well of phosphoric acid solution 2N. Absorbance was read at 450 nm using a microplate reader (Infinite 200, Tecan).

The detection range for this method, while being not as sensitive as luminescent ELISA, is still good and suitable for use in analysis of biological samples. Total and free KDM1A standard curves exhibited linear behavior ($r2>0.99$). The LLOD of colorimetric ELISA is around 200 pg of KDM1A and the detection range (0.25-2.5 ng). As

Example 6. Amplified Luminescent Proximity Homogeneous Assay to Detect Total and Free KDM1A The Amplified Luminescent Proximity Homogeneous Assay (Alpha) technology is a homogeneous immunoassay platform that is an alternative to classical ELISA assays such as the one described in Example 5.2.

The AlphaLISA assay detects the proximity of a first detection agent containing 250 nM latex donor beads containing phthalocyanine that release singlet oxygen after irradiation at 680 nM to a second detection agent containing similar sized acceptor beads containing Europium that emit a narrow peak of light at 615 nM after absorption of singlet oxygen. The AlphaPlex assay allows detection of multiple analytes in the same assay volume and works similarly, but two acceptor beads are used (second and third detection agents) containing respectively Terbium or Samarium and emit light at 545 nM or 645 nM after absorption. Effective singlet oxygen transfer occurs when donor and acceptor beads are separated by a distance of less than 200 nm.

The anti-KDM1A antibodies mAb-825 and mAb-844 selected (see example 5.1) to bind in close proximity to each other and to the protruding KDM1A chemoprobe example 1.6 on the surface of KDM1A. Binding of the chemoprobe did not affect the binding of the antibodies, nor did binding to the surface of mAb-844 interfere with binding of mAb-825 in the experimental settings used. The AlphaLisa/AlphaPlex format for the chemoprobe based immune assay was developed to assess KDM1A target engagement.

For example, anti-KDM1A antibody (mAb-844) was conjugated to AlphaLISA acceptor beads (Perkin Elmer #6772001) to generate a first detection agent, and anti-KDM1A antibody (mAb-825) was conjugated to AlphaLISA donor beads (Perkin Elmer #6762013) to generate a second detection agent that together form a detection system that can be used to determine total KDM1A levels. The first detection reagent can also be used in combination with a third detection reagent, streptavidin-coated AlphaLISA donor beads (Perkin Elmer #6760002), targeting the biotin tag bearing KDM1A chemoprobe example 1.6, to form a second detection system that can be used to detect free KDM1A levels. AlphaLISA assay and conjugation of antibodies to the donor and acceptor beads was performed according to the vendor's instructions.

Figure 6B:
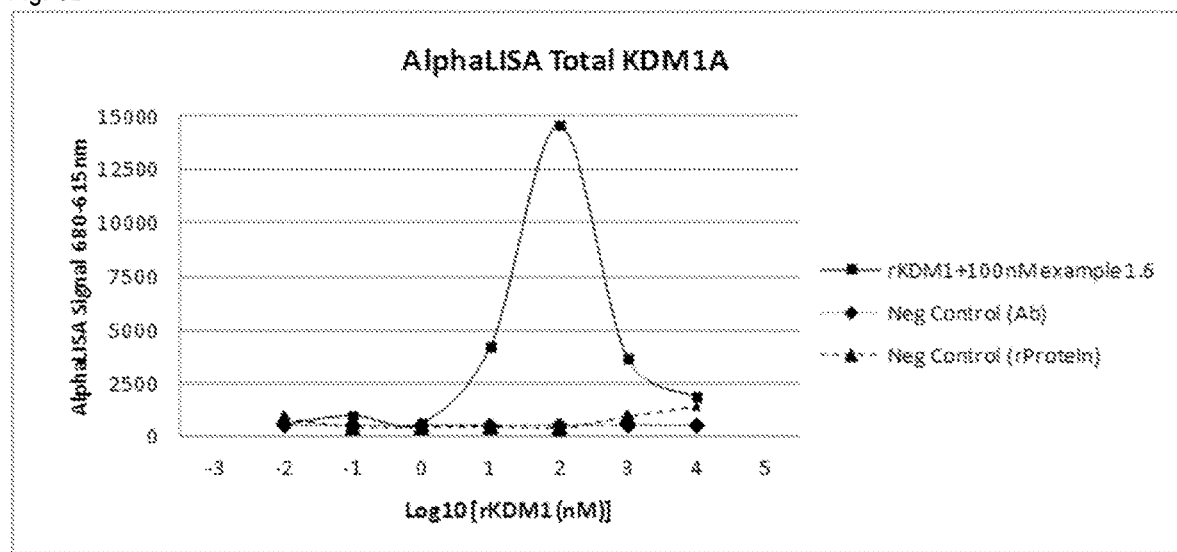
Figure 6C:
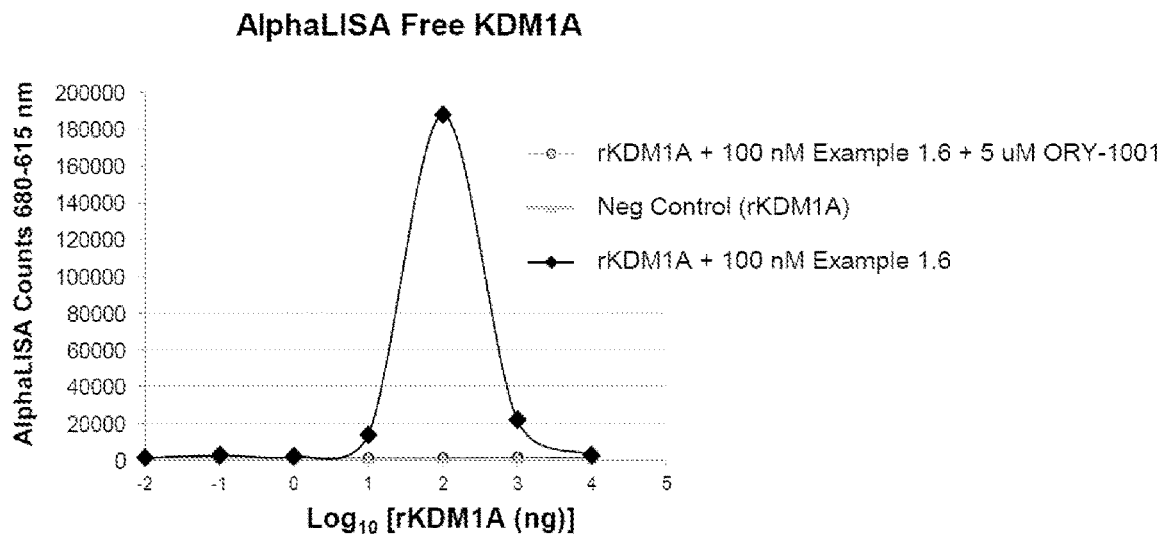

To illustrate the use of AlphaLISA to detect total and free KDM1A, a dilution series of human rKDM1A was prepared, incubated with 100 nM chemoprobe example 1.6 and mixed with anti-KDM1A mAb-844 conjugated AlphaLISA acceptor beads and either anti-KDM1A mAb-825 conjugated AlphaLISA donor beads or streptavidin coated AlphaLISA donor beads to detect free (FIG. 6A) or total (FIG. 6B) KDM1A respectively. The resulting curves are bell-shaped and characterized by a titratable signal decrease (hook effect) following a plateau obtained after an initial concentration-dependent signal increase, a pattern typical for AlphaLISA assays. The maximum signal to background ratio was obtained with 100 nM rKDM1A, i.e. at equimolar concentrations of chemoprobe and enzyme. As expected, the free KDM1A signal was blocked by pretreatment of the enzyme with ORY-1001 (5 uM), as the KDM1A inhibitor binds to KDM1A, so that there is no free KDM1A available for binding to the KDM1A chemoprobe; see FIG. 6C, where rhombi corresponds to rKDM1A+KDM1A chemoprobe (Example 1.6, 100 nM), circles correspond to rKDM1A+KDM1A chemoprobe (Example 1.6, 100 nM)+ORY-1001 (5 uM) and triangles correspond to negative control (rKDM1A protein alone).

For the multiplex assay, the phthalocyanine containing Alphaplex donor beads can be coupled to one of the anti-KDM1A antibodies (p.e. mAb-825) and Terbium containing Acceptor Beads to the second anti-KDM1A antibody (p.e mAb-844) and Samarium containing AlphaPLEX 645 Streptavidin Acceptor Beads can be used to bind the chemoprobe example 1.6 or vice versa, and detect total and free KDM1A simultaneously.

Example 7. Use of Chemoprobe for Assessment of KDM1A Target Engagement in Cells The chemoprobe-based immunoassay described above can be used to assess KDM1A target engagement in cells, as shown below.

7.1 Method

To establish a dose curve, MV(4;11) cells were treated for 96h with vehicle or increasing doses of ORY-1001. Cells were lysed and protein extracts were obtained in the presence of 25 nM of chemoprobe (example 1.6) as described in example 5.2. Total protein extracts were quantified and 1 ug of total protein was used to perform the target engagement analysis as described above, using the luminescent substrate.

7.2 Target Engagement Calculation

After treatment of cells with a KDM1A inhibitor such as ORY-1001, a part of free KDM1A enzyme can be occupied by the compound. When the KDM1A from these cells is exposed to an excess of the KDM1A chemoprobe such as example 1.6, it will rapidly bind to the FAD cofactor and tag the free KDM1A. The chemoprobes and the method described herein can be used to assess direct KDM1A occupation (target engagement) of ORY-1001 or any other KDM1A inhibitor in cells, tissues and/or other biological samples that express KDM1A.

To determine the target engagement (TE), a relative quantification method was used, in which the target engagement in a given sample X was calculated relative to a reference sample REF (pre-treatment or vehicle) of the same nature. After raw data processing (robust elimination of outliers in replica analysis points according to Grubbs criteria and subtraction of blank signal), the target engagement was calculated as $TE_X = 1 - (R_X/R_{REF})$; where $R_X = (RLU_{Free,X}/RLU_{Total,X})$ and $R_{REF} = (RLU_{Free,REF}/RLU_{Total,REF})$ or, expressed in %

$TE_X(\%) = 100 - ((R_X(\%)/R_{REF}(\%)) \times 100)$; where $R_X(\%) = (RLU_{Free,X}/RLU_{Total,X}) \times 100$ and $R_{REF}(\%) = (RLU_{Free,REF}/RLU_{Total,REF}) \times 100$.

7.3 Results

Figure 7:
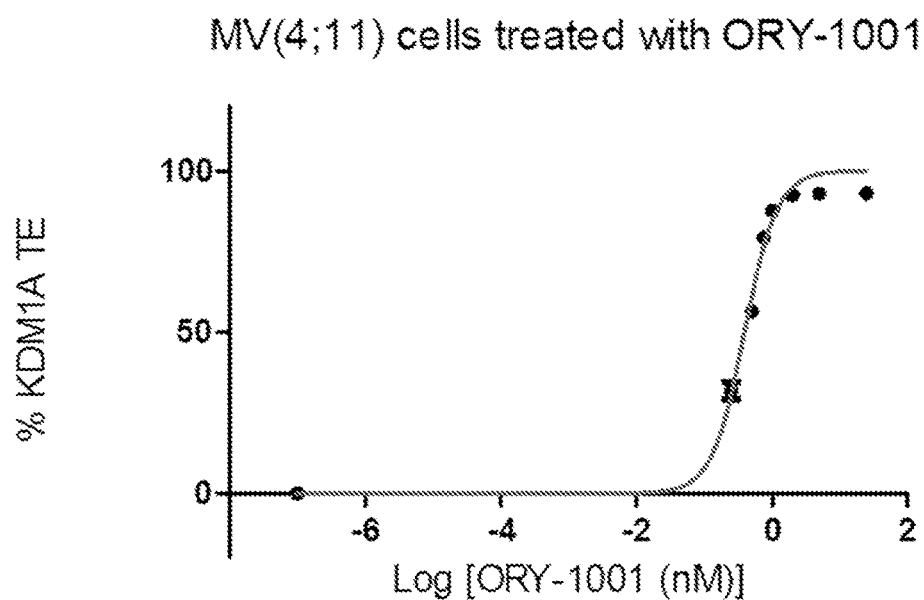
FIG. 7: IC50 determination of KDM1A target engagement in cells (MV4;11) treated with ORY-1001 and using the luminescent chemoprobe immunoassay described in example 7.

Total and free KDM1A levels, measured in RLUs, were determined following the conditions described in example 5.2, and target engagement was calculated following the method described in 7.2 above. FIG. 7 shows the % of target engagement plotted against ORY-1001 concentration, and the IC50 value for target engagement of ORY-1001 to KDM1A in MV(4;11) was calculated to be 0.35 nM using Graph Prism Software.

Figure 8A:
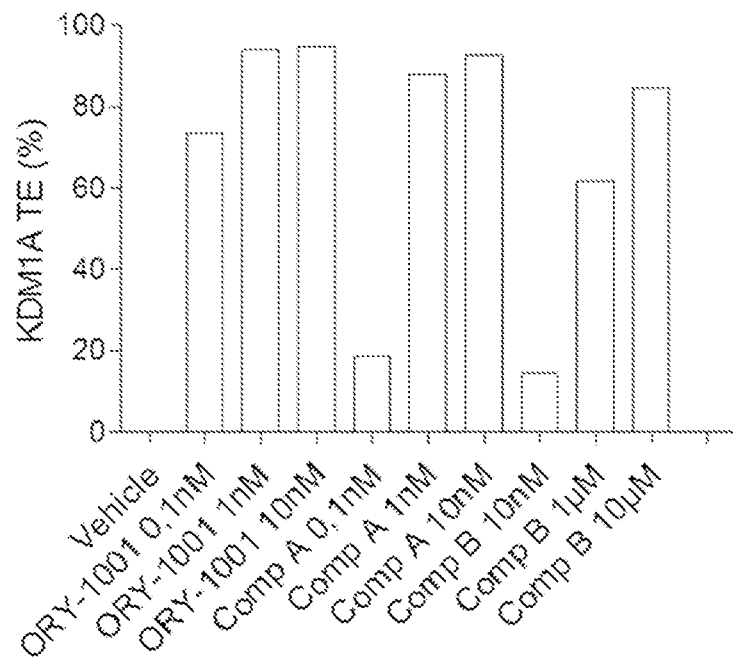
FIGS. 8A, 8B and 8C: KDM1A Target engagement in cells after treatment with different KDM1A inhibitors detailed in example 7.

Using the same method, we have also evaluated KDM1A target engagement by other KDM1A inhibitors such as compound A and compound B after 24 h of treatment in MV(4;11) cells. Compound A (or Comp A) is the compound with chemical name (trans)-2-Phenyl-N-(piperidin-4-ylmethyl)cyclopropan-1-amine, which is disclosed in example 5 of WO2013/057320. Compound B (or Comp B) is parnate, also known as tranylcypromine, with chemical name trans-2-Phenylcyclopropylamine. The results are shown in FIG. 8A, where the % of KDM1A target engagement for ORY-1001 (at 0.1, 1 and 10 nM), Comp A (at 0.1, 1 and 10 nM) and Comp B (at 10 nM, 1 mcM and 10 mcM) are plotted. FIG. 8A shows a dose-responsive cellular target engagement in accordance with their biochemical KDM1A activity ($IC50_{LSD1}$=0.018 uM, 0.022 uM and 15 uM for ORY-1001, comp A and B, respectively).

Figure 8B:
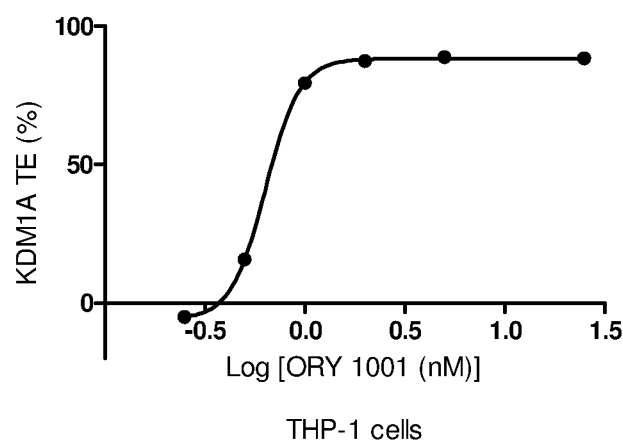
Figure 8C:
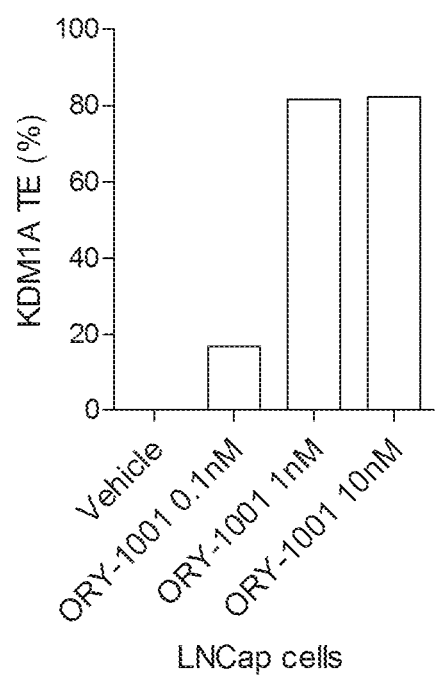

The methods and chemoprobes disclosed herein have also been used to determine target engagement of KDM1A inhibitors in additional cell lines, including other leukemic cell lines like THP-1 and solid tumor cell lines like prostate cancer and small cell lung cancer (SCLC) cell lines. For example, leukemia THP-1 cells or prostate cancer LNCap cells were treated for 24 h with ORY-1001 (at concentrations in the range 0.25-25 nM in THP-1 cells, at 0.1, 1 and 10 nM in LNCap cells), then lysed in Cell Lysis Buffer 1× (Cell Signaling Technology) in presence of the chemoprobe example 1.6 (25 nM) as described above, and free and total KDM1A levels were determined as described in Example 5.2 and used to calculate target engagement as described above. The % of Target engagement obtained in THP-1 cells treated with ORY-1001 is shown in FIG. 8B. The results show a dose-responsive cellular target engagement, with a calculated IC50 value using Graph Prism Software for target engagement of ORY-1001 to KDM1A in THP-1 cells of 0.6 nM. The target engagement data obtained in LNCap cells treated with ORY-1001 is shown in FIG. 8C, where a clear KDM1A target engagement of the KDM1A inhibitor tested is seen.

The results provided in this Example 7 show that the chemoprobe-based methods of the invention can be used to reliably determine target engagement of KDM1A inhibitors in different kinds of cells, including leukemic and solid tumor cells.

Example 8. Use of Chemoprobe for Assessment of In Vivo KDM1A Target Engagement Using Ex Vivo Samples The chemoprobes and chemoprobe-based methods of the invention have been successfully used to determine KDM1A target engagement in living subjects like animals (for example rat or mice) and humans that have been treated with a KDM1A inhibitor, using samples taken from said subjects (ex vivo samples).

For example, as shown in sections 8.1 to 8.3, rats or mice have been administered a KDM1A inhibitor at different doses or vehicle, and samples have then been obtained from said animals (for example blood samples, or tissue or organ samples) and analyzed to determine free and total KDM1A levels in said samples, which have been used to determine KDM1A target engagement by the KDM1A inhibitor as described above. Likewise, using the same approach, KDM1A target engagement has also been shown in humans treated with a KDM1A inhibitor, as described in more detail in Example 9 below.

8.1. Samples Preparation and Obtention of Protein Extracts from Cells was Performed as Described in Example 5

Frozen tissues were homogenized with a mortar and pestle chilled on dry ice. Powdered samples were resuspended in lysis buffer and forced through a 18 gauge blunt syringe needle to lyse the cells, proteins were then extracted as described above for cell pellets (example 5.2). Isolation of PBMCs from peripheral blood was also as described in example 5.2.

8.2. Assay Protocol and Calculation of TE: Same as Described in Example 7.1 and 7.2

8.3. Results

The luminescent ELISA method was used to assess KDM1A target engagement using ex-vivo samples of rats treated with ORY-1001 by oral gavage during 4 consecutive days. Four different doses were used (1, 3, 10 and 30 ug/kg/day). The KDM1A target engagement was calculated as described previously (see example 7), where $R_X$ corresponds to each condition analyzed and $R_{REF}$ is the sample corresponding to vehicle (non treated) rat PBMCs. FIG. 9A summarizes the KDM1A target engagement (in %) in pooled rat PBMC (n=3) treated with ORY-1001 at each dose tested and isolated two hours after last administration, and FIG. 9B shows the KDM1A target engagement (in %) in pooled rat lung (n=3) from the same animals treated with ORY-1001. A clear dose-response of KDM1A target engagement was observed to ORY-1001 treatment in both PBMCs and lung.

Figure 9C:
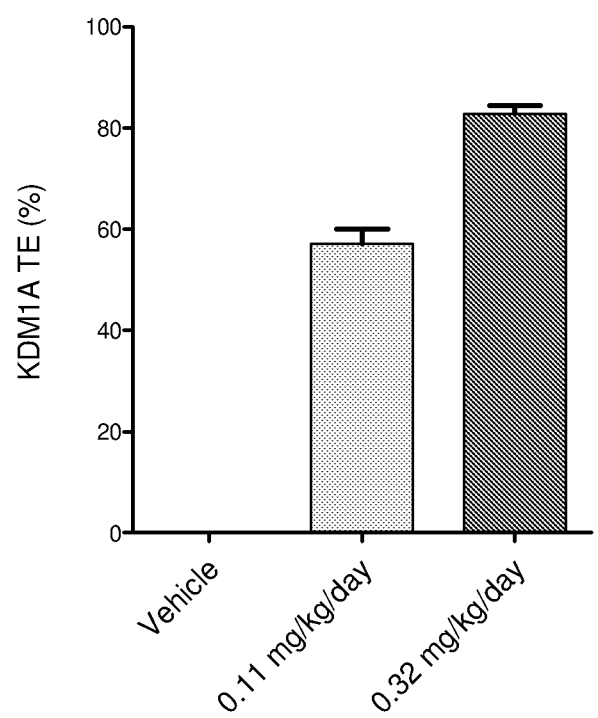

The methods of the invention have also been used to determine KDM1A target engagement in SAMP8 mice (a non-transgenic model for neurodegeneration reminiscent of Alzheimer's disease) which have been treated with the KDM1A inhibitor designated as Compound C. Compound C is the compound with chemical name (−) 5-((((trans)-2-(4-(benzyloxy)phenyl)cyclopropyl)amino)methyl)-1,3,4-oxadiazol-2-amine, which is described in WO2012/013728. This compound inhibits KDM1A with an IC50 (biochemical assay) of 101 nM, is orally available and has been shown to cross the blood-brain barrier. Female SAMP8 mice were treated with Compound C starting at 5 months of age and during 2 months. Mice were randomly distributed in three groups, receiving vehicle or Compound C at 0.11 mg/kg/day or 0.32 mg/kg/day, respectively. Compound C was diluted in vehicle (1.8% hydroxypropyl-beta-cyclodextrin, Sigma-Aldrich) and administered in drinking water. The dose was calculated according to the animal water consumption average per cage and adjusted weekly. Compound C (or vehicle) was available for 5 days followed by a 2 day clearance in a weekly period. After 2 months of treatment, animals were sacrificed and brains were dissected and snap frozen on dry ice for further TE analysis, which was performed following the procedure described previously. The results are shown in FIG. 9C, which shows the mean % KDM1A target engagement for each dose of Comp C tested; a clear dose-response of KDM1A target engagement was observed to Compound C treatment in brain.

The data reported in this Example 8 confirm the usefulness of the chemoprobes and chemoprobe-based methods of the invention to monitor KDM1A target engagement in living organisms.

Example 9. Use of Chemoprobe for Analysis of Pharmacodynamics and Assessment of KDM1A Target Turn-Over The chemoprobes and methods according to the invention have been used to quantify KDM1A target engagement and assess pharmacodynamics of binding of KDM1A inhibitors to KDM1A in animals and humans. In this type of study, typically animals (for example rats or mice) or humans (for example in the course of a clinical trial either using healthy volunteers or patients) are administered a KDM1A inhibitor, either as a single dose or as repeated doses (over several days or months) and samples are taken from said subjects at different time points, for example before start of the treatment with the KDM1A inhibitor and at different times after treatment has started, and target engagement is determined in said samples using the methods described above.

Rats:

Obtention of proteins extracts, assay protocol and calculation of TE as described in example 8.1, 7.1 and 7.2 respectively.

Figure 10:
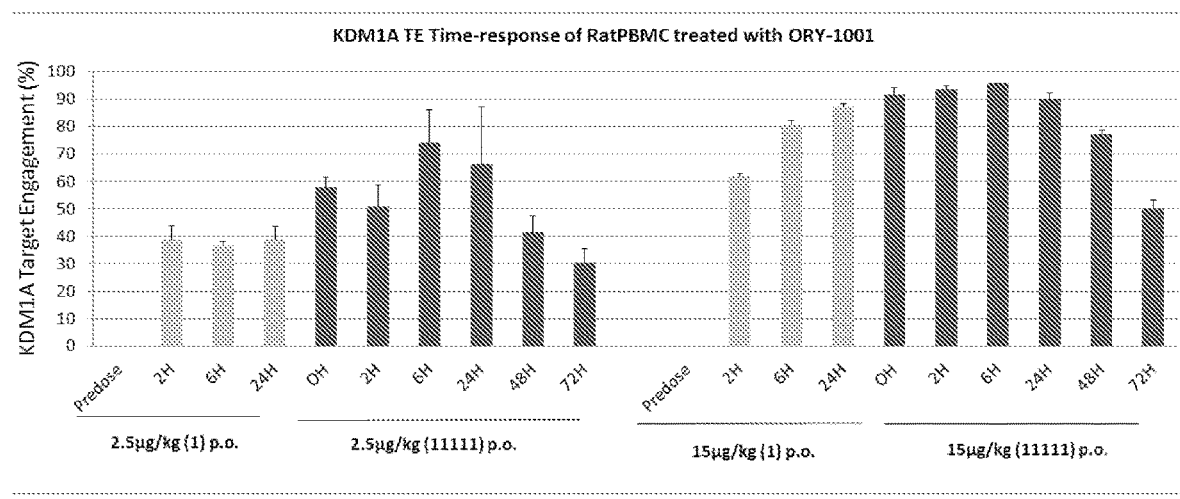
FIG. 10: Determination of dynamics of KDM1A target engagement in rat pooled PBMCs treated with ORY-1001 according to the conditions detailed in example 9.

To assess the dynamics of target engagement in vivo, vehicle or ORY-1001 was administered p.o. to rats either 1 day or during 5 consecutive days, at a dose of 2.5 and 15 ug/kg/day. PBMCs were obtained pre-dose (before starting the drug administration) and 2, 6, 24 h after the single dose administration, or pre-dose (i.e. 0h) and 2, 6, 24, 48 and 72 h after the last drug administration in the multiple dose administration. Total and free KDM1A protein levels in PBMCs were assessed using 0.5 ug of total protein extracts. FIG. 10 shows the percentage of KDM1A target engagement of pooled rat PBMCs (n=3) treated with ORY-1001 (2.5 and 15 ug/Kg/day) administered orally as a single dose (1) and as a multiple dose (during 5 days, 11111). The KDM1A target engagement was calculated as described previously (see section 7.2)), where $R_X$ corresponds to each time-point analyzed and $R_{REF}$ is the sample corresponding to the pre-dose of rat PBMC. FIG. 10 shows a clear time- and dose-response in KDM1A target engagement. At the same dose level, target engagement after multiple administrations is higher than single administration. Also as shown in FIG. 10, after the last dose in absence of further treatment, the percentage of KDM1A target engagement gradually decreases.

Humans

Figure 11:
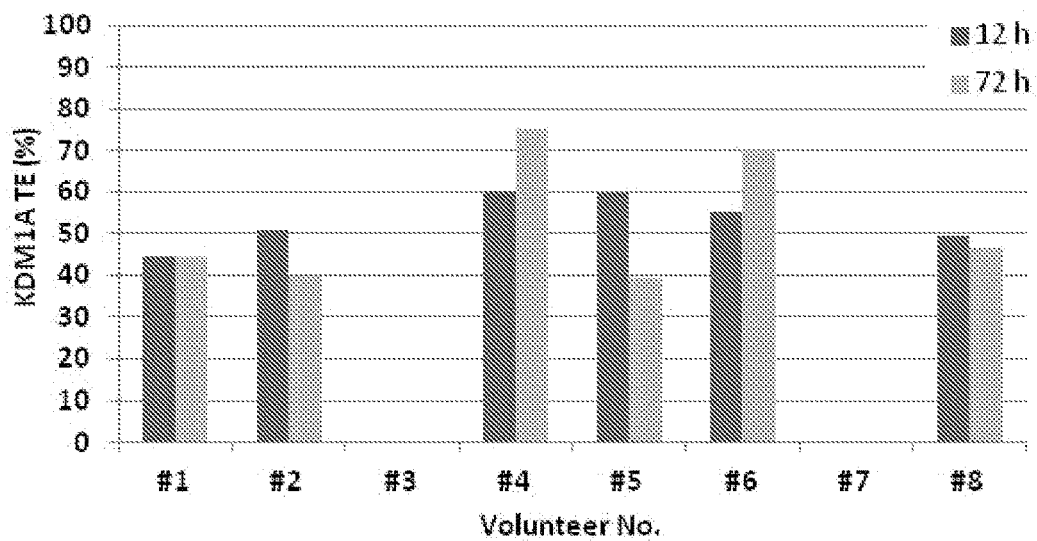
FIG. 11: Determination of KDM1A target engagement in PBMCs of human healthy volunteers treated with Compound C as described in example 9.

A Phase I clinical study has been performed to characterize the safety, tolerability, pharmacokinetics and pharmacodynamics of Compound C in healthy volunteers. The first stage of this clinical study is a randomized, double-blind, dose escalation study, in which the KDM1A inhibitor was administered as a single oral dose in capsules. Up to five different dose levels were tested in cohorts of 8 volunteers, randomized to receive either Compound C (n=6) or placebo (n=2). As part of the pharmacodynamic evaluations in this clinical study, KDM1A target engagement (TE) was assessed at pre-treatment, and 12 and 72 h after drug administration. Briefly, blood samples (10 mL) were collected in EDTA-K2 tubes from all the treated volunteers (active drug and placebo, n=8 per dose level) and PBMCs pellets obtained by density gradient centrifugation in Leucosep™ tubes and stored at −90° C. until analysis. Only PBMC samples meeting pre-established sample quality control criteria are used for the TE analysis. In particular, samples with signs of hemolysis and/or with traces of red cells are discarded. KDM1A TE values obtained for each volunteer in the cohort of volunteers corresponding to the single dose of 1.5 mg of Compound C are shown in FIG. 11. Clear KDM1A target engagement was observed at 12 and 72 h post-administration in 6 volunteers, whereas KDM1A TE levels of 0% was observed in the remaining two subjects. These results show that the chemoprobes and methods of the invention are useful to determine KDM1A target engagement by KDM1A inhibitors in human clinical samples.

Example 10. Chemoprobe Mediated Chemoproteomics of KDM1A

The KDM1A chemoprobe can be used to chemoprecipitate KDM1A containing complexes and to identify KDM1A interacting protein partners by means of Western blot analysis, antibody microarray analysis or mass spectrometry.

Selected chemoprobes (example 1.1 and 1.6) are incubated with cell extracts obtained from vehicle or KDM1A inhibitor (here used as a negative control) treated THP-1 or MV(4;11). Cells are lysed in 1× Cell Lysis Buffer (Cell Signaling; #9803) containing 1× Complete Mini, Protease Inhibitor Cocktail Tablets (ROCHE; #11836153001) and KDM1A chemoprobe example 1.6 (5 NM for pull down) is added to frozen cell pellets at a ratio of 200 µL Cell Lysis Buffer to 10-mg of cell pellet ($10^7$ cells are used). Tubes are incubated for 5 min on ice and briefly sonicated to achieve lysis. The resulting extracts are centrifuged 10 min at 14.000×g at 4° C. Supernatants are collected and quantified by Bradford assay (BIO-RAD; #500-0006) following manufacturer's instructions. 250 µL of Dynabeads M-280 Streptavidin (ThermoFisher Scientific; #11205D) are used as a capture agent and are washed 3 times and resuspended in 250 µL PBS. Protein extracts (containing the chemoprobe) are then added and incubated for 60 min in ice using gentle rotation.

The chemoprobe-KDM1A complex bound to the streptavidin beads is separated using a magnet and washed 4 times in PBS or Cell Lysis Buffer, prior to elution. The eluted proteins may then be analyzed using different techniques like western blot, antibody array analysis or mass spectrometry, as described for example below.

Western Blot:

After the last wash, samples are resuspended in 25 µL of 3× denaturing Sample Buffer Samples are separated on a 10% Bis-Tris NuPAGE® Novex® Precast gel (Invitrogen; #P0301BOX) following manufacturer's instructions. Gels are transferred onto nitrocellulose membrane (GE Healthcare; #RPN303D) for immunodetection by semi-dry transfer. N-specific binding sites are blocked by incubating membranes in blocking buffer (5% non-fat dry milk in PBS-Tween 0.1%) at RT for 1 h. Nitrocellulose membrane are incubated in blocking buffer with an anti-KDM1A antibody (Cell Signaling; #2184) diluted 1:1000 over night (O/N) at 4° C. or with antibodies of interest as a primary detection reagent; according to the vendor's instructions. After 5 washes in PBS-Tween 0.5%, the membrane is incubated with a peroxidase-conjugated secondary antibody (Jackson Immunoresearch; #711-035-152) diluted 1:5000 for 1 h at RT as a secondary detection reagent. Signal is detected by enhanced chemiluminescence (ECL, Amersham, GE Healthcare; #W9643350) using a GeneGnome HR System (Syngene).

Antibody Array Analysis

The chemoprobe precipitates obtained from the vehicle and the KDM1A inhibitor treated cells are labeled according to the vendor's instructions using the Amersham Cy5 or Cy3 Monoreactive Dye Pack (GE Healthcare PA25001/PA23001), respectively. Antibody microarrays containing potential capture agents to the KDM1A interacting proteins in the chemoprobe bound KDM1A complex are incubated overnight in 1×PBS/0.2% NP-40 and then incubated for 1 h at room temperature in blocking buffer sodium tetraborate decahydrate (2.85 g/100 ml) ethanolamine (453 ul/100 ml), in Agilent slide gaskets (1-well) and hybridization chambers; protected from light in an Agilent gasket rotator at speed 5. After this, the gaskets are dismounted and 500 ul of Cy3/Cy5 labeled protein is pipetted on the slide and mounted in the gasket for 1 h in the same conditions as used for blocking.

After this incubation, the slides open in wash buffer 3 and washed for 5 min in wash buffer 1 (2×PBS 0.5% NP-40), 2× in wash buffer 2 (1×PBS/0.5% NP-40); 2× in wash buffer 3 (1×PBS/0.2% NP-40) and aqua milliQ (3×), after which they are dried and scanned in an Agilent scanner. Data acquisition is performed using PC_Scan (Agilent Scan Software v.7.0 o sup.).

Mass Spectrometry:

Elution for mass spectrometry protein identification can be performed incubating the Dynabeads in 2% SDS for 45 minutes (in a heating block at 95 C) or by incubation in 8 M Urea pH 8.5 for 30 minutes (at room temperature).

Proteins are then treated with Dithiothreitol (DTT) and Iodoacetamide (IAA) to break disulfite bonds, prior to Tricloroacetic acid (TCA)/aceton precipitation and overnight (16 hours approximately) digestion with 1 g of porcine Tripsin. After stopping the reaction with 1 L of formic acid 1%, 1-5NL are injected for separation in the HPLC AS2nanoULTRA (EKSIGENT) apparatus. Protein identification has been performed using a LQT-Velos-Orbitrap (Thermo Scientific) mass spectrometer.

For example, a KDM1A chemoproteomic analysis using MS for protein identification was performed as follows:

To identify interacting proteins and transcription factors recruiting KDM1A to its target sites in the genome, pull-down experiments were performed in MV (4;11) cells with an active KDM1A-specific chemoprobe, using KDM1A inhibited cells or a mock pull down product as controls. Specifically, MV (4;11) cells were treated with either DMSO (0.1%) or with an irreversible KDM1A inhibitor (200 nM). Pellets of $10^7$ cells were prepared after 4 days of treatment and frozen at −80° C. For the pulldown, cells were resuspended in 400 μL of Cell Lysis Buffer (Cell Signaling) supplemented with 100 nM KDM1A chemoprobe of example 1.6. Samples were maintained in ice for 5 minutes, prior to sonication and high speed centrifugation to separate cellular debris. Cleared lysates were then incubated 1 hour on ice, to allow binding of the chemoprobe. For the pull-down, 150 μL of streptavidin beads (Life Technologies) were added to 450 μg of protein in 300 μL of Cell Lysis Buffer and incubated for 30 minutes at room temperature on a spinning wheel. After magnetic isolation, the beads were washed 5 times with ice-cold PBS to remove non-specific binding. Elution was performed using 25 μL of 1% SDS, incubating the beads for 15 minutes at 95° C. Eluted protein were precipitated with Trichloroacetic Acid, resuspended in 8M urea pH 8.0 and digested overnight with porcine trypsin (1 μg). Peptides were identified by LC-MS, using an AS2nanoULTRA HPLC system (Eksingent) for separation and a LTQ-Velos-Orbitrap detector (Thermo Scientific). Protein lists were processed by String (string-db.org) (76), for generating the final graphical representation of the protein networks associated to KDM1A. Proteins enriched by chemoprobe pull-down in untreated relative to treated MV (4;11) cells included, among others, components of the CoREST complex, in accordance with published reports in the scientific literature that have described KDM1A to be associated with CoREST. This confirms the KDM1A chemoprobes of the invention are useful to identify KDM1A interacting protein partners.

Example 11: Chromatin Immuno Precipitation (ChIP) Assays

ChIP assays can be performed using for example the SimpleChIP Enzymatic Chromatin IP Kit (Cell Signaling, 9003), according the supplier's indications. Briefly, THP-1 cells are treated with vehicle or 20 nM ORY-1001 for 96h, fixed with 1% formaldehyde (v/v) for 10 min at room temperature. Fixation is stopped by addition of glycine. Cell are lyzed in presence of a KDM1A chemoprobe including a biotin tag (example 1.6) and chromatin digested with the micrococcal nuclease from S. aureus (Roche) for 20 min at 37° C. and sonicated with bath sonicator (CD-4820 COBOS) 5×30s ON/OFF at high power to produce chromatin fragments of 150-300 bp. Lysates are subjected to pull-down using magnetic streptavidin beads as a capture agent. After pull down of chromatin complexes, the protein-DNA cross-links are reversed and DNA is purified. Pulled-down sequences are analyzed by next-generation sequencing analysis (ChIP-Seq) or by qPCR using specific primers of a gene of interest.

Example 12: Chemohistochemistry

The KDM1A chemoprobe incorporating a label or tag, such as fluorescein labeled or biotin labeled probes, can be used for histological localization of KDM1A in fresh or fixed tissues. If active KDM1A is present in the sample the probe will be able to join covalently to the enzyme habilitating direct localization by fluorescence if the fluorescein labeled probe is used and/or by secondary detection using an antibody against fluorescein or streptavidin (if the biotin labeled probe is used) conjugated to a fluorophore. Alternative to fluorescence, enzymatic secondary detection could be used using horseradish peroxidase, alkaline phosphatase or any other enzymatic reaction with a chromogenic product. The assay would allow locating active KDM1A in any cellular or tissue compartment. Combined with immune detection of KDM1A the assay would be used to calculate the free/total KDM1A ratio in the target tissue.

Unless defined otherwise, all technical and scientific terms used herein have the same meaning as commonly understood by one of ordinary skill in the art to which this invention pertains.

All publications, patents and patent applications cited herein are hereby incorporated herein by reference in their entireties.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains and as may be applied to the essential features hereinbefore set forth and as follows in the appended claims.

The invention claimed is:

1. A method for in vitro determining a level of free KDM1A in a sample, wherein said method comprises
   (i) contacting or exposing KDM1A to a chemoprobe, wherein said chemoprobe is a compound of formula (I)

P-L-Z                          (I)

or a salt thereof,
   wherein:
   P is a tag or label;
   L is a divalent $C_{6-100}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— and —NR$^1$—SO$_2$—, and wherein L provides a distance of at least 6 atoms between P and Z;
   R$^1$ is hydrogen or $C_{1-4}$ alkyl; and
   Z is a radical of a KDM1A inhibitor; and
   (ii) determining said level of free KDM1A employing said chemoprobe in said sample.

2. The method of claim 1, wherein said method further comprises to determine a level of total KDM1A in said sample.

3. The method of claim 1, wherein said method further comprises determining target engagement of a KDM1A inhibitor in said sample.

4. The method of claim 3, wherein the determination of said target engagement comprises:
   (i) calculating the ratio between free KDM1A level in the sample and the free KDM1A level in a reference sample; or
   (ii) calculating the ratio between free KDM1A level and total KDM1A level in the sample; or
   (iii) calculating the ratio $R_X/R_{REF}$, wherein $R_X$ is the ratio of the free KDM1A level and the total KDM1A level in the sample and $R_{REF}$ is the ratio of the free KDM1A level and total KDM1A level in the reference sample.

5. The method of claim 4, wherein the target engagement is determined as 1 minus the ratio calculated according to any of (i), (ii) or (iii), wherein 1 corresponds to full target engagement and 0 corresponds to absence of target engagement.

6. A method for in vitro determining target engagement of an inhibitor of KDM1A in a sample,
   wherein said method comprises:
   (i) contacting or exposing KDM1A to a chemoprobe, wherein said (i) chemoprobe is a compound of formula (I)

P-L-Z                          (I)

or a salt thereof,
   wherein:
   P is a tag or label;
   L is a divalent $C_{6-100}$ hydrocarbon group, wherein one or more carbon atoms comprised in said hydrocarbon group are each optionally replaced by a heteroatom selected independently from O, S and N, wherein one or more carbon atoms comprised in said hydrocarbon group are each optionally replaced by a group selected independently from the group consisting of —C(=O)—, —NR$^1$—, —NR$^1$—C(=O)—, —C(=O)—NR$^1$—, —NR$^1$—C(=O)—NR$^1$—, —NR$^1$—C(=S)—NR$^1$—, —O—C(=O)—NR$^1$—, —NR$^1$—C(=O)—O—, —C(=O)—O—, —O—C(=O)—, —SO$_2$—NR$^1$— and —NR$^1$—SO$_2$—, and wherein L provides a distance of at least 6 atoms between P and Z;
   R$^1$ is hydrogen or $C_{1-4}$ alkyl; and
   Z is a radical of a KDM1A inhibitor;
   (ii) determining a level of free KDM1A employing said chemoprobe in said sample;

(iii) determining a level of total KDM1A in said sample;
(iv) determining a level of free KDM1A employing said chemoprobe in a reference sample;
(v) determining a level of total KDM1A in said reference sample;
(vi) calculating the ratio A/B, wherein A is the ratio of the free KDM1A level and the total KDM1A level in the sample and B is the ratio of the free KDM1A level and the total KDM1A level in the reference sample; and
(vii) determining target engagement as 1 minus the ratio calculated in step (vi).

7. The method of claim 1, wherein said sample is obtained from a subject that has been administered a KDM1A inhibitor.

8. The method of claim 3, wherein said inhibitor of KDM1A is an irreversible inhibitor of KDM1A.

9. The method of claim 8, wherein said irreversible KDM1A inhibitor is (trans)-N1-(((1R,2S)-2-phenylcyclopropyl)cyclohexane-1,4-diamine, (−) 5-((((trans)-2-(4-(benzyloxy)phenyl)cyclopropyl)amino)methyl)-1,3,4-oxadiazol-2-amine, or 4-((4-((((1R,2S)-2-phenylcyclopropyl)amino)methyl) piperidin-1-yl)methyl)benzoic acid, or a salt thereof.

10. The method of claim 1, wherein the chemoprobe is used to capture or detect free KDM1A.

11. The method of claim 10, wherein P in the chemoprobe is a tag and the chemoprobe is captured or detected by a suitable capture or detection agent.

12. The method of claim 1, wherein Z is a radical of an irreversible KDM1A inhibitor comprising a 2-cyclyl-cyclopropylamino moiety.

13. The method of claim 1, wherein Z is a radical of an irreversible KDM1A inhibitor which is a 2-(hetero)arylcyclopropylamino compound.

* * * * *